US012715856B2

(12) United States Patent
Yeung et al.

(10) Patent No.: US 12,715,856 B2
(45) Date of Patent: Aug. 25, 2026

(54) COMPOUNDS USEFUL AS IMMUNOMODULATORS

(71) Applicant: Bristol-Myers Squibb Company, Princeton, NJ (US)

(72) Inventors: Kap-Sun Yeung, Madison, CT (US); Denis R. St. Laurent, Newington, CT (US); Li-Qiang Sun, Newtown, PA (US); Zhiwei Yin, Glastonbury, CT (US); Katharine A. Grant-Young, Vieques, PR (US); Paul Michael Scola, Cambridge, MA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1179 days.

(21) Appl. No.: 17/766,483

(22) PCT Filed: Oct. 1, 2020

(86) PCT No.: PCT/US2020/053667

§ 371 (c)(1),
(2) Date: Apr. 4, 2022

(87) PCT Pub. No.: WO2021/067521

PCT Pub. Date: Apr. 8, 2021

(65) Prior Publication Data

US 2024/0124417 A1 Apr. 18, 2024

Related U.S. Application Data

(60) Provisional application No. 62/910,721, filed on Oct. 4, 2019.

(51) Int. Cl.

| | |
|---|---|
| ***C07D 401/14*** | (2006.01) |
| ***A61K 31/4439*** | (2006.01) |
| ***A61K 31/4545*** | (2006.01) |
| ***A61K 31/497*** | (2006.01) |
| ***A61K 31/501*** | (2006.01) |
| ***A61K 31/506*** | (2006.01) |
| ***C07D 401/12*** | (2006.01) |
| ***C07D 403/14*** | (2006.01) |
| ***C07D 413/14*** | (2006.01) |
| ***C07D 417/14*** | (2006.01) |
| ***C07D 471/04*** | (2006.01) |
| ***C07D 513/04*** | (2006.01) |

(52) U.S. Cl.

CPC ........ *C07D 401/14* (2013.01); *A61K 31/4439* (2013.01); *A61K 31/4545* (2013.01); *A61K 31/497* (2013.01); *A61K 31/501* (2013.01); *A61K 31/506* (2013.01); *C07D 401/12* (2013.01); *C07D 403/14* (2013.01); *C07D 413/14* (2013.01); *C07D 417/14* (2013.01); *C07D 471/04* (2013.01); *C07D 513/04* (2013.01)

(58) Field of Classification Search

None

See application file for complete search history.

(56) References Cited

U.S. PATENT DOCUMENTS

| | | | |
|---|---|---|---|
| 9,850,225 | B2 | 12/2017 | Chupak et al. |
| 9,872,852 | B2 | 1/2018 | Chupak et al. |
| 10,144,706 | B2 | 12/2018 | Yeung et al. |
| 10,590,105 | B2 | 3/2020 | Yeung et al. |
| 10,745,382 | B2 | 8/2020 | Yeung et al. |
| 10,882,844 | B2 | 1/2021 | Yeung et al. |
| 11,046,675 | B2 | 6/2021 | Yeung et al. |
| 11,414,418 | B2 | 8/2022 | Yeung et al. |
| 11,578,054 | B2 | 2/2023 | Yeung et al. |

FOREIGN PATENT DOCUMENTS

| | | | |
|---|---|---|---|
| EP | 2011788 | A1 | 1/2009 |
| WO | WO 2015034820 | A1 | 3/2015 |
| WO | WO 2015160641 | A2 | 10/2015 |
| WO | WO 2017066227 | A1 | 4/2017 |
| WO | WO 2018005374 | A1 | 1/2018 |
| WO | WO 2018009505 | A1 | 1/2018 |
| WO | WO 2018044963 | A1 | 3/2018 |
| WO | WO 2018118848 | A1 | 6/2018 |
| WO | WO 2018183171 | A1 | 10/2018 |
| WO | WO 2019023575 | A1 | 1/2019 |
| WO | WO 2019147662 | A1 | 8/2019 |
| WO | WO 2019169123 | A1 | 9/2019 |
| WO | WO 2019191624 | A1 | 10/2019 |

OTHER PUBLICATIONS

Guzik, K., et al., "Small-Molecule Inhibitors of the Programmed Cell Death-1/Programmed Death-Ligand 1 (PD-1/PD-L1) Interaction via Transiently Induced Protein States and Dimerization of PD-L1," *Journal of Medicinal Chemistry*, 60(13):5857-5867, American Chemical Society, United States (Jul. 2017).

*Primary Examiner* — Juliet C Switzer
*Assistant Examiner* — Dawanna Shar-Day White
(74) *Attorney, Agent, or Firm* — Sterne, Kessler, Goldstein & Fox P.L.L.C.

(57) ABSTRACT

The present disclosure generally relates to compounds useful as immunomodulators. Provided herein are compounds, compositions comprising such compounds, and methods of their use. The disclosure further pertains to pharmaceutical compositions comprising at least one compound according to the disclosure that are useful for the treatment of various diseases, including cancer and infectious diseases.

2 Claims, No Drawings

73COMPOUNDS USEFUL AS IMMUNOMODULATORS

CROSS REFERENCE TO RELATED APPLICATION

This application claims the priority of U.S. Provisional Application Ser. No. 62/910,721 filed Oct. 4, 2019 which is herein incorporated by reference.

The present disclosure generally relates to compounds useful as inhibitors of the PD-1/PD-L1 protein/protein and CD80/PD-L1 protein/protein interactions. Provided herein are compounds, compositions comprising such compounds, and methods of their use. The disclosure further pertains to pharmaceutical compositions comprising at least one compound according to the disclosure that are useful for the treatment of various diseases, including cancer and infectious diseases.

Programmed death-1 (CD279) is a receptor on T cells that has been shown to suppress activating signals from the T cell receptor when bound by either of its ligands, Programmed death-ligand 1 (PD-L1, CD274, B7-H1) or PD-L2 (CD273, B7-DC) (Sharpe et al., *Nat. Imm.* 2007). When PD-1 expressing T cells contact cells expressing its ligands, functional activities in response to antigenic stimuli, including proliferation, cytokine secretion, and cytolytic activity are reduced. PD-1/PD-Ligand interactions down regulate immune responses during resolution of an infection or tumor, or during the development of self tolerance (Keir Me, Butte M J, Freeman G J, et al. *Annu. Rev. Immunol.* 2008; 26: Epub). Chronic antigen stimulation, such as that which occurs during tumor disease or chronic infections, results in T cells that express elevated levels of PD-1 and are dysfunctional with respect to activity towards the chronic antigen (reviewed in Kim and Ahmed, Curr Opin Imm, 2010). This is termed "T cell exhaustion". B cells also display PD-1/PD-ligand suppression and "exhaustion".

PD-L1 has also been shown to interact with CD80 (Butte M J et al., *Immunity* 27:111-122 (2007)). The interaction of PD-L1/CD80 on expressing immune cells has been shown to be an inhibitory one. Blockade of this interaction has been shown to abrogate this inhibitory interaction (Paterson A M, et al., *J Immunol.,* 187:1097-1105 (2011); Yang J, et al. *J Immunol*. August 1; 187(3):1113-9 (2011)).

Blockade of the PD-1/PD-L1 interaction using antibodies to PD-L1 has been shown to restore and augment T cell activation in many systems. Patients with advanced cancer benefit from therapy with a monoclonal antibody to PD-L1 (Brahmer et al., *New Engl J Med* 2012). Preclinical animal models of tumors have shown that blockade of the PD-1/PD-L1 pathway by monoclonal antibodies can enhance the immune response and result in the immune response to a number of histologically distinct tumors (Dong H, Chen L. *J Mol Med.* 2003; 81(5):281-287; Dong H, Strome S E, Salamoa D R, et al. *Nat Med.* 2002; 8(8):793-800).

Interference with the PD-1/PD-L1 interaction has also shown enhanced T cell activity in chronic infection systems. Chronic lymphocytic chorio meningitis virus infection of mice also exhibits improved virus clearance and restored immunity with blockade of PD-L1 (Barber D L, Wherry E J, Masopust D, et al. *Nature* 2006; 439(7077):682-687).

Humanized mice infected with HIV-1 show enhanced protection against viremia and reduced viral depletion of CD4+ T cells (Palmer et al., *J. Immunol* 2013). Blockade of PD-1/PD-L1 through monoclonal antibodies to PD-L1 can restore in vitro antigen-specific functionality to T cells from HIV patients (Day, *Nature* 2006; Petrovas, *J. Exp. Med.* 2006; Trautman, *Nature Med.* 2006; D'Souza, *J. Jmmunol.* 2007; Zhang, *Blood* 2007; Kaufmann, *Nature Imm.* 2007; Kasu, *J. Immunol.* 2010; Porichis, *Blood* 2011), HCV patients [Golden-Mason, *J Virol.* 2007; Jeung, J. Leuk. *Biol.* 2007; Urbani, *J. Hepatol.* 2008; Nakamoto, *PLoS Path.* 2009; Nakamoto, *Gastroenterology* 2008] or HBV patients (Boni, *J. Virol.* 2007; Fisicaro, *Gastro.* 2010; Fisicaro et al., *Gastroenterology,* 2012; Boni et al., *Gastro.,* 2012; Penna et al., *J Hep,* 2012; Raziorrough, *Hepatology* 2009; Liang, *World J Gastro.* 2010; Zhang, *Gastro.* 2008).

Blockade of the PD-L1/CD80 interaction has also been shown to stimulate immunity (Yang J., et al., *J Immunol.* August 1; 187(3):1113-9 (2011)). The immune stimulation resulting from blockade of the PD-L1/CD80 interaction has been shown to be enhanced through combination with blockade of further PD-1/PD-L1 or PD-1/PD-L2 interactions.

Alterations in immune cell phenotypes are hypothesized to be an important factor in septic shock (Hotchkiss, et al., *Nat Rev Immunol* (2013)). These include increased levels of PD-1 and PD-L1 and T ceoll apoptosis (Guignant, et al, *Crit. Care* (2011)). Antibodies directed to PD-L1 can reduce the level of Immune cell apoptosis (Zhang et al, *Crit. Care* (2011)). Furthermore, mice lacking PD-1 expression are more resistant to septic shock symptoms than wildtype mice (Yang J., et al. *J Immunol*. August 1; 187(3):1113-9 (2011)). Studies have revealed that blockade of the interactions of PD-L1 using antibodies can suppress inappropriate immune responses and ameliorate disease symptoms.

In addition to enhancing immunologic responses to chronic antigens, blockade of the PD-1/PD-L1 pathway has also been shown to enhance responses to vaccination, including therapeutic vaccination in the context of chronic infection (S. J. Ha, S. N. Mueller, E. J. Wherry et al., *The Journal of Experimental Medicine*, vol. 205, no. 3, pp. 543-555, 2008.; A. C. Finnefrock, A. Tang, F. Li et al., *The Journal of Immunology*, vol. 182, no. 2, pp. 980-987, 2009; M.-Y. Song, S.-H. Park, H. J. Nam, D.-H. Choi, and Y.-C. Sung, *The Journal of Immunotherapy*, vol. 34, no. 3, pp. 297-306, 2011).

The PD-1 pathway is a key inhibitory molecule in T cell exhaustion that arises from chronic antigen stimulation during chronic infections and tumor disease. Blockade of the PD-1/PD-L1 interaction through targeting the PD-L1 protein has been shown to restore antigen-specific T cell immune functions in vitro and in vivo, including enhanced responses to vaccination in the setting of tumor or chronic infection.

Accordingly, agents that block the interaction of PD-L1 with either PD-1 or CD80 are desired.

Applicants found potent compounds that have activity as inhibitors of the interaction of PD-L1 with PD-1 and CD80, and thus may be useful for therapeutic administration to enhance immunity in cancer or infections, including therapeutic vaccine. These compounds are provided to be useful as pharmaceuticals with desirable stability, bioavailability, therapeutic index, and toxicity values that are important to their drugability.

In a first aspect, the present disclosure provides a compound of formula (I)

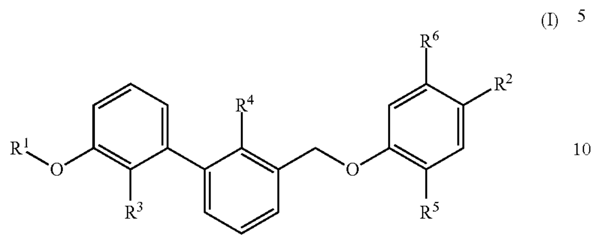

(I)

wherein $R^1$ is —$(CH_2)_n$—$R^{1a}$;

$R^{1a}$ is —$NHCH_2CH(OH)CH_2OH$ or a mono or bicyclic heterocyclyl group with one or more heteroatoms selected from —O—, —N—, —S—, and $NR^7$, or $C_3$-$C_8$ cycloalkyl, all of which are substituted with 0-2 $R^{1b}$;

$R^{1b}$ is hydrogen, $C_1$-$C_6$ alkyl, hydroxyl, heterocyclyl, haloalkyl, hydroxyalkyl or —$NHCO(C_1$-$C_3$ alkyl);

$R^2$ is —$(CH_2)_m$—$(NR_7)_p$—$(CH_2)_m$—$(CR^8R^{8a})_s$—$R^{2a}$;

$R^{2a}$ is a mono or bicyclic heterocyclyl group with one or more heteroatoms selected from —O—, —N— and —S—, substituted with 0-2 $R^{2b}$;

$R^{2b}$ is a mono or bicyclic heterocyclyl group with one or more heteroatoms selected from —O—, —N— and —S—, $C_1$-$C_3$ alkyl, halogen, CN, $CONH_2$, $NH_2$, phenyl, $C_3$-$C_8$ cycloalkyl, hydroxyalkyl, alkoxyalkyl, benzyl or haloalkyl, said heterocyclyl group substituted with 0-2 $R^{2c}$ or 0-1 $R^{2d}$;

$R^{2c}$ is hydrogen or $C_1$-$C_3$ alkyl;

$R^{2d}$ is oxo;

$R^3$ is hydrogen, $C_1$-$C_3$ alkyl or halogen;

$R^4$ is hydrogen, $C_1$-$C_3$ alkyl or halogen;

$R^5$ is hydrogen, $C_1$-$C_3$ alkyl or halogen;

$R^6$ is O—$(CH_2)_n$—$R^{6a}$;

$R^{6a}$ is $C_1$-$C_4$ alkyl or a mono or bicyclic heterocyclyl group with one or more heteroatoms selected from —O—, —N— and —S—, substituted with 0-3 $R^{6b}$;

$R^{6b}$ is $C_1$-$C_3$ alkyl, CN, halogen or trityl;

$R^7$ is H, $C_1$-$C_3$ alkyl or alkoxyalkyl;

$R^8$ is hydrogen, $C_1$-$C_3$ alkyl or carboxy;

$R^{8a}$ is hydrogen or $C_1$-$C_3$ alkyl;

alternatively, $R^8$ and $R^{8a}$ may be combined, together with the carbon atom to which they are attached, to form a 4- to 6-membered carbocycle, and wherein the carbocycle is substituted with 0 to 2 $R^9$;

$R^9$ is $C_1$-$C_3$ alkyl, halogen, CN, alkoxy, alkoxyalkyl, phenyl, benzyl, phenoxy or benzyloxy;

m is 0, 1 or 2;

n is 0, 1, 2, 3 or 4;

p is 0 or 1; and s is 0 or 1;

or a pharmaceutically acceptable salt thereof.

In a second aspect, the present disclosure provides a compound of formula (II)

(II)

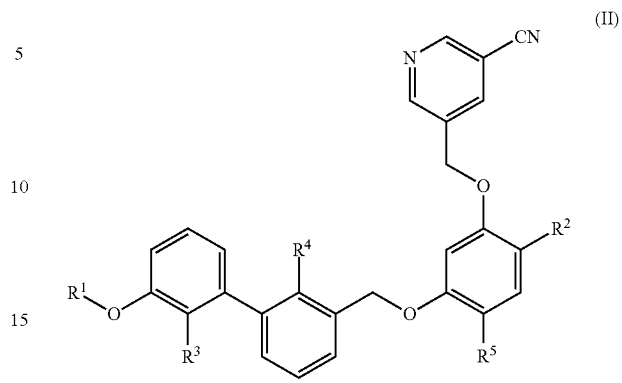

wherein $R^1$ is —$(CH_2)_n$—$R^{1a}$;

$R^{1a}$ is —$NHCH_2CH(OH)CH_2OH$ or a mono or bicyclic heterocyclyl group with one or more heteroatoms selected from —O—, —N—, —S— and $NR^7$, or $C_3$-$C_8$ cycloalkyl, all of which are substituted with 0-2 $R^{1b}$;

$R^{1b}$ is hydrogen, $C_1$-$C_6$ alkyl, hydroxyl, heterocyclyl, haloalkyl, hydroxyalkyl or —$NHCO(C_1$-$C_3$ alkyl);

$R^2$ is —$(CH_2)_m$—$(NR_7)_p$—$(CH_2)_m$—$(CHR^8)_s$—$R^{2a}$;

$R^{2a}$ is a mono or bicyclic heterocyclyl group with one or more heteroatoms selected from —O—, —N— and —S—, substituted with 0-2 $R^{2b}$;

$R^{2b}$ is a mono or bicyclic heterocyclyl group with one or more heteroatoms selected from —O—, —N— and —S—, $C_1$-$C_3$ alkyl, halogen, CN, $CONH_2$, $NH_2$, phenyl, $C_3$-$C_8$ cycloalkyl, hydroxyalkyl, alkoxyalkyl, benzyl or haloalkyl, said heterocyclyl group substituted with 0-2 $R^{2c}$ or 0-1 $R^{2d}$;

$R^{2c}$ is hydrogen or $C_1$-$C_3$ alkyl;

$R^{2d}$ is oxo;

$R^3$ is hydrogen, $C_1$-$C_3$ alkyl or halogen;

$R^4$ is hydrogen, $C_1$-$C_3$ alkyl or halogen;

$R^5$ is hydrogen, $C_1$-$C_3$ alkyl or halogen;

$R^7$ is hydrogen or $C_1$-$C_3$ alkyl;

$R^8$ is hydrogen, $C_1$-$C_3$ alkyl or carboxy;

m is 0, 1 or 2;

n is 0, 1, 2, 3 or 4;

p is 0 or 1; and s is 0 or 1;

or a pharmaceutically acceptable salt thereof.

In a third aspect, the present disclosure provides a compound of formula (II)

(II)

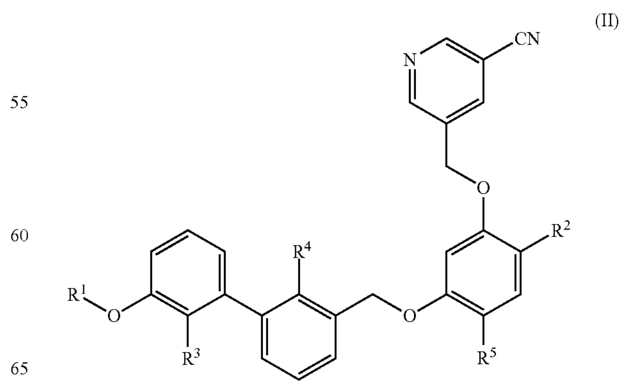

wherein $R^1$ is $—(CH_2)_n—R^{1a}$;

$R^{1a}$ is $—NHCH_2CH(OH)CH_2OH$ or a mono or bicyclic heterocyclyl group with one or more heteroatoms selected from —O—, —N—, —S—, and $NR^7$, or $C_3$-$C_8$ cycloalkyl, all of which are substituted with 0-2 $R^{1b}$;

$R^{1b}$ is hydrogen, $C_1$-$C_6$ alkyl, hydroxyl, heterocyclyl, haloalkyl, hydroxyalkyl or $—NHCO(C_1$-$C_3$ alkyl);

$R^2$ is $—(CH_2)_m—(NR_7)_p—(CH_2)_m—(CHR^8)_s—R^{2a}$;

$R^{2a}$ is a mono or bicyclic heterocyclyl group with one or more heteroatoms selected from —O—, —N— and —S—, substituted with 0-2 $R^{2b}$;

$R^{2b}$ is pyrazole, imidazole, triazole, tetrazole, $C_1$-$C_3$ alkyl, halogen, CN, $CONH_2$, $NH_2$, phenyl, cyclopropyl, hydroxyalkyl, alkoxyalkyl, benzyl or $CF_3$, said pyrazole, imidazole, triazole or tetrazole group substituted with 0-2 $R^{2c}$ or 0-1 $R^{2d}$;

$R^{2c}$ is hydrogen or $C_1$-$C_3$ alkyl;

$R^{2d}$ is oxo;

$R^3$ is hydrogen, $C_1$-$C_3$ alkyl or halogen;

$R^4$ is hydrogen, $C_1$-$C_3$ alkyl or halogen;

$R^5$ is hydrogen, $C_1$-$C_3$ alkyl or halogen;

$R^7$ is hydrogen or $C_1$-$C_3$ alkyl;

$R^8$ is hydrogen, $C_1$-$C_3$ alkyl or carboxy;

m is 0, 1 or 2;

n is 0, 1, 2, 3 or 4;

p is 0 or 1; and s is 0 or 1;

or a pharmaceutically acceptable salt thereof.

In a fourth aspect, the present disclosure provides a compound of formula (II)

(II)

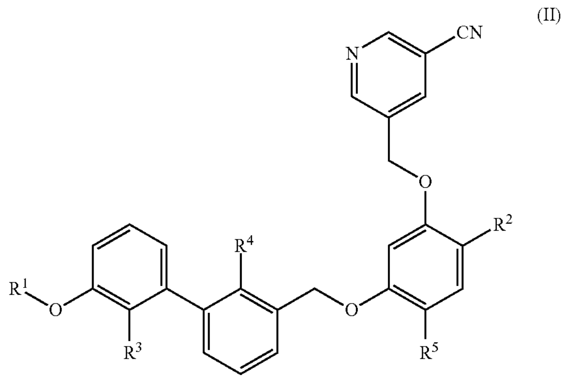

wherein $R^1$ is $—(CH_2)_n—R^{1a}$;

$R^{1a}$ is $—NHCH_2CH(OH)CH_2OH$ or a mono heterocyclyl group with one or more heteroatoms selected from —O—, —N—, —S—, and $NR^7$, or $C_3$-$C_8$ cycloalkyl, all of which are substituted with 0-2 $R^{1b}$;

$R^{1b}$ is hydrogen, $C_1$-$C_6$ alkyl, hydroxyl, heterocyclyl, haloalkyl or $—NHCO(C_1$-$C_3$ alkyl);

$R^2$ is $—(CH_2)_m—(NR^7)_p—(CH_2)_m—(CHR^8)_s—R^{2a}$;

$R^{2a}$ is piperidine, pyrrolidine, pyrazole, pyridine, pyrazine, pyridazine, pyrimidine, imidazole, triazole, tetrazole, thiazole, isoxazole, oxazole, oxadiazole, indazole, indole, pyrazolo-piperidine or benzo-imidazole, substituted with 0-2 $R^{2b}$;

$R^{2b}$ is pyrazole, imidazole, triazole, tetrazole, $C_1$-$C_3$ alkyl, halogen, CN, $—CH_2OH$, $CONH_2$, $NH_2$, phenyl, cyclopropyl, alkoxyalkyl, benzyl or $CF_3$, said pyrazole, imidazole, triazole or tetrazole group substituted with 0-2 $R^{2C}$ or 0-1 $R^{2d}$;

$R^{2c}$ is hydrogen or $C_1$-$C_3$ alkyl;

$R^{2d}$ is oxo;

$R^3$ is hydrogen, $C_1$-$C_3$ alkyl or halogen;

$R^4$ is hydrogen, $C_1$-$C_3$ alkyl or halogen;

$R^5$ is hydrogen, $C_1$-$C_3$ alkyl or halogen;

$R^7$ is hydrogen or $C_1$-$C_3$ alkyl;

$R^8$ is hydrogen, $C_1$-$C_3$ alkyl or carboxy;

m is 0, 1 or 2;

n is 0, 1, 2, 3 or 4;

p is 0 or 1; and s is 0 or 1;

or a pharmaceutically acceptable salt thereof.

In a fifth aspect, the present disclosure provides a compound of formula (II)

(II)

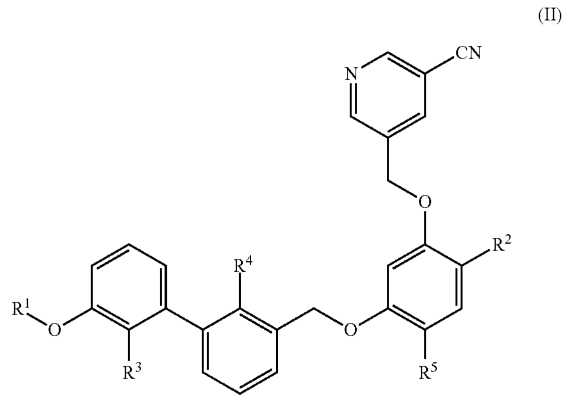

wherein $R^1$ is $—(CH_2)_n—R^{1a}$;

$R^{1a}$ is $—NHCH_2CH(OH)CH_2OH$, pyrrolidine substituted with 0-2 $R^{1b}$ or piperidine substituted with 0-2 $R^{1b}$;

$R^{1b}$ is hydrogen, $C_1$-$C_6$ alkyl, hydroxyl, heterocyclyl or haloalkyl;

$R^2$ is $—(CH_2)_m—(NR^7)_p—(CH_2)_m—(CHR^8)_s—R^{2a}$;

$R^{2a}$ is piperidine, pyrrolidine, pyrazole, pyridine, pyrazine, pyridazine, pyrimidine, imidazole, triazole, tetrazole, thiazole, isoxazole, oxazole, oxadiazole, pyrazolo-piperidine or benzo-imidazole, substituted with 0-2 $R^{2b}$;

$R^{2b}$ is pyrazole, imidazole, triazole, tetrazole, $C_1$-$C_3$ alkyl, halogen, CN, $—CH_2OH$, $CONH_2$, $NH_2$, phenyl, cyclopropyl, alkoxyalkyl, benzyl or $CF_3$, said pyrazole, imidazole, triazole or tetrazole group substituted with 0-2 $R^{2c}$ or 0-1 $R^{2d}$;

$R^{2c}$ is hydrogen or $C_1$-$C_3$ alkyl;

$R^{2d}$ is oxo;

$R^3$ is hydrogen, $C_1$-$C_3$ alkyl or halogen;

$R^4$ is hydrogen, $C_1$-$C_3$ alkyl or halogen;

$R^5$ is hydrogen, $C_1$-$C_3$ alkyl or halogen;

$R^7$ is hydrogen or $C_1$-$C_3$ alkyl;

$R^8$ is hydrogen, $C_1$-$C_3$ alkyl or carboxy;

m is 0, 1 or 2;

n is 0, 1, 2, 3 or 4;

p is 0 or 1; and s is 0 or 1;

or a pharmaceutically acceptable salt thereof.

In another aspect, the present disclosure provides a compound of formula (I)

(I)

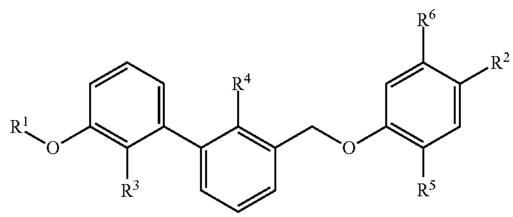

wherein $R^1$ is —$(CH_2)_n$—$R^{1a}$;

$R^{1a}$ is a mono or bicyclic heterocyclyl group with one or more heteroatoms selected from —O—, —N—, —S—, and $NR^7$, or $C_3$-$C_8$ cycloalkyl, all of which are substituted with 0-2 $R^{1b}$;

$R^{1b}$ is hydrogen, $C_1$-$C_6$ alkyl, hydroxyl, heterocyclyl or haloalkyl;

$R^2$ is —$(CH_2)_m$—$(NR^7)_p$—$(CH_2)_m$—$R^{2a}$;

$R^{2a}$ is a mono or bicyclic heterocyclyl group with one or more heteroatoms selected from —O—, —N— and —S—, substituted with 0-2 $R^{2b}$;

$R^{2b}$ is a mono or bicyclic heterocyclyl group with one or more heteroatoms selected from —O—, —N— and —S—, $C_1$-$C_3$ alkyl, halogen, CN, $CONH_2$, $NH_2$, phenyl, $C_3$-$C_8$ cycloalkyl, alkoxyalkyl, benzyl or haloalkyl, said heterocyclyl group substituted with 0-2 $R^{2c}$;

$R^{2c}$ is hydrogen or $C_1$-$C_3$ alkyl;

$R^3$ is hydrogen, $C_1$-$C_3$ alkyl or halogen;

$R^4$ is hydrogen, $C_1$-$C_3$ alkyl or halogen;

$R^5$ is hydrogen, $C_1$-$C_3$ alkyl or halogen;

$R^6$ is —O—$(CH_2)_n$—$R^{6a}$;

$R^{6a}$ is a mono or bicyclic heterocyclyl group with one or more heteroatoms selected from —O—, —N— or —S—, substituted with 0-3 $R^{6b}$;

$R^{6b}$ is $C_1$-$C_3$ alkyl, CN, halogen or trityl;

$R^7$ is H or $C_1$-$C_3$ alkyl;

m is 0, 1 or 2;

n is 0, 1, 2, 3 or 4; and p is 0 or 1;

or a pharmaceutically acceptable salt thereof.

In another aspect, the present disclosure provides a compound of formula (II)

(II)

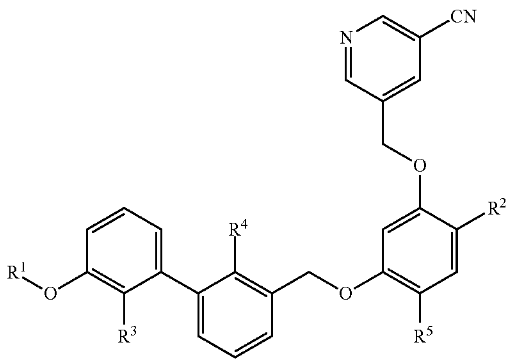

wherein $R^1$ is —$(CH_2)_n$—$R^{1a}$;

$R^{1a}$ is a mono or bicyclic heterocyclyl group with one or more heteroatoms selected from —O—, —N—, —S—, and $NR_7$, or $C_3$-$C_8$ cycloalkyl, all of which are substituted with 0-2 $R^{1b}$;

$R^{1b}$ is hydrogen, $C_1$-$C_6$ alkyl, hydroxyl, heterocyclyl or haloalkyl;

$R^2$ is —$(CH_2)_m$—$(NR_7)_p$—$(CH_2)_m$—$R^{2a}$;

$R^{2a}$ is a mono or bicyclic heterocyclyl group with one or more heteroatoms selected from —O—, —N— or —S—, substituted with 0-2 $R^{2b}$;

$R^{2b}$ is a mono or bicyclic heterocyclyl group with one or more heteroatoms selected from —O—, —N— or —S—, $C_1$-$C_3$ alkyl, halogen, CN, $CONH_2$, $NH_2$, phenyl, $C_3$-$C_8$ cycloalkyl, alkoxyalkyl, benzyl or haloalkyl, said heterocyclyl group substituted with 0-2 $R^{2c}$;

$R^{2c}$ is hydrogen or $C_1$-$C_3$ alkyl;

$R^3$ is hydrogen, $C_1$-$C_3$ alkyl or halogen;

$R^4$ is hydrogen, $C_1$-$C_3$ alkyl or halogen;

$R^5$ is hydrogen, $C_1$-$C_3$ alkyl or halogen;

$R^7$ is hydrogen or $C_1$-$C_3$ alkyl;

m is 0, 1 or 2;

n is 0, 1, 2, 3 or 4; and p is 0 or 1;

or a pharmaceutically acceptable salt thereof.

In another aspect, the present disclosure provides a compound of formula (II)

(II)

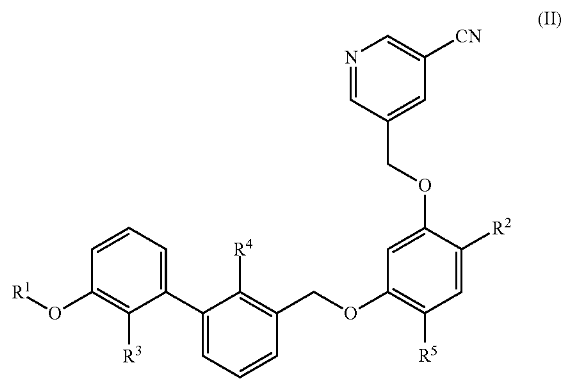

wherein $R^1$ is —$(CH_2)_n$—$R^{1a}$;

$R^{1a}$ is a mono or bicyclic heterocyclyl group with one or more heteroatoms selected from —O—, —N—, —S—, and $NR^7$, or $C_3$-$C_8$ cycloalkyl, all of which are substituted with 0-2 $R^{1b}$;

$R^{1b}$ is hydrogen, $C_1$-$C_6$ alkyl, hydroxyl, heterocyclyl or haloalkyl;

$R^2$ is —$(CH_2)_m$—$(NR^7)_p$—$(CH_2)_m$—$R^{2a}$;

$R^{2a}$ is a mono or bicyclic heterocyclyl group with one or more heteroatoms selected from —O—, —N— and —S—, substituted with 0-2 $R^{2b}$;

$R^{2b}$ is pyrazole, imidazole, triazole, tetrazole, $C_1$-$C_3$ alkyl, halogen, CN, $CONH_2$, $NH_2$, phenyl, cyclopropyl, alkoxyalkyl, benzyl or $CF_3$, said pyrazole, imidazole, triazole or tetrazole group substituted with 0-2 $R^{2c}$;

$R^{2c}$ is hydrogen or $C_1$-$C_3$ alkyl;

$R^3$ is hydrogen, $C_1$-$C_3$ alkyl or halogen;

$R^4$ is hydrogen, $C_1$-$C_3$ alkyl or halogen;

$R^5$ is hydrogen, $C_1$-$C_3$ alkyl or halogen;

$R^7$ is hydrogen or $C_1$-$C_3$ alkyl;

m is 0, 1 or 2;

n is 0, 1, 2, 3 or 4; and p is 0 or 1;

or a pharmaceutically acceptable salt thereof.

In another aspect, the present disclosure provides a compound of formula (II)

(II)

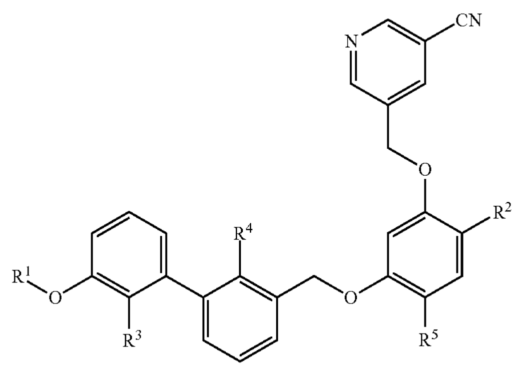

wherein $R^1$ is —$(CH_2)_n$—$R^{1a}$;

$R^{1a}$ is a mono or bicyclic heterocyclyl group with one or more heteroatoms selected from —O—, —N—, —S— and $NR^7$, or $C_3$-$C_8$ cycloalkyl, all of which are substituted with 0-2 $R^{1b}$;

$R^{1b}$ is hydrogen, $C_1$-$C_6$ alkyl, hydroxyl, heterocyclyl or haloalkyl;

$R^2$ is —$(CH_2)_m$—$(NR^7)_p$—$(CH_2)_m$—$R^{2a}$;

$R^{2a}$ is piperidine, pyrrolidine, pyrazole, pyridine, pyrazine, pyridazine, pyrimidine, imidazole, triazole, tetrazole, thiazole, isoxazole, oxazole, oxadiazole, indazole, indole, pyrazolo-piperidine or benzo-imidazole, substituted with 0-2 $R^{2b}$;

$R^{2b}$ is pyrazole, imidazole, triazole, tetrazole, $C_1$-$C_3$ alkyl, halogen, CN, $CONH_2$, $NH_2$, phenyl, cyclopropyl, alkoxyalkyl, benzyl or $CF_3$, said pyrazole, imidazole, triazole or tetrazole group substituted with 0-2 $R^{2c}$;

$R^{2c}$ is hydrogen or $C_1$-$C_3$ alkyl;

$R^3$ is hydrogen, $C_1$-$C_3$ alkyl or halogen;

$R^4$ is hydrogen, $C_1$-$C_3$ alkyl or halogen;

$R^5$ is hydrogen, $C_1$-$C_3$ alkyl or halogen;

$R^7$ is hydrogen or $C_1$-$C_3$ alkyl;

m is 0, 1 or 2;

n is 0, 1, 2, 3 or 4; and p is 0 or 1;

or a pharmaceutically acceptable salt thereof.

In another aspect, the present disclosure provides a compound of formula (II)

(II)

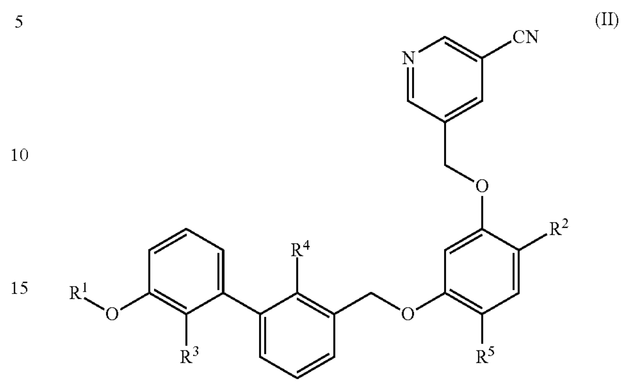

wherein $R^1$ is —$(CH_2)_n$—$R^{1a}$;

$R^{1a}$ is pyrrolidine or piperidine substituted with 0-2 $R^{1b}$;

$R^{1b}$ is hydrogen, $C_1$-$C_6$ alkyl, hydroxyl, heterocyclyl or haloalkyl;

$R^2$ is —$(CH_2)_m$—$(NR^7)_p$—$(CH_2)_m$—$R^{2a}$;

$R^{2a}$ is piperidine, pyrrolidine, pyrazole, pyridine, pyrazine, pyridazine, pyrimidine, imidazole, triazole, tetrazole, thiazole, isoxazole, oxazole, oxadiazole, pyrazolo-piperidine or benzo-imidazole, substituted with 0-2 $R^{2b}$;

$R^{2b}$ is pyrazole, imidazole, triazole, tetrazole, $C_1$-$C_3$ alkyl, halogen, CN, $CONH_2$, $NH_2$, phenyl, cyclopropyl, alkoxyalkyl, benzyl or $CF_3$, said pyrazole, imidazole, triazole or tetrazole group substituted with 0-2 $R^{2c}$;

$R^{2c}$ is hydrogen or $C_1$-$C_3$ alkyl;

$R^3$ is hydrogen, $C_1$-$C_3$ alkyl or halogen;

$R^4$ is hydrogen, $C_1$-$C_3$ alkyl or halogen;

$R^5$ is hydrogen, $C_1$-$C_3$ alkyl or halogen;

$R^7$ is hydrogen or $C_1$-$C_3$ alkyl;

m is 0, 1 or 2;

n is 0, 1, 2, 3 or 4; and p is 0 or 1;

or a pharmaceutically acceptable salt thereof.

In another aspect, there is provided a compound selected from the exemplified examples, or a pharmaceutically acceptable salt thereof.

In another aspect, there is provided a compound selected from any subset list of compounds within the scope of any of the above aspects.

In another aspect, there is provided a compound which is 5-((2-(((1-(1H-Tetrazol-5-yl)ethyl)(methyl)amino)methyl)-4-chloro-5-((3'-(3-((R)-3-hydroxypyrrolidin-1-yl)propoxy)-2,2'-dimethyl-[1,1'-biphenyl]-3-yl)methoxy)phenoxy) methyl)nicotinonitrile (1005), 5-((2-(((2-(1H-Tetrazol-5-yl)propyl)(methyl)amino)methyl)-4-chloro-5-((3'-(3-((R)-3-hydroxypyrrolidin-1-yl)propoxy)-2,2'-dimethyl-[1,1'-biphenyl]-3-yl)methoxy)phenoxy) methyl)nicotinonitrile (1006), 5-((4-Chloro-5-((3'-(3-((R)-3-hydroxypyrrolidin-1-yl)propoxy)-2,2'-dimethyl-[1,1'-biphenyl]-3-yl)methoxy)-2-((2-(5-oxo-2,5-dihydro-1H-1,2,4-triazol-3-yl)piperidin-1-yl)-methyl)phenoxy)methyl)nicotinonitrile (1010), 5-((2-(((2-(1H-Tetrazol-5-yl)propyl)amino)methyl)-4-chloro-5-((3'-(3-((R)-3-hydroxy-pyrrolidin-1-yl)propoxy)-2,2'-dimethyl-[1,1'-biphenyl]-3-yl)methoxy)phenoxy)methyl)-nicotinonitrile (1013), 2-((5-Chloro-4-((2'-chloro-2-methyl-3'-((1-methylpiperidin-3-yl)methoxy)-[1,1'-biphenyl]-3-yl)methoxy)-2-((5- cyanopyridin-3-yl)methoxy)benzyl)amino)-2-(3,5-dimethyl-1H-pyrazol-4-yl)acetic acid (1027), 2-((5-Chloro-4-((2'-chloro-2-methyl-3'-((1-methylpiperidin-3-yl)methoxy)-[1,1'-biphenyl]-3-yl)methoxy)-2-((5-cyanopyridin-3-yl)methoxy)benzyl)amino)-2-(1-methyl-1H-pyrazol-4-yl)acetic acid (1028), 5-((4-Chloro-5-((2'-chloro-2-methyl-3'-((1-methylpiperidin-3-yl)methoxy)-[1,1'-biphenyl]-3-yl)methoxy)-2-((3-(hydroxymethyl)-1-methyl-1,3a,4,6,7,7a-hexahydro-5H-pyrazolo[4,3-c]pyridin-5-yl)methyl)phenoxy)methyl) nicotinonitrile (1029), 5-((2-(((1-(1H-Tetrazol-5-yl)ethyl)(methyl)amino)methyl)-4-chloro-5-((3'-(3-(((S)-2,3-dihydroxypropyl)amino) propoxy)-2,2'-dimethyl-[1,1'-biphenyl]-3-yl)methoxy)-phenoxy)methyl)nicotinonitrile (1030), 5-((2-(((2-(1H-Tetrazol-5-yl)propyl)(methyl)amino) methyl)-4-chloro-5-((3'-(3-(((S)-2,3-dihydroxy-propyl) amino)propoxy)-2,2'-dimethyl-[1,1'-biphenyl]-3-yl) methoxy)-phenoxy)methyl)nicotinonitrile (1031), 5-((2-(((1-(1H-Tetrazol-5-yl)ethyl)(methyl)amino)methyl)-4-chloro-5-((2'-chloro-3'-(3-(((S)-2,3-dihydroxypropyl) amino)propoxy)-2-methyl-[1,1'-biphenyl]-3-yl) methoxy)-phenoxy)methyl)-nicotinonitrile (1034), 5-((2-(((2-(1H-Tetrazol-5-yl)propyl)(methyl)amino) methyl)-4-chloro-5-((2'-chloro-3'-(3-(((S)-2,3-dihydroxy-propyl)amino)propoxy)-2-methyl-[1,1'-biphenyl]-3-yl) methoxy)-phenoxy)methyl)nicotinonitrile (1035), N-(1-(3-((3'-((4-(((1-(1H-Tetrazol-5-yl)ethyl)(methyl) amino)methyl)-2-chloro-5-((5-cyanopyridin-3-yl) methoxy)phenoxy)methyl)-2,2'-dimethyl-[1,1'-biphenyl]-3-yl)oxy)-propyl)piperidin-4-yl)acetamide (1040), N-(1-(3-((3'-((4-(((1-(1H-Tetrazol-5-yl)ethyl)amino) methyl)-2-chloro-5-((5-cyanopyridin-3-yl)methoxy)phenoxy)methyl)-2,2'-dimethyl-[1,1'-biphenyl]-3-yl)oxy) propyl)piperidin-4-yl)acetamide (1043), N-(1-(3-((3'-((4-(((2-(2H-Tetrazol-5-yl)propyl)(methyl) amino)methyl)-2-chloro-5-((5-cyanopyridin-3-yl) methoxy)phenoxy)methyl)-2,2'-dimethyl-[1,1'-biphenyl]-3-yl)oxy)-propyl)piperidin-4-yl)acetamide (1047), (R)-4-(((5-chloro-4-((3'-(3-(3-hydroxypyrrolidin-1-yl) propoxy)-2,2'-dimethyl-[1,1'-biphenyl]-3-yl)methoxy)-2-((5-methyl-1H-imidazol-4-yl)methoxy)benzyl)amino) methyl)pyrimidine-2-carbonitrile (2042), N-(1-(3-((3'-((4-(((2-(1H-Tetrazol-5-yl)propyl)amino) methyl)-2-chloro-5-((5-cyano-pyridin-3-yl)methoxy)phenoxy)methyl)-2,2'-dimethyl-[1,1'-biphenyl]-3-yl)oxy) propyl)-piperidin-4-yl)acetamide (1050), (R)-4-(((5-chloro-4-((3'-(3-(3-hydroxypyrrolidin-1-yl) propoxy)-2,2'-dimethyl-[1,1'-biphenyl]-3-yl)methoxy)-2-((5-methyl-1-trityl-1H-imidazol-4-yl)methoxy)benzyl) amino)methyl)pyrimidine-2-carbonitrile (2043), (R)-1-(3-((3'-((4-((((1H-imidazol-2-yl)methyl)amino) methyl)-2-chloro-5-(pyrimidin-5-ylmethoxy)phenoxy) methyl)-2,2'-dimethyl-[1,1'-biphenyl]-3-yl)oxy)propyl) pyrrolidin-3-ol (2050), (R)-1-(3-((3'-((4-((((1H-pyrazol-4-yl)methyl)amino) methyl)-2-chloro-5-(pyrimidin-5-ylmethoxy)phenoxy) methyl)-2,2'-dimethyl-[1,1'-biphenyl]-3-yl)oxy)propyl) pyrrolidin-3-ol (2051), N-((1H-pyrazol-4-yl)methyl)-1-(5-chloro-4-((2'-chloro-2-methyl-3'-((1-methylpiperidin-3-yl)methoxy)-[1,1'-biphenyl]-3-yl)methoxy)-2-(pyridazin-3-ylmethoxy)phenyl)methanamine (2054), N-((1H-imidazol-2-yl)methyl)-1-(5-chloro-4-((2'-chloro-2-methyl-3'-((1-methylpiperidin-3-yl)methoxy)-[1,1'-biphenyl]-3-yl)methoxy)-2-(pyridazin-3-ylmethoxy)phenyl)methanamine (2055), N-((1H-pyrazol-4-yl)methyl)-1-(5-chloro-4-((2'-chloro-2-methyl-3'-((1-methylpiperidin-3-yl)methoxy)-[1,1'-biphenyl]-3-yl)methoxy)-2-methoxyphenyl)methanamine (2056), N-((1H-imidazol-2-yl)methyl)-1-(5-chloro-4-((2'-chloro-2-methyl-3'-((1-methylpiperidin-3-yl)methoxy)-[1,1'-biphenyl]-3-yl)methoxy)-2-methoxyphenyl)methanamine (2057), N-(5-chloro-4-((2'-chloro-2-methyl-3'-((1-methylpiperidin-3-yl)methoxy)-[1,1'-biphenyl]-3-yl)methoxy)-2-(pyrazin-2-ylmethoxy)benzyl)-1-(pyridazin-3-yl)methanamine (2058), N-(5-chloro-4-((2'-chloro-2-methyl-3'-((1-methylpiperidin-3-yl)methoxy)-[1,1'-biphenyl]-3-yl)methoxy)-2-(pyrazin-2-ylmethoxy)benzyl)-1-(pyrimidin-2-yl)methanamine (2059), N-((1H-imidazol-4-yl)methyl)-1-(5-chloro-4-((2'-chloro-2-methyl-3'-((1-methylpiperidin-3-yl)methoxy)-[1,1'-biphenyl]-3-yl)methoxy)-2-(pyrazin-2-ylmethoxy)phenyl) methanamine (2060), ((R)-5-((4-chloro-5-((3'-(3-(3-hydroxypyrrolidin-1-yl) propoxy)-2,2'-dimethyl-[1,1'-biphenyl]-3-yl)methoxy)-2-((1-methyl-1,4,6,7-tetrahydro-5H-imidazo[4,5-c]pyridin-5-yl)methyl)phenoxy)methyl)nicotinonitrile (2502), (R)-5-((4-chloro-5-((3'-(3-(3-hydroxypyrrolidin-1-yl) propoxy)-2,2'-dimethyl-[1,1'-biphenyl]-3-yl)methoxy)-2-((2-methyl-6,7-dihydrothiazolo[5,4-c]pyridin-5(4H) yl)methyl)phenoxy)methyl)nicotinonitrile (2503), (R)-5-((4-chloro-5-((3'-(3-(3-hydroxypyrrolidin-1-yl) propoxy)-2,2'-dimethyl-[1,1'-biphenyl]-3-yl)methoxy)-2-((1,4,6,7-tetrahydro-5H-pyrazolo[4,3-c]pyridin-5-yl) methyl)phenoxy)methyl)nicotinonitrile (2512), (R)-5-((4-chloro-5-((3'-(3-(3-hydroxypyrrolidin-1-yl) propoxy)-2,2'-dimethyl-[1,1'-biphenyl]-3-yl)methoxy)-2-((1,4,6,7-tetrahydro-5H-imidazo[4,5-c]pyridin-5-yl) methyl)phenoxy)methyl)nicotinonitrile (2515), (R)-5-((4-chloro-2-(((2-(5-chloro-1H-benzo[d]imidazol-2-yl)ethyl)amino)methyl)-5-((3'-(3-(3-hydroxypyrrolidin-1-yl)propoxy)-2,2'-dimethyl-[1,1'-biphenyl]-3-yl) methoxy)phenoxy)methyl)nicotinonitrile (2516), (R)-5-((2-(((benzo[d]thiazol-2-ylmethyl)amino)methyl)-4-chloro-5-((3'-(3-(3-hydroxypyrrolidin-1-yl)propoxy)-2, 2'-dimethyl-[1,1'-biphenyl]-3-yl)methoxy)phenoxy) methyl)nicotinonitrile (2549)

(R)-5-((2-(((benzo[d]thiazol-2-ylmethyl)(methyl)amino) methyl)-4-chloro-5-((3'-(3-(3-hydroxypyrrolidin-1-yl) propoxy)-2,2'-dimethyl-[1,1'-biphenyl]-3-yl)methoxy) phenoxy)methyl)nicotinonitrile (2554)

(R)-5-((4-chloro-5-((3'-(3-(3-hydroxypyrrolidin-1-yl) propoxy)-2,2'-dimethyl-[1,1'-biphenyl]-3-yl)methoxy)-2-((((1-methyl-1H-indazol-3-yl)methyl)amino)methyl) phenoxy)methyl)nicotinonitrile (2555)

5-((4-chloro-5-((3'-(3-((R)-3-hydroxypyrrolidin-1-yl) propoxy)-2,2'-dimethyl-[1,1'-biphenyl]-3-yl)methoxy)-2-(((4,5,6,7-tetrahydro-1H-indazol-5-yl)amino)methyl) phenoxy)methyl)nicotinonitrile (2563)

5-((4-chloro-5-((3'-(3-((R)-3-hydroxypyrrolidin-1-yl) propoxy)-2,2'-dimethyl-[1,1'-biphenyl]-3-yl)methoxy)-2-((methyl(4,5,6,7-tetrahydro-1H-indazol-5-yl)amino) methyl)phenoxy)methyl)nicotinonitrile (2564)

(R)-5-((4-chloro-5-((3'-(3-(3-hydroxypyrrolidin-1-yl) propoxy)-2,2'-dimethyl-[1,1'-biphenyl]-3-yl)methoxy)-2-(((imidazo[1,5-a]pyridin-3-ylmethyl)amino)methyl) phenoxy)methyl)nicotinonitrile (2565)

(R)-5-((4-chloro-5-((3'-(3-(3-hydroxypyrrolidin-1-yl) propoxy)-2,2'-dimethyl-[1,1'-biphenyl]-3-yl)methoxy)-2-

((1-phenyl-1,4,6,7-tetrahydro-5H-pyrazolo[4,3-c]pyridin-5-yl)methyl)phenoxy)methyl)nicotinonitrile (2567)

(R)-5-((4-chloro-5-((3'-(3-(3-hydroxypyrrolidin-1-yl)propoxy)-2,2'-dimethyl-[1,1'-biphenyl]-3-yl)methoxy)-2-((1,4,5,7-tetrahydro-6H-pyrazolo[3,4-c]pyridin-6-yl)methyl)phenoxy)methyl)nicotinonitrile (2569)

(R)-5-((4-chloro-2-((((4,5-diethyl-1H-imidazol-2-yl)methyl)(2-methoxyethyl)amino)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile (2571)

5-((4-chloro-5-((2'-chloro-2-methyl-3'-((1-methylpiperidin-3-yl)methoxy)-[1,1'-biphenyl]-3-yl)methoxy)-2-((1,4,6,7-tetrahydro-5H-imidazo[4,5-c]pyridin-5-yl)methyl)phenoxy)methyl)nicotinonitrile (2583)

5-((4-chloro-5-((2'-chloro-2-methyl-3'-((1-methylpiperidin-3-yl)methoxy)-[1,1'-biphenyl]-3-yl)methoxy)-2-((1,4,6,7-tetrahydro-5H-pyrazolo[4,3-c]pyridin-5-yl)methyl)phenoxy)methyl)nicotinonitrile (2587)

5-((4-chloro-5-((2'-chloro-2-methyl-3'-((1-methylpiperidin-3-yl)methoxy)-[1,1'-biphenyl]-3-yl)methoxy)-2-((1,4,5,7-tetrahydro-6H-pyrazolo[3,4-c]pyridin-6-yl)methyl)phenoxy)methyl)nicotinonitrile (2589)

5-((4-chloro-5-((2'-chloro-2-methyl-3'-((1-methylpiperidin-3-yl)methoxy)-[1,1'-biphenyl]-3-yl)methoxy)-2-((1,4,5,7-tetrahydro-6H-pyrazolo[3,4-c]18yridine-6-yl)methyl)phenoxy)methyl)nicotinonitrile (2589)

5-((4-chloro-5-((2'-chloro-2-methyl-3'-((1-methylpiperidin-3-yl)methoxy)-[1,1'-biphenyl]-3-yl)methoxy)-2-((1-methyl-1,4,6,7-tetrahydro-5H-imidazo[4,5-c]pyridin-5-yl)methyl)phenoxy)methyl)nicotinonitrile (2592)

5-((2-(((2-(1H-benzo[d]imidazol-2-yl)ethyl)amino)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile (2593)

5-((4-chloro-5-((2'-chloro-2-methyl-3'-((1-methylpiperidin-3-yl)methoxy)-[1,1'-biphenyl]-3-yl)methoxy)-2-((2-methyl-6,7-dihydrothiazolo[5,4-c]pyridin-5(4H)-yl)methyl)phenoxy)methyl)nicotinonitrile (2600)

5-((4-chloro-5-((2'-chloro-2-methyl-3'-((1-methylpiperidin-3-yl)methoxy)-[1,1'-biphenyl]-3-yl)methoxy)-2-(((4,5,6,7-tetrahydro-1H-indazol-5-yl)amino)methyl)phenoxy)methyl)nicotinonitrile (2601)

5-((2-(((benzo[d]thiazol-2-ylmethyl)amino)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile (2611)

5-((4-chloro-5-((2'-chloro-2-methyl-3'-((1-methylpiperidin-3-yl)methoxy)-[1,1'-biphenyl]-3-yl)methoxy)-2-((((6-(trifluoromethyl)-[1,2,4]triazolo[4,3-a]pyridin-3-yl)methyl)amino)methyl)phenoxy)methyl)nicotinonitrile (2619)

5-((2-(((2-(1,2,4-oxadiazol-3-yl)propan-2-yl)amino)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile (2620)

5-((4-chloro-5-((2'-chloro-2-methyl-3'-((1-methylpiperidin-3-yl)methoxy)-[1,1'-biphenyl]-3-yl)methoxy)-2-(((imidazo[1,5-a]pyridin-3-ylmethyl)amino)methyl) phenoxy)methyl)nicotinonitrile (2623)

5-((2-(((2-(1,2,4-oxadiazol-3-yl)propan-2-yl-1,1,1,3,3,3-d6)amino)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile (2623)

5-((2-(((3-(benzyloxy)-1-(1,2,4-oxadiazol-3-yl)cyclobutyl)amino)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile (2625)

5-((2-((2-(1H-Pyrazol-4-yl)piperidin-1-yl)methyl)-4-chloro-5-((3'-(3-((R)-3-hydroxy-pyrrolidin-1-yl)propoxy)-2,2'-dimethyl-[1,1'-biphenyl]-3-yl)methoxy)phenoxy)methyl)-nicotinonitrile (1011)

5-((2-((2-(1H-Pyrazol-4-yl)piperidin-1-yl)methyl)-4-chloro-5-((2'-chloro-2-methyl-3'-((1-methylpiperidin-3-yl)methoxy)-[1,1'-biphenyl]-3-yl)methoxy)phenoxy)methyl)-nicotinonitrile (1020), or 5-((2-((2-(1H-Pyrazol-3-yl)piperidin-1-yl)methyl)-4-chloro-5-((2'-chloro-2-methyl-3'-((1-methylpiperidin-3-yl)methoxy)-[1,1'-biphenyl]-3-yl)methoxy)phenoxy)methyl)-nicotinonitrile (1021), or a pharmaceutically acceptable salt thereof.

The present disclosure also provides a pharmaceutical composition comprising a compound of formula (I), or a pharmaceutically acceptable salt thereof, and a pharmaceutically acceptable carrier.

In another aspect, the present disclosure provides a compound of the present invention, or a pharmaceutically acceptable salt thereof, or a pharmaceutical composition thereof, for use as a medicament.

In another aspect, the present disclosure provides a compound of the present invention, or a pharmaceutically acceptable salt thereof, or a pharmaceutical composition thereof, for use in the manufacture of a medicament for treatment of cancer in a subject in need thereof.

In another aspect, the present disclosure provides a compound of the present invention, or a pharmaceutically acceptable salt thereof, for use in enhancing, stimulating, modulating and/or increasing an immune response in a subject in need thereof, comprising administering to the subject a therapeutically effective amount of said compound or a pharmaceutically acceptable salt thereof.

In another aspect, the present disclosure provides a compound of the present invention, or a pharmaceutically acceptable salt thereof, for use in inhibiting growth, proliferation, or metastasis of cancer cells in a subject in need thereof, comprising administering to the subject a therapeutically effective amount of said compound or a pharmaceutically acceptable salt thereof.

In another aspect, the present disclosure provides a method of enhancing, stimulating, modulating and/or increasing the immune response in a subject in need thereof, said method comprising administering to the subject a therapeutically effective amount of a compound of formula (I), or a pharmaceutically acceptable salt thereof. In a first embodiment of the third aspect, the method further comprises administering an additional agent prior to, after, or simultaneously with the compound of formula (I), or the pharmaceutically acceptable salt thereof. In a second embodiment, the additional agent is an antimicrobial agent, an antiviral agent, a cytotoxic agent, a gene expression modulatory agent, and/or an immune response modifier.

In another aspect, the present disclosure provides a method of inhibiting growth, proliferation, or metastasis of cancer cells in a subject in need thereof, said method comprising administering to the subject a therapeutically effective amount of a compound of formula (I), or a pharmaceutically acceptable salt. In a first embodiment of the fourth aspect, the cancer is selected from melanoma, renal cell carcinoma, squamous non-small cell lung cancer (NSCLC), non-squamous NSCLC, colorectal cancer, castration-resistant prostate cancer, ovarian cancer, gastric cancer, hepatocellular carcinoma, pancreatic carcinoma, squamous cell carcinoma of the head and neck, carcinomas of the esophagus, gastrointestinal tract and breast, and a hematological malignancy.

In another aspect, the present disclosure provides a method of treating an infectious disease in a subject in need thereof, the method comprising administering to the subject a therapeutically effective amount of a compound of formula (I), or a pharmaceutically acceptable salt thereof. In a first embodiment of the fifth aspect, the infectious disease is caused by a virus. In a second embodiment of the fifth aspect, the virus is selected from HIV, Hepatitis A, Hepatitis B, Hepatitis C, Hepatitis D, herpes viruses, papillomaviruses, and influenza.

In another aspect, the present disclosure provides a method of treating septic shock in a subject in need thereof, the method comprising administering to the subject a therapeutically effective amount of a compound of formula (I), or a pharmaceutically acceptable salt thereof.

Unless specifically stated otherwise herein, references made in the singular may also include the plural. For example, "a" and "an" may refer to either one, or one or more.

As used herein, the phase "compound(s) or pharmaceutically acceptable salts thereof" refers to at least one compound, at least one salt of the compounds, or a combination thereof. For example, compounds of formula (I) or pharmaceutically acceptable salts thereof includes a compound of formula (I); two compounds of formula (I); a salt of a compound of formula (I); a compound of formula (I) and one or more salts of the compound of formula (I); and two or more salts of a compound of formula (I).

Unless otherwise indicated, any atom with unsatisfied valences is assumed to have hydrogen atoms sufficient to satisfy the valences.

Throughout the specification, groups and substituents thereof may be chosen by one skilled in the field to provide stable moieties and compounds.

Listed below are definitions of various terms used to describe the present disclosure. These definitions apply to the terms as they are used throughout the specification (unless they are otherwise limited in specific instances) either individually or as part of a larger group. The definitions set forth herein take precedence over definitions set forth in any patent, patent application, and/or patent application publication incorporated herein by reference.

The term "$C_1$-$C_3$ alkyl" as used herein, refers to a group derived from a straight or branched chain saturated hydrocarbon containing from one to three carbon atoms.

The term "$C_1$-$C_6$ alkyl" as used herein, refers to a group derived from a straight or branched chain saturated hydrocarbon containing from one to six carbon atoms.

The term "amido" as used herein, refers to $-C(O)NH_2$.

The term "aminocarbonyl" as used herein, refers to $-C(O)NH_2$.

The term "aminocarbonyl($C_1$-$C_3$alkyl)" as used herein, refers to an aminocarbonyl group attached to the parent molecular moiety through a $C_1$-$C_3$alkyl group.

The term "carbonyl" as used herein, refers to $-C(O)-$.

The term "carboxy" as used herein, refers to $-CO_2H$.

The term "carboxy$C_2$-$C_6$alkenyl" as used herein, refers to a carboxy group attached to the parent molecular moiety through a $C_2$-$C_6$alkenyl group.

The term "carboxy$C_1$-$C_6$ alkyl" as used herein, refers to a carboxy group attached to the parent molecular moiety through a $C_1$-$C_6$alkyl group.

The term "cyano" as used herein, refers to $-CN$.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The term "($C_3$-$C_6$ cycloalkyl)$C_1$-$C_3$ alkyl" as used herein, refers to a $C_1$-$C_3$ alkyl group substituted with a $C_3$-$C_6$ cycloalkyl group.

The terms "halo" and "halogen" as used herein, refer to F, Cl, Br, or I.

The term "halo$C_1$-$C_4$alkoxy" as used herein, refers to a halo$C_1$-$C_4$alkyl group attached to the parent molecular moiety through an oxygen atom.

The term "halo$C_1$-$C_3$ alkyl" as used herein, refers to a $C_1$-$C_3$ alkyl group substituted with one, two, or three halogen atoms.

The term "hydroxyalkyl" includes both branched and straight-chain saturated alkyl groups substituted with one or more hydroxyl groups. For example, "hydroxyalkyl" includes $-CH_2OH$, $-CH_2CH_2OH$, and $C_{1-4}$ hydroxyalkyl.

The term "nitro" as used herein, refers to $-NO_2$.

The term "oxo" as used herein, refers to $=0$.

The term "heteroatom" refers to oxygen (O), sulfur (S), and nitrogen (N).

The terms "heterocyclo", "heterocyclic", or "heterocyclyl" may be used interchangeably and refer to cyclic groups having at least one saturated or partially saturated nonaromatic ring and wherein one or more of the rings have at least one heteroatom (O, S or N), said heteroatom containing ring preferably having 1 to 3 heteroatoms independently selected from O, S, and/or N. The ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The heterocyclo group may be attached at any available nitrogen or carbon atom. The heterocyclo ring may be unsubstituted or may contain one or more substituents as valence allows.

Exemplary monocyclic heterocyclyl groups include pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolidinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, tetrahydro-1,1-dioxothienyl, dihydroisoindolyl, and tetrahydroquinolinyl.

The term heterocyclyl also encompasses heteroaryl compounds.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, and pyrrolopyridyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of formula (I) can form salts which are also within the scope of this disclosure. Unless otherwise indicated, reference to an inventive compound is understood to include reference to one or more salts thereof. The term "salt(s)" denotes acidic and/or basic salts formed with inorganic and/or organic acids and bases. In addition, the term "salt(s) may include zwitterions (inner salts), e.g., when a compound of formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the disclosure. Salts of the compounds of the formula (I) may be formed, for example, by reacting a compound of the formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylene-diamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

Various forms of prodrugs are well known in the art and are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985);

c) *A Textbook of Drug Design and Development*, P. Krogsgaard-Larson and H. Bundgaard, eds. Ch 5, pgs 113-191 (Harwood Academic Publishers, 1991); and d) *Hydrolysis in Drug and Prodrug Metabolism*, Bernard Testa and Joachim M. Mayer, (Wiley-VCH, 2003).

Compounds of the present disclosure may contain stereoisomers, wherein asymmetric or chiral centers are present. Specific stereochemistry may be designated by the symbols "R" or "S" depending on the configuration of substituents around the chiral carbon atom. The present invention contemplates various stereoisomers (i.e., enantiomers and diastereomers) and mixtures thereof and is intended to encompass all stereoisomers that bind to PD-L1. Individual stereoisomers of compounds of the present invention may be prepared synthetically from commercially available starting materials which contain asymmetric or chiral centers or by preparation of racemic mixtures followed by resolution well-known to those of ordinary skill in the art.

In addition, compounds of formula (I), subsequent to their preparation, can be isolated and purified to obtain a composition containing an amount by weight equal to or greater than 99% of a compound of formula (I) ("substantially pure"), which is then used or formulated as described herein. Such "substantially pure" compounds of formula (I) are also contemplated herein as part of the present disclosure.

"Stable compound" and "stable structure" are meant to indicate a compound that is sufficiently robust to survive isolation to a useful degree of purity from a reaction mixture, and formulation into an efficacious therapeutic agent. The present disclosure is intended to embody stable compounds.

"Therapeutically effective amount" is intended to include an amount of a compound of the present disclosure alone or an amount of the combination of compounds claimed or an amount of a compound of the present disclosure in combination with other active ingredients effective to inhibit PD-1/PD-L1 protein/protein and/or CD80/PD-L1 protein/protein interactions, or effective to treat or prevent cancer or infectious disease, such as septic shock, HIV or Hepatitis B, Hepatitis C, and Hepatitis D.

As used herein, "treating" or "treatment" cover the treatment of a disease-state in a mammal, particularly in a human, and may include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state. The terms "preventing" and "inhibiting" should not be read into any claims related to treatment unless explicitly included.

The compounds of the present disclosure are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed. For example, methyl ($—CH_3$) also includes deuterated methyl groups such as $—CD_3$.

Compounds in accordance with formula (I) and/or pharmaceutically acceptable salts thereof can be administered by any means suitable for the condition to be treated, which can depend on the need for site-specific treatment or quantity of formula (I) compound to be delivered. Also embraced within this disclosure is a class of pharmaceutical compositions comprising a compound of formula (I) and/or pharmaceutically acceptable salts thereof; and one or more non-toxic, pharmaceutically-acceptable carriers and/or diluents and/or adjuvants (collectively referred to herein as "carrier" materials) and, if desired, other active ingredients. The compounds of formula (I) may be administered by any suitable route, preferably in the form of a pharmaceutical composition adapted to such a route, and in a dose effective for the treatment intended. The compounds and compositions of the present disclosure may, for example, be administered orally, mucosally, rectally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the disclosure can contain at least one agent selected from sweetening agents, flavoring agents, coloring agents, demulcents, antioxidants, and preserving agents.

A tablet can, for example, be prepared by admixing at least one compound of formula (I) and/or at least one pharmaceutically acceptable salt thereof with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of formula (I) and/or at least one salt thereof with at least one inert solid diluent, such as, for example, calcium carbonate; calcium phosphate; and kaolin.

Soft gelatin capsules can, for example, be prepared by mixing at least one compound of formula (I) and/or at least one pharmaceutically acceptable salt thereof with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of formula (I) and/or at least one pharmaceutically acceptable salt thereof with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of formula (I) and/or at least one pharmaceutically acceptable salt thereof in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of formula (I) and/or at least one pharmaceutically acceptable salt thereof with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of formula (I) and/or at least one pharmaceutically acceptable salt thereof can, for example, be prepared as an oil-in-water emulsion. The oily phase of the emulsions comprising compounds of formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present disclosure include Tween 60, Span 80, cetostearyl alcohol, myristyl alcohol, glyceryl monostearate, sodium lauryl sulfate, glyceryl distearate alone or with a wax, or other materials well known in the art.

The compounds of formula (I) and/or at least one pharmaceutically acceptable salt thereof can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of formula (I) in an oily phase, such as, for example, a mixture of soybean oil and lecithin; 2) combining the formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this disclosure include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this disclosure can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this disclosure depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this disclosure are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this disclosure comprise at least one compound of formula (I) and/or at least one pharmaceutically acceptable salt thereof, and optionally an additional agent selected from any pharmaceutically acceptable carrier, adjuvant, and vehicle. Alternate compositions of this disclosure comprise a compound of the formula (I) described herein, or a prodrug thereof, and a pharmaceutically acceptable carrier, adjuvant, or vehicle.

The compounds of the disclosure inhibit the PD-1/PD-L1 protein/protein resulting in a PD-L1 blockade. The blockade of PD-L1 can enhance the immune response to cancerous cells and infectious diseases in mammals, including humans.

In one aspect, the present disclosure relates to treatment of a subject in vivo using a compound of formula (I) or a salt thereof such that growth of cancerous tumors is inhibited. A compound of formula (I) or a salt thereof may be used alone to inhibit the growth of cancerous tumors. Alternatively, a compound of formula (I) or a salt thereof may be used in conjunction with other immunogenic agents or standard cancer treatments, as described below.

In one embodiment, the disclosure provides a method of inhibiting growth of tumor cells in a subject, comprising administering to the subject a therapeutically effective amount of a compound of formula (I) or a salt thereof.

In one embodiment, a method is provided for treating cancer comprising administering to a patient in need thereof, a therapeutically effective amount of a compound of formula (I) or a salt thereof. Examples of cancers include those whose growth may be inhibited using compounds of the disclosure include cancers typically responsive to immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, the disclosure includes refractory or recurrent malignancies whose growth may be inhibited using the compounds of the disclosure.

Examples of other cancers that may be treated using the methods of the disclosure include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present disclosure is also useful for treatment of metastatic cancers, especially metastatic cancers that express PD-L1 (Iwai et al. (2005) *Int. Immunol.* 17:133-144).

Optionally, the compounds of formula (I) or salts thereof can be combined with another immunogenic agent, such as cancerous cells, purified tumor antigens (including recombinant proteins, peptides, and carbohydrate molecules), cells, and cells transfected with genes encoding immune stimulating cytokines (He et al (2004) J. Immunol. 173: 4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF.

In humans, some tumors have been shown to be immunogenic such as melanomas. It is anticipated that by raising the threshold of T cell activation by PD-L1 blockade, tumor responses are expected to be activated in the host.

The PD-L1 blockade can be combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology. Fifth Edition). In one of these strategies, a vaccine is prepared using autologous or allogenenic tumor cells. These cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sci. U.S.A. 90: 3539-43).

The study of gene expression and large scale gene expression patterns in various tumors has led to the definition of so called tumor specific antigens (Rosenberg, S A (1999) Immunity 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. PD-L1 blockade may be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) Science 266: 2011-2013). (These somatic tissues may be protected from immune attack by various means). Tumor antigen may also be "neo-antigens" expressed in cancer cells because of somatic mutations that alter protein sequence or create fusion proteins between two unrelated sequences (ie. bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV, HDV and HCV) and Kaposi's Herpes Sarcoma Virus (KHSV). Another form of tumor specific antigen which may be used in conjunction with PD-L1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) Science 269:1585-1588; Tamura, Y. et al. (1997) Science 278:117-120).

Dendritic cells (DC) are potent antigen presenting cells that can be used to prime antigen-specific responses. DC's can be produced ex vivo and loaded with various protein and peptide antigens as well as tumor cell extracts (Nestle, F. et al. (1998) Nature Medicine 4: 328-332). DCs may also be transduced by genetic means to express these tumor antigens as well. DCs have also been fused directly to tumor cells for the purposes of immunization (Kugler, A. et al. (2000) Nature Medicine 6:332-336). As a method of vaccination, DC immunization may be effectively combined with PD-L1 blockade to activate more potent anti-tumor responses.

PD-L1 blockade may also be combined with standard cancer treatments. PD-L1 blockade may be effectively combined with chemotherapeutic regimes. In these instances, it may be possible to reduce the dose of chemotherapeutic reagent administered (Mokyr, M. et al. (1998) *Cancer Research* 58: 5301-5304). An example of such a combination is a compound of this disclosure in combination with dacarbazine for the treatment of melanoma. Another example of such a combination is a compound of this disclosure in combination with interleukin-2 (IL-2) for the treatment of melanoma. The scientific rationale behind the combined use of PD-L1 blockade and chemotherapy is that cell death, that is a consequence of the cytotoxic action of most chemotherapeutic compounds, should result in increased levels of tumor antigen in the antigen presentation pathway. Other combination therapies that may result in synergy with PD-L1 blockade through cell death are radiation, surgery, and hormone deprivation. Each of these protocols creates a source of tumor antigen in the host. Angiogenesis inhibitors may also be combined with PD-L1 blockade. Inhibition of angiogenesis leads to tumor cell death which may feed tumor antigen into host antigen presentation pathways.

The compounds of this disclosure can also be used in combination with bispecific compounds that target Fc alpha or Fc gamma receptor-expressing effectors cells to tumor cells (see, e.g., U.S. Pat. Nos. 5,922,845 and 5,837,243). Bispecific compounds can be used to target two separate antigens. For example anti-Fc receptor/anti tumor antigen (e.g., Her-2/neu) bispecific compounds have been used to target macrophages to sites of tumor. This targeting may more effectively activate tumor specific responses. The T cell arm of these responses would be augmented by the use of PD-L1 blockade. Alternatively, antigen may be delivered directly to DCs by the use of bispecific compounds which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) *J. Exp. Med.* 163: 1037-1050), IL-10 (Howard, M. & O'Garra, A. (1992) *Immunology Today* 13: 198-200), and Fas ligand (Hahne, M. et al. (1996) Science 274: 1363-1365). Inhibitors that bind to and block each of these entities may be used in combination with the compounds of this disclosure to counteract the effects of the immunosuppressive agent and favor tumor immune responses by the host.

Compounds that activate host immune responsiveness can be used in combination with PD-L1 blockade. These include molecules on the surface of dendritic cells which activate DC function and antigen presentation. Anti-CD40 compounds are able to substitute effectively for T cell helper activity (Ridge, J. et al. (1998) *Nature* 393: 474-478) and can be used in conjunction with PD-L1 blockade (Ito, N. et al. (2000) *Immunobiology* 201 (5) 527-40). Activating compounds to T cell costimulatory molecules such as CTLA-4 (e.g., U.S. Pat. No. 5,811,097), OX-40 (Weinberg, A. et al. (2000) *Immunol* 164: 2160-2169), 4-1BB (Melero, I. et al. (1997) *Nature Medicine* 3: 682-685 (1997), and ICOS (Hutloff, A. et al. (1999) *Nature* 397: 262-266) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. PD-L1 blockade can be used to increase the effectiveness of the donor engrafted tumor specific T cells.

Other methods of the disclosure are used to treat patients who have been exposed to particular toxins or pathogens. Accordingly, another aspect of the disclosure provides a method of treating an infectious disease in a subject comprising administering to the subject a therapeutically effective amount of a compound of formula (I) or salts thereof.

Similar to its application to tumors as discussed above, the compound of formula (I) or salts thereof can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to HIV, Hepatitis (A, B, C or D), Influenza, Herpes, Giardia, Malaria, Leishmania, Staphylococcus aureus, Pseudomonas Aeruginosa. PD-L1 blockade is particularly useful against established infections by agents such as HIV that present altered antigens over the course of the infections. These novel epitopes are recognized as foreign at the time of administration, thus provoking a strong T cell response that is not dampened by negative signals through PD-1.

Some examples of pathogenic viruses causing infections treatable by methods of the disclosure include HIV, hepatitis (A, B, C, or D), herpes viruses (e.g., VZV, HSV-1, HAV-6, HHv-7, HHV-8, HSV-2, CMV, and Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the disclosure include chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lymes disease bacteria.

Some examples of pathogenic fungi causing infections treatable by methods of the disclosure include Candida (albicans, krusei, glabrata, tropicalis, etc.), Cryptococcus neoformans, Aspergillus (fumigatus, niger, etc.), Genus Mucorales (mucor, absidia, rhizophus), Sporothrix schenkii, Blastomyces dermatitidis, Paracoccidioides brasiliensis, Coccidioides immitis and Histoplasma capsulatum.

Some examples of pathogenic parasites causing infections treatable by methods of the disclosure include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis.*

In all of the above methods, PD-L1 blockade can be combined with other forms of immunotherapy such as cytokine treatment (e.g., interferons, GM-CSF, G-CSF, IL-2), or bispecific antibody therapy, which provides for enhanced presentation of tumor antigens (see, e.g., Holliger (1993) Proc. Natl. Acad. Sci. USA 90:6444-6448; Poljak (1994) Structure 2:1121-1123), vaccines, or agents that modify gene expression.

The compounds of this disclosure may provoke and amplify autoimmune responses. Indeed, induction of anti-tumor responses using tumor cell and peptide vaccines reveals that many anti-tumor responses involve anti-self reactivities (depigmentation observed in anti-CTLA-4+GM-CSF-modified B 16 melanoma in van Elsas et al. supra; depigmentation in Trp-2 vaccinated mice (Overwijk, W. et al. (1999) *Proc. Natl. Acad. Sci. U.S.A.* 96: 2982-2987); autoimmune prostatitis evoked by TRAMP tumor cell vaccines (Hurwitz, A. (2000) supra), melanoma peptide antigen vaccination and vitilago observed in human clinical trials (Rosenberg, S A and White, D E (1996) *J. Immunother Emphasis Tumor Immunol* 19 (1): 81-4).

Therefore, it is possible to consider using anti-PD-L1 blockade in conjunction with various self proteins in order to devise vaccination protocols to efficiently generate immune responses against these self proteins for disease treatment. For example, Alzheimer's disease involves inappropriate accumulation of A.beta.peptide in amyloid deposits in the brain; antibody responses against amyloid are able to clear these amyloid deposits (Schenk et al., (1999) Nature 400: 173-177).

Other self proteins may also be used as targets such as IgE for the treatment of allergy and asthma, and TNF.alpha. for rheumatoid arthritis. Finally, antibody responses to various hormones may be induced by the use of a compound of formula (I) or salts thereof. Neutralizing antibody responses to reproductive hormones may be used for contraception. Neutralizing antibody response to hormones and other soluble factors that are required for the growth of particular tumors may also be considered as possible vaccination targets.

Analogous methods as described above for the use of anti-PD-L1 antibody can be used for induction of therapeutic autoimmune responses to treat patients having an inappropriate accumulation of other self-antigens, such as amyloid deposits, including A.beta. in Alzheimer's disease, cytokines such as TNF alpha, and IgE.

The compounds of this disclosure may be used to stimulate antigen-specific immune responses by co-administration of a compound of formula (I) or salts thereof with an antigen of interest (e.g., a vaccine). Accordingly, in another aspect the disclosure provides a method of enhancing an immune response to an antigen in a subject, comprising administering to the subject: (i) the antigen; and (ii) a compound of formula (I) or salts thereof, such that an immune response to the antigen in the subject is enhanced. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

As previously described, the compounds of the disclosure can be co-administered with one or more other therapeutic agents, e.g., a cytotoxic agent, a radiotoxic agent or an immunosuppressive agent. The compounds of the disclosure can be administered before, after or concurrently with the other therapeutic agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, decarbazine and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/mL dose once every 21 days. Co-administration of a compound of formula (I) or salts thereof, with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Also within the scope of the present disclosure are kits comprising a compound of formula (I) or salts thereof and instructions for use. The kit can further contain at least one additional reagent. Kits typically include a label indicating the intended use of the contents of the kit. The term label includes any writing, or recorded material supplied on or with the kit, or which otherwise accompanies the kit.

The above other therapeutic agents, when employed in combination with the compounds of the present disclosure, may be used, for example, in those amounts indicated in the Physicians' Desk Reference (PDR) or as otherwise determined by one of ordinary skill in the art. In the methods of the present disclosure, such other therapeutic agent(s) may be administered prior to, simultaneously with, or following the administration of the inventive compounds.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

The following scheme illustrates the synthesis of Example 1001 to Example 1059. The reductive amination was performed by using the penultimate aldehyde (25 to 100 mg) with 0.6 to 1 equivalent of borane-2-picoline complex, 1 to 2 equivalents of amine and 5 equivalents of AcOH in dry DMF (0.04-0.06 M) at rt for 16 to 40 hours. If necessary, additional amine and reducing agent were added after 16 h to ensure reaction completion.

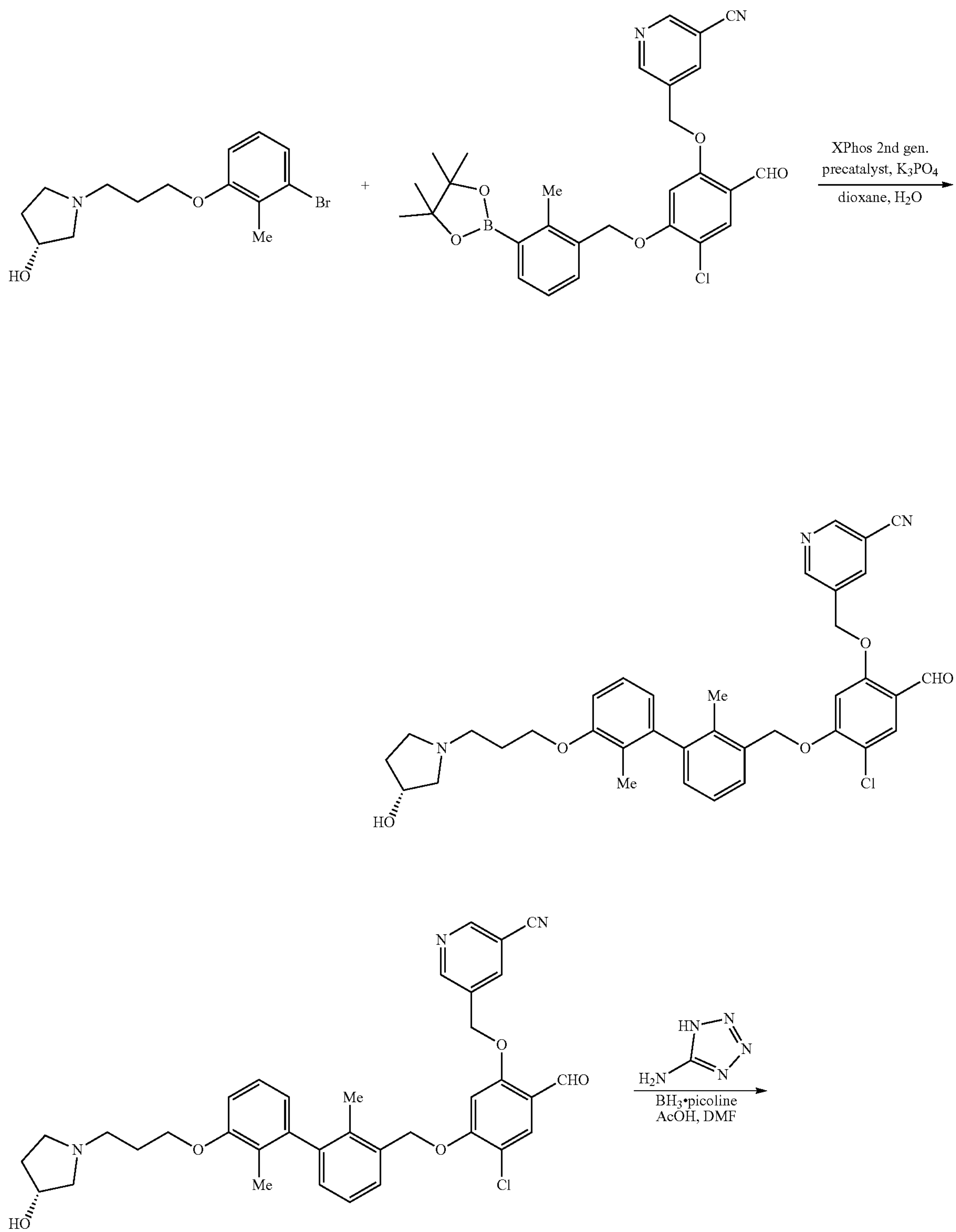

-continued

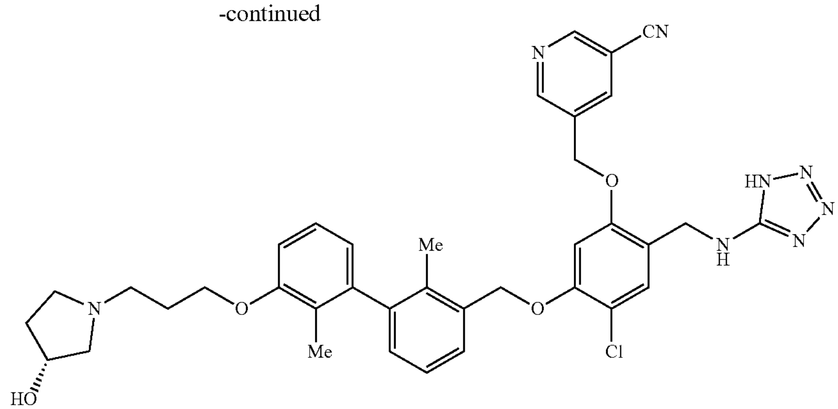

Example 1001

Intermediate: 5-Chloro-2-hydroxy-4-((2-methyl-3-(4,4,5,5-tetramethyl-1,3,2-dioxaborolan-2-yl)benzyl)oxy)benzaldehyde

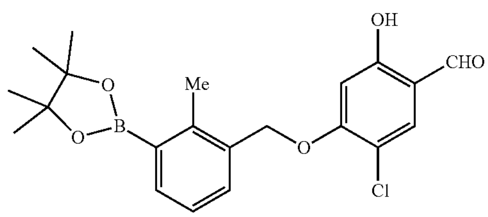 [SMILES: Cc1c(COc2cc(O)c(C=O)cc2Cl)cccc1B1OC(C)(C)C(C)(C)O1]

A solution of DIAD (1.79 g, 8.87 mmol) in THF (50 mL) was added dropwise to a cold (0° C.) solution of (2-methyl-3-(4,4,5,5-tetramethyl-1,3,2-dioxaborolan-2-yl)phenyl)-methanol (2.0 g, 8.06 mmol), 5-chloro-2,4-dihydroxybenzaldehyde (1.39 g, 8.06 mmol), and triphenylphosphine (2.33 g, 8.87 mmol) in anhydrous THF (50 mL) under nitrogen. The resulting yellow solution was allowed to warm to room temperature and stir for 16 h before the solvent was removed in vacuo. The residue was then purified by silica gel column chromatography (Biotage 40M, 0-20% ethyl acetate/hexanes) to give 1.95 g (57%) of 5-chloro-2-hydroxy-4-((2-methyl-3-(4,4,5,5-tetramethyl-1,3,2-dioxaborolan-2-yl)benzyl)oxy)benzaldehyde as a white solid. LCMS: $t_R$ (retention time)=2.15 min., m/z=389.2 $(M+H)^+$. LCMS conditions: Injection Vol=1 μL; Gradient=0-100% B; Gradient Time=2 min; Flow Rate=1 ml/min; Wavelength=220 nm; Mobile Phase A=10:90 acetonitrile:water with 0.1% trifluoroacetic acid; Mobile Phase B=90:10 acetonitrile:water with 0.1% trifluoroacetic acid; Column=Phenomenex Luna C18, 2.0×50 mm, 3 U (μm); Oven Temp=40° C.

$^1$H NMR (400 MHz, $CDCl_3$) δ 11.45 (s, 1H), 9.72 (s, 1H), 7.83-7.79 (m, 1H), 7.57-7.53 (m, 2H), 7.28-7.23 (m, 1H), 6.62 (s, 1H), 5.19 (s, 2H), 2.59 (s, 3H), 1.40-1.37 (m, 12H).

Intermediate: 5-((4-Chloro-2-formyl-5-((2-methyl-3-(4,4,5,5-tetramethyl-1,3,2-dioxaborolan-2-yl)-benzyl)oxy)phenoxy)methyl)nicotinonitrile

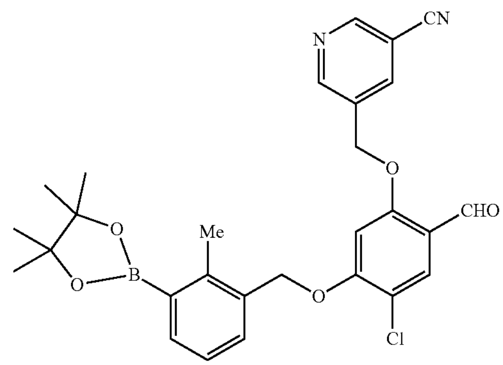 [SMILES: Cc1c(COc2cc(OCc3cncc(C#N)c3)c(C=O)cc2Cl)cccc1B1OC(C)(C)C(C)(C)O1]

A suspension of 5-chloro-2-hydroxy-4-((2-methyl-3-(4,4,5,5-tetramethyl-1,3,2-dioxaborolan-2-yl)benzyl)oxy)benzaldehyde (1.50 g, 3.73 mmol), 5-(chloromethyl)-nicotinonitrile (0.74 g, 4.84 mmol), and cesium carbonate (1.76 g, 5.40 mmol) in DMF (15 mL) was stirred at room temperature overnight. The solvent was removed, and the residue was partitioned between dichloromethane and water. The aqueous phase was separated and extracted once more with dichloromethane. The combined organic extract was washed with brine and then dried over sodium sulfate. The drying agent was removed by filtration and the solvent removed in vacuo. The resulting residue was purified by silica gel column chromatography (Biotage 40M, 0-50% ethyl acetate/hexanes) to give 1.48 g (77%) of 5-((4-chloro-2-formyl-5-((2-methyl-3-(4,4,5,5-tetramethyl-1,3,2-dioxaborolan-2-yl)-benzyl)oxy)phenoxy)methyl)nicotinonitrile as a white solid. LCMS: $t_R$=2.15 min, m/z=505.3 $(M+H)^+$. LCMS conditions: Injection Vol=1 μL; Gradient=0-100% B; Gradient Time=2 min; Flow Rate=1 ml/min; Wavelength=220 nm; Mobile Phase A=10:90 acetonitrile:water with 0.1% trifluoroacetic acid; Mobile Phase B=90:10 acetonitrile:water with 0.1% trifluoroacetic acid; Column=Phenomenex Luna $C_{18}$, 2.0×50 mm, 3 U; Oven Temp=40° C.

$^1$H NMR (500 MHz, $CDCl_3$) δ 10.29 (s, 1H), 8.93 (d, J=1.6 Hz, 1H), 8.91 (d, J=1.7 Hz, 1H), 8.08 (s, 1H), 7.94 (s,

1H), 7.81 (d, J=7.3 Hz, 1H), 7.48 (d, J=7.4 Hz, 1H), 7.25 (t, J=7.5 Hz, 1H), 6.58 (s, 1H), 5.25 (s, 2H), 5.19 (s, 2H), 2.61 (s, 3H), 1.40 (s, 12H).

Intermediate: 1-Bromo-3-(3-bromopropoxy)-2-methylbenzene

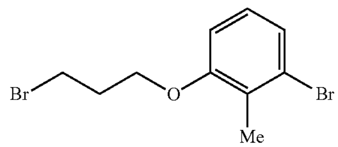

Potassium carbonate (9.24 g, 66.8 mmol) was added in one portion to a stirred solution of 3-bromo-2-methylphenol (10.0 g, 53.5 mmol) and 1,3-dibromopropane (54.3 mL, 535 mmol) in dry acetone (400 mL). The suspension was stirred at rt for 6 days before the mixture was suction-filtered to remove the salts. The filtrate was then concentrated in vacuo to a light yellow oil which was transferred to a 250 mL RBF (round bottomed flask) and distilled under high vacuum using a short-path distillation head to remove all of the excess 1,3-dibromopropane which came off between 28-32° C. (bath temp=70° C.) as a colorless liquid. Afterward, there was isolated in the distillation pot the crude desired product as a light yellow-colored oil which was used without further purification and was stored in the refrigerator when not needed.

LCMS: $t_R$=1.76 min; LCMS conditions: Injection Vol=3 μL; Gradient=2-98% B; Gradient Time=1.5 min; Flow Rate=0.8 ml/min; Wavelength=220 nm; Mobile Phase A=0: 100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

$^1$H NMR (500 MHz, $CDCl_3$) δ 7.18 (d, J=8.0 Hz, 1H), 7.02 (t, J=8.1 Hz, 1H), 6.81 (d, J=8.0 Hz, 1H), 4.11 (t, J=5.8 Hz, 2H), 3.63 (t, J=6.4 Hz, 2H), 2.39-2.34 (m, 2H), 2.33 (s, 3H).

Intermediate: (R)-1-(3-(3-Bromo-2-methylphenoxy) propyl)pyrrolidin-3-ol

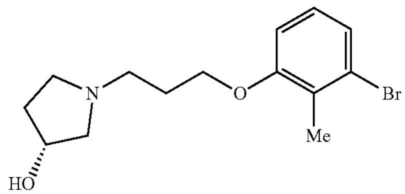 [SMILES: Cc1c(Br)cccc1OCCCN1CC[C@@H](O)C1]

A stirred suspension of 1-bromo-3-(3-chloropropoxy)-2-methylbenzene (5.15 g, 19.54 mmol), (R)-pyrrolidin-3-ol hydrochloride (3.62 g, 29.30 mmol), powdered potassium carbonate (4.05 g, 29.3 mmol) and sodium iodide (2.93 g, 19.54 mmol) in anhydrous DMF (100 mL) was heated at 80° C. for 16 h. The solvent was then removed in vacuo and the residue was partitioned between ethyl acetate and water. The aqueous phase was separated and extracted once more with ethyl acetate. The organic extracts were combined, washed with brine, dried over $MgSO_4$, filtered and concentrated to yield a residue which was then taken up in a small amount of dichloromethane and charged to a RediSepRf normal phase silica gel Teledyne ISCO 80 g disposable column which was first eluted with dichloromethane for 200 mL, followed by 0-100% B for 1500 mL where solvent B=methanol and solvent A=dichloromethane. Fractions containing the desired product were combined and dried via centrifugal evaporation. There was isolated the product (R)-1-(3-(3-bromo-2-methylphenoxy)propyl)pyrrolidin-3-ol (5.1 g, 83% yield) as caramel-colored oils. A small portion of the crude material (~33 mg) was purified via preparative LCMS with the following conditions: Column: XBridge C18, 19×200 mm, 5 U; Mobile Phase A: 5:95 acetonitrile: water with 10 mM ammonium acetate; Mobile Phase B: 95:5 acetonitrile:water with 10 mM ammonium acetate; Gradient: 12-52% B over 20 min, then a 5 min hold at 100% B; Flow: 20 mL/min. Fractions containing the desired product were combined and dried via centrifugal evaporation. The yield of the product was 25.1 mg, and its estimated purity by LCMS analysis was 98%. Two analytical LCMS injections were used to determine the final purity. Injection 1 conditions: Column: Waters Acquity UPLC BEH C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1.0 mL/min; Detection: UV at 220 nm. Injection 1 results: Purity: 98.2%; Observed Mass: 314.0; Retention Time: 1.37 min. Injection 2 conditions: Column: Waters Acquity UPLC BEH C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1.0 mL/min; Detection: UV at 220 nm. Injection 2 results: Purity: 98.5%; Observed Mass: 314.0; Retention Time: 1.38 min.

Intermediate: (R)-5-((4-Chloro-2-formyl-5-((3'-(3-(3-hydroxypyrrolidin-1-yl)propoxy)-2,2'-dimethyl-[1,1'-biphenyl]-3-yl)methoxy)phenoxy)methyl)nicotinonitrile

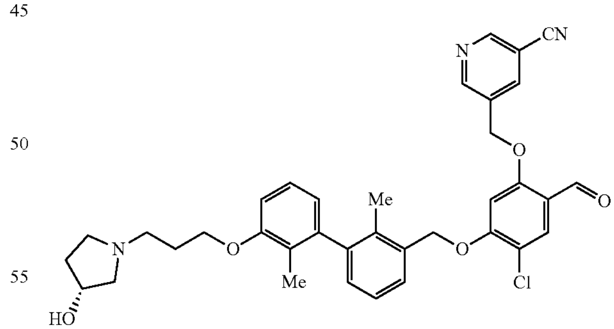

Second generation XPhos precatalyst (0.076 g, 0.096 mmol) was added in one portion to an argon-degassed mixture of (R)-1-(3-(3-bromo-2-methylphenoxy)propyl)-pyrrolidin-3-ol (0.73 g, 2.31 mmol), 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (1.0 g, 1.93 mmol) and potassium phosphate (1.02 g, 4.82 mmol) in THE (14 mL), dioxane (2 mL) and water (4 mL) at rt. The vial was sealed and the resultant suspension was stirred at rt for 16 h before it was placed in the freezer for 3 days. Afterwards, the mixture was diluted with ethyl acetate and water and the aqueous phase was separated and extracted with ethyl acetate one more time. The combined organic extract was washed with brine, dried over $MgSO_4$, filtered and concentrated. The crude product was taken up in a small amount of dichloromethane and charged to a RediSepRf normal phase silica gel Teledyne ISCO 80 g disposable column which was first eluted with dichloromethane for 300 mL, followed by 0-20% B for 2200 mL where solvent B=methanol and solvent A=dichloromethane. After concentration of the eluant, there was isolated the desired product, (R)-5-((4-chloro-2-formyl-5-((3'-(3-(3-hydroxypyrrolidin-1-yl)propoxy)-2,2'-dimethyl-[1,1'-biphenyl]-3-yl)-methoxy)phenoxy)methyl)nicotinonitrile (800.8 mg, 70% yield) as a yellow foam.

LCMS: $t_R$=1.14 min; LCMS (ESI) m/z=626.15 $[M+H]^+$. LCMS conditions: Injection Vol=3 μL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

$^1$H NMR (500 MHz, DMSO-d6) δ 10.24 (s, 1H), 9.05 (m, 2H), 8.57 (t, J=2.0 Hz, 1H), 7.74 (s, 1H), 7.53 (d, J=6.8 Hz, 1H), 7.33-7.26 (m, 2H), 7.21 (t, J=7.9 Hz, 1H), 7.12 (m, 1H), 6.97 (d, J=8.0 Hz, 1H), 6.69 (d, J=7.1 Hz, 1H), 5.50 (s, 2H), 5.43 (m, 2H), 4.66 (d, J=4.6 Hz, 1H), 4.22-4.15 (m, 1H), 4.10-4.00 (m, 2H), 2.70 (dd, J=9.4, 6.2 Hz, 1H), 2.60-2.53 (m, 3H), 2.49-2.29 (m, 2H), 2.05 (s, 3H), 1.96 (m, 1H), 1.91 (m, 2H), 1.83 (s, 3H), 1.60-1.46 (m, 1H).

Example 1001: (R)-5-((2-(((1H-Tetrazol-5-yl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile

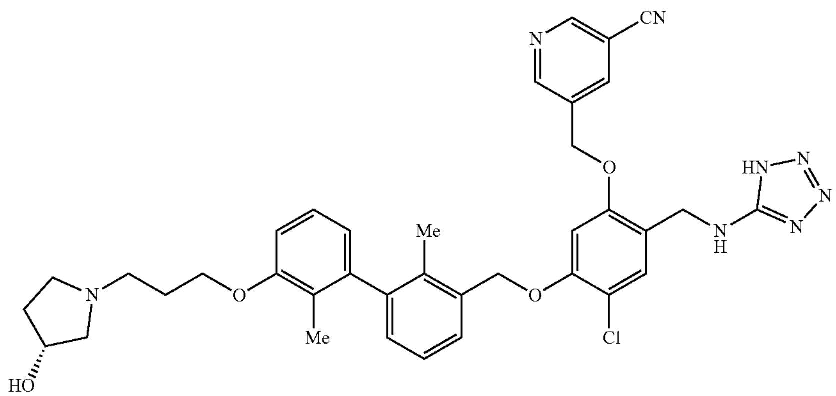 [SMILES: Cc1c(COc2cc(OCc3cncc(C#N)c3)c(CNc3nnn[nH]3)cc2Cl)cccc1-c1cccc(OCCCN2CC[C@@H](O)C2)c1C]

Borane-2-picoline complex (5.1 mg, 0.048 mmol) was added in one portion to a stirred solution of (R)-5-((4-chloro-2-formyl-5-((3'-(3-(3-hydroxypyrrolidin-1-yl)-propoxy)-2,2'-dimethyl-[1,1'-biphenyl]-3-yl)methoxy)phenoxy)methyl)nicotinonitrile (50.0 mg, 0.080 mmol), 1H-tetrazol-5-amine (10.2 mg, 0.12 mmol) and acetic acid (100 μL, 1.75 mmol) in dry DMF (2 mL) at rt. The mixture was stirred at rt for 16 h before the mixture was concentrated using nitrogen stream. Afterwards, MeOH was added and the resultant suspension was filtered through a nylon syringe filter and purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 18-58% B over 24 min, then a 4 min hold at 100% B; Flow: 20 mL/min. Fractions containing the desired product were combined and dried via centrifugal evaporation. The yield of the product was 19.0 mg, and its estimated purity by LCMS analysis was 97%. Analytical LCMS was used to determine the final purity. Injection 1 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 1 results: Purity: 97.1%; Observed Mass: 695.15; Retention Time: 1.59 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 2 results: Purity: 97.4%; Observed Mass: 695.16; Retention Time: 1.53 min.

Example 1002: (R)-5-((2-((((1H-Tetrazol-5-yl)methyl)amino)methyl)-4-chloro-5-((3'-(3-(3-hydroxy-pyrrolidin-1-yl)propoxy)-2,2'-dimethyl-[1,1'-biphenyl]-3-yl)methoxy)phenoxy)methyl)-nicotinonitrile

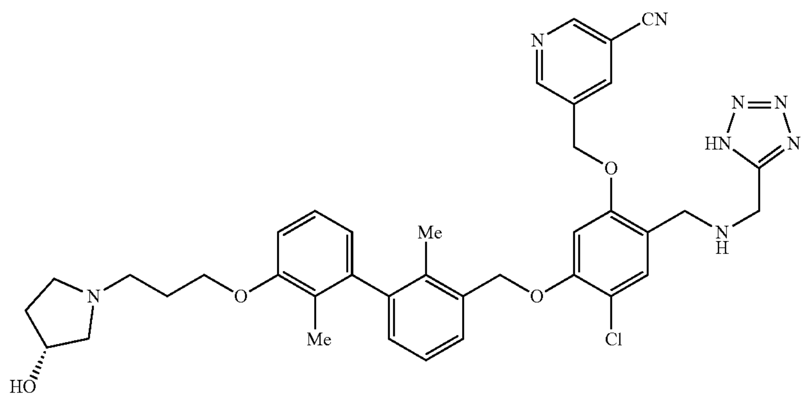 [SMILES: Cc1c(COc2cc(OCc3cncc(C#N)c3)c(CNCc3nnn[nH]3)cc2Cl)cccc1-c1cccc(OCCCN2CC[C@@H](O)C2)c1C]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 13-53% B over 23 min, then a 6 min hold at 100% B; Flow: 20 mL/min. Fractions containing the desired product were combined and dried via centrifugal evaporation. The material was further purified via preparative LCMS with the following conditions: Column: XBridge C18, 19×200 mm, 5 U; Mobile Phase A: 5:95 methanol:water with 10 mM ammonium acetate; Mobile Phase B: 95:5 methanol:water with 10 mM ammonium acetate; Gradient: 28-68% B over 30 min, then a 7 min hold at 100% B; Flow: 20 mL/min. Fractions containing the desired product were combined and dried via centrifugal evaporation. The yield of the product as a bis-acetic acid salt was 18.2 mg, and its estimated purity by LCMS analysis was 100%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 100.0%; Observed Mass: 709.24; Retention Time: 1.39 min. Injection 2 conditions: Column: Waters XBridge C18, 2.1×50 mm, 1.7 U; Mobile Phase A: 5:95 methanol:water with 10 mM ammonium acetate; Mobile Phase B: 95:5 methanol:water with 10 mM ammonium acetate; Temperature: 50° C.; Gradient: 0-100% B over 3.5 min, then a 0.5 min hold at 100% B; Flow: 0.5 mL/min; Detection: MS and UV (220 nm). Injection 2 results: Purity: 100.0%; Observed Mass: 709.22; Retention Time: 2.93 min. Injection 3 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 3 results: Purity: 100.0%; Observed Mass: 709.21; Retention Time: 1.4 min.

Example 1003: 5-((2-((3-(1H-Imidazol-2-yl)piperidin-1-yl)methyl)-4-chloro-5-((3'-(3-((R)-3-hydroxypyrrolidin-1-yl)propoxy)-2,2'-dimethyl-[1,1'-biphenyl]-3-yl)methoxy)phenoxy)methyl)-nicotinonitrile

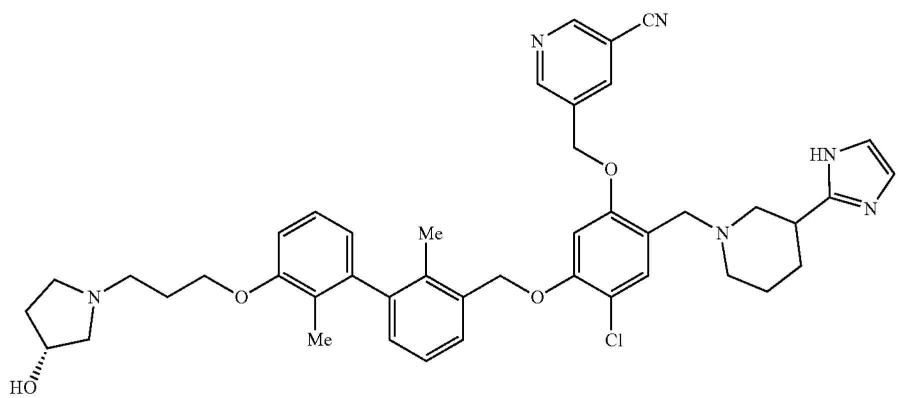 [SMILES: Cc1c(COc2cc(OCc3cncc(C#N)c3)c(CN3CCCC(c4ncc[nH]4)C3)cc2Cl)cccc1-c1cccc(OCCCN2CC[C@@H](O)C2)c1C]

The crude material was purified via preparative LCMS using the following conditions: Column: Waters XBridge C18, 19×200 mm, 5U: Mobile Phase A was 5:95 acetonitrile:water with 10 mM ammonium acetate and Mobile Phase B was 95:5 acetonitrile:water with 10 mM ammonium acetate at a gradient of 26-80% B over 27 min with a 4 min hold at a flow rate of 20 mL/min. Fractions containing the desired product were combined and dried via centrifugal evaporation. The yield of the product was 33.9 mg, and its estimated purity by LCMS analysis was 99%. Two analytical LCMS injections were used to determine the final purity. Injection 1 conditions: Column: Waters Acquity UPLC BEH C18, 2.1×50 mm, 1.7 U; Mobile Phase A=5:95 acetonitrile:water with 10 mM ammonium acetate; Mobile Phase B=95:5 acetonitrile:water with 10 mM ammonium acetate at a temperature of 50° C. at a gradient of 0-100% B over 3 min with a 0.75 min hold at 100% B at a flow rate of 1.0 mL/min at a UV wavelength of 220 nm. Injection 1 results: Retention time=1.718 min; ESI-MS (+) m/z=762.3 $(M+H)^+$. Injection 2 conditions: Column: Waters Acquity UPLC BEH C18, 2.1×50 mm, 1.7 U; Mobile Phase A=5:95 acetonitrile:water with 0.1% trifluoroacetic acid; Mobile Phase B=95:5 acetonitrile:water with 0.1% trifluoroacetic acid at a temperature of 50° C. at a gradient of 0-100% B over 3 min with a 0.75 min hold at 100% B at a flow rate of 1.0 mL/min at a UV wavelength of 220 nm. Injection 2 results: Retention time=1.336 min; ESI-MS (+) m/z=762.3 $(M+H)^+$.

$^1H$ NMR (500 MHz, DMSO-d6) δ 8.99 (dd, J=4.9, 1.8 Hz, 2H), 8.38 (s, 1H), 7.49 (d, J=7.6 Hz, 1H), 7.33 (s, 1H), 7.27 (t, J=7.6 Hz, 1H), 7.20 (t, J=7.8 Hz, 1H), 7.14-7.04 (m, 2H), 6.96 (d, J=8.2 Hz, 1H), 6.82 (s, 2H), 6.68 (d, J=7.3 Hz, 1H), 5.32 (s, 2H), 5.26 (s, 2H), 4.19 (m, 1H), 4.08 (m, 2H), 3.34-3.37 (m, 4H), 2.94 (m, 1H), 2.71 (m, 1H), 2.78 (m, 1H), 2.71 (m, 1H), 2.65-2.56 (m, 3H), 2.49-2.41 (m, 1H), 2.35 (dd, J=9.8, 3.7 Hz, 1H), 2.14 (m, 1H), 2.05 (s, 3H), 2.00 (m, 3H), 1.84 (s, 3H), 1.68 (m, 1H), 1.57 (m, 2H), 1.46 (m, 1H).

Example 1004: (R)-5-((2-(((2-(2H-Tetrazol-5-yl)ethyl)(methyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)-methyl)nicotinonitrile

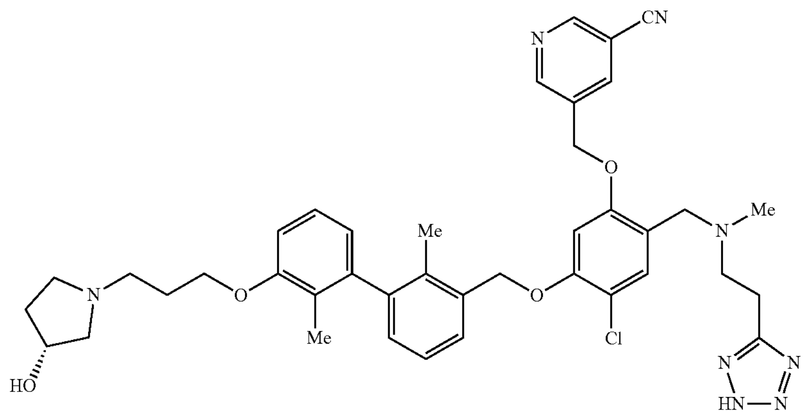 [SMILES: Cc1c(COc2cc(OCc3cncc(C#N)c3)c(CN(C)CCc3nn[nH]n3)cc2Cl)cccc1-c1cccc(OCCCN2CC[C@@H](O)C2)c1C]

The crude material was purified via preparative LCMS using the following conditions: Column: Waters XBridge C18, 19×200 mm, 5 U; Mobile Phase A=5:95 acetonitrile: water with 10 mM ammonium acetate; Mobile Phase B=95:5 acetonitrile:water with 10 mM ammonium acetate at a gradient of 14-57% B over 21 min with a 4 min hold at a flow rate of 20 mL/min. Fractions containing the desired product were combined and dried via centrifugal evaporation. The yield of the product was 25.1 mg, and its estimated purity by LCMS analysis was 100%. Two analytical LCMS injections were used to determine the final purity. Injection 1 conditions: Column: Waters Acquity UPLC BEH C18, 2.1×50 mm, 1.7 U; Mobile Phase A=5:95 acetonitrile:water with 10 mM ammonium acetate; Mobile Phase B=95:5 acetonitrile:water with 10 mM ammonium acetate at a temperature of 50° C. at a gradient of 0-100% B over 3 min with a 0.75 min hold at 100% B at a flow rate of 1.0 mL/min and at a UV wavelength of 220 nm. Injection 1 results: Retention time=1.396 min; ESI-MS (+) m/z=738.2 $(M+H)^+$. Injection 2 conditions: Column: Waters Acquity UPLC BEH C18, 2.1×50 mm, 1.7 U; Mobile Phase A=5:95 acetonitrile: water with 0.1% trifluoroacetic acid; Mobile Phase B=95:5 acetonitrile:water with 0.1% trifluoroacetic acid at a temperature of 50° C. at a gradient of 0-100% B over 3 min with a 0.75 min hold at 100% B at a flow rate of 1.0 mL/min and at a UV wavelength of 220 nm. Injection 2 results: Retention time=1.388 min; ESI-MS (+) m/z=738.2 $(M+H)^+$.

$^1$H NMR (500 MHz, DMSO-d6) δ 8.97 (m, 2H), 8.41 (s, 1H), 7.49 (d, J=7.3 Hz, 1H), 7.30 (s, 1H), 7.27 (m, 1H), 7.20 (m, 1H), 7.12-7.04 (m, 2H), 6.96 (d, J=7.9 Hz, 1H), 6.69 (d, J=7.3 Hz, 1H), 5.31 (s, 2H), 5.25 (s, 2H), 4.21 (m, 1H), 4.07 (m, 3H), 3.51 (s, 1H), 2.89 (m, 2H), 2.79-2.68 (m, 3H), 2.66-2.56 (m, 3H), 2.47 (m, 1H), 2.38 (dd, J=9.6, 3.5 Hz, 1H), 2.21 (s, 3H), 2.05 (s, 3H), 2.03-1.93 (m, 3H), 1.84 (s, 3H), 1.63-1.49 (m, 1H).

Example 1005: 5-((2-(((1-(1H-Tetrazol-5-yl)ethyl)(methyl)amino)methyl)-4-chloro-5-((3'-(3-((R)-3-hydroxypyrrolidin-1-yl)propoxy)-2,2'-dimethyl-[1,1'-biphenyl]-3-yl)methoxy)phenoxy) methyl) nicotinonitrile

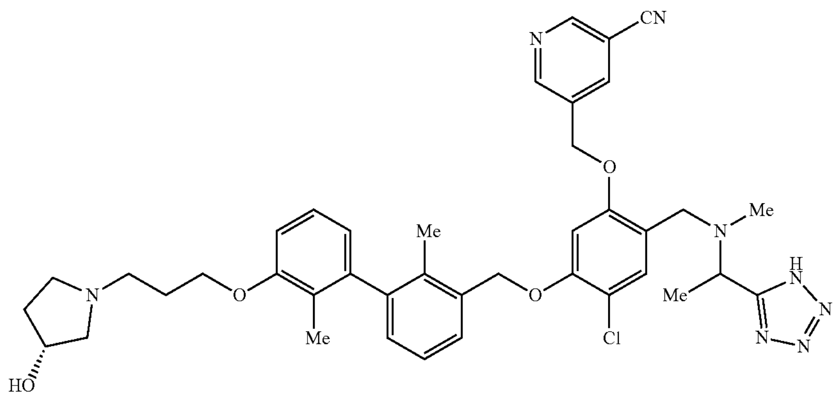 [SMILES: Cc1c(COc2cc(OCc3cncc(C#N)c3)c(CN(C)C(C)c3nnn[nH]3)cc2Cl)cccc1-c1cccc(OCCCN2CC[C@@H](O)C2)c1C]

The crude material was purified via preparative LCMS using the following conditions: Column: Waters XBridge C18, 19×200 mm, 5 U; Mobile Phase A=5:95 acetonitrile: water with 10 mM ammonium acetate and Mobile Phase B=95:5 acetonitrile:water with 10 mM ammonium acetate at a gradient of 12-52% B over 20 min with a 5 min hold at a flow rate of 20 mL/min. Fractions containing the desired product were combined and dried via centrifugal evaporation. The yield of the product was 23.3 mg, and its estimated purity by LCMS analysis was 100%. Two analytical LCMS injections were used to determine the final purity. Injection 1 conditions: Column: Waters Acquity UPLC BEH C18, 2.1×50 mm, 1.7 U; Mobile Phase A=5:95 acetonitrile:water with 10 mM ammonium acetate; Mobile Phase B=95:5 acetonitrile:water with 10 mM ammonium acetate at a temperature of 50° C. at a gradient of 0-100% B over 3 min with a 0.75 min hold at 100% B at a flow rate of 1.0 mL/min and at a UV wavelength of 220 nm. Injection 1 results: Retention time=1.496 min; ESI-MS (+) m/z=738.3 $(M+H)^+$. Injection 2 conditions: Column: Waters Acquity UPLC BEH, C18, 2.1×50 mm, 1.7 U; Mobile Phase A=5:95 acetonitrile:water with 0.1% trifluoroacetic acid; Mobile Phase B=95:5 acetonitrile:water with 0.1% trifluoroacetic acid at a temperature of 50° C. at a gradient of 0-100% B over 3 min with a 0.75 min hold at 100% B at a flow rate of 1.0 mL/min and at a UV wavelength of 220 nm. Injection 2 results: Retention time=1.464 min; ESI-MS (+) m/z=738.3 $(M+H)^+$.

$^1$H NMR (500 MHz, DMSO-d6) δ 9.05-8.88 (m, 2H), 8.41 (s, 1H), 7.48 (d, J=7.3 Hz, 1H), 7.43 (s, 1H), 7.26 (t, J=7.5 Hz, 1H), 7.20 (t, J=7.8 Hz, 1H), 7.10-7.02 (m, 2H), 6.96 (d, J=8.2 Hz, 1H), 6.68 (d, J=7.3 Hz, 1H), 5.31 (s, 2H), 5.24 (s, 2H), 4.21 (m, 1H), 4.18-4.12 (m, 1H), 4.11-4.01 (m, 1H), 3.58-3.41 (m, 2H), 3.19 (s, 3H), 2.75 (dd, J=9.8, 6.1 Hz, 1H), 2.68-2.55 (m, 3H), 2.40 (dd, J=9.6, 3.5 Hz, 1H), 2.09 (s, 3H), 2.04 (s, 3H), 1.94 (m, 2H), 1.84 (s, 3H), 1.65-1.51 (m, 1H), 1.40 (d, J=6.7 Hz, 3H).

Example 1006: 5-((2-(((2-(1H-Tetrazol-5-yl)propyl)(methyl)amino)methyl)-4-chloro-5-((3'-(3-((R)-3-hydroxypyrrolidin-1-yl)propoxy)-2,2'-dimethyl-[1,1'-biphenyl]-3-yl)methoxy)phenoxy) methyl) nicotinonitrile

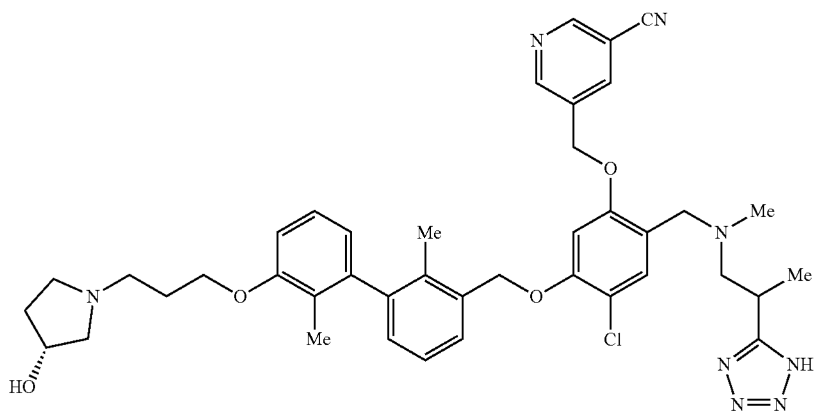 [SMILES: Cc1c(COc2cc(OCc3cncc(C#N)c3)c(CN(C)CC(C)c3nnn[nH]3)cc2Cl)cccc1-c1cccc(OCCCN2CC[C@@H](O)C2)c1C]

The crude material was purified via preparative LCMS using the following conditions: Column: Waters XBridge C18, 19×200 mm, 5 U; Mobile Phase A=5:95 acetonitrile: water with 10 mM ammonium acetate and Mobile Phase B=95:5 acetonitrile:water with 10 mM ammonium acetate at a gradient of 15-55% B over 20 min with a 4 min hold at a flow rate of 20 mL/min. Fractions containing the desired product were combined and dried via centrifugal evaporation. The yield of the product was 24.5 mg, and its estimated purity by LCMS analysis was 99%. Two analytical LCMS injections were used to determine the final purity. Injection 1 conditions: Column: Waters Acquity UPLC BEH C18, 2.1×50 mm, 1.7 U; Mobile Phase A=5:95 acetonitrile:water with 10 mM ammonium acetate; Mobile Phase B=95:5 acetonitrile:water with 10 mM ammonium acetate at a temperature of 50° C. at a gradient of 0-100% B over 3 min with a 0.75 min hold at 100% B at a flow rate of 1.0 mL/min and at a UV wavelength of 220 nm. Injection 1 results: Retention time=1.538 min; ESI-MS (+) m/z=752.3 $(M+H)^+$. Injection 2 conditions: Column: Waters Acquity UPLC BEH C18, 2.1×50 mm, 1.7 U; Mobile Phase A was 5:95 acetonitrile:water with 0.1% trifluoroacetic acid; Mobile Phase B was 95:5 acetonitrile:water with 0.1% trifluoroacetic acid at a temperature of 50° C. at a gradient of 0-100% B over 3 min with a 0.75 min hold at 100% B at a flow rate of 1.0 mL/min and at a UV wavelength of 220 nm. Injection 2 results: Retention time=1.475 min; ESI-MS (+) m/z=752.3 $(M+H)^+$.

$^1$H NMR (500 MHz, DMSO-d6) δ 8.98 (m, 2H), 8.37 (s, 1H), 7.49 (d, J=7.3 Hz, 1H), 7.31-7.16 (m, 3H), 7.09-7.04 (m, 2H), 6.96 (d, J=8.2 Hz, 1H), 6.68 (d, J=7.3 Hz, 1H), 5.27 (m, 4H), 4.21 (m, 1H), 4.13-4.03 (m, 2H), 3.58-3.42 (m, 2H), 3.29 (m, 1H), 3.19 (s, 1H), 2.75 (dd, J=9.8, 6.1 Hz, 1H), 2.69-2.54 (m, 5H), 2.39 (dd, J=9.8, 3.7 Hz, 1H), 2.16 (s, 3H), 2.05 (s, 3H), 2.02-1.93 (m, 3H), 1.84 (s, 3H), 1.57 (m, 1H), 1.21 (d, J=6.7 Hz, 3H).

Example 1007: (R)-5-((2-((((1H-Tetrazol-5-yl)methyl)(ethyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy) methyl)nicotinonitrile

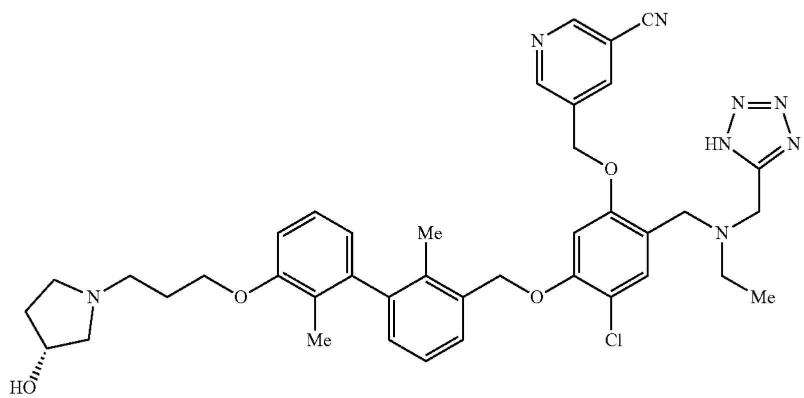 [SMILES: CCN(Cc1nnn[nH]1)Cc1cc(Cl)c(OCc2cccc(-c3cccc(OCCCN4CC[C@@H](O)C4)c3C)c2C)cc1OCc1cncc(C#N)c1]

The crude material was purified via preparative LCMS using the following conditions: Column: Waters XBridge C18, 19×200 mm, 5 U; Mobile Phase A=5:95 acetonitrile: water with 10 mM ammonium acetate; Mobile Phase B=95:5 acetonitrile:water with 10 mM ammonium acetate at a gradient of 18-58% B over 22 min with a 4 min hold at a flow rate of 20 mL/min. Fractions containing the desired product were combined and dried via centrifugal evaporation. The yield of the product was 22.1 mg, and its estimated purity by LCMS analysis was 98%. Two analytical LCMS injections were used to determine the final purity. Injection 1 conditions: Column: Waters Acquity UPLC BEH C18, 2.1×50 mm, 1.7 U; Mobile Phase A=5:95 acetonitrile:water with 10 mM ammonium acetate; Mobile Phase B=95:5 acetonitrile:water with 10 mM ammonium acetate at a temperature of 50° C. at a gradient of 0-100% B over 3 min with a 0.75 min hold at 100% B at a flow rate of 1.0 mL/min and at a UV wavelength of 220 nm. Injection 1 results: Retention time=1.531 min; ESI-MS (+) m/z=738.3 $(M+H)^+$. Injection 2 conditions: Column: Waters Acquity UPLC BEH C18, 2.1×50 mm, 1.7 U; Mobile Phase A was 5:95 acetonitrile:water with 0.1% trifluoroacetic acid; Mobile Phase B was 95:5 acetonitrile:water with 0.1% trifluoroacetic acid at a temperature of 50° C. at a gradient of 0-100% B over 3 min with a 0.75 min hold at 100% B at a flow rate of 1.0 mL/min and at a UV wavelength of 220 nm. Injection 2 results: Retention time=1.467 min; ESI-MS (+) m/z=738.3 $(M+H)^+$.

$^1$H NMR (500 MHz, DMSO-d6) δ 8.89 (m, 2H), 8.42 (s, 1H), 7.57 (s, 1H), 7.49 (d, J=7.6 Hz, 1H), 7.27 (t, J=7.6 Hz, 1H), 7.20 (t, J=7.8 Hz, 1H), 7.11-7.01 (m, 2H), 6.96 (d, J=7.9 Hz, 1H), 6.69 (d, J=7.6 Hz, 1H), 5.31 (s, 2H), 5.25 (s, 2H), 4.22 (m, 1H), 4.14-4.00 (m, 2H), 3.96-3.87 (m, 1H), 3.83 (m, 1H), 3.70 (m, 1H), 3.59 (m, 1H), 3.57-3.41 (m, 2H), 3.19 (m, 2H), 2.78 (dd, J=9.8, 6.1 Hz, 1H), 2.72-2.58 (m, 2H), 2.48-2.37 (m, 2H), 2.05 (s, 3H), 1.95 (m, 2H), 1.84 (s, 3H), 1.67-1.47 (m, 1H), 1.07-0.89 (m, 3H).

Example 1008: 5-((2-((3-(4H-1,2,4-Triazol-3-yl)piperidin-1-yl)methyl)-4-chloro-5-((3'-(3-((R)-3-hydroxypyrrolidin-1-yl)propoxy)-2,2'-dimethyl-[1,1'-biphenyl]-3-yl)methoxy)phenoxy)-methyl)nicotinonitrile

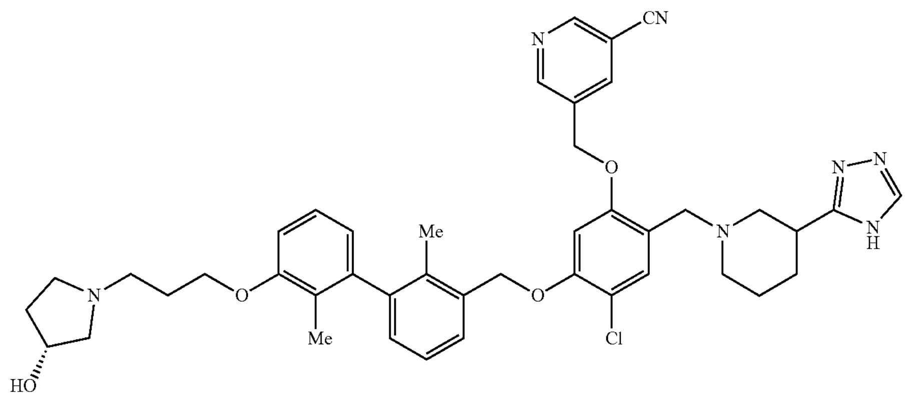 [SMILES: Cc1c(COc2cc(OCc3cncc(C#N)c3)c(CN3CCCC(c4nnc[nH]4)C3)cc2Cl)cccc1-c1cccc(OCCCN2CC[C@@H](O)C2)c1C]

The crude material was purified via preparative LCMS using the following conditions: Column: Waters XBridge C18, 19×200 mm, 5 U; Mobile Phase A=5:95 acetonitrile: water with 10 mM ammonium acetate; Mobile Phase B=95:5 acetonitrile:water with 10 mM ammonium acetate at a gradient of 18-58% B over 20 min with a 5 min hold at a flow rate of 20 mL/min. Fractions containing the desired product were combined and dried via centrifugal evaporation. The yield of the product was 45.1 mg, and its estimated purity by LCMS analysis was 99%. Two analytical LCMS injections were used to determine the final purity. Injection 1 conditions: Column: Waters Acquity UPLC BEH C18, 2.1×50 mm, 1.7 U; Mobile Phase A=5:95 acetonitrile:water with 10 mM ammonium acetate; Mobile Phase B=95:5 acetonitrile:water with 10 mM ammonium acetate at a temperature of 50° C. at a gradient of 0-100% B over 3 min with a 0.75 min hold at 100% B at a flow rate of 1.0 mL/min and at a UV wavelength of 220 nm. Injection 1 results: Retention time=1.727 min; ESI-MS (+) m/z=762.3 $(M+H)^+$. Injection 2 conditions: Column: Waters Acquity UPLC BEH C18, 2.1×50 mm, 1.7 U; Mobile Phase A=5:95 acetonitrile: water with 0.1% trifluoroacetic acid; Mobile Phase B=95:5 acetonitrile:water with 0.1% trifluoroacetic acid at a temperature of 50° C. at a gradient of 0-100% B over 3 min with a 0.75 min hold at 100% B at a flow rate of 1.0 mL/min and at a UV wavelength of 220 nm. Injection 2 results: Retention time=1.423 min; ESI-MS (+) m/z=762.3 $(M+H)^+$.

$^1$H NMR (500 MHz, DMSO-d6) δ 8.99 (m, 2H), 8.38 (s, 1H), 8.00 (s, 1H), 7.49 (d, J=7.0 Hz, 1H), 7.33 (s, 1H), 7.27 (t, J=7.5 Hz, 1H), 7.20 (t, J=7.9 Hz, 1H), 7.12-7.05 (m, 2H), 6.96 (d, J=7.9 Hz, 1H), 6.68 (d, J=7.3 Hz, 1H), 5.32 (s, 2H), 5.26 (s, 2H), 4.17 (m, 1H), 4.13-4.01 (m, 2H), 3.56-3.42 (m, 2H), 3.19 (s, 1H), 2.99 (m, 1H), 2.96-2.88 (m, 1H), 2.82-2.75 (m, 1H), 2.72 (m, 1H), 2.66-2.53 (m, 5H), 2.48-2.42 (m, 1H), 2.36 (m, 1H), 2.18 (br t, J=10.5 Hz, 1H), 2.05 (s, 3H), 2.02-1.92 (m, 2H), 1.84 (s, 3H), 1.75-1.66 (m, 1H), 1.64-1.44 (m, 3H).

Example 1009: 5-((2-((2-(1H-Imidazol-2-yl)piperidin-1-yl)methyl)-4-chloro-5-((3'-(3-((R)-3-hydroxypyrrolidin-1-yl)propoxy)-2,2'-dimethyl-[1,1'-biphenyl]-3-yl)methoxy)phenoxy)methyl)-nicotinonitrile

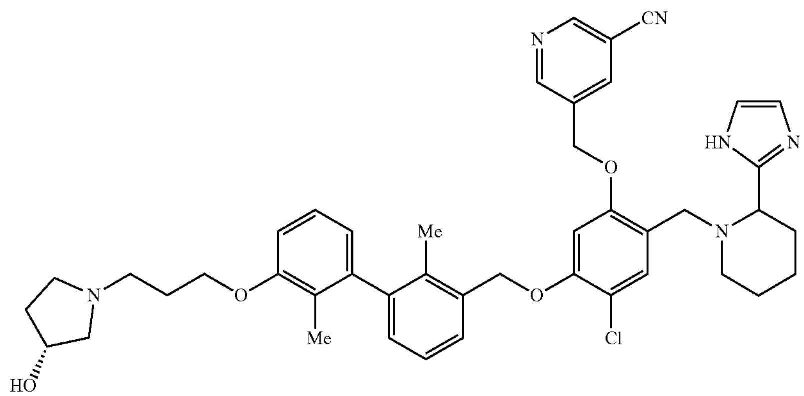 [SMILES: Cc1c(COc2cc(OCc3cncc(C#N)c3)c(CN3CCCCC3c3ncc[nH]3)cc2Cl)cccc1-c1cccc(OCCCN2CC[C@@H](O)C2)c1C]

The crude material was purified via preparative LCMS using the following conditions: Column: Waters XBridge C18, 19×200 mm, 5 U; Mobile Phase A=5:95 acetonitrile: water with 10 mM ammonium acetate; Mobile Phase B=95:5 acetonitrile:water with 10 mM ammonium acetate at a gradient of 30-75% B over 25 min with a 4 min hold at a flow rate of 20 mL/min. Fractions containing the desired product were combined and dried via centrifugal evaporation. The yield of the product was 28.4 mg, and its estimated purity by LCMS analysis was 99%. Two analytical LCMS injections were used to determine the final purity. Injection 1 conditions: Column: Waters Acquity UPLC BEH C18, 2.1×50 mm, 1.7 U; Mobile Phase A=5:95 acetonitrile:water with 10 mM ammonium acetate; Mobile Phase B=95:5 acetonitrile:water with 10 mM ammonium acetate at a temperature of 50° C. at a gradient of 0-100% B over 3 min with a 0.75 min hold at 100% B at a flow rate of 1.0 mL/min and at a UV wavelength of 220 nm. Injection 1 results: Retention time=1.883 min; ESI-MS (+) m/z=761.3 $(M+H)^+$. Injection 2 conditions: Column: Waters Acquity UPLC BEH C18, 2.1×50 mm, 1.7 U; Mobile Phase A=5:95 acetonitrile: water with 0.1% trifluoroacetic acid; Mobile Phase B=95:5 acetonitrile:water with 0.1% trifluoroacetic acid at a temperature of 50° C. at a gradient of 0-100% B over 3 min with a 0.75 min hold at 100% B at a flow rate of 1.0 mL/min and at a UV wavelength of 220 nm. Injection 2 results: Retention time=1.483 min; ESI-MS (+) m/z=761.2 $(M+H)^+$.

$^1$H NMR (500 MHz, DMSO-d6) δ 8.99 (m, 1H), 8.92 (d, J=2.1 Hz, 1H), 8.33 (s, 1H), 7.47 (d, J=7.3 Hz, 1H), 7.39 (s, 1H), 7.26 (t, J=7.6 Hz, 1H), 7.22-7.15 (m, 1H), 7.07 (d, J=7.3 Hz, 1H), 7.02 (s, 1H), 6.96 (d, J=8.2 Hz, 1H), 6.93-6.76 (br.s., 2H), 6.68 (d, J=7.6 Hz, 1H), 5.25 (s, 2H), 5.22 (s, 2H), 4.20 (m, 1H), 4.08 (m, 2H), 3.52-3.38 (m, 2H), 3.24-3.08 (m, 2H), 2.86-2.77 (m, 1H), 2.77-2.66 (m, 1H), 2.66-2.55 (m, 4H), 2.49-2.40 (m, 1H), 2.39-2.30 (m, 1H), 2.03 (s, 3H), 1.95 (m, 3H), 1.83 (s, 3H), 1.77 (m, 3H), 1.64 (m, 2H), 1.43-1.25 (m, 1H).

Example 1010: 5-((4-Chloro-5-((3'-(3-((R)-3-hydroxypyrrolidin-1-yl)propoxy)-2,2'-dimethyl-[1,1'-biphenyl]-3-yl)methoxy)-2-((2-(5-oxo-2,5-dihydro-1H-1,2,4-triazol-3-yl)piperidin-1-yl)-methyl)phenoxy)methyl)nicotinonitrile

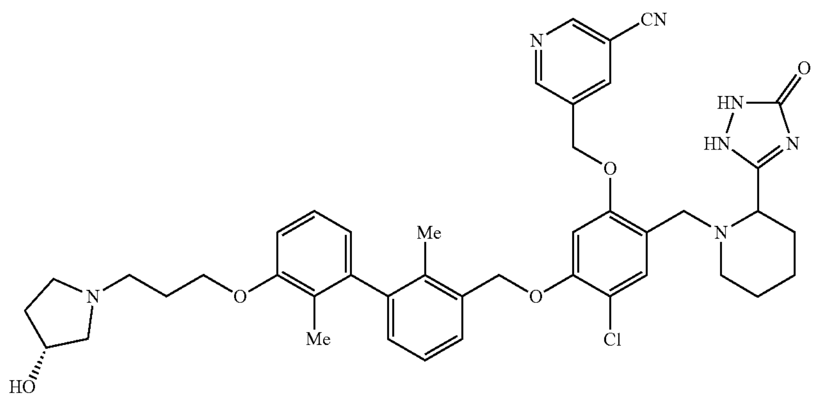 [SMILES: Cc1c(COc2cc(OCc3cncc(C#N)c3)c(CN3CCCCC3c3nc(=O)[nH][nH]3)cc2Cl)cccc1-c1cccc(OCCCN2CC[C@@H](O)C2)c1C]

The crude material was purified via preparative LCMS using the following conditions: Column: Waters XBridge C18, 19×200 mm, 5 U; Mobile Phase A=5:95 acetonitrile: water with 10 mM ammonium acetate; Mobile Phase B=95:5 acetonitrile:water with 10 mM ammonium acetate at a gradient of 22-62% B over 24 min with a 4 min hold at a flow rate of 20 mL/min. Fractions containing the desired product were combined and dried via centrifugal evaporation. The yield of the product was 23.1 mg, and its estimated purity by LCMS analysis was 100%. Two analytical LCMS injections were used to determine the final purity. Injection 1 conditions: Column: Waters Acquity UPLC BEH C18, 2.1×50 mm, 1.7 U; Mobile Phase A=5:95 acetonitrile:water with 10 mM ammonium acetate; Mobile Phase B=95:5 acetonitrile:water with 10 mM ammonium acetate at a temperature of 50° C. at a gradient of 0-100% B over 3 min with a 0.75 min hold at 100% B at a flow rate of 1.0 mL/min and at a UV wavelength of 220 nm. Injection 1 results: Retention time=1.844 min; ESI-MS (+) m/z=778.2 $(M+H)^+$. Injection 2 conditions: Column: Waters Acquity UPLC BEH C18, 2.1×50 mm, 1.7 U; Mobile Phase A=5:95 acetonitrile: water with 0.1% trifluoroacetic acid; Mobile Phase B=95:5 acetonitrile:water with 0.1% trifluoroacetic acid at a temperature of 50° C. at a gradient of 0-100% B over 3 min with a 0.75 min hold at 100% B at a flow rate of 1.0 mL/min and at a UV wavelength of 220 nm. Injection 2 results: Retention time=1.408 min; ESI-MS (+) m/z=778.3 $(M+H)^+$.

$^1$H NMR (500 MHz, DMSO-d6) δ 11.17-10.94 (br.s., 1H), 8.98 (d, J=1.8 Hz, 1H), 8.95 (d, J=1.8 Hz, 1H), 8.36 (s, 1H), 7.48 (m, 2H), 7.26 (t, J=7.6 Hz, 1H), 7.20 (t, J=7.9 Hz, 1H), 7.07 (d, J=7.5 Hz, 1H), 7.04 (s, 1H), 6.96 (d, J=7.9 Hz, 1H), 6.68 (d, J=7.6 Hz, 1H), 5.29 (s, 2H), 5.23 (s, 2H), 4.19 (m, 1H), 4.08 (m, 2H), 3.40 (m, 1H), 3.19 (m, 1H), 2.77 (m, 1H), 2.60 (m, 2H), 2.59 (m, 3H), 2.43 (m, 1H), 2.35 (dd, J=9.6, 3.8 Hz, 1H), 2.04 (s, 3H), 1.99 (m, 4H), 1.83 (s, 3H), 1.80-1.67 (m, 3H), 1.59-1.51 (m, 2H), 1.45 (m, 1H), 1.36-1.26 (m, 1H).

Example 1011: 5-((2-((2-(1H-Pyrazol-4-yl)piperidin-1-yl)methyl)-4-chloro-5-((3'-(3-((R)-3-hydroxypyrrolidin-1-yl)propoxy)-2,2'-dimethyl-[1,1'-biphenyl]-3-yl)methoxy)phenoxy)methyl)-nicotinonitrile

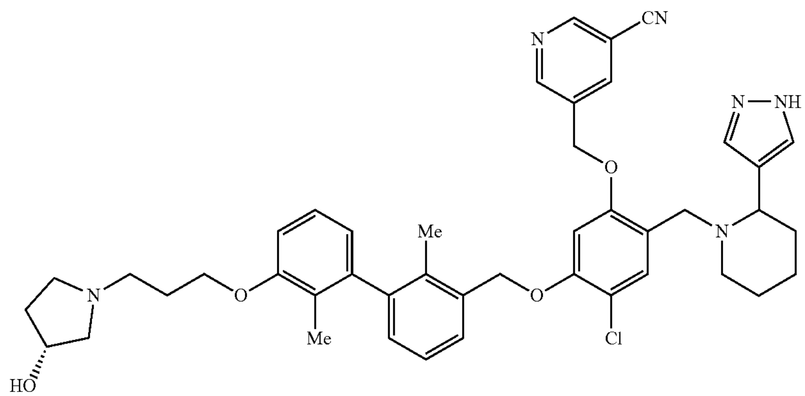 [SMILES: Cc1c(COc2cc(OCc3cncc(C#N)c3)c(CN3CCCCC3c3cn[nH]c3)cc2Cl)cccc1-c1cccc(OCCCN2CC[C@@H](O)C2)c1C]

The crude material was purified via preparative LCMS using the following conditions: Column: Waters XBridge C18, 19×200 mm, 5 U; Mobile Phase A=5:95 acetonitrile: water with 10 mM ammonium acetate; Mobile Phase B=95:5 acetonitrile:water with 10 mM ammonium acetate at a gradient of 18-58% B over 15 min with a 5 min hold at a flow rate of 20 mL/min. Fractions containing the desired product were combined and dried via centrifugal evaporation. The yield of the product was 60 mg, and its estimated purity by LCMS analysis was 95%. Two analytical LCMS injections were used to determine the final purity. Injection 1 conditions: Column: Waters Acquity UPLC BEH C18, 2.1×50 mm, 1.7 U; Mobile Phase A=5:95 acetonitrile:water with 10 mM ammonium acetate; Mobile Phase B=95:5 acetonitrile:water with 10 mM ammonium acetate at a temperature of 50° C. at a gradient of 0-100% B over 3 min with a 0.75 min hold at 100% B at a flow rate of 1.0 mL/min and at a UV wavelength of 220 nm. Injection 1 results: Retention time=1.806 min; ESI-MS (+) m/z=761.3 $(M+H)^+$. Injection 2 conditions: Column: Waters Acquity UPLC BEH C18, 2.1×50 mm, 1.7 U; Mobile Phase A=5:95 acetonitrile: water with 0.1% trifluoroacetic acid; Mobile Phase B=95:5 acetonitrile:water with 0.1% trifluoroacetic acid at a temperature of 50° C. at a gradient of 0-100% B over 3 min with a 0.75 min hold at 100% B at a flow rate of 1.0 mL/min and at a UV wavelength of 220 nm. Injection 2 results: Retention time=1.470 min; ESI-MS (+) m/z=761.4 $(M+H)^+$.

$^1$H NMR (500 MHz, DMSO-d6) δ 8.99 (d, J=1.8 Hz, 1H), 8.94 (d, J=1.8 Hz, 1H), 8.33 (s, 1H), 7.48 (m, 3H), 7.29-7.13 (m, 3H), 7.11-7.01 (m, 2H), 6.96 (d, J=7.9 Hz, 1H), 6.68 (d, J=7.6 Hz, 1H), 5.27 (s, 2H), 5.22 (s, 2H), 4.19 (m, 1H), 4.05 (m, 2H), 3.77 (m 2H), 3.27 (d, J=8.5 Hz, 1H), 3.03 (m, 1H), 2.74 (m, 2H), 2.59 (m, 3H), 2.48-2.39 (m, 2H), 2.35 (m, 2H), 2.03 (s, 3H), 1.91 (m, 2H), 1.89-1.68 (m, 3H), 1.71 (m, 2H), 1.55 (m, 3H), 1.32 (m, 1H).

Example 1012: 5-((2-((2-(1H-Tetrazol-5-yl)piperidin-1-yl)methyl)-4-chloro-5-((3'-(3-((R)-3-hydroxypyrrolidin-1-yl)propoxy)-2,2'-dimethyl-[1,1'-biphenyl]-3-yl)methoxy)phenoxy)methyl)-nicotinonitrile

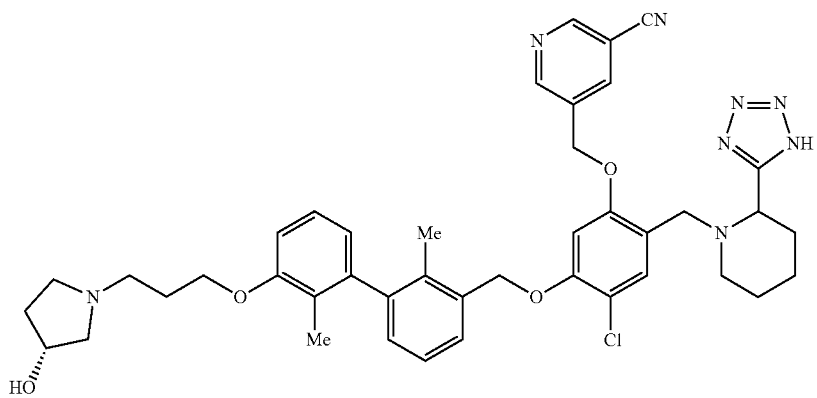 [SMILES: Cc1c(COc2cc(OCc3cncc(C#N)c3)c(CN3CCCCC3c3nnn[nH]3)cc2Cl)cccc1-c1cccc(OCCCN2CC[C@@H](O)C2)c1C]

The crude material was purified via preparative LCMS using the following conditions: Column: Waters XBridge C18, 19×200 mm, 5 U; Mobile Phase A=5:95 acetonitrile: water with 10 mM ammonium acetate; Mobile Phase B=95:5 acetonitrile:water with 10 mM ammonium acetate at a gradient of 17-57% B over 20 min with a 5 min hold at a flow rate of 20 mL/min. Fractions containing the desired product were combined and dried via centrifugal evaporation. The yield of the product was 35.1 mg, and its estimated purity by LCMS analysis was 100%. Two analytical LCMS injections were used to determine the final purity. Injection 1 conditions: Column: Waters Acquity UPLC BEH C18, 2.1×50 mm, 1.7 U; Mobile Phase A=5:95 acetonitrile:water with 10 mM ammonium acetate; Mobile Phase B=95:5 acetonitrile:water with 10 mM ammonium acetate at a temperature of 50° C. at a gradient of 0-100% B over 3 min with a 0.75 min hold at 100% B at a flow rate of 1.0 mL/min and at a UV wavelength of 220 nm. Injection 1 results: Retention time=1.542 min; ESI-MS (+) m/z=763.3 $(M+H)^+$. Injection 2 conditions: Column: Waters Acquity UPLC BEH C18, 2.1×50 mm, 1.7 U; Mobile Phase A=5:95 acetonitrile:

water with 0.1% trifluoroacetic acid; Mobile Phase B=95:5 acetonitrile:water with 0.1% trifluoroacetic acid at a temperature of 50° C. at a gradient of 0-100% B over 3 min with a 0.75 min hold at 100% B at a flow rate of 1.0 mL/min and at a UV wavelength of 220 nm. Injection 2 results: Retention time=1.491 min; ESI-MS (+) m/z=763.3 $(M+H)^+$.

$^1$H NMR (500 MHz, DMSO-d6) δ 8.97 (s, 1H), 8.94 (br s, 1H), 8.38 (s, 1H), 7.47 (d, J=7.3 Hz, 1H), 7.39 (s, 1H), 7.25 (t, J=7.6 Hz, 1H), 7.20 (t, J=7.7 Hz, 1H), 7.06 (d, J=7.3 Hz, 1H), 7.00 (s, 1H), 6.96 (d, J=8.2 Hz, 1H), 6.68 (d, J=7.6 Hz, 1H), 5.25 (s, 2H), 5.22 (s, 2H), 4.22 (m, 1H), 4.12-4.02 (m, 2H), 3.84 (m, 1H), 3.24 (m, 2H), 2.88 (m, 1H), 2.79 (m, 1H), 2.75-2.61 (m, 3H), 2.65 (m, 1H), 2.44 (m, 1H), 2.17 (m, 1H), 2.03 (s, 3H), 1.88-1.73 (m, 2H), 1.87 (m, 1H), 1.83 (s, 3H), 1.77 (m, 3H), 1.58 (m, 3H), 1.42-1.34 (m, 1H).

Example 1013: 5-((2-(((2-(1H-Tetrazol-5-yl)propyl)amino)methyl)-4-chloro-5-((3'-(3-((R)-3-hydroxypyrrolidin-1-yl)propoxy)-2,2'-dimethyl-[1,1'-biphenyl]-3-yl)methoxy)phenoxy)methyl)-nicotinonitrile

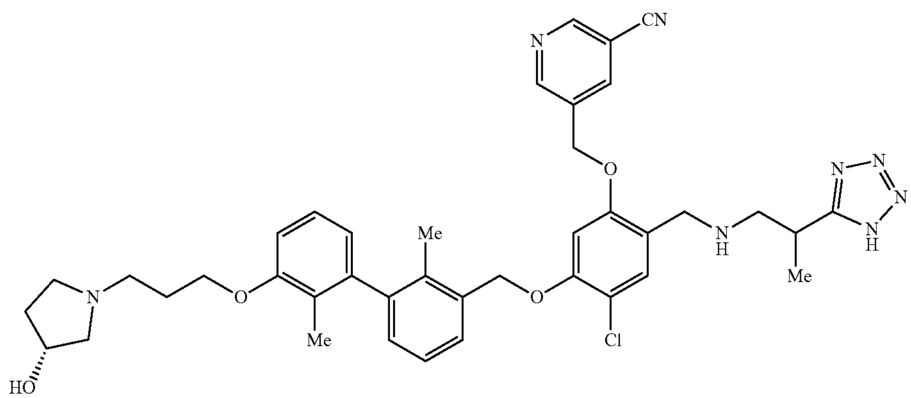 [SMILES: Cc1c(COc2cc(OCc3cncc(C#N)c3)c(CNCC(C)c3nnn[nH]3)cc2Cl)cccc1-c1cccc(OCCCN2CC[C@@H](O)C2)c1C]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 10-50% B over 20 min, then a 4 min hold at 100% B; Flow: 20 mL/min. Fractions containing the desired product were combined and dried via centrifugal evaporation. The yield of the product was 10.5 mg, and its estimated purity by LCMS analysis was 96%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 96.3%; Observed Mass: 737.24; Retention Time: 1.51 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 96.2%; Observed Mass: 737.22; Retention Time: 1.48 min.

Example 1014: (R)-5-((4-Chloro-5-((3'-(3-(3-hydroxypyrrolidin-1-yl)propoxy)-2,2'-dimethyl-[1,1'-biphenyl]-3-yl)methoxy)-2-(((2-(1-methyl-1H-tetrazol-5-yl)ethyl)amino)methyl)-phenoxy)methyl)nicotinonitrile

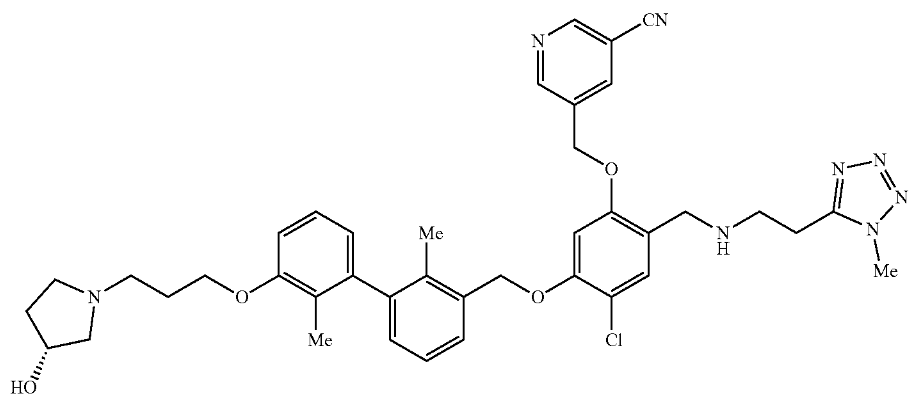 [SMILES: Cc1c(COc2cc(OCc3cncc(C#N)c3)c(CNCCc3nnnn3C)cc2Cl)cccc1-c1cccc(OCCCN2CC[C@@H](O)C2)c1C]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 15-55% B over 25 min, then a 4 min hold at 100% B; Flow: 20 mL/min. Fractions containing the desired product were combined and dried via centrifugal evaporation. The material was further purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 9-49% B over 26 min, then a 2 min hold at 100% B; Flow: 20 mL/min. Fractions containing the desired product were combined and dried via centrifugal evaporation. The yield of the product was 6.8 mg, and its estimated purity by LCMS analysis was 96%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 97.2%; Observed Mass: 737.23; Retention Time: 1.53 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 96.5%; Observed Mass: 737.24; Retention Time: 1.44 min.

Example 1015: 5-((2-((2-(1H-Tetrazol-5-yl)pyrrolidin-1-yl)methyl)-4-chloro-5-((3'-(3-((R)-3-hydroxypyrrolidin-1-yl)propoxy)-2,2'-dimethyl-[1,1'-biphenyl]-3-yl)methoxy)phenoxy)methyl)-nicotinonitrile

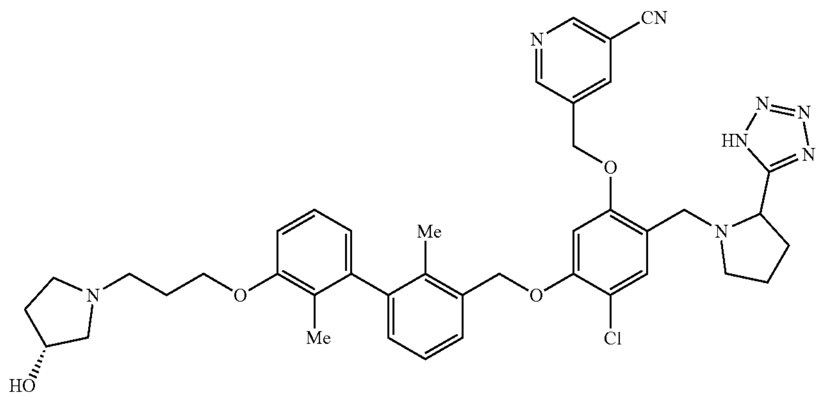 [SMILES: Cc1c(COc2cc(OCc3cncc(C#N)c3)c(CN3CCCC3c3nnn[nH]3)cc2Cl)cccc1-c1cccc(OCCCN2CC[C@@H](O)C2)c1C]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 10-50% B over 25 min, then a 4 min hold at 100% B; Flow: 20 mL/min. Fractions containing the desired product were combined and dried via centrifugal evaporation. The yield of the product was 24.8 mg, and its estimated purity by LCMS analysis was 100%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 100.0%; Observed Mass: 749.21; Retention Time: 1.43 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 100.0%; Observed Mass: 749.24; Retention Time: 1.43 min.

Example 1016: (R)-5-((2-((((1H-Tetrazol-5-yl)methyl)(methyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)-methyl)nicotinonitrile

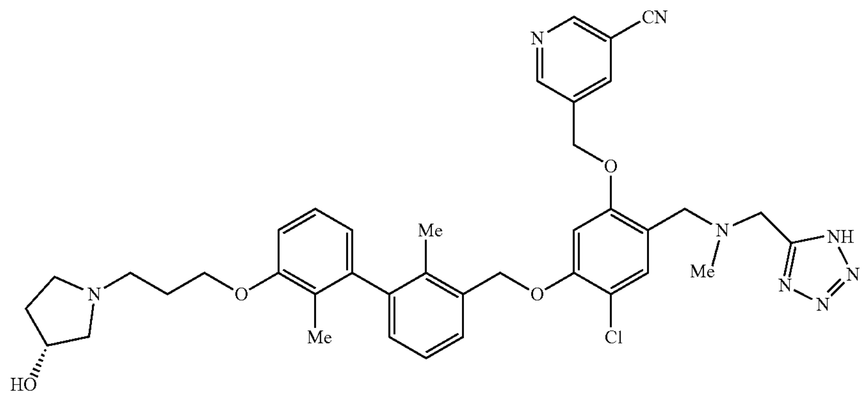 [SMILES: Cc1c(COc2cc(OCc3cncc(C#N)c3)c(CN(C)Cc3nnn[nH]3)cc2Cl)cccc1-c1cccc(OCCCN2CC[C@@H](O)C2)c1C]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 12-52% B over 20 min, then a 5 min hold at 100% B; Flow: 20 mL/min. Fractions containing the desired product were combined and dried via centrifugal evaporation. The yield of the product was 10.6 mg, and its estimated purity by LCMS analysis was 99%. Analytical LCMS was used to determine the final purity. Injection 1 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 1 results: Purity: 100.0%; Observed Mass: 723.22; Retention Time: 1.44 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 2 results: Purity: 98.7%; Observed Mass: 723.25; Retention Time: 1.52 min.

Example 1017: 5-((2-((3-(1H-Tetrazol-5-yl)pyrrolidin-1-yl)methyl)-4-chloro-5-((3'-(3-((R)-3-hydroxypyrrolidin-1-yl)propoxy)-2,2'-dimethyl-[1,1'-biphenyl]-3-yl)methoxy)phenoxy)methyl)-nicotinonitrile

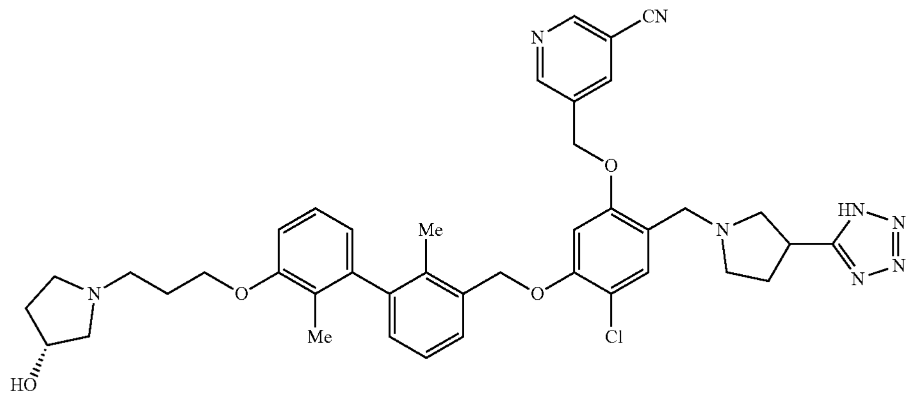 [SMILES: Cc1c(COc2cc(OCc3cncc(C#N)c3)c(CN3CCC(c4nnn[nH]4)C3)cc2Cl)cccc1-c1cccc(OCCCN2CC[C@@H](O)C2)c1C]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 5-45% B over 20 min, then a 5 min hold at 100% B; Flow: 20 mL/min. Fractions containing the desired product were combined and dried via centrifugal evaporation. The yield of the product was 17.1 mg, and its estimated purity by LCMS analysis was 97%. Analytical LCMS was used to determine the final purity. Injection 1 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 1 results: Purity: 96.8%; Observed Mass: 749.24; Retention Time: 1.46 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 2 results: Purity: 98.9%; Observed Mass: 749.25; Retention Time: 1.48 min.

Example 1018: 5-((2-((3-(1H-Tetrazol-5-yl)piperidin-1-yl)methyl)-4-chloro-5-((3'-(3-((R)-3-hydroxypyrrolidin-1-yl)propoxy)-2,2'-dimethyl-[1,1'-biphenyl]-3-yl)methoxy)phenoxy)methyl)-nicotinonitrile

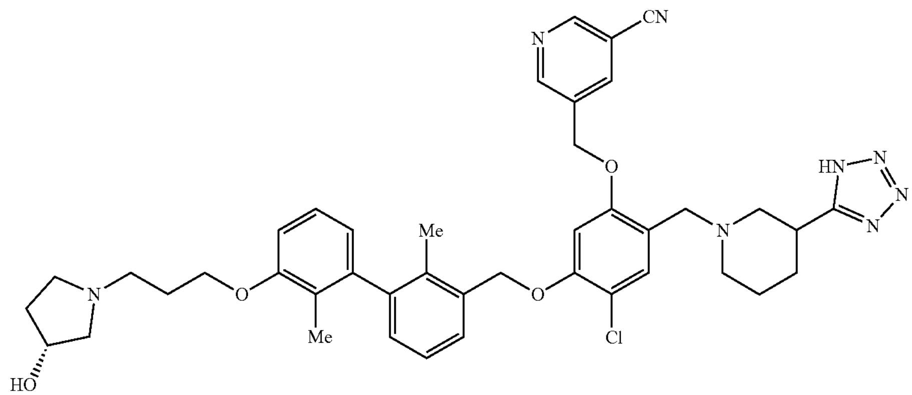 [SMILES: Cc1c(COc2cc(OCc3cncc(C#N)c3)c(CN3CCCC(c4nnn[nH]4)C3)cc2Cl)cccc1-c1cccc(OCCCN2CC[C@@H](O)C2)c1C]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 6-51% B over 20 min, then a 5 min hold at 100% B; Flow: 20 mL/min. Fractions containing the desired product were combined and dried via centrifugal evaporation. The yield of the product was 16.5 mg, and its estimated purity by LCMS analysis was 94%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 94.4%; Observed Mass: 763.26; Retention Time: 1.52 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 93.8%; Observed Mass: 763.23; Retention Time: 1.47 min.

Intermediate: 3-((3-Bromo-2-chlorophenoxy)methyl)-1-methylpiperidine

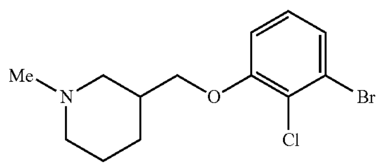 [SMILES: CN1CCCC(COc2cccc(Br)c2Cl)C1]

Potassium carbonate (0.80 g, 5.78 mmol) was added in one portion to a stirred solution of 3-bromo-2-chlorophenol (0.50 g, 2.41 mmol) and 3-(bromomethyl)-1-methylpiperidine hydrobromide (0.66 g, 2.41 mmol) in dry DMF (10 mL). The suspension was stirred at 60° C. for 16 h. After cooling to rt, the mixture was then diluted with ethyl acetate and water. The aqueous phase was separated, and extracted once more with ethyl acetate. The combined organic extract was washed with brine, dried over $MgSO_4$, filtered and concentrated to yield an oil which was taken up in a small amount of dichloromethane and charged to a RediSepRf normal phase silica gel Teledyne ISCO 24 g disposable column which was first eluted with dichloromethane for 100 mL, followed by 0-10% B for 650 mL where solvent B=methanol and solvent A=dichloromethane. After concentration of the eluant, there was isolated the desired product, 3-((3-bromo-2-chlorophenoxy)methyl)-1-methylpiperidine (585.5 mg, 76% yield) as a colorless oil.

LCMS: $t_R$=0.97 min; LCMS (ESI) m/z=317.85 and 319.90 $[M+H]^+$. LCMS conditions: Injection Vol=3 μL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

$^1H$ NMR (500 MHz, $CDCl_3$) δ 7.21 (dd, J=8.1, 1.0 Hz, 1H), 7.05 (t, J=8.1 Hz, 1H), 6.85 (d, J=8.2 Hz, 1H), 4.06-3.64 (m, 2H), 2.96 (br d, J=10.2 Hz, 1H), 2.74 (br d, J=10.4 Hz, 1H), 2.29 (s, 3H), 2.24-2.14 (m, 1H), 1.99 (br t, J=10.4 Hz, 1H), 1.91 (br t, J=10.2 Hz, 1H), 1.84-1.77 (m, 1H), 1.77-1.69 (m, 1H), 1.69-1.59 (m, 1H), 1.26-1.10 (m, 1H).

Intermediate: 5-((4-Chloro-5-((2'-chloro-2-methyl-3'-((1-methylpiperidin-3-yl)methoxy)-[1,1'-biphenyl]-3-yl)methoxy)-2-formylphenoxy)methyl)nicotinonitrile

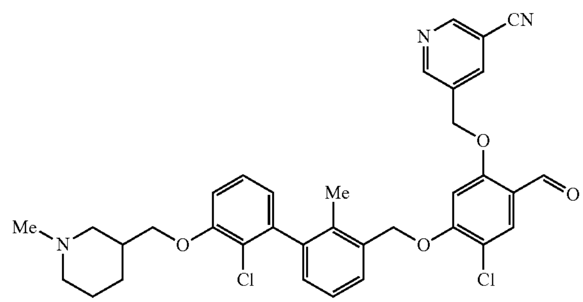 [SMILES: Cc1c(COc2cc(OCc3cncc(C#N)c3)c(C=O)cc2Cl)cccc1-c1cccc(OCC2CCCN(C)C2)c1Cl]

Second generation XPhos precatalyst (76 mg, 0.096 mmol) was added in one portion to an argon-degassed mixture of 3-((3-bromo-2-chlorophenoxy)methyl)-1-methylpiperidine (369 mg, 1.16 mmol), 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (500 mg, 0.96 mmol) and potassium phosphate (511 mg, 2.41 mmol) in THE (7 mL) and water (2 mL) at rt. The vial was then sealed and the resultant suspension was stirred at rt for 16 h before ethyl acetate and water were added. The mixture was shaken and the aqueous layer was separated, and extracted once more with ethyl acetate. The combined ethyl acetate extract was then washed with brine, dried over $MgSO_4$, filtered and concentrated to yield a yellowish-orange oil which was taken up in a small amount of dichloromethane and charged to a RediSepRf normal phase silica gel Teledyne ISCO 40 g disposable column which was first eluted with dichloromethane for 150 mL, followed by 0-15% B for 1500 mL where solvent B=methanol and solvent A=dichloromethane. After concentration of the eluant, there was isolated the desired product (638.3 mg) as a yellow foam which was used as obtained. LCMS: $t_R$=1.32 min; LCMS (ESI) m/z=630.05 and 632.00 $[M+H]^+$. LCMS conditions: Injection Vol=3 μL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

Example 1020: 5-((2-((2-(1H-Pyrazol-4-yl)piperidin-1-yl)methyl)-4-chloro-5-((2'-chloro-2-methyl-3'-((1-methylpiperidin-3-yl)methoxy)-[1,1'-biphenyl]-3-yl)methoxy)phenoxy)methyl)-nicotinonitrile

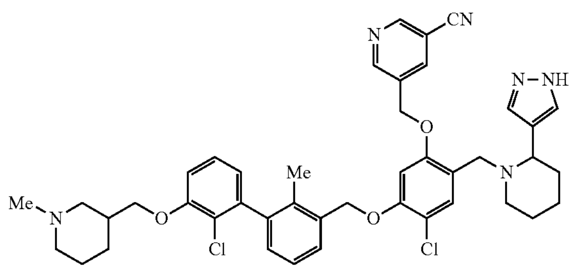 [SMILES: Cc1c(COc2cc(OCc3cncc(C#N)c3)c(CN3CCCCC3c3cn[nH]c3)cc2Cl)cccc1-c1cccc(OCC2CCCN(C)C2)c1Cl]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 36-76% B over 25 min, then a 4 min hold at 100% B; Flow: 20 mL/min. Fractions containing the desired product were combined and dried via centrifugal evaporation. The yield of the product was 14.0 mg, and its estimated purity by LCMS analysis was 95%. Analytical LCMS was used to determine the final purity. Injection 1 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 1 results: Purity: 97.1%; Observed Mass: 765.31; Retention Time: 1.51 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 2 results: Purity: 94.9%; Observed Mass: 765.27; Retention Time: 1.92 min.

$^1$H NMR (500 MHz, DMSO-d6) δ 9.01 (s, 1H), 8.96 (s, 1H), 8.36 (s, 1H), 7.53-7.47 (m, 3H), 7.38-7.32 (m, 1H), 7.31-7.24 (m, 2H), 7.16 (br d, J=8.2 Hz, 1H), 7.10 (br d, J=7.6 Hz, 1H), 7.04 (s, 1H), 6.84 (d, J=7.6 Hz, 1H), 5.27 (br s, 2H), 5.22 (br s, 2H), 4.04-3.91 (m, 2H), 3.22 (br d, J=10.7 Hz, 1H), 3.17 (s, 1H), 2.96 (br d, J=13.7 Hz, 1H), 2.87-2.81 (m, 1H), 2.77-2.70 (m, 1H), 2.64 (br s, 1H), 2.16 (s, 3H), 2.09-2.01 (m, 5H), 1.79-1.74 (m, 2H), 1.78-1.73 (m, 2H), 1.67-1.59 (m, 2H), 1.58-1.44 (m, 4H), 1.38-1.27 (m, 2H), 1.23 (br s, 1H), 1.17-1.04 (m, 1H).

Example 1021: 5-((2-((2-(1H-Pyrazol-3-yl)piperidin-1-yl)methyl)-4-chloro-5-((2'-chloro-2-methyl-3'-((1-methyl-piperidin-3-yl)methoxy)-[1,1'-biphenyl]-3-yl)methoxy)phenoxy)methyl)-nicotinonitrile

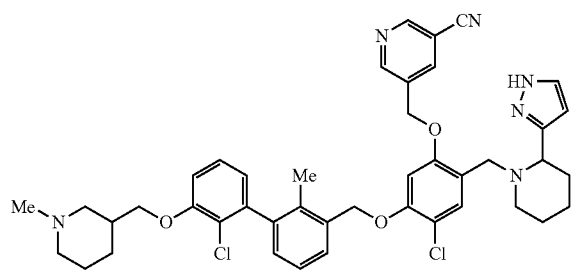 [SMILES: Cc1c(COc2cc(OCc3cncc(C#N)c3)c(CN3CCCCC3c3cc[nH]n3)cc2Cl)cccc1-c1cccc(OCC2CCCN(C)C2)c1Cl]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 34-74% B over 20 min, then a 4 min hold at 100% B; Flow: 20 mL/min. Fractions containing the desired product were combined and dried via centrifugal evaporation. The yield of the product was 22.7 mg, and its estimated purity by LCMS analysis was 99%. Analytical LCMS was used to determine the final purity. Injection 1 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 1 results: Purity: 100.0%; Observed Mass: 765.21; Retention Time: 1.52 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 2 results: Purity: 99.3%; Observed Mass: 765.25; Retention Time: 2.1 min.

$^1$H NMR (600 MHz, DMSO-d6) δ 9.01 (s, 1H), 8.95 (s, 1H), 8.37 (s, 1H), 7.51 (d, J=7.7 Hz, 1H), 7.47 (s, 1H), 7.34 (d, J=7.7 Hz, 1H), 7.33 (s, 1H), 7.28 (t, J=7.5 Hz, 1H), 7.16 (d, J=8.4 Hz, 1H), 7.11 (d, J=7.7 Hz, 1H), 7.05 (s, 1H), 6.85 (d, J=7.7 Hz, 1H), 6.13 (s, 1H), 5.28-5.24 (m, 2H), 5.23-5.20 (m, 2H), 4.04-3.92 (m, 2H), 3.04 (br d, J=14.3 Hz, 1H), 2.88-2.80 (m, 1H), 2.77 (br d, J=11.4 Hz, 1H), 2.69-2.60 (m, 1H), 2.17 (s, 3H), 2.06 (s, 5H), 1.99-1.82 (m, 3H), 1.79-1.62 (series of m, 6H), 1.60-1.45 (2m, 4H), 1.38-1.28 (m, 1H), 1.18-1.07 (m, 1H).

Example 1022: 5-((4-Chloro-5-((2'-chloro-2-methyl-3'-((1-methylpiperidin-3-yl)methoxy)-[1,1'-biphenyl]-3-yl)methoxy)-2-((2-(1-methyl-1H-pyrazol-4-yl)piperidin-1-yl)methyl)phenoxy)-methyl) nicotinonitrile

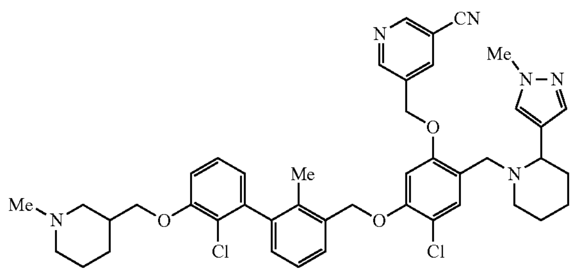 [SMILES: Cc1c(COc2cc(OCc3cncc(C#N)c3)c(CN3CCCCC3c3cnn(C)c3)cc2Cl)cccc1-c1cccc(OCC2CCCN(C)C2)c1Cl]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 31-76% B over 20 min, then a 5 min hold at 100% B; Flow: 20 mL/min. Fractions containing the desired product were combined and dried via centrifugal evaporation. The yield of the product was 17.0 mg, and its estimated purity by LCMS analysis was 98%. Analytical LCMS was used to determine the final purity. Injection 1 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 1 results: Purity: 100.0%; Observed Mass: 779.22; Retention Time: 1.52 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 2 results: Purity: 98.3%; Observed Mass: 779.26; Retention Time: 2.11 min.

Example 1023: 5-((4-Chloro-5-((2'-chloro-2-methyl-3'-((1-methylpiperidin-3-yl)methoxy)-[1,1'-biphenyl]-3-yl)methoxy)-2-((3-(1-methyl-1H-pyrazol-4-yl)piperidin-1-yl)methyl)-phenoxy)methyl) nicotinonitrile

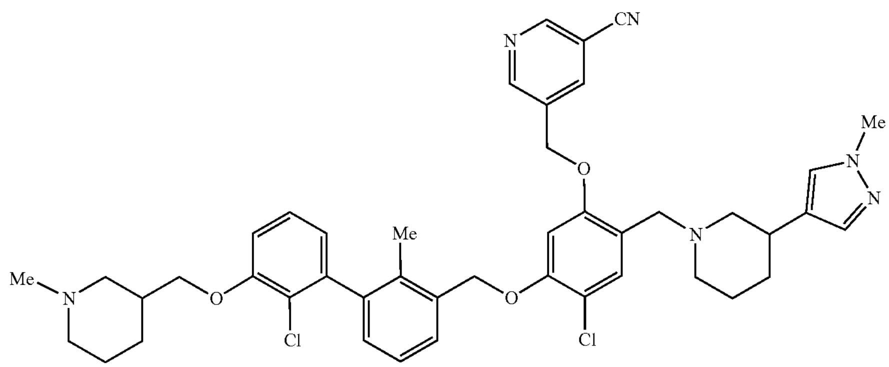 [SMILES: Cc1c(COc2cc(OCc3cncc(C#N)c3)c(CN3CCCC(c4cnn(C)c4)C3)cc2Cl)cccc1-c1cccc(OCC2CCCN(C)C2)c1Cl]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 33-73% B over 20 min, then a 4 min hold at 100% B; Flow: 20 mL/min. Fractions containing the desired product were combined and dried via centrifugal evaporation. The yield of the product was 16.1 mg, and its estimated purity by LCMS analysis was 94%. Analytical LCMS was used to determine the final purity. Injection 1 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 1 results: Purity: 94.6%; Observed Mass: 779.25; Retention Time: 1.51 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 2 results: Purity: 94.1%; Observed Mass: 779.21; Retention Time: 2.12 min.

$^1$H NMR (600 MHz, DMSO-d6) δ 9.02-9.00 (br s, 1H), 9.00 (br s, 1H), 8.39 (br s, 1H), 7.53 (br d, J=7.7 Hz, 1H), 7.43 (s, 1H), 7.35 (t, J=7.9 Hz, 1H), 7.31 (s, 1H), 7.30 (t, J=7.9 Hz, 2H), 7.22 (s, 1H), 7.17 (br d, J=8.4 Hz, 1H), 7.14-7.10 (m, 2H), 6.85 (d, J=7.3 Hz, 1H), 5.33 (s, 2H), 5.29-5.22 (m, 2H), 4.05-3.92 (m, 2H), 3.74 (s, 2H), 2.90-2.80 (m, 2H), 2.74 (br d, J=9.9 Hz, 1H), 2.70-2.60 (m, 2H), 2.19 (br s, 4H), 2.10-2.03 (m, 2H), 2.07 (s, 3H), 2.01-1.87 (m, 4H), 1.91 (s, 3H), 1.86-1.80 (m, 1H), 1.80-1.72 (s, 2H), 1.70-1.61 (m, 2H), 1.58-1.46 (m, 2H), 1.28-1.19 (m, 1H), 1.18-1.07 (m, 1H).

Example 1024: 5-((2-((3-(1H-Pyrazol-5-yl)piperidin-1-yl)methyl)-4-chloro-5-((2'-chloro-2-methyl-3'-((1-methylpiperidin-3-yl)methoxy)-[1,1'-biphenyl]-3-yl)methoxy)phenoxy)methyl)-nicotinonitrile

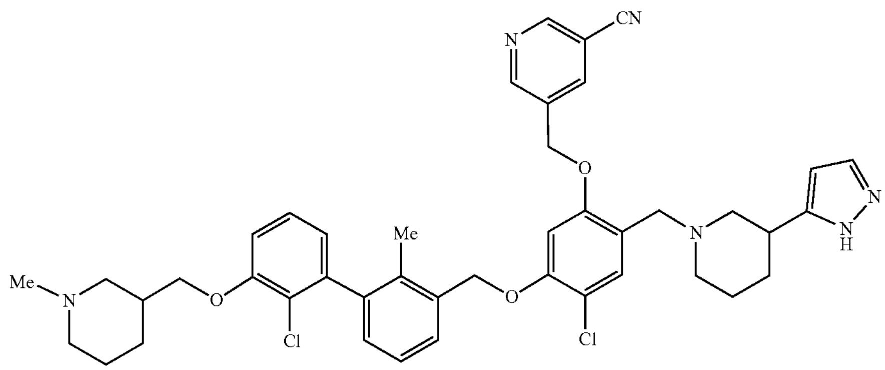 [SMILES: Cc1c(COc2cc(OCc3cncc(C#N)c3)c(CN3CCCC(c4ccn[nH]4)C3)cc2Cl)cccc1-c1cccc(OCC2CCCN(C)C2)c1Cl]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 26-71% B over 20 min, then a 5 min hold at 100% B; Flow: 20 mL/min. Fractions containing the desired product were combined and dried via centrifugal evaporation. The yield of the product was 31.1 mg, and its estimated purity by LCMS analysis was 99%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 98.7%; Observed Mass: 765.16; Retention Time: 1.82 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 100.0%; Observed Mass: 765.19; Retention Time: 1.52 min.

Example 1025: 5-((2-((2-(1H-Pyrazol-4-yl)pyrrolidin-1-yl)methyl)-4-chloro-5-((2'-chloro-2-methyl-3'-((1-methylpiperidin-3-yl)methoxy)-[1,1'-biphenyl]-3-yl)methoxy)phenoxy)methyl)-nicotinonitrile

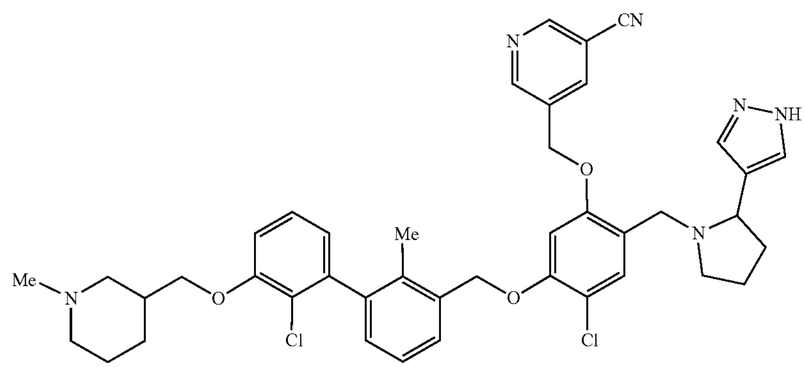 [SMILES: Cc1c(COc2cc(OCc3cncc(C#N)c3)c(CN3CCCC3c3cn[nH]c3)cc2Cl)cccc1-c1cccc(OCC2CCCN(C)C2)c1Cl]

The crude material was purified via preparative LCMS with the following conditions: Column: XBridge C18, 19×200 mm, 5 U; Mobile Phase A: 5:95 acetonitrile:water with 0.1% trifluoroacetic acid; Mobile Phase B: 95:5 acetonitrile:water with 0.1% trifluoroacetic acid; Gradient: 12-52% B over 25 min, then a 4 min hold at 100% B; Flow: 20 mL/min. Fractions containing the desired product were combined and dried via centrifugal evaporation. The yield of the product was 10.0 mg, and its estimated purity by LCMS analysis was 97%. Analytical LCMS was used to determine the final purity. Injection 1 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 1 results: Purity: 97.4%; Observed Mass: 751.23; Retention Time: 1.46 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 2 results: Purity: 97.4%; Observed Mass: 751.17; Retention Time: 1.86 min.

Example 1026: 5-((2-((2-(1H-Pyrazol-5-yl)pyrrolidin-1-yl)methyl)-4-chloro-5-((2'-chloro-2-methyl-3'-((1-methylpiperidin-3-yl)methoxy)-[1,1'-biphenyl]-3-yl)methoxy)phenoxy)methyl)-nicotinonitrile

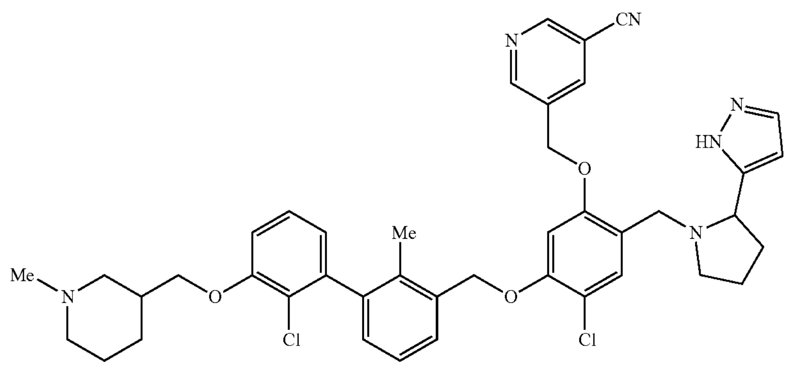 [SMILES: Cc1c(COc2cc(OCc3cncc(C#N)c3)c(CN3CCCC3c3ccn[nH]3)cc2Cl)cccc1-c1cccc(OCC2CCCN(C)C2)c1Cl]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 25-65% B over 25 min, then a 4 min hold at 100% B; Flow: 20 mL/min. Fractions containing the desired product were combined and dried via centrifugal evaporation. The material was purified a second time via preparative LCMS with the following conditions: Column: XBridge C18, 19×200 mm, 5 U; Mobile Phase A: 5:95 acetonitrile:water with 0.1% trifluoroacetic acid; Mobile Phase B: 95:5 acetonitrile:water with 0.1% trifluoroacetic acid; Gradient: 8-48% B over 25 min, then a 4 min hold at 100% B; Flow: 20 mL/min. Fractions containing the desired product were combined and dried via centrifugal evaporation. The yield of the product was 20.3 mg, and its estimated purity by LCMS analysis was 97%. Analytical LCMS was used to determine the final purity. Injection 1 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 1 results: Purity: 96.7%; Observed Mass: 751.25; Retention Time: 1.49 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 2 results: Purity: 96.7%; Observed Mass: 751.21; Retention Time: 1.99 min.

$^1$H NMR (600 MHz, DMSO-d6) δ 9.05 (br s, 1H), 8.91 (br s, 1H), 8.38 (br s, 1H), 7.75-7.61 (m, 1H), 7.53 (br d, J=7.7 Hz, 2H), 7.53-7.44 (m, 1H), 7.38 (t, J=7.9 Hz, 1H), 7.30 (t, J=7.5 Hz, 1H), 7.19 (br d, J=8.4 Hz, 2H), 7.19-7.14

(m, 1H), 7.11 (br d, J=7.3 Hz, 1H), 6.88 (d, J=7.3 Hz, 1H), 6.45-6.31 (m, 1H), 5.29 (br s, 4H), 4.14-4.05 (m, 1H), 4.04-3.95 (m, 1H), 2.81 (s, 3H), 2.44-2.25 (m, 2H), 2.24-2.11 (m, 1H), 2.09-1.96 (m, 2H), 2.07 (s, 3H), 1.96-1.83 (m, 3H), 1.77-1.66 (m, 2H), 1.33 (br s, 1H).

Example 1027: 2-((5-Chloro-4-((2'-chloro-2-methyl-3'-((1-methylpiperidin-3-yl)methoxy)-[1,1'-biphenyl]-3-yl)methoxy)-2-((5-cyanopyridin-3-yl)methoxy)benzyl)amino)-2-(3,5-dimethyl-1H-pyrazol-4-yl)acetic Acid

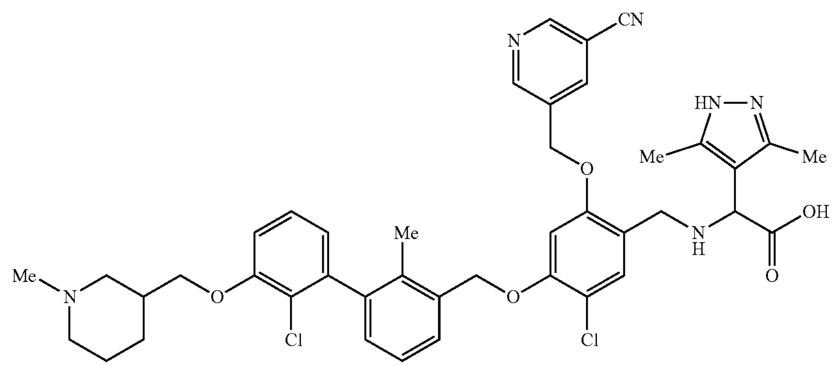 [SMILES: Cc1n[nH]c(C)c1C(NCc1cc(Cl)c(OCc2cccc(-c3cccc(OCC4CCCN(C)C4)c3Cl)c2C)cc1OCc1cncc(C#N)c1)C(=O)O]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 15% B, 15-55% B over 25 minutes, then a 5-minute hold at 100% B; Flow Rate: 20 mL/min; Column Temperature: 25 C. Fraction collection was triggered by MS signals. Fractions containing the desired product were combined and dried via centrifugal evaporation. The yield of the product was 6.2 mg, and its estimated purity by LCMS analysis was 94%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 783.17; Retention Time: 1.6 min. Injection 2 conditions: Column: Waters XBridge C18, 2.1 mm×50 mm, 1.7 m particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 94.1%; Observed Mass: 783.18; Retention Time: 1.4 min.

Example 1028: 2-((5-Chloro-4-((2'-chloro-2-methyl-3'-((1-methylpiperidin-3-yl)methoxy)-[1,1'-biphenyl]-3-yl)methoxy)-2-((5-cyanopyridin-3-yl)methoxy)benzyl)amino)-2-(1-methyl-1H-pyrazol-4-yl)acetic Acid

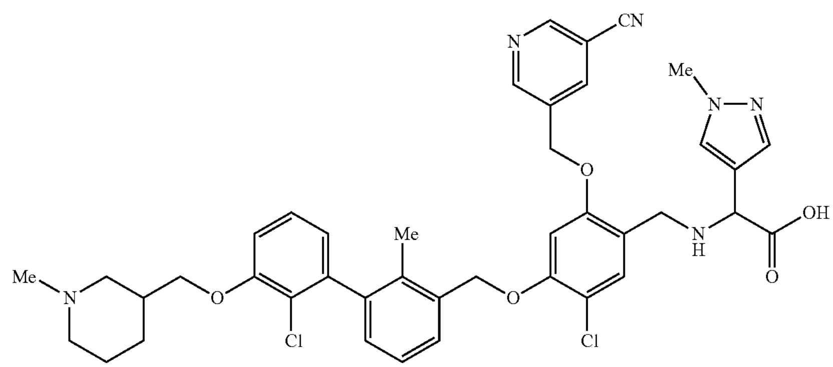 [SMILES: Cc1c(COc2cc(OCc3cncc(C#N)c3)c(CNC(C(=O)O)c3cnn(C)c3)cc2Cl)cccc1-c1cccc(OCC2CCCN(C)C2)c1Cl]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 8-48% B over 25 min, then a 4 min hold at 100% B; Flow Rate: 20 mL/min; Column Temperature: 25° C. Fractions containing the desired product were combined and dried via centrifugal evaporation. The yield of the product was 4.7 mg, and its estimated purity by LCMS analysis was 96%. Analytical LCMS was used to determine the final purity. Injection 1 conditions: Column: Waters XBridge C18, 2.1×50 mm, 1.7 U; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 1 results: Purity: 95.7%; Observed Mass: 769.18; Retention Time: 1.45 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 2 results: Purity: 98.3%; Observed Mass: 769.16; Retention Time: 1.5 min.

Example 1029: 5-((4-Chloro-5-((2'-chloro-2-methyl-3'-((1-methylpiperidin-3-yl)methoxy)-[1,1'-biphenyl]-3-yl)methoxy)-2-((3-(hydroxymethyl)-1-methyl-1,3a,4,6,7,7a-hexahydro-5H-pyrazolo[4,3-c]pyridin-5-yl)methyl)phenoxy)methyl)nicotinonitrile

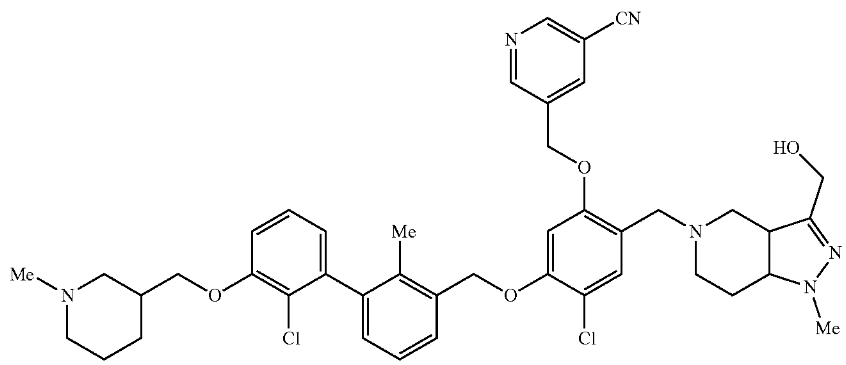 [SMILES: Cc1c(COc2cc(OCc3cncc(C#N)c3)c(CN3CCC4C(C3)C(CO)=NN4C)cc2Cl)cccc1-c1cccc(OCC2CCCN(C)C2)c1Cl]

The crude material was purified via preparative LCMS with the following conditions: Column: XBridge C18, 19×200 mm, 5 U; Mobile Phase A: 5:95 acetonitrile:water with 0.1% trifluoroacetic acid; Mobile Phase B: 95:5 acetonitrile:water with 0.1% trifluoroacetic acid; Gradient: 13-53% B over 20 min, then a 4 min hold at 100% B; Flow Rate: 20 mL/min; Column Temperature: 25° C. Fractions containing the desired product were combined and dried via centrifugal evaporation. The yield of the product was 2.1 mg, and its estimated purity by LCMS analysis was 99%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 100.0%; Observed Mass: 781.22; Retention Time: 1.87 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 99.4%; Observed Mass: 781.2; Retention Time: 1.44 min.

Intermediate: (S)-3-((3-(3-Bromo-2-methylphenoxy) propyl)amino)propane-1,2-diol

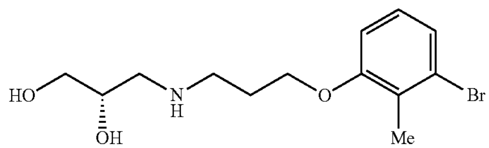 [SMILES: Cc1c(Br)cccc1OCCCNC[C@H](O)CO]

Hunig's base (1.70 mL, 9.74 mmol) was added in one portion to a stirred solution of 1-bromo-3-(3-bromopropoxy)-2-methylbenzene (1.0 g, 3.25 mmol) and (S)-3-aminopropane-1,2-diol (1.48 g, 16.23 mmol) in dry DMF (30 mL). The mixture was then heated to 60° C. for 16 h before it was concentrated with nitrogen stream. The resultant residue was diluted with methanol (up to 10 mL), filtered through a Whatman 13 mm PVDF syringe filter (45 μM), placed into five preparative HPLC sample vials (2 mL) and purified by preparative HPLC in several portions (10-100% B over a 12 min gradient @ 40 ml/min) using a SunFire C18 column (30×100 mm, 5 U) where Mobile Phase A: 5:95 acetonitrile:water with 10 mM ammonium acetate and Mobile Phase B: 95:5 acetonitrile:water with 10 mM ammonium acetate. Fractions containing the desired product were combined and dried via centrifugal evaporation. There was isolated the purified product, (S)-3-((3-(3-bromo-2-methylphenoxy)propyl)amino)-propane-1,2-diol (944.3 mg, 91% yield) as a colorless oil which solidified to a white solid on standing in the freezer.

LCMS: $t_R$=1.07 min; LCMS (ESI) m/z=318.05 and 320.05 $[M+H]^+$. LCMS conditions: Injection Vol=3 μL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

$^1$H NMR (500 MHz, METHANOL-d4) δ 7.16 (d, J=7.9 Hz, 1H), 7.05 (t, J=8.1 Hz, 1H), 6.92 (d, J=8.2 Hz, 1H), 4.12 (t, J=5.8 Hz, 2H), 3.90 (br dd, J=8.5, 3.6 Hz, 1H), 3.63-3.47 (m, 2H), 3.26-3.19 (m, 2H), 3.16 (dd, J=12.5, 3.1 Hz, 1H), 3.00 (dd, J=12.5, 9.2 Hz, 1H), 2.32 (s, 3H), 2.25-2.14 (m, 2H).

Intermediate: (S)-5-((4-Chloro-5-((3'-(3-((2,3-dihydroxypropyl)amino)propoxy)-2,2'-dimethyl-[1,1'-biphenyl]-3-yl)methoxy)-2-formylphenoxy)methyl) nicotinonitrile

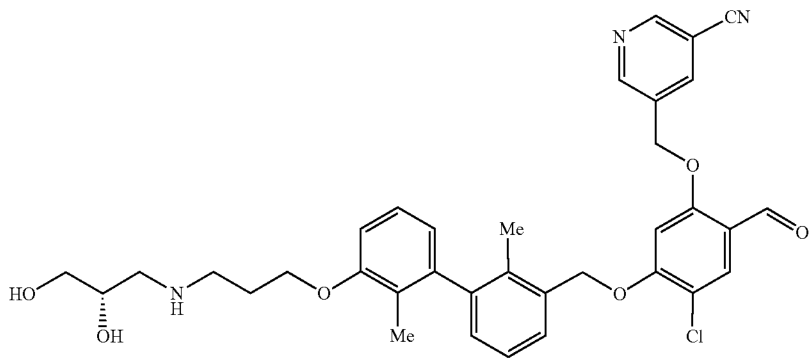 [SMILES: Cc1c(COc2cc(OCc3cncc(C#N)c3)c(C=O)cc2Cl)cccc1-c1cccc(OCCCNC[C@H](O)CO)c1C]

Second generation XPhos precatalyst (76 mg, 0.096 mmol) was added in one portion to an argon-degassed mixture of (S)-3-((3-(3-bromo-2-methylphenoxy)propyl) amino)-propane-1,2-diol (368 mg, 1.16 mmol), 5-((4-chloro-2-formyl-5-((2-methyl-3-(4,4,5,5-tetramethyl-1,3,2-dioxaborolan-2-yl)benzyl)oxy)phenoxy)methyl) nicotinonitrile (500 mg, 0.96 mmol) and potassium phosphate (511 mg, 2.41 mmol) in THE (10 mL) and water (2 mL) at rt. The vial was then sealed and the resultant suspension was stirred at rt for 16 h before it was diluted with ethyl acetate and water. The aqueous layer was separated, and extracted once more with ethyl acetate. The combined organic extract was washed with brine, dried over $MgSO_4$, filtered and concentrated to yield a brownish-orange foam (847.6 mg) as the desired product which was used as obtained.

LCMS $t_R$=1.21 min; LCMS (ESI) m/z=630.40 $[M+H]^+$. LCMS conditions: Injection Vol=3 μL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

Example 1030: 5-((2-(((1-(1H-Tetrazol-5-yl)ethyl) (methyl)amino)methyl)-4-chloro-5-((3'-(3-(((S)-2,3-dihydroxypropyl)amino)propoxy)-2,2'-dimethyl-[1, 1'-biphenyl]-3-yl)methoxy)-phenoxy)methyl) nicotinonitrile

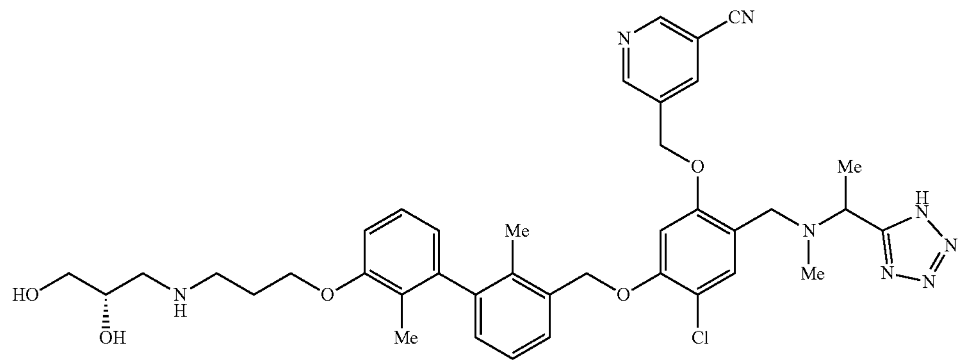 [SMILES: Cc1c(COc2cc(OCc3cncc(C#N)c3)c(CN(C)C(C)c3nnn[nH]3)cc2Cl)cccc1-c1cccc(OCCCNC[C@H](O)CO)c1C]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 9-49% B over 20 min, then a 5 min hold at 100% B; Flow: 20 mL/min. Fractions containing the desired product were combined and dried via centrifugal evaporation. The yield of the product was 1.9 mg, and its estimated purity by LCMS analysis was 96%. Analytical LCMS was used to determine the final purity. Injection 1 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 1 results: Purity: 98.3%; Observed Mass: 741.17; Retention Time: 1.42 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 2 results: Purity: 96.3%; Observed Mass: 741.21; Retention Time: 1.4 min.

Example 1031: 5-((2-(((2-(1H-Tetrazol-5-yl)propyl)(methyl)amino)methyl)-4-chloro-5-((3'-(3-(((S)-2,3-dihydroxy-propyl)amino)propoxy)-2,2'-dimethyl-[1,1'-biphenyl]-3-yl)methoxy)-phenoxy)methyl)nicotinonitrile

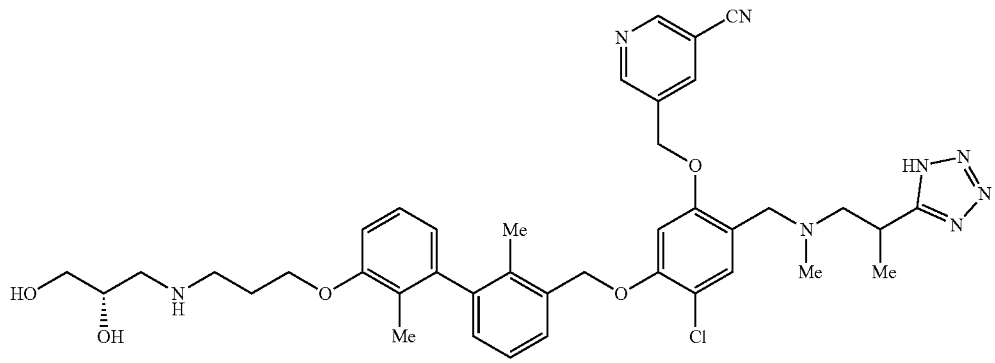 [SMILES: Cc1c(COc2cc(OCc3cncc(C#N)c3)c(CN(C)CC(C)c3nnn[nH]3)cc2Cl)cccc1-c1cccc(OCCCNC[C@H](O)CO)c1C]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 10-55% B over 20 min, then a 5 min hold at 100% B; Flow: 20 mL/min. Fractions containing the desired product were combined and dried via centrifugal evaporation. The material was purified a second time via preparative LCMS with the following conditions: Column: XBridge C18, 19×200 mm, 5 U; Mobile Phase A: 5:95 acetonitrile:water 0.1% trifluoroacetic acid; Mobile Phase B: 95:5 acetonitrile: water 0.1% trifluoroacetic acid; Gradient: 7-47% B over 20 min, then a 5 min hold at 100% B; Flow: 20 mL/min. Fractions containing the desired product were combined and dried via centrifugal evaporation. The yield of the product was 1.6 mg, and its estimated purity by LCMS analysis was 98%. Analytical LCMS was used to determine the final purity. Injection 1 conditions: Column: Waters XBridge C18, 2.1×50 mm, 1.7 U; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 1 results: Purity: 100.0%; Observed Mass: 755.24; Retention Time: 1.43 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 2 results: Purity: 97.8%; Observed Mass: 755.26; Retention Time: 1.46 min.

Intermediate: 1-Bromo-3-(3-bromopropoxy)-2-chlorobenzene

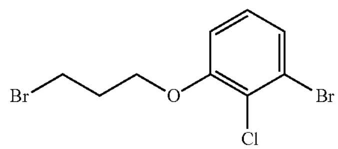 [SMILES: Clc1c(Br)cccc1OCCCBr]

Potassium carbonate (8.33 g, 60.3 mmol) was added in one portion to a stirred solution of 3-bromo-2-chlorophenol (10.0 g, 48.2 mmol) and 1,3-dibromopropane (48.9 mL, 482 mmol) in dry acetone (400 mL). The suspension was stirred at rt for 5 d before the mixture was suction-filtered to remove the salts. The filtrate was then concentrated in vacuo to a light yellow oil which was transferred to a 250 mL RBF and distilled under high vacuum using a short-path distillation head to remove all of the excess 1,3-dibromopropane which came off between 38-40° C. (bath temp=70° C.) as a colorless liquid. Afterward, there was isolated in the distillation pot the crude desired product as a viscous, honey-colored oil which was used as obtained and was stored in the refrigerator when not needed.

LCMS: $t_R$=1.46 min; LCMS conditions: Injection Vol=3 µL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

$^1$H NMR (500 MHz, $CDCl_3$) δ 7.26 (dd, J=8.0, 1.1 Hz, 1H), 7.09 (t, J=8.2 Hz, 1H), 6.91 (d, J=8.4 Hz, 1H), 4.18 (t, J=5.8 Hz, 2H), 3.67 (t, J=6.3 Hz, 2H), 2.38 (quin, J=6.0 Hz, 2H).

Intermediate: (S)-3-((3-(3-Bromo-2-chlorophenoxy)propyl)amino)propane-1,2-diol

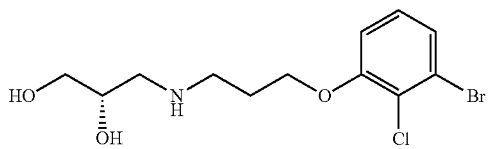 [SMILES: OC[C@@H](O)CNCCCOc1cccc(Br)c1Cl]

Hunig's base (1.6 mL, 9.13 mmol) was added in one portion to a stirred solution of 1-bromo-3-(3-bromopropoxy)-2-chlorobenzene (1.0 g, 3.04 mmol) and (S)-3-aminopropane-1,2-diol (1.4 g, 15.22 mmol) in dry DMF (30 mL). The mixture was then heated to 60° C. for 16 h before it was cooled to rt and concentrated with nitrogen stream. The resultant residue was diluted with methanol (up to 10 mL), filtered through a Whatman 13 mm PVDF syringe filter (45 µM), placed into five preparative HPLC vials (2 mL) and purified in several portions (10-100% B over a 12 min gradient @ 40 ml/min) using a SunFire $C_{18}$ column (30×100 mm, 5 U) where Mobile Phase A: 5:95 acetonitrile:water with 10 mM ammonium acetate and Mobile Phase B: 95:5 acetonitrile:water with 10 mM ammonium acetate. Fractions containing the desired product were combined and dried via centrifugal evaporation. There was isolated the purified product, (S)-3-((3-(3-bromo-2-chlorophenoxy)propyl)amino)-propane-1,2-diol (971.0 mg, 94% yield) as a light yellow viscous oil which solidified to a very light yellow solid on standing in the freezer overnight.

LCMS: $t_R$=1.04 min; LCMS (ESI) m/z=338.00 and 340.00 $[M+H]^+$. LCMS conditions: Injection Vol=3 µL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

$^1$H NMR (500 MHz, METHANOL-d4) δ 7.30 (dd, J=8.0, 0.9 Hz, 1H), 7.19 (t, J=8.2 Hz, 1H), 7.12-7.05 (m, 1H), 4.21 (t, J=5.7 Hz, 2H), 3.91 (br dd, J=8.7, 3.6 Hz, 1H), 3.63-3.50 (m, 2H), 3.35 (s, 1H), 3.29-3.24 (m, 2H), 3.18 (dd, J=12.5, 3.1 Hz, 1H), 3.02 (dd, J=12.5, 9.3 Hz, 1H), 2.32-2.16 (m, 2H).

Intermediate: (S)-5-((4-Chloro-5-((2'-chloro-3'-(3-((2,3-dihydroxypropyl)amino)propoxy)-2-methyl-[1,1'-biphenyl]-3-yl)methoxy)-2-formylphenoxy)methyl)nicotinonitrile

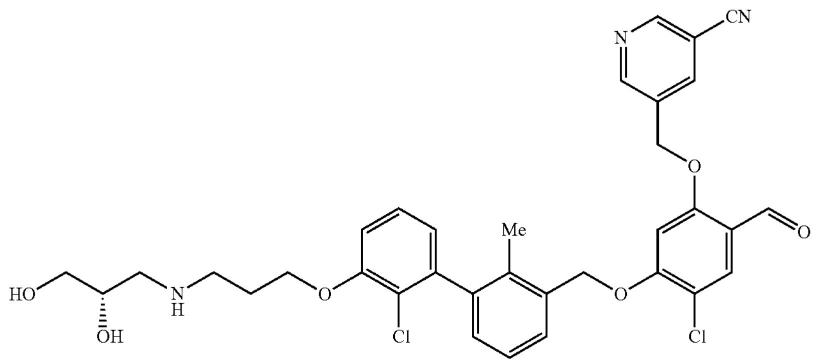 [SMILES: Cc1c(COc2cc(OCc3cncc(C#N)c3)c(C=O)cc2Cl)cccc1-c1cccc(OCCCNC[C@H](O)CO)c1Cl]

Second generation XPhos precatalyst (76 mg, 0.096 mmol) was added in one portion to an argon-degassed mixture of (S)-3-((3-(3-bromo-2-chlorophenoxy)propyl) amino)-propane-1,2-diol (392 mg, 1.16 mmol), 5-((4-chloro-2-formyl-5-((2-methyl-3-(4,4,5,5-tetramethyl-1,3,2-dioxaborolan-2-yl)benzyl)oxy)phenoxy)methyl) nicotinonitrile (500 mg, 0.96 mmol) and potassium phosphate (511 mg, 2.41 mmol) in THE (10 mL) and water (2 mL) at rt. The vial was then sealed and the resultant suspension was stirred at rt for 16 h before it was diluted with ethyl acetate and water. The aqueous layer was separated, and extracted once more with ethyl acetate. The combined organic extract was washed with brine, dried over $MgSO_4$, filtered and concentrated to yield a brownish-orange foam (775.1 mg) as the product which was used as obtained.

LCMS: $t_R$=1.19 min; LCMS (ESI) m/z=650.35 $[M+H]^+$. LCMS conditions: Injection Vol=3 μL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

Example 1032: 5-((2-((2-(1H-Pyrazol-4-yl)piperidin-1-yl)methyl)-4-chloro-5-((2'-chloro-3'-(3-(((S)-2,3-dihydroxypropyl)amino)propoxy)-2-methyl-[1,1'-biphenyl]-3-yl)methoxy)phenoxy)-methyl) nicotinonitrile

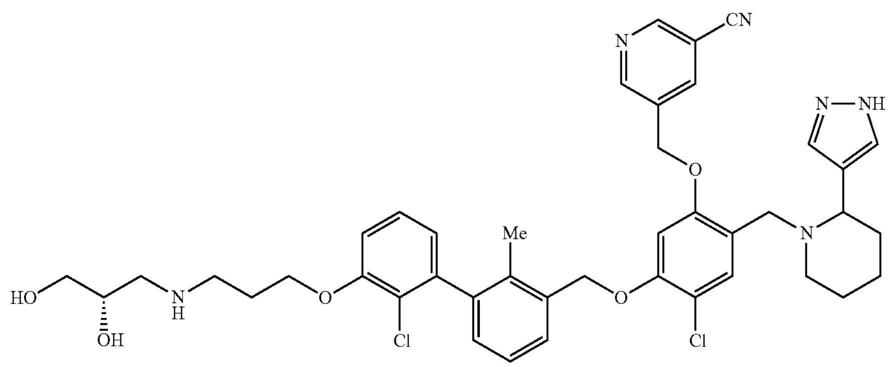 [SMILES: Cc1c(COc2cc(OCc3cncc(C#N)c3)c(CN3CCCCC3c3cn[nH]c3)cc2Cl)cccc1-c1cccc(OCCCNC[C@H](O)CO)c1Cl]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 21-61% B over 20 min, then a 4 min hold at 100% B; Flow: 20 mL/min. Fractions containing the desired product were combined and dried via centrifugal evaporation. The yield of the product was 2.0 mg, and its estimated purity by LCMS analysis was 93%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 92.8%; Observed Mass: 785.18; Retention Time: 1.55 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile: water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 94.1%; Observed Mass: 785.18; Retention Time: 1.4 min.

Example 1033: 5-((2-((3-(1H-Tetrazol-5-yl)pyrrolidin-1-yl)methyl)-4-chloro-5-((2'-chloro-3'-(3-(((S)-2,3-dihydroxypropyl)amino)propoxy)-2-methyl-[1,1'-biphenyl]-3-yl)methoxy)phenoxy)-methyl)nicotinonitrile

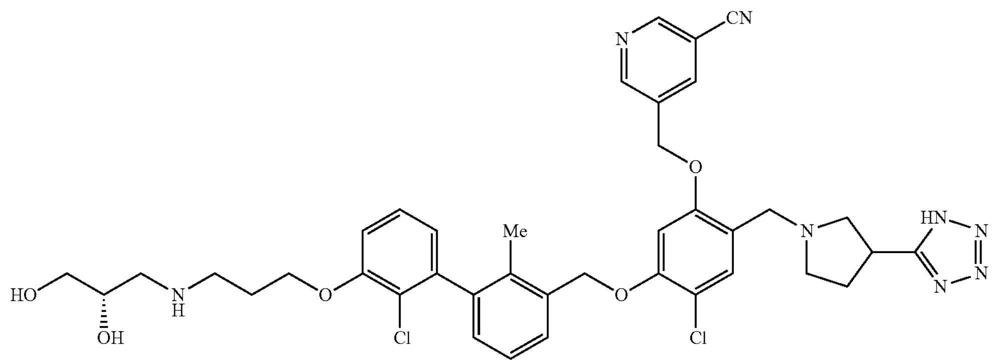 [SMILES: Cc1c(COc2cc(OCc3cncc(C#N)c3)c(CN3CCC(c4nnn[nH]4)C3)cc2Cl)cccc1-c1cccc(OCCCNC[C@H](O)CO)c1Cl]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 12-52% B over 20 min, then a 4 min hold at 100% B; Flow: 20 mL/min. Fractions containing the desired product were combined and dried via centrifugal evaporation. The yield of the product was 1.6 mg, and its estimated purity by LCMS analysis was 95%. Analytical LCMS was used to determine the final purity. Injection 1 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 1 results: Purity: 95.0%; Observed Mass: 773.19; Retention Time: 1.39 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 2 results: Purity: 96.6%; Observed Mass: 773.19; Retention Time: 1.37 min.

Example 1034: 5-((2-(((1-(1H-Tetrazol-5-yl)ethyl)(methyl)amino)methyl)-4-chloro-5-((2'-chloro-3'-(3-(((S)-2,3-dihydroxypropyl)amino)propoxy)-2-methyl-[1,1'-biphenyl]-3-yl)methoxy)-phenoxy)methyl)-nicotinonitrile

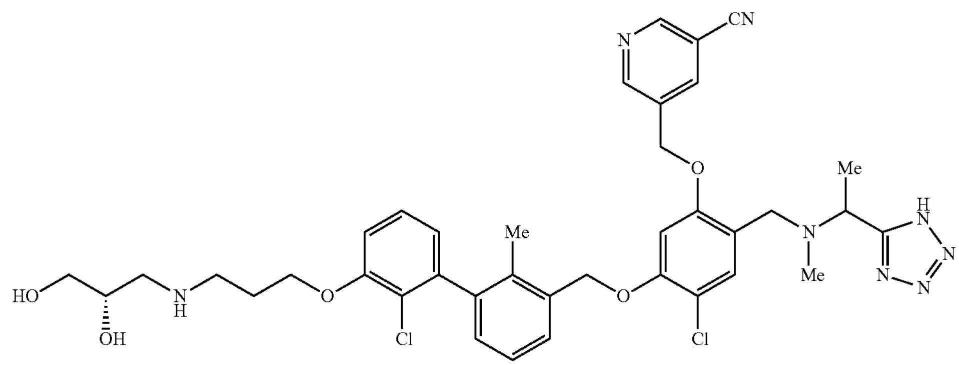 [SMILES: Cc1c(COc2cc(OCc3cncc(C#N)c3)c(CN(C)C(C)c3nnn[nH]3)cc2Cl)cccc1-c1cccc(OCCCNC[C@H](O)CO)c1Cl]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 12-52% B over 20 min, then a 6 min hold at 100% B; Flow: 20 mL/min. Fractions containing the desired product were combined and dried via centrifugal evaporation. The yield of the product was 1.9 mg, and its estimated purity by LCMS analysis was 90%. Analytical LCMS was used to determine the final purity. Injection 1 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 1 results: Purity: 93.5%; Observed Mass: 761.13; Retention Time: 1.39 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 2 results: Purity: 90.1%; Observed Mass: 761.11; Retention Time: 1.4 min.

Example 1035: 5-((2-(((2-(1H-Tetrazol-5-yl)propyl)(methyl)amino)methyl)-4-chloro-5-((2'-chloro-3'-(3-(((S)-2,3-dihydroxypropyl)amino)propoxy)-2-methyl-[1,1'-biphenyl]-3-yl)methoxy)-phenoxy)methyl)nicotinonitrile

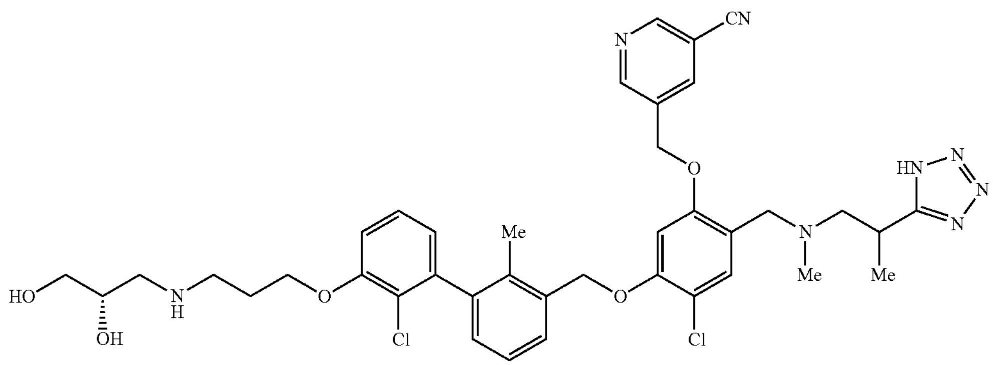 [SMILES: Cc1c(COc2cc(OCc3cncc(C#N)c3)c(CN(C)CC(C)c3nnn[nH]3)cc2Cl)cccc1-c1cccc(OCCCNC[C@H](O)CO)c1Cl]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 14-54% B over 20 min, then a 4 min hold at 100% B; Flow: 20 mL/min. Fractions containing the desired product were combined and dried via centrifugal evaporation. The material was purified a second time via preparative LCMS with the following conditions: Column: XBridge C18, 19×200 mm, 5 U; Mobile Phase A: 5:95 acetonitrile:water with 0.1% trifluoroacetic acid; Mobile Phase B: 95:5 acetonitrile:water with 0.1% trifluoroacetic acid; Gradient: 6-51% B over 20 min, then a 5 min hold at 100% B; Flow: 20 mL/min. Fractions containing the desired product were combined and dried via centrifugal evaporation. The yield of the product was 2.0 mg, and its estimated purity by LCMS analysis was 99%. Analytical LCMS was used to determine the final purity. Injection 1 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 1 results: Purity: 98.9%; Observed Mass: 775.18; Retention Time: 1.41 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 2 results: Purity: 99.2%; Observed Mass: 775.16; Retention Time: 1.42 min.

Intermediate: N-(1-(3-(3-Bromo-2-methylphenoxy)propyl)piperidin-4-yl)acetamide

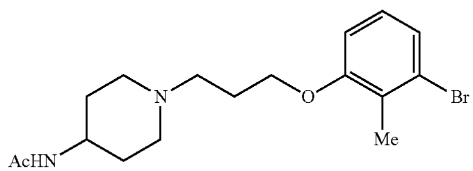

Potassium carbonate (607 mg, 4.40 mmol) was added in one portion to a stirred solution of 1-bromo-3-(3-bromopropoxy)-2-methylbenzene (542 mg, 1.76 mmol) and N-(piperidin-4-yl)acetamide (250 mg, 1.76 mmol) in dry DMF (7 mL). The mixture was then heated to 60° C. for 16 h before the solvent was removed with nitrogen stream overnight. The residue was then taken up in dichloromethane, and the suspension was sonicated for 5 min and suction-filtered to remove the excess potassium carbonate. The filtrate was then charged to a RediSepRf normal phase silica gel Teledyne ISCO 24 g disposable column which was first eluted with dichloromethane for 150 mL, followed by 0-20% B for 600 mL where solvent B=methanol and solvent A=dichloromethane. Fractions containing the desired product were combined and dried via centrifugal evaporation. There was isolated the desired product, N-(1-(3-(3-bromo-2-methylphenoxy)propyl)piperidin-4-yl)acetamide (0.42 g, 64.4% yield) as a white solid.

LCMS: $t_R$=1.07 min; LCMS (ESI) m/z=368.95 and 370.90 $[M+H]^+$. LCMS conditions: Injection Vol=3 μL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

$^1$H NMR (500 MHz, $CDCl_3$) δ 7.14 (d, J=7.9 Hz, 1H), 6.99 (t, J=8.0 Hz, 1H), 6.77 (d, J=8.0 Hz, 1H), 5.31 (br d, J=7.3 Hz, 1H), 4.00 (t, J=6.1 Hz, 2H), 3.87-3.74 (m, 1H), 2.87 (br d, J=11.3 Hz, 2H), 2.53 (t, J=7.4 Hz, 3H), 2.31 (s, 3H), 2.12 (br t, J=10.9 Hz, 3H), 2.02-1.88 (m, 5H), 1.98 (s, 3H), 1.50-1.38 (m, 2H).

Intermediate: N-(1-(3-((3'-((2-Chloro-5-((5-cyanopyridin-3-yl)methoxy)-4-formylphenoxy)methyl)-2,2'-dimethyl-[1,1'-biphenyl]-3-yl)oxy)propyl)piperidin-4-yl)acetamide

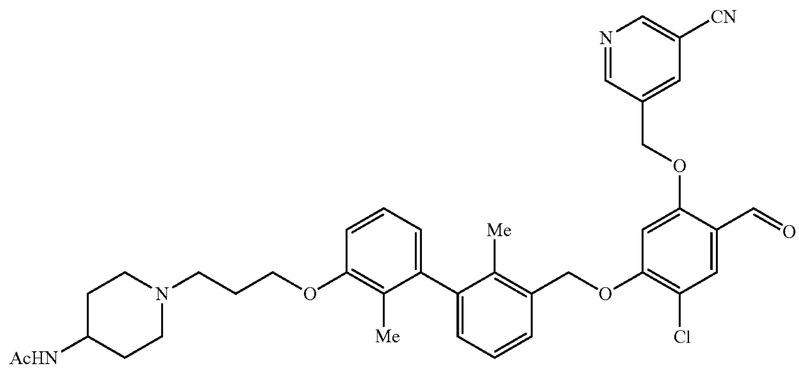

Second generation XPhos precatalyst (76 mg, 0.096 mmol) was added in one portion to an argon-degassed mixture of N-(1-(3-(3-bromo-2-methylphenoxy)propyl)piperidin-4-yl)acetamide (427 mg, 1.16 mmol), 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (500 mg, 0.96 mmol) and potassium phosphate (511 mg, 2.41 mmol) in THE (10 mL) and water (2 mL) at rt. The vial was then sealed and the resultant suspension was stirred at rt for 16 h before the mixture was diluted with ethyl acetate and water. The aqueous layer was separated, and extracted once more with ethyl acetate. The combined organic extract was washed with brine, dried over $MgSO_4$, filtered and concentrated to yield a yellow foam as the crude product which was taken up in a small amount of dichloromethane and charged to a RediSepRf normal phase silica gel Teledyne ISCO 40 g disposable column which was first eluted with dichloromethane for 100 mL, followed by 0-20% B for 1250 mL where solvent B=methanol and solvent A=dichloromethane. Fractions containing the desired product were combined and dried via centrifugal evaporation. There was isolated the desired product, N-(1-(3-((3'-((2-chloro-5-((5-cyanopyridin-3-yl)methoxy)-4-formyl-phenoxy)methyl)-2,2'-dimethyl-[1,1'-biphenyl]-3-yl)oxy)propyl)piperidin-4-yl)acetamide (644.0 mg, 98% yield) as a yellow solid. LCMS: $t_R$=1.22 min; LCMS (ESI) m/z=681.15 $[M+H]^+$. LCMS conditions: Injection Vol=3 μL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

Example 1036: N-(1-(3-((3'-((4-(((1H-Tetrazol-5-yl)amino)methyl)-2-chloro-5-((5-cyanopyridin-3-yl)-methoxy)phenoxy)methyl)-2,2'-dimethyl-[1,1'-biphenyl]-3-yl)oxy)propyl)piperidin-4-yl)-acetamide

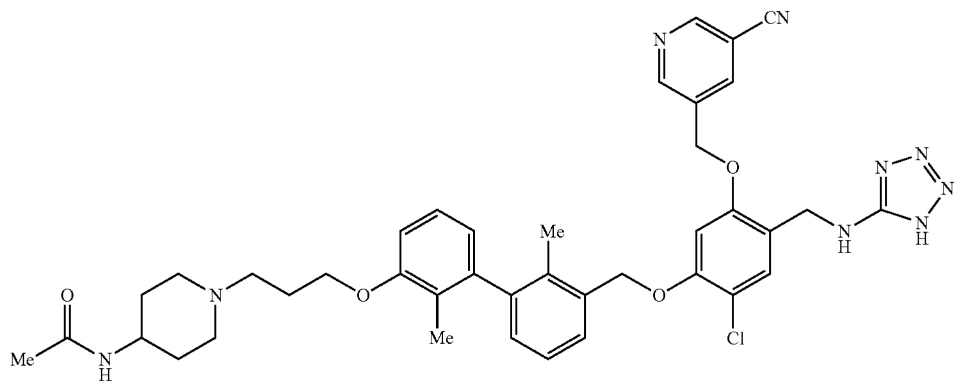 [SMILES: CC(=O)NC1CCN(CCCOc2cccc(-c3cccc(COc4cc(OCc5cncc(C#N)c5)c(CNc5nnn[nH]5)cc4Cl)c3C)c2C)CC1]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 16-56% B over 22 min, then a 6 min hold at 100% B; Flow: 20 mL/min. Fractions containing the desired product were combined and dried via centrifugal evaporation. The yield of the product was 16.2 mg, and its estimated purity by LCMS analysis was 98%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 100.0%; Observed Mass: 750.23; Retention Time: 1.58 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 98.2%; Observed Mass: 750.25; Retention Time: 1.61 min.

Example 1037: N-(1-(3-((3'-((4-(((2-(2H-Tetrazol-5-yl)ethyl)(methyl)amino)methyl)-2-chloro-5-((5-cyanopyridin-3-yl)methoxy)phenoxy)methyl)-2,2'-dimethyl-[1,1'-biphenyl]-3-yl)oxy)-propyl)piperidin-4-yl)acetamide

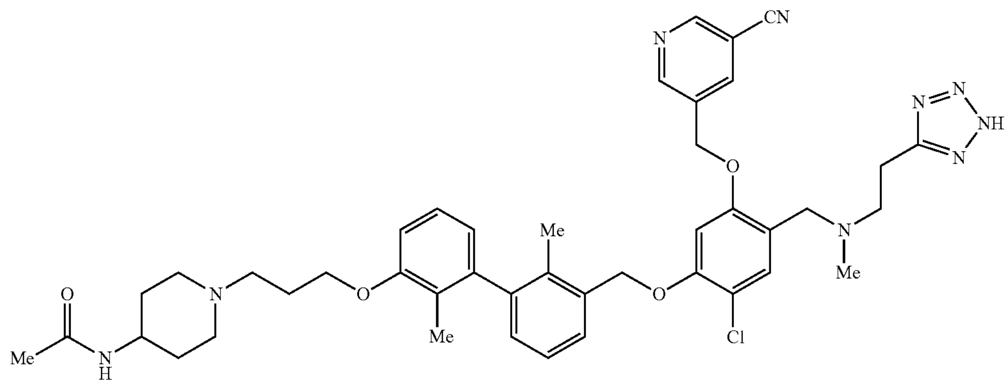 [SMILES: CC(=O)NC1CCN(CCCOc2cccc(-c3cccc(COc4cc(OCc5cncc(C#N)c5)c(CN(C)CCc5nn[nH]n5)cc4Cl)c3C)c2C)CC1]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 10-50% B over 25 min, then a 6 min hold at 100% B; Flow: 20 mL/min. Fractions containing the desired product were combined and dried via centrifugal evaporation. The material was purified a second time via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 6-46% B over 25 min, then a 3 min hold at 100% B; Flow: 20 mL/min. Fractions containing the desired product were combined and dried via centrifugal evaporation. The yield of the product was 6.5 mg, and its estimated purity by LCMS analysis was 94%. Analytical LCMS was used to determine the final purity. Injection 1 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 1 results: Purity: 94.3%; Observed Mass: 792.28; Retention Time: 1.61 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 2 results: Purity: 95.9%; Observed Mass: 792.27; Retention Time: 1.42 min.

Example 1038: N-(1-(3-((3'-((4-((3-(1H-Imidazol-2-yl)piperidin-1-yl)methyl)-2-chloro-5-((5-cyano-pyridin-3-yl)methoxy)phenoxy)methyl)-2,2'-dimethyl-[1,1'-biphenyl]-3-yl)oxy)propyl)-piperidin-4-yl) acetamide

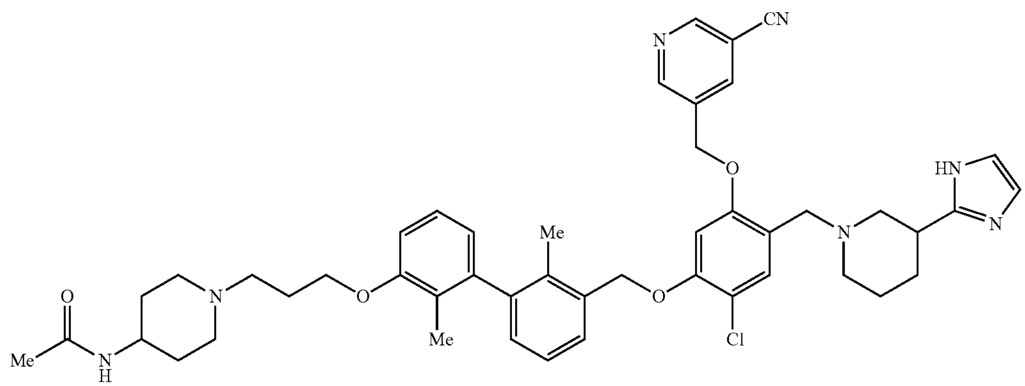 [SMILES: CC(=O)NC1CCN(CCCOc2cccc(-c3cccc(COc4cc(OCc5cncc(C#N)c5)c(CN5CCCC(c6ncc[nH]6)C5)cc4Cl)c3C)c2C)CC1]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 20-60% B over 23 min, then a 6 min hold at 100% B; Flow: 20 mL/min. Fractions containing the desired product were combined and dried via centrifugal evaporation. The yield of the product was 14.5 mg, and its estimated purity by LCMS analysis was 93%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 94.6%; Observed Mass: 816.3; Retention Time: 1.84 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile: water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 92.9%; Observed Mass: 816.32; Retention Time: 1.34 min.

Example 1039: N-(1-(3-((3'-((4-((3-(4H-1,2,4-Triazol-3-yl)piperidin-1-yl)methyl)-2-chloro-5-((5-cyano-pyridin-3-yl)methoxy)phenoxy)methyl)-2,2'-dimethyl-[1,1'-biphenyl]-3-yl)oxy)propyl)-piperidin-4-yl)acetamide

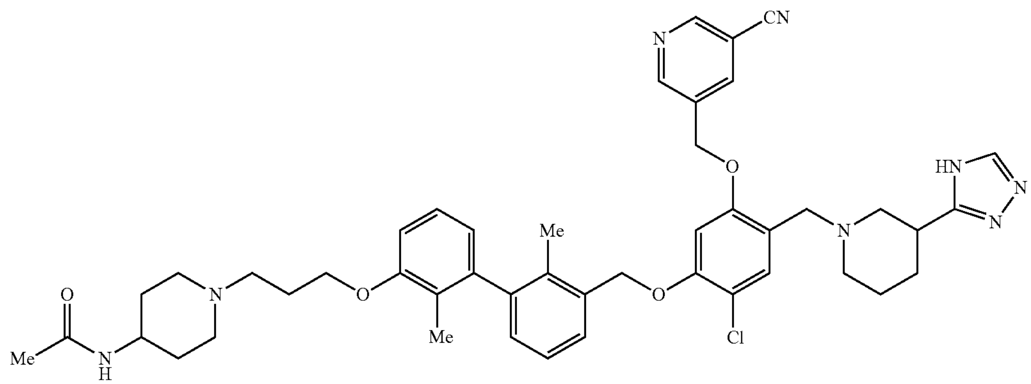 [SMILES: CC(=O)NC1CCN(CCCOc2cccc(-c3cccc(COc4cc(OCc5cncc(C#N)c5)c(CN5CCCC(c6nnc[nH]6)C5)cc4Cl)c3C)c2C)CC1]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 23-63% B over 20 min, then a 6 min hold at 100% B; Flow: 20 mL/min. Fractions containing the desired product were combined and dried via centrifugal evaporation. The yield of the product was 13.3 mg, and its estimated purity by LCMS analysis was 92%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 94.5%; Observed Mass: 817.28; Retention Time: 1.82 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 92.4%; Observed Mass: 817.32; Retention Time: 1.44 min.

Example 1040: N-(1-(3-((3'-((4-(((1-(1H-Tetrazol-5-yl)ethyl)(methyl)amino)methyl)-2-chloro-5-((5-cyanopyridin-3-yl)methoxy)phenoxy)methyl)-2,2'-dimethyl-[1,1'-biphenyl]-3-yl)oxy)-propyl)piperidin-4-yl)acetamide

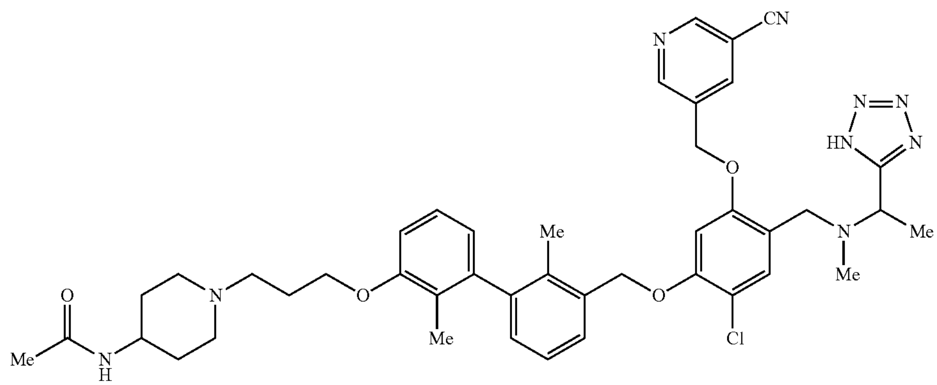 [SMILES: CC(=O)NC1CCN(CCCOc2cccc(-c3cccc(COc4cc(OCc5cncc(C#N)c5)c(CN(C)C(C)c5nnn[nH]5)cc4Cl)c3C)c2C)CC1]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 16-56% B over 20 min, then a 6 min hold at 100% B; Flow: 20 mL/min. Fractions containing the desired product were combined and dried via centrifugal evaporation. The material was purified a second time via preparative LCMS with the following conditions: Column: XBridge C18, 19×200 mm, 5 U; Mobile Phase A: 5:95 methanol: water with 10 mM ammonium acetate; Mobile Phase B: 95:5 methanol: water with 10 mM ammonium acetate; Gradient: 36-76% B over 20 min, then a 4 min hold at 100% B; Flow: 20 mL/min. Fractions containing the desired product were combined and dried via centrifugal evaporation. The material was purified a third time via preparative LCMS with the following conditions: Column: XBridge Phenyl, 19×200 mm, 5 U; Mobile Phase A: 5:95 acetonitrile:water with 10 mM ammonium acetate; Mobile Phase B: 95:5 acetonitrile: water with 10 mM ammonium acetate; Gradient: 5-48% B over 28 min, then a 4 min hold at 100% B; Flow: 20 mL/min. Fractions containing the desired product were combined and dried via centrifugal evaporation. The yield of the product was 3.2 mg, and its estimated purity by LCMS analysis was 100%. Analytical LCMS was used to determine the final purity. Injection 1 conditions: Column: Waters XBridge C18, 2.1×50 mm, 1.7 U; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 100.0%; Observed Mass: 792.26; Retention Time: 1.55 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 100.0%; Observed Mass: 792.3; Retention Time: 1.45 min.

Example 1041: N-(1-(3-((3'-((4-((3-(1H-Tetrazol-5-yl)piperidin-1-yl)methyl)-2-chloro-5-((5-cyano-pyridin-3-yl)methoxy)phenoxy)methyl)-2,2'-dimethyl-[1,1'-biphenyl]-3-yl)oxy)propyl)-piperidin-4-yl)acetamide

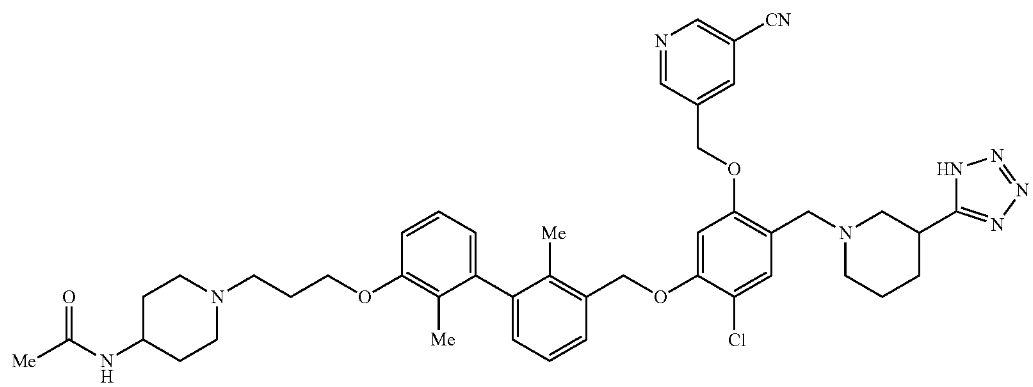 [SMILES: CC(=O)NC1CCN(CCCOc2cccc(-c3cccc(COc4cc(OCc5cncc(C#N)c5)c(CN5CCCC(c6nnn[nH]6)C5)cc4Cl)c3C)c2C)CC1]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 10-50% B over 20 min, then a 6 min hold at 100% B; Flow: 20 mL/min. Fractions containing the desired product were combined and dried via centrifugal evaporation. The yield of the product was 13.0 mg, and its estimated purity by LCMS analysis was 99%. Analytical LCMS was used to determine the final purity. Injection 1 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 1 results: Purity: 98.6%; Observed Mass: 818.29; Retention Time: 1.47 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 2 results: Purity: 100.0%; Observed Mass: 818.29; Retention Time: 1.56 min.

Example 1042: N-(1-(3-((3'-((4-((3-(1H-Tetrazol-5-yl)pyrrolidin-1-yl)methyl)-2-chloro-5-((5-cyano-pyridin-3-yl)methoxy)phenoxy)methyl)-2,2'-dimethyl-[1,1'-biphenyl]-3-yl)oxy)propyl)-piperidin-4-yl)acetamide

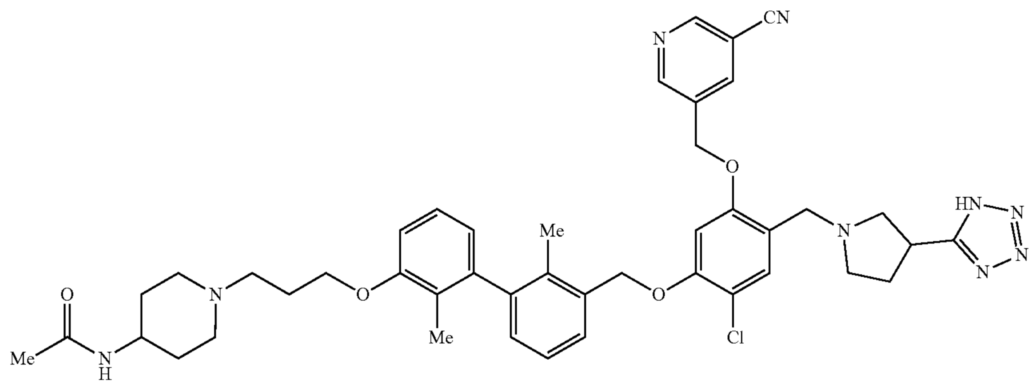 [SMILES: CC(=O)NC1CCN(CCCOc2cccc(-c3cccc(COc4cc(OCc5cncc(C#N)c5)c(CN5CCC(c6nnn[nH]6)C5)cc4Cl)c3C)c2C)CC1]

The crude material was purified via preparative LCMS with the following conditions: Column: XBridge C18, 19×200 mm, 5 U; Mobile Phase A: 5:95 acetonitrile:water 0.1% trifluoroacetic acid; Mobile Phase B: 95:5 acetonitrile: water 0.1% trifluoroacetic acid; Gradient: 10-50% B over 20 min, then a 6 min hold at 100% B; Flow: 20 mL/min. Fractions containing the desired product were combined and dried via centrifugal evaporation. The yield of the product was 18.2 mg, and its estimated purity by LCMS analysis was 100%. Analytical LCMS was used to determine the final purity. Injection 1 conditions: Column: Waters XBridge C18, 2.1×50 mm, 1.7 U; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 100.0%; Observed Mass: 804.29; Retention Time: 1.52 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 100.0%; Observed Mass: 804.31; Retention Time: 1.45 min.

Example 1043: N-(1-(3-((3'-((4-(((1-(1H-Tetrazol-5-yl)ethyl)amino)methyl)-2-chloro-5-((5-cyanopyridin-3-yl)methoxy)phenoxy)methyl)-2,2'-dimethyl-[1,1'-biphenyl]-3-yl)oxy)propyl)piperidin-4-yl) acetamide

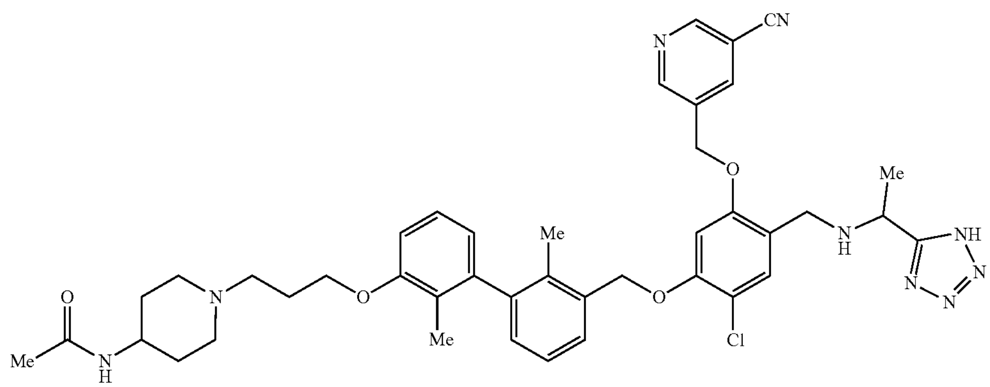 [SMILES: CC(=O)NC1CCN(CCCOc2cccc(-c3cccc(COc4cc(OCc5cncc(C#N)c5)c(CNC(C)c5nnn[nH]5)cc4Cl)c3C)c2C)CC1]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 10-50% B over 20 min, then a 5 min hold at 100% B; Flow: 20 mL/min. Fractions containing the desired product were combined and dried via centrifugal evaporation. The yield of the product was 17.4 mg, and its estimated purity by LCMS analysis was 99%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 98.7%; Observed Mass: 778.29; Retention Time: 1.48 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 98.6%; Observed Mass: 778.22; Retention Time: 1.46 min.

Example 1044: N-(1-(3-((3'-((4-((((1H-Tetrazol-5-yl)methyl)(methyl)amino)methyl)-2-chloro-5-((5-cyanopyridin-3-yl)methoxy)phenoxy)methyl)-2,2'-dimethyl-[1,1'-biphenyl]-3-yl)oxy)-propyl)piperidin-4-yl)acetamide

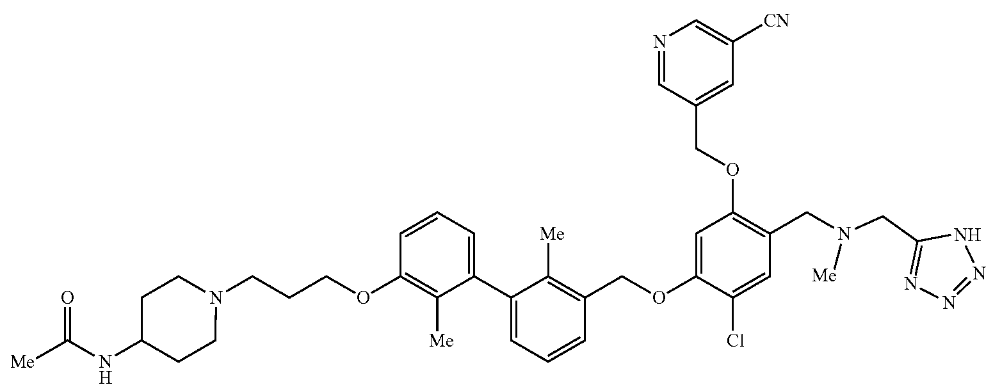 [SMILES: CC(=O)NC1CCN(CCCOc2cccc(-c3cccc(COc4cc(OCc5cncc(C#N)c5)c(CN(C)Cc5nnn[nH]5)cc4Cl)c3C)c2C)CC1]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 13-53% B over 20 min, then a 5 min hold at 100% B; Flow: 20 mL/min. Fractions containing the desired product were combined and dried via centrifugal evaporation. The yield of the product was 8.6 mg, and its estimated purity by LCMS analysis was 91%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 100.0%; Observed Mass: 778.28; Retention Time: 1.55 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 90.8%; Observed Mass: 778.3; Retention Time: 1.44 min.

Example 1045: N-(1-(3-((3'-((4-((2-(1H-Imidazol-2-yl)piperidin-1-yl)methyl)-2-chloro-5-((5-cyano-pyridin-3-yl)methoxy)phenoxy)methyl)-2,2'-dimethyl-[1,1'-biphenyl]-3-yl)oxy)propyl)-piperidin-4-yl) acetamide

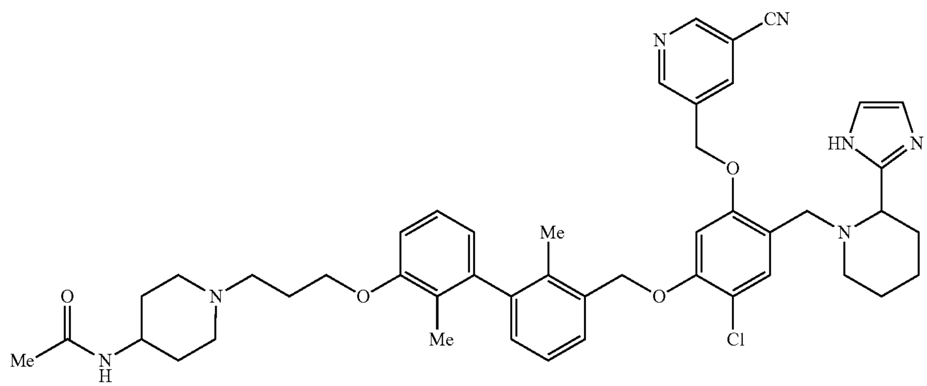 [SMILES: CC(=O)NC1CCN(CCCOc2cccc(-c3cccc(COc4cc(OCc5cncc(C#N)c5)c(CN5CCCCC5c5ncc[nH]5)cc4Cl)c3C)c2C)CC1]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 25-65% B over 20 min, then a 4 min hold at 100% B; Flow: 20 mL/min. Fractions containing the desired product were combined and dried via centrifugal evaporation. The yield of the product was 9.4 mg, and its estimated purity by LCMS analysis was 98%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 98.2%; Observed Mass: 816.29; Retention Time: 1.99 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 98.0%; Observed Mass: 816.29; Retention Time: 1.52 min.

Example 1046: N-(1-(3-((3'-((4-((((1H-Tetrazol-5-yl)methyl)amino)methyl)-2-chloro-5-((5-cyanopyridin-3-yl)methoxy)phenoxy)methyl)-2,2'-dimethyl-[1,1'-biphenyl]-3-yl)oxy)propyl)piperidin-4-yl) acetamide

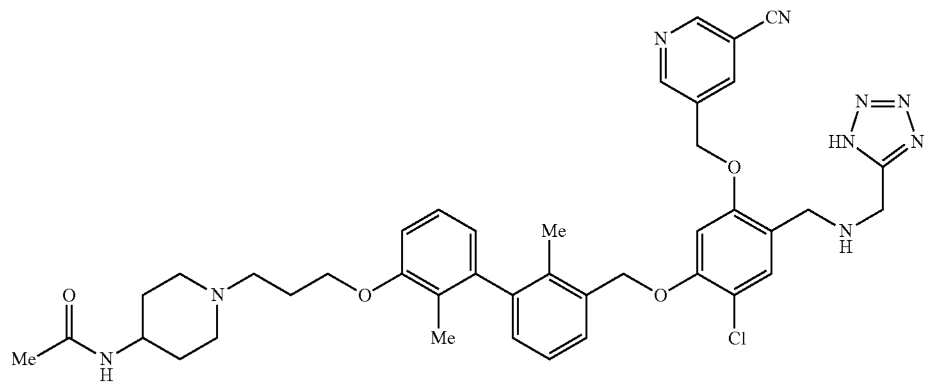 [SMILES: CC(=O)NC1CCN(CCCOc2cccc(-c3cccc(COc4cc(OCc5cncc(C#N)c5)c(CNCc5nnn[nH]5)cc4Cl)c3C)c2C)CC1]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 17-57% B over 15 min, then a 5 min hold at 100% B; Flow: 20 mL/min. Fractions containing the desired product were combined and dried via centrifugal evaporation. The material was purified a second time via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 10-50% B over 20 min, then a 5 min hold at 100% B; Flow: 20 mL/min. Fractions containing the desired product were combined and dried via centrifugal evaporation. The yield of the product was 1.9 mg, and its estimated purity by LCMS analysis was 81%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 84.6%; Observed Mass: 764.25; Retention Time: 1.5 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 81.4%; Observed Mass: 764.26; Retention Time: 1.45 min.

Example 1047: N-(1-(3-((3'-((4-(((2-(2H-Tetrazol-5-yl)propyl)(methyl)amino)methyl)-2-chloro-5-((5-cyanopyridin-3-yl)methoxy)phenoxy)methyl)-2,2'-dimethyl-[1,1'-biphenyl]-3-yl)oxy)-propyl)piperidin-4-yl)acetamide

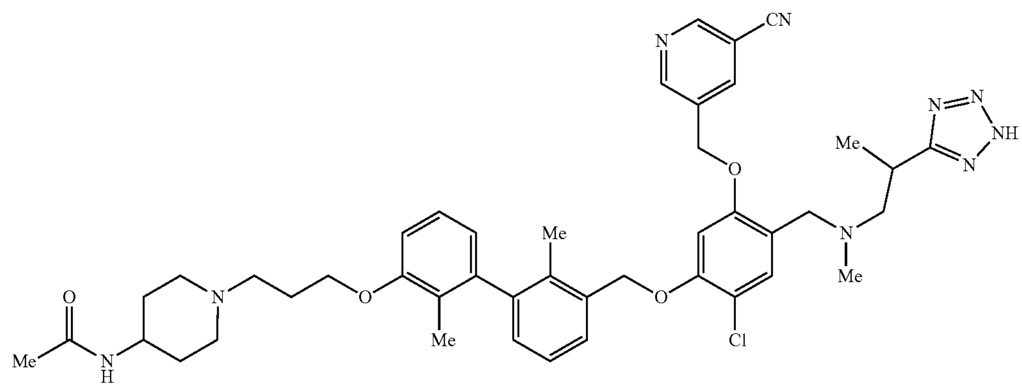 [SMILES: CC(=O)NC1CCN(CCCOc2cccc(-c3cccc(COc4cc(OCc5cncc(C#N)c5)c(CN(C)CC(C)c5nn[nH]n5)cc4Cl)c3C)c2C)CC1]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 20-60% B over 15 min, then a 5 min hold at 100% B; Flow: 20 mL/min. Fractions containing the desired product were combined and dried via centrifugal evaporation. The yield of the product was 16.7 mg, and its estimated purity by LCMS analysis was 97%. Analytical LCMS was used to determine the final purity. Injection 1 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 1 results: Purity: 97.8%; Observed Mass: 806.28; Retention Time: 1.46 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 2 results: Purity: 97.1%; Observed Mass: 806.34; Retention Time: 1.57 min.

Example 1048: N-(1-(3-((3'-((4-((2-(1H-Tetrazol-5-yl)piperidin-1-yl)methyl)-2-chloro-5-((5-cyano-pyridin-3-yl)methoxy)phenoxy)methyl)-2,2'-dimethyl-[1,1'-biphenyl]-3-yl)oxy)propyl)-piperidin-4-yl) acetamide

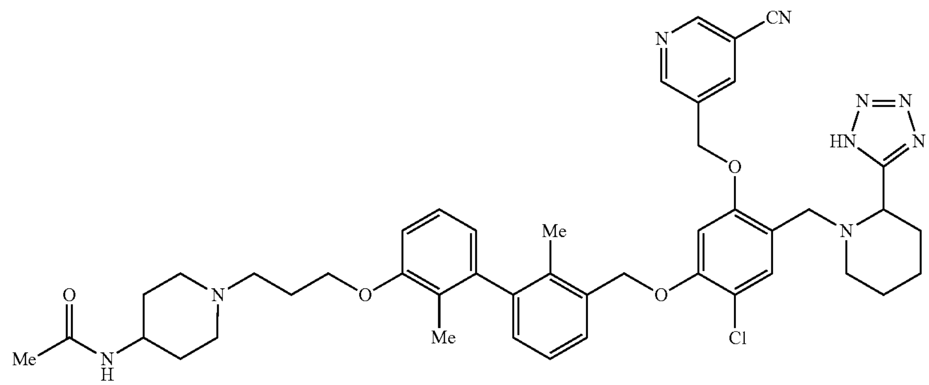 [SMILES: CC(=O)NC1CCN(CCCOc2cccc(-c3cccc(COc4cc(OCc5cncc(C#N)c5)c(CN5CCCCC5c5nnn[nH]5)cc4Cl)c3C)c2C)CC1]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 12-53% B over 25 min, then a 5 min hold at 100% B; Flow: 20 mL/min. Fractions containing the desired product were combined and dried via centrifugal evaporation. The yield of the product was 14.2 mg, and its estimated purity by LCMS analysis was 98%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 98.6%; Observed Mass: 818.28; Retention Time: 1.59 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 97.9%; Observed Mass: 818.28; Retention Time: 1.49 min.

Example 1049: N-(1-(3-((3'-((2-Chloro-5-((5-cyanopyridin-3-yl)methoxy)-4-(((2-(1-methyl-1H-tetrazol-5-yl)ethyl)amino)methyl)phenoxy)methyl)-2,2'-dimethyl-[1,1'-biphenyl]-3-yl)oxy)-propyl)piperidin-4-yl)acetamide

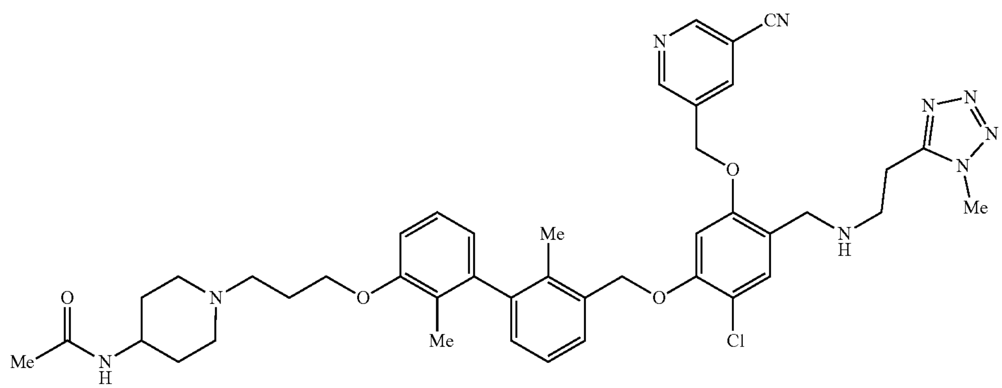 [SMILES: CC(=O)NC1CCN(CCCOc2cccc(-c3cccc(COc4cc(OCc5cncc(C#N)c5)c(CNCCc5nnnn5C)cc4Cl)c3C)c2C)CC1]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 10-50% B over 20 min, then a 5 min hold at 100% B; Flow: 20 mL/min. Fractions containing the desired product were combined and dried via centrifugal evaporation. The yield of the product was 11.4 mg, and its estimated purity by LCMS analysis was 98%. Analytical LCMS was used to determine the final purity. Injection 1 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 1 results: Purity: 97.7%; Observed Mass: 792.21; Retention Time: 1.45 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 2 results: Purity: 100.0%; Observed Mass: 792.26; Retention Time: 1.75 min.

Example 1050: N-(1-(3-((3'-((4-(((2-(1H-Tetrazol-5-yl)propyl)amino)methyl)-2-chloro-5-((5-cyano-pyridin-3-yl)methoxy)phenoxy)methyl)-2,2'-dimethyl-[1,1'-biphenyl]-3-yl)oxy)propyl)-piperidin-4-yl) acetamide

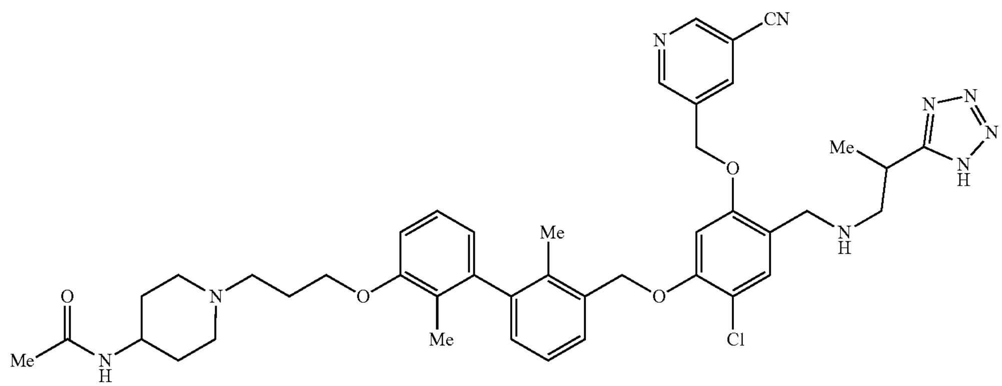 [SMILES: CC(=O)NC1CCN(CCCOc2cccc(-c3cccc(COc4cc(OCc5cncc(C#N)c5)c(CNCC(C)c5nnn[nH]5)cc4Cl)c3C)c2C)CC1]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 7-48% B over 21 min, then a 4 min hold at 100% B; Flow: 20 mL/min. Fractions containing the desired product were combined and dried via centrifugal evaporation. The material was purified a second time via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 12-53% B over 21 min, then a 4 min hold at 100% B; Flow: 20 mL/min. Fractions containing the desired product were combined and dried via centrifugal evaporation. The yield of the product was 15.3 mg, and its estimated purity by LCMS analysis was 100%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 100.0%; Observed Mass: 792.28; Retention Time: 1.54 min. Injection 2 conditions: Column: Waters Xbridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 100.0%; Observed Mass: 792.26; Retention Time: 1.46 min.

Example 1051: N-(1-(3-((3'-((4-((2-(1H-Tetrazol-5-yl)pyrrolidin-1-yl)methyl)-2-chloro-5-((5-cyano-pyridin-3-yl)methoxy)phenoxy)methyl)-2,2'-dimethyl-[1,1'-biphenyl]-3-yl)oxy)propyl)-piperidin-4-yl)acetamide

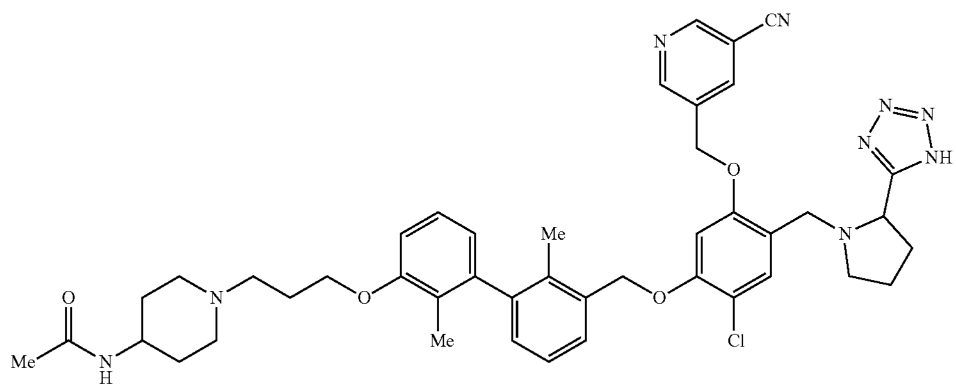 [SMILES: CC(=O)NC1CCN(CCCOc2cccc(-c3cccc(COc4cc(OCc5cncc(C#N)c5)c(CN5CCCC5c5nnn[nH]5)cc4Cl)c3C)c2C)CC1]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 6-46% B over 25 min, then a 4 min hold at 100% B; Flow: 20 mL/min. Fractions containing the desired product were combined and dried via centrifugal evaporation. The yield of the product was 17.3 mg, and its estimated purity by LCMS analysis was 97%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 100.0%; Observed Mass: 804.28; Retention Time: 1.55 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 97.1%; Observed Mass: 804.25; Retention Time: 1.45 min.

Example 1052: N-(1-(3-((3'-((2-Chloro-5-((5-cyanopyridin-3-yl)methoxy)-4-((3-(1-methyl-1H-pyrazol-4-yl)pyrrolidin-1-yl)methyl)phenoxy)methyl)-2,2'-dimethyl-[1,1'-biphenyl]-3-yl)oxy)-propyl)piperidin-4-yl)acetamide

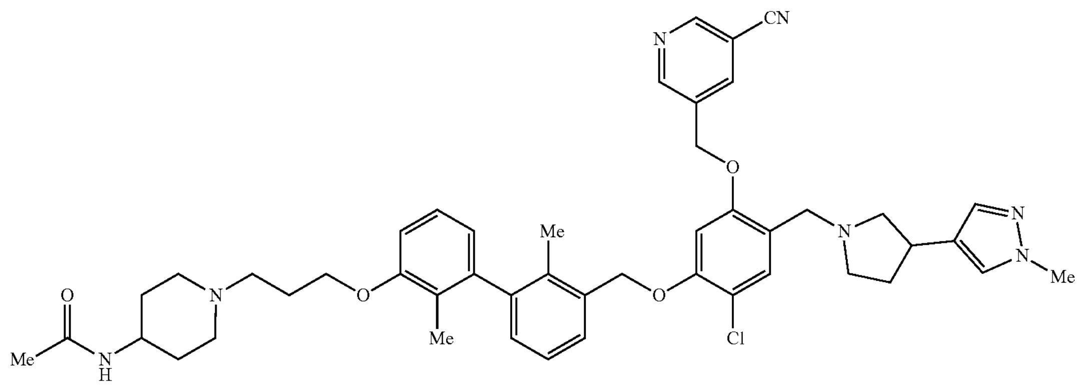 [SMILES: CC(=O)NC1CCN(CCCOc2cccc(-c3cccc(COc4cc(OCc5cncc(C#N)c5)c(CN5CCC(c6cnn(C)c6)C5)cc4Cl)c3C)c2C)CC1]

The crude material was purified via preparative LCMS with the following conditions: Column: XBridge C18, 200 mm×19 mm, 5 U; Mobile Phase A: 5:95 acetonitrile:water with 10 mM ammonium acetate; Mobile Phase B: 95:5 acetonitrile:water with 10 mM ammonium acetate; Gradient: 29-69% B over 25 min, then a 4 min hold at 100% B; Flow Rate: 20 mL/min; Column Temperature: 25° C. Fractions containing the desired product were combined and dried via centrifugal evaporation. The yield of the product was 18.9 mg, and its estimated purity by LCMS analysis was 94%. Analytical LCMS was used to determine the final purity. Injection 1 conditions: Column: Waters XBridge C18, 2.1×50 mm, 1.7 U; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 99.0%; Observed Mass: 816.34; Retention Time: 1.86 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B;

Flow: 1 mL/min; Detection: MS and UV (220 nm). Injection 2 results: Purity: 94.5%; Observed Mass: 816.34; Retention Time: 1.47 min.

Example 1053: N-(1-(3-((3'-((4-((2-(1H-Pyrazol-3-yl)piperidin-1-yl)methyl)-2-chloro-5-((5-cyano-pyridin-3-yl)methoxy)phenoxy)methyl)-2,2'-dimethyl-[1,1'-biphenyl]-3-yl)oxy)propyl)-piperidin-4-yl) acetamide

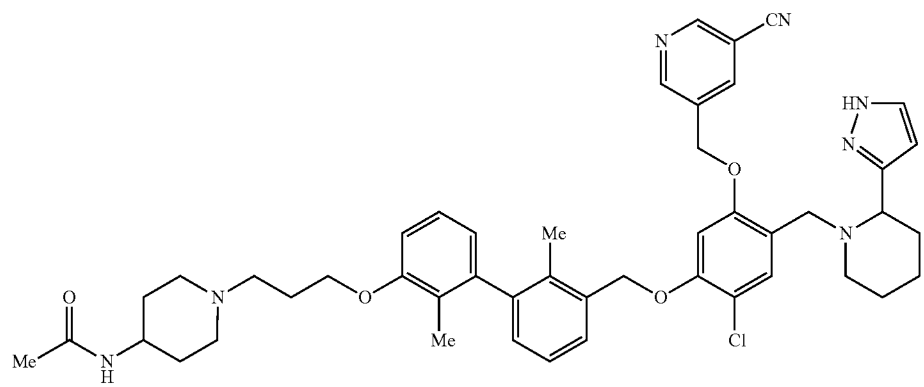 [SMILES: CC(=O)NC1CCN(CCCOc2cccc(-c3cccc(COc4cc(OCc5cncc(C#N)c5)c(CN5CCCCC5c5cc[nH]n5)cc4Cl)c3C)c2C)CC1]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 35-75% B over 22 min, then a 4 min hold at 100% B; Flow: 20 mL/min. Fractions containing the desired product were combined and dried via centrifugal evaporation. The material was purified a second time via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 30-75% B over 28 min, then a 4 min hold at 100% B; Flow: 20 mL/min. Fractions containing the desired product were combined and dried via centrifugal evaporation. The yield of the product was 8.2 mg, and its estimated purity by LCMS analysis was 100%. Analytical LCMS was used to determine the final purity. Injection 1 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 1 results: Purity: 100.0%; Observed Mass: 816.29; Retention Time: 1.49 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 2 results: Purity: 100.0%; Observed Mass: 816.3; Retention Time: 1.95 min.

Example 1054: N-(1-(3-((3'-((2-Chloro-5-((5-cyano-pyridin-3-yl)methoxy)-4-((2-(1-methyl-1H-pyrazol-4-yl)piperidin-1-yl)methyl)phenoxy)methyl)-2,2'-dimethyl-[1,1'-biphenyl]-3-yl)oxy)-propyl)piperidin-4-yl)acetamide

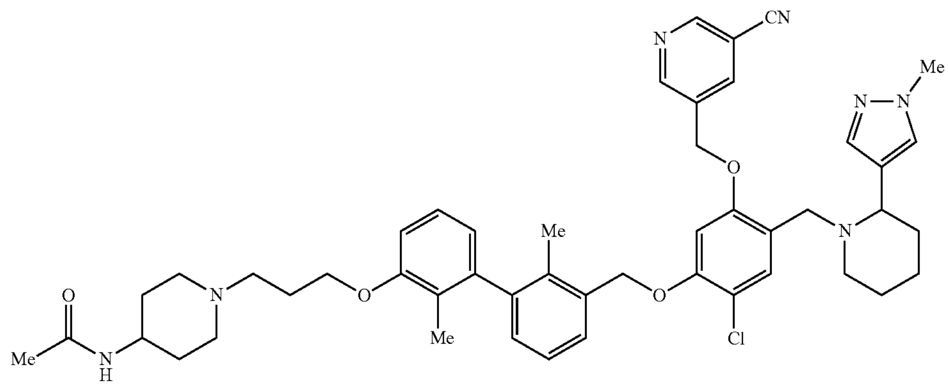 [SMILES: CC(=O)NC1CCN(CCCOc2cccc(-c3cccc(COc4cc(OCc5cncc(C#N)c5)c(CN5CCCCC5c5cnn(C)c5)cc4Cl)c3C)c2C)CC1]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 26-66% B over 25 min, then a 4 min hold at 100% B; Flow: 20 mL/min. Fractions containing the desired product were combined and dried via centrifugal evaporation. The yield of the product was 5.1 mg, and its estimated purity by LCMS analysis was 98%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 100.0%; Observed Mass: 830.3; Retention Time: 1.67 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 98.0%; Observed Mass: 830.32; Retention Time: 1.48 min.

Intermediate: N-(1-(3-(3-Bromo-2-chlorophenoxy)propyl)piperidin-4-yl)acetamide

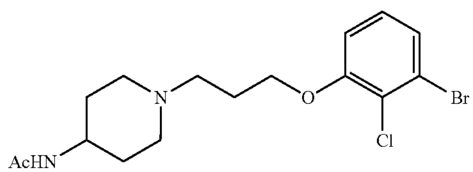 [SMILES: CC(=O)NC1CCN(CCCOc2cccc(Br)c2Cl)CC1]

Potassium carbonate (2.43 g, 17.58 mmol) was added in one portion to a stirred solution of 1-bromo-3-(3-bromopropoxy)-2-chlorobenzene (2.31 g, 7.03 mmol) and N-(piperidin-4-yl)acetamide (1.00 g, 7.03 mmol) in dry acetonitrile (20 mL) and DMF (10 mL). The mixture was then heated to 60° C. for 16 h before it was cooled to rt and diluted with ethyl acetate and water. The aqueous phase was separated and extracted once more with ethyl acetate. The combined organic phase was washed with brine, dried over $MgSO_4$, filtered and concentrated to 14 vol to yield the product, N-(1-(3-(3-bromo-2-chlorophenoxy)-propyl)piperidin-4-yl)acetamide (1.13 g, 41.2% yield) as a white solid after suction-filtration. The filtrate was concentrated, taken up in a minimal amount of dichloromethane, and charged to a RediSepRf normal phase silica gel Teledyne ISCO 40 g disposable column which was first eluted with dichloromethane for 150 mL, followed by 0-20% B for 1300 mL where solvent B=methanol and solvent A=dichloromethane. Fractions containing the desired product were combined and dried via centrifugal evaporation. There was isolated additional product, N-(1-(3-(3-bromo-2-chlorophenoxy)propyl)piperidin-4-yl)acetamide (0.62 g, 22.4% yield) as a white solid.

LCMS: $t_R$=0.86 min; LCMS (ESI) m/z=388.90 and 390.90 $[M+H]^+$. LCMS conditions: Injection Vol=3 μL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

$^1$H NMR (500 MHz, $CDCl_3$) δ 7.23 (dd, J=8.1, 1.2 Hz, 1H), 7.07 (t, J=8.2 Hz, 1H), 6.88 (dd, J=8.2, 0.9 Hz, 1H), 5.38-5.10 (m, 1H), 4.08 (t, J=6.2 Hz, 2H), 3.94-3.64 (m, 1H), 2.86 (br d, J=11.7 Hz, 2H), 2.55 (t, J=7.3 Hz, 2H), 2.13 (br t, J=11.0 Hz, 2H), 2.05-1.99 (m, 2H), 1.98 (s, 3H), 1.94 (br d, J=12.1 Hz, 2H), 1.43 (qd, J=11.6, 3.7 Hz, 2H).

Intermediate: N-(1-(3-((2-Chloro-3'-((2-chloro-5-((5-cyanopyridin-3-yl)methoxy)-4-formylphenoxy)-methyl)-2'-methyl-[1,1'-biphenyl]-3-yl)oxy)propyl)piperidin-4-yl)acetamide

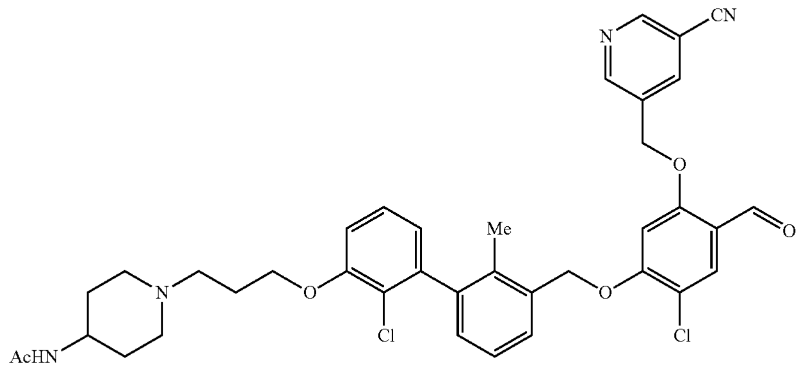 [SMILES: CC(=O)NC1CCN(CCCOc2cccc(-c3cccc(COc4cc(OCc5cncc(C#N)c5)c(C=O)cc4Cl)c3C)c2Cl)CC1]

Second generation XPhos precatalyst (38 mg, 0.048 mmol) was added in one portion to an argon-degassed mixture of N-(1-(3-(3-bromo-2-chlorophenoxy)propyl) piperidin-4-yl)acetamide (451 mg, 1.16 mmol), 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (500 mg, 0.96 mmol) and potassium phosphate (511 mg, 2.41 mmol) in THE (10 mL) and water (2.5 mL) at rt. The vial was then sealed and the resultant suspension was stirred at rt for 16 h before it was diluted with ethyl acetate and water. The aqueous phase was separated, and extracted once more with ethyl acetate. The combined organic extract was washed with brine, dried over $MgSO_4$, filtered and concentrated. The crude product was taken up in a small amount of dichloromethane and charged to a RediSepRf normal phase silica gel Teledyne ISCO 40 g disposable column which was first eluted with dichloromethane for 100 mL, followed by 0-20% B for 1450 mL where solvent B=methanol and solvent A=dichloromethane. Fractions containing the desired product were combined and dried via centrifugal evaporation. There was isolated the desired product, N-(1-(3-((2-chloro-3'-((2-chloro-5-((5-cyanopyridin-3-yl)methoxy)-4-formylphenoxy)methyl)-2'-methyl-[1,1'-biphenyl]-3-yl)oxy)propyl)piperidin-4-yl)acetamide (586.3 mg, 87% yield) as a yellow solid.

LCMS: $t_R$=1.19 min; LCMS (ESI) m/z=701.00 $[M+H]^+$. LCMS conditions: Injection Vol=3 μL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

Example 1055: N-(1-(3-((3'-((4-((2-(1H-Tetrazol-5-yl)piperidin-1-yl)methyl)-2-chloro-5-((5-cyano-pyridin-3-yl)methoxy)phenoxy)methyl)-2-chloro-2'-methyl-[1,1'-biphenyl]-3-yl)oxy)-propyl)-piperidin-4-yl)acetamide

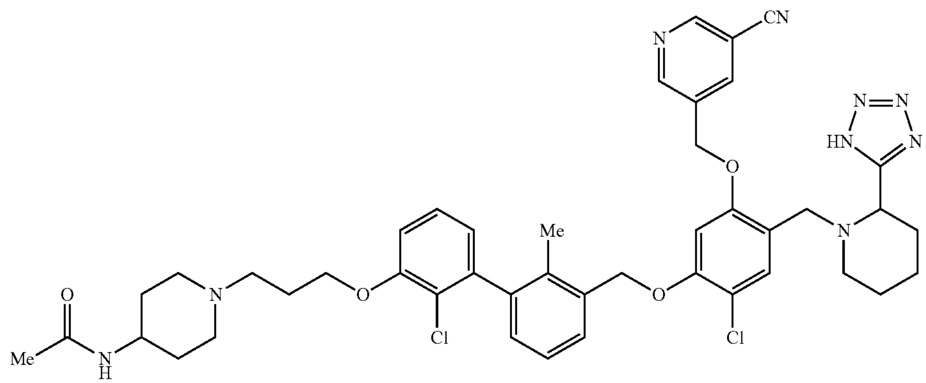 [SMILES: CC(=O)NC1CCN(CCCOc2cccc(-c3cccc(COc4cc(OCc5cncc(C#N)c5)c(CN5CCCCC5c5nnn[nH]5)cc4Cl)c3C)c2Cl)CC1]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 14-54% B over 20 min, then a 5 min hold at 100% B; Flow: 20 mL/min. Fractions containing the desired product were combined and dried via centrifugal evaporation. The yield of the product was 7.9 mg, and its estimated purity by LCMS analysis was 98%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 97.7%; Observed Mass: 838.21; Retention Time: 1.54 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 98.1%; Observed Mass: 838.26; Retention Time: 1.46 min.

Example 1056: N-(1-(3-((3'-((4-(((1H-Tetrazol-5-yl) amino)methyl)-2-chloro-5-((5-cyanopyridin-3-yl)-methoxy)phenoxy)methyl)-2-chloro-2'-methyl-[1,1'-biphenyl]-3-yl)oxy)propyl)piperidin-4-yl)acetamide

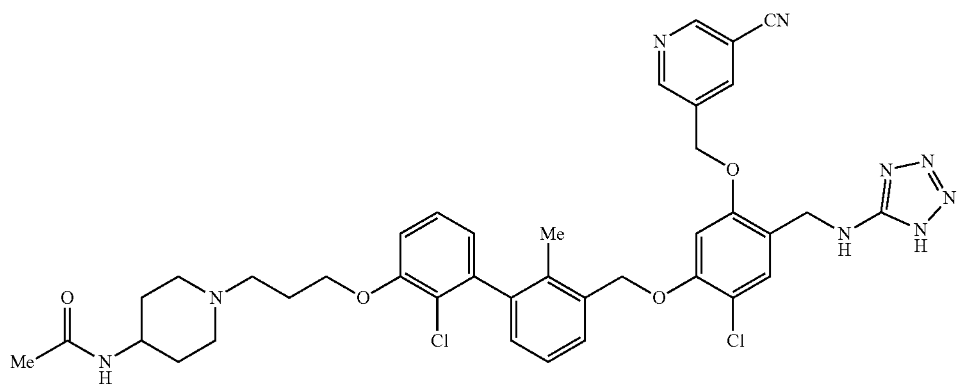 [SMILES: CC(=O)NC1CCN(CCCOc2cccc(-c3cccc(COc4cc(OCc5cncc(C#N)c5)c(CNc5nnn[nH]5)cc4Cl)c3C)c2Cl)CC1]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 15-55% B over 25 min, then a 4 min hold at 100% B; Flow: 20 mL/min. Fractions containing the desired product were combined and dried via centrifugal evaporation. The yield of the product was 11.4 mg, and its estimated purity by LCMS analysis was 98%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 98.6%; Observed Mass: 770.14; Retention Time: 1.55 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 98.1%; Observed Mass: 770.19; Retention Time: 1.57 min.

Example 1057: N-(1-(3-((3'-((4-((((1H-Tetrazol-5-yl)methyl)amino)methyl)-2-chloro-5-((5-cyano-pyridin-3-yl)methoxy)phenoxy)methyl)-2-chloro-2'-methyl-[1,1'-biphenyl]-3-yl)oxy)-propyl)piperidin-4-yl)acetamide

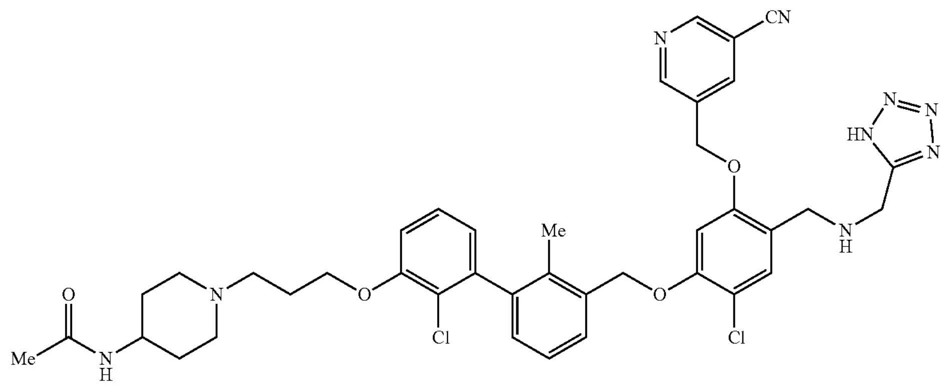 [SMILES: CC(=O)NC1CCN(CCCOc2cccc(-c3cccc(COc4cc(OCc5cncc(C#N)c5)c(CNCc5nnn[nH]5)cc4Cl)c3C)c2Cl)CC1]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 5-48% B over 25 min, then a 5 min hold at 100% B; Flow: 20 mL/min. Fractions containing the desired product were combined and dried via centrifugal evaporation. The yield of the product was 14.8 mg, and its estimated purity by LCMS analysis was 94%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 94.0%; Observed Mass: 784.22; Retention Time: 1.48 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile: water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 94.2%; Observed Mass: 784.22; Retention Time: 1.39 min.

Example 1058: N-(1-(3-((3'-((4-((3-(1H-Tetrazol-5-yl)pyrrolidin-1-yl)methyl)-2-chloro-5-((5-cyano-pyridin-3-yl)methoxy)phenoxy)methyl)-2-chloro-2'-methyl-[1,1'-biphenyl]-3-yl)oxy)-propyl)piperidin-4-yl)acetamide

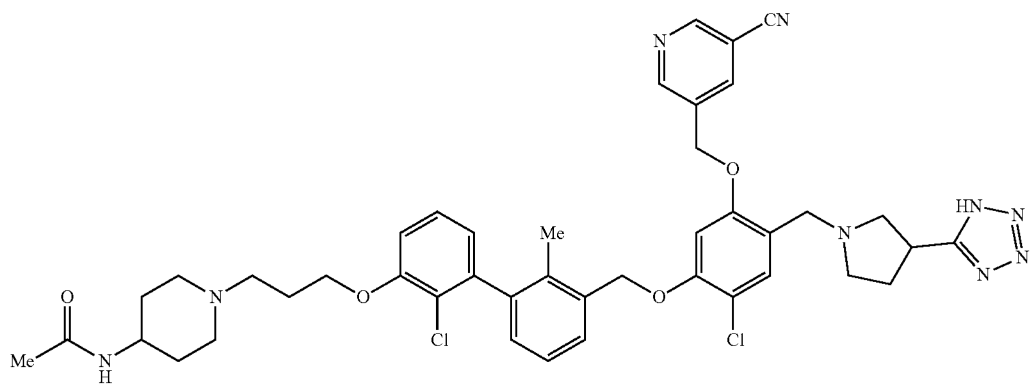 [SMILES: CC(=O)NC1CCN(CCCOc2cccc(-c3cccc(COc4cc(OCc5cncc(C#N)c5)c(CN5CCC(c6nnn[nH]6)C5)cc4Cl)c3C)c2Cl)CC1]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 10-60% B over 20 min, then a 5 min hold at 100% B; Flow: 20 mL/min. Fractions containing the desired product were combined and dried via centrifugal evaporation. The yield of the product was 13.2 mg, and its estimated purity by LCMS analysis was 91%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 91.3%; Observed Mass: 824.19; Retention Time: 1.48 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile: water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 91.1%; Observed Mass: 824.27; Retention Time: 1.42 min.

Example 1059: N-(1-(3-((3'-((4-((2-(1H-Pyrazol-4-yl)piperidin-1-yl)methyl)-2-chloro-5-((5-cyano-pyridin-3-yl)methoxy)phenoxy)methyl)-2-chloro-2'-methyl-[1,1'-biphenyl]-3-yl)oxy)-propyl)piperidin-4-yl)acetamide

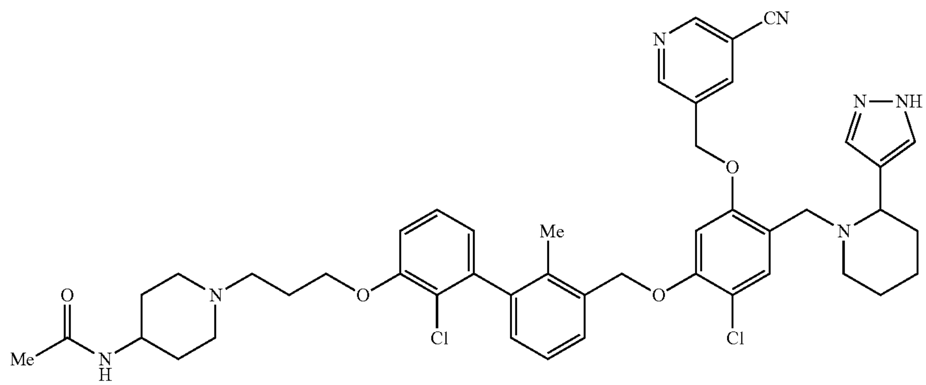 [SMILES: CC(=O)NC1CCN(CCCOc2cccc(-c3cccc(COc4cc(OCc5cncc(C#N)c5)c(CN5CCCCC5c5cn[nH]c5)cc4Cl)c3C)c2Cl)CC1]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 19-59% B over 25 min, then a 4 min hold at 100% B; Flow: 20 mL/min. Fractions containing the desired product were combined and dried via centrifugal evaporation. The yield of the product was 8.5 mg, and its estimated purity by LCMS analysis was 98%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 99.3%; Observed Mass: 836.17; Retention Time: 1.81 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 97.8%; Observed Mass: 836.21; Retention Time: 1.43 min.

Examples in the 2000 series were prepared in a manner analogous to those described above.

Example 2001: (R)-5-((2-((((1H-pyrazol-3-yl)methyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile

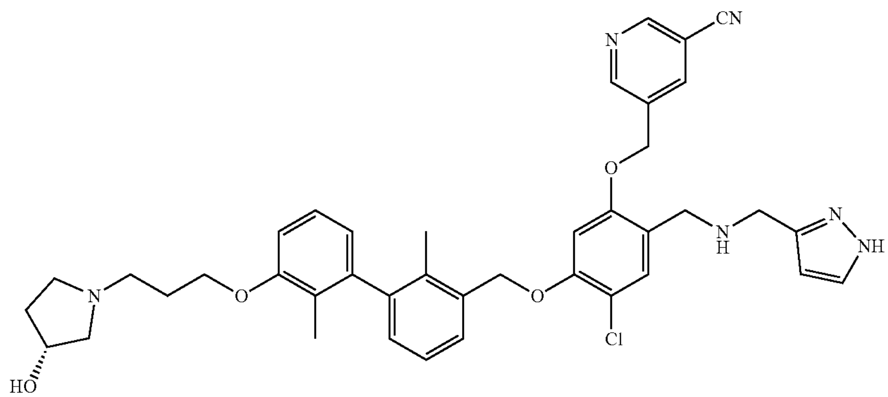 [SMILES: Cc1c(COc2cc(OCc3cncc(C#N)c3)c(CNCc3cc[nH]n3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-65% B over 24 minutes, then a 5-minute hold at 100% B; Flow: 20 mL/min. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.3%; Observed Mass: 707.18; Retention Time: 1.43 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.1%; Observed Mass: 707.2; Retention Time: 1.44 min.

Example 2002: (R)-5-((2-((((1H-1,2,4-triazol-5-yl)methyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile

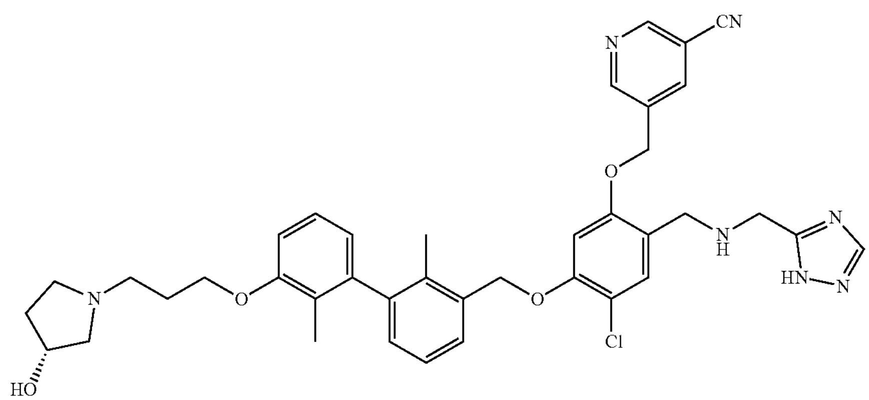 [SMILES: Cc1c(COc2cc(OCc3cncc(C#N)c3)c(CNCc3ncn[nH]3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55% B over 25 minutes, then a 5-minute hold at 100% B; Flow: 20 mL/min. Fractions containing the desired product were combined and dried via centrifugal evaporation and its estimated purity by LCMS analysis was 98%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.7%; Observed Mass: 708.26; Retention Time: 1.39 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.7%; Observed Mass: 708.26; Retention Time: 1.48 min.

Example 2003: (R)-5-((2-((((1H-imidazol-4-yl)methyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile

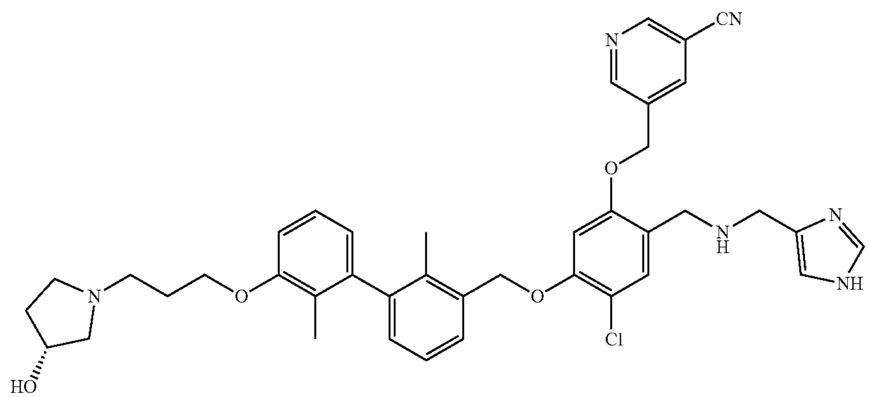 [SMILES: Cc1c(COc2cc(OCc3cncc(C#N)c3)c(CNCc3c[nH]cn3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55% B over 20 minutes, then a 5-minute hold at 100% B; Flow: 20 mL/min. Fractions containing the desired product were combined and dried via centrifugal evaporation and its estimated purity by LCMS analysis was 94%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 94.1%; Observed Mass: 707.19; Retention Time: 1.32 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.4%; Observed Mass: 707.21; Retention Time: 1.38 min.

Example 2004: (R)-5-((2-((((1H-imidazol-2-yl)methyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile

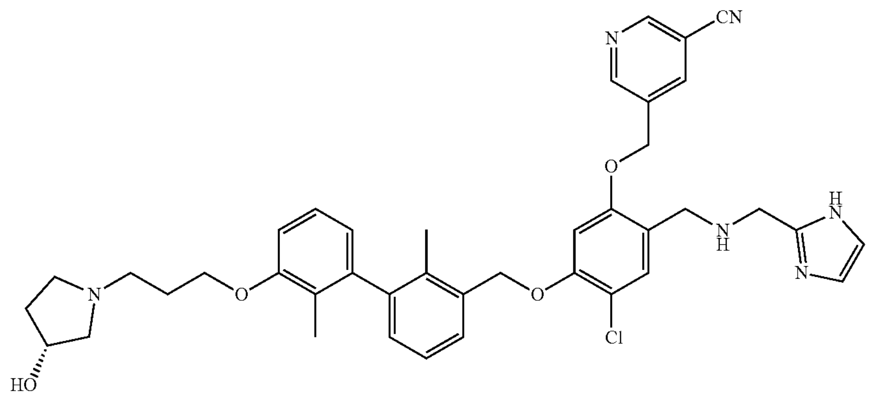 [SMILES: Cc1c(COc2cc(OCc3cncc(C#N)c3)c(CNCc3ncc[nH]3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 25-65% B over 20 minutes, then a 5-minute hold at 100% B; Flow: 20 mL/min. Fractions containing the desired product were combined and dried via centrifugal evaporation and its estimated purity by LCMS analysis was 94%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 707.23; Retention Time: 1.51 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 94.3%; Observed Mass: 707.22; Retention Time: 1.35 min.

Example 2005: (R)-5-((2-((((1H-pyrazol-3-yl)methyl)(methyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile

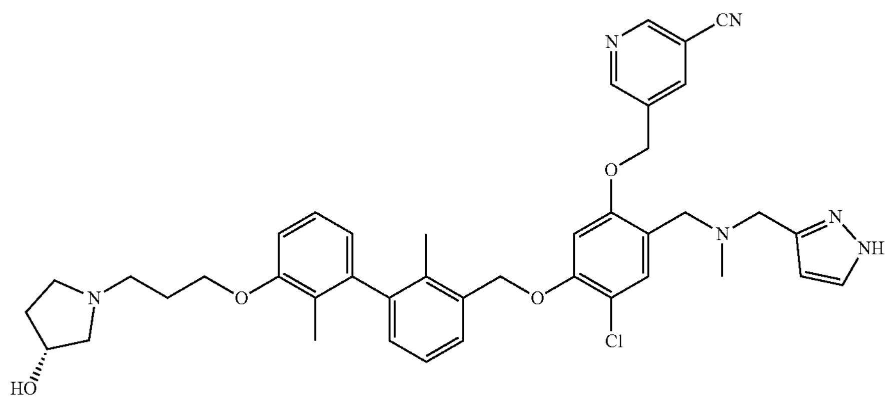 [SMILES: Cc1c(COc2cc(OCc3cncc(C#N)c3)c(CN(C)Cc3cc[nH]n3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 35-75% B over 19 minutes, then a 4-minute hold at 100% B; Flow: 20 mL/min. Fractions containing the desired product were combined and dried via centrifugal evaporation and its estimated purity by LCMS analysis was 98%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.6%; Observed Mass: 721.24; Retention Time: 1.44 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 721.23; Retention Time: 1.78 min.

Example 2006: (R)-5-((2-((((1H-1,2,4-triazol-5-yl)methyl)(methyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile

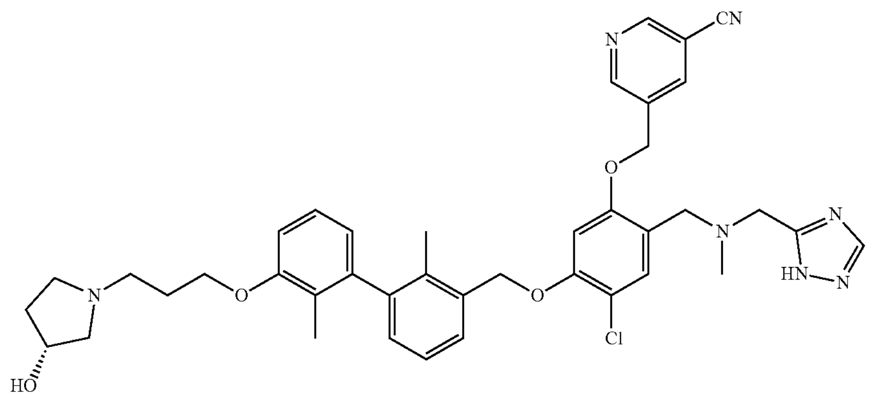 [SMILES: Cc1c(COc2cc(OCc3cncc(C#N)c3)c(CN(C)Cc3ncn[nH]3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 28-68% B over 20 minutes, then a 4-minute hold at 100% B; Flow: 20 mL/min. Fractions containing the desired product were combined and dried via centrifugal evaporation and its estimated purity by LCMS analysis was 94%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 94.2%; Observed Mass: 722.33; Retention Time: 1.47 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 94.4%; Observed Mass: 722.28; Retention Time: 1.7 min.

Example 2007: (R)-5-((2-((((1H-imidazol-4-yl)methyl)(methyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile

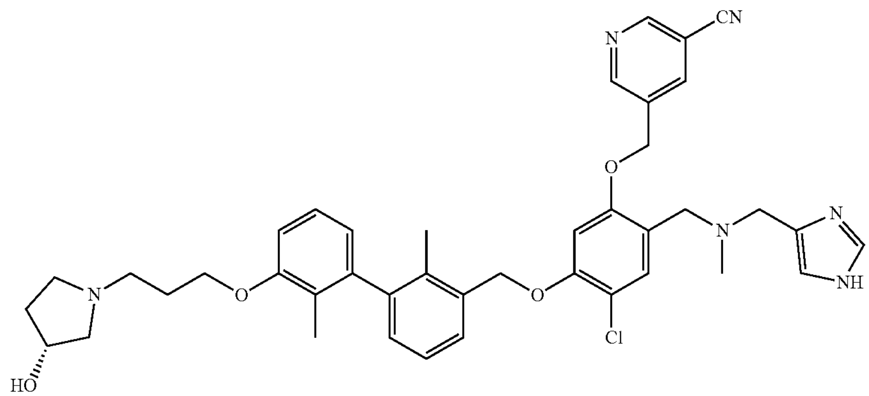 [SMILES: Cc1c(COc2cc(OCc3cncc(C#N)c3)c(CN(C)Cc3c[nH]cn3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 20 minutes, then a 4-minute hold at 100% B; Flow: 20 mL/min. Fractions containing the desired product were combined and dried via centrifugal evaporation and its estimated purity by LCMS analysis was 98%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.1%; Observed Mass: 721.31; Retention Time: 1.37 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 721.31; Retention Time: 1.57 min.

Example 2008: (R)-5-((2-((((1H-imidazol-2-yl)methyl)(methyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile

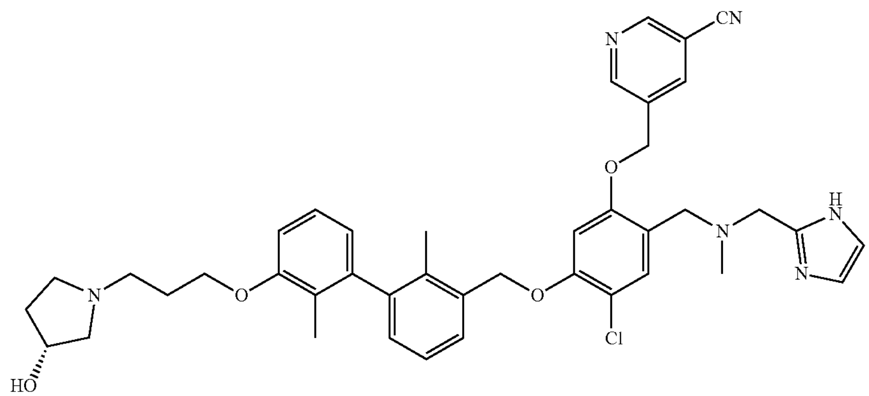 [SMILES: Cc1c(COc2cc(OCc3cncc(C#N)c3)c(CN(C)Cc3ncc[nH]3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 28-68% B over 20 minutes, then a 4-minute hold at 100% B; Flow: 20 mL/min. Fractions containing the desired product were combined and dried via centrifugal evaporation and its estimated purity by LCMS analysis was 94%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 93.7%; Observed Mass: 721.26; Retention Time: 1.43 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.1%; Observed Mass: 721.26; Retention Time: 1.73 min.

Example 2009: 5-((2-((((1H-1,2,4-triazol-5-yl)methyl)amino)methyl)-4-chloro-5-((2'-chloro-3'-(3-(4-hydroxy-4-(hydroxymethyl)piperidin-1-yl)propoxy)-2-methyl-[1,1'-biphenyl]-3-yl)methoxy)phenoxy)methyl)nicotinonitrile

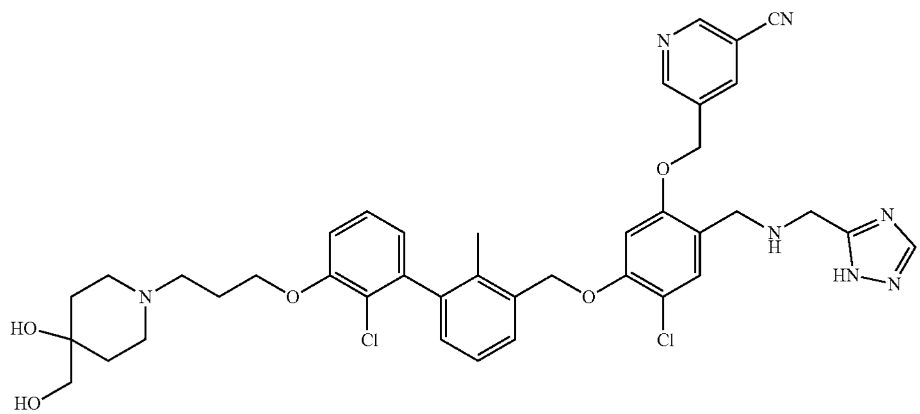

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 14-58% B over 20 minutes, then a 6-minute hold at 100% B; Flow: 20 mL/min. Fractions containing the desired product were combined and dried via centrifugal evaporation and its estimated purity by LCMS analysis was 98%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 772.14, 772.14; Retention Time: 1.57, 1.61 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.0%; Observed Mass: 772.16; Retention Time: 1.31 min.

Example 2010: 5-((2-((((1H-imidazol-4-yl)methyl)amino)methyl)-4-chloro-5-((2'-chloro-3'-(3-(4-hydroxy-4-(hydroxymethyl)piperidin-1-yl)propoxy)-2-methyl-[1,1'-biphenyl]-3-yl)methoxy)phenoxy)methyl)nicotinonitrile

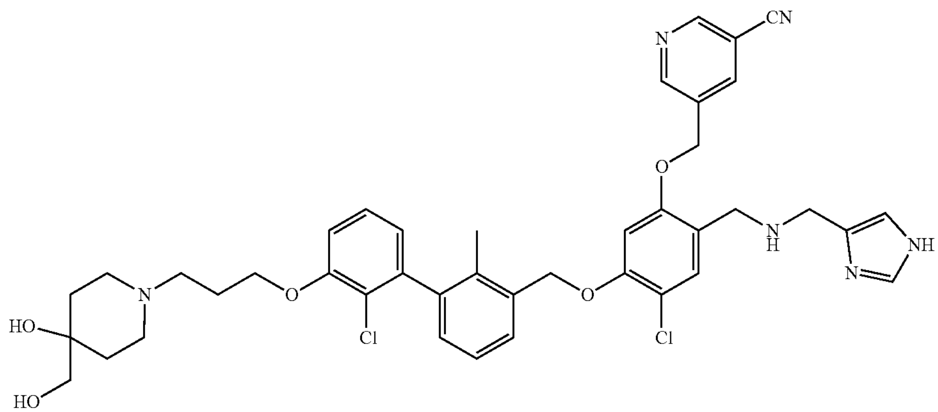

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 25 minutes, then a 6-minute hold at 100% B; Flow: 20 mL/min. Fractions containing the desired product were combined and dried via centrifugal evaporation and its estimated purity by LCMS analysis was 99%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.5%; Observed Mass: 771.17; Retention Time: 1.32 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.7%; Observed Mass: 771.16; Retention Time: 1.24 min.

Example 2011: 5-((2-((((1H-imidazol-2-yl)methyl)amino)methyl)-4-chloro-5-((2'-chloro-3'-(3-(4-hydroxy-4-(hydroxymethyl)piperidin-1-yl)propoxy)-2-methyl-[1,1'-biphenyl]-3-yl)methoxy)phenoxy)methyl)nicotinonitrile

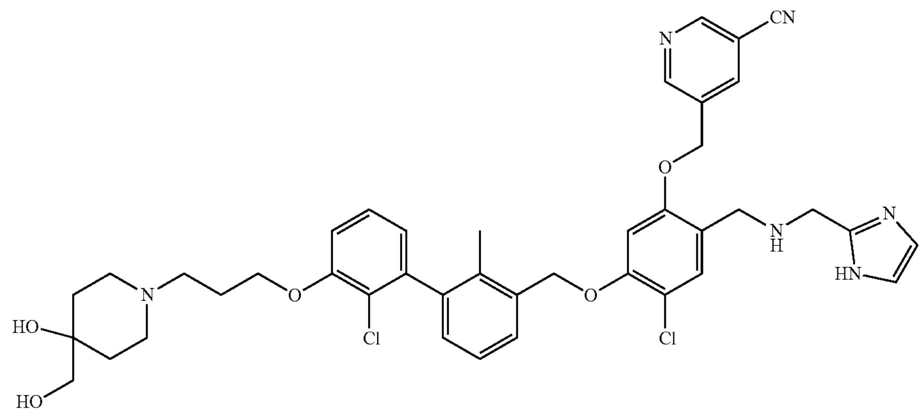 [SMILES: Cc1c(COc2cc(OCc3cncc(C#N)c3)c(CNCc3ncc[nH]3)cc2Cl)cccc1-c1cccc(OCCCN2CCC(O)(CO)CC2)c1Cl]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 11-51% B over 25 minutes, then a 6-minute hold at 100% B; Flow: 20 mL/min. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.4%; Observed Mass: 771.17; Retention Time: 1.44 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.1%; Observed Mass: 771.16; Retention Time: 1.27 min.

Example 2012: 5-((2-((((1H-pyrazol-3-yl)methyl)amino)methyl)-4-chloro-5-((2'-chloro-3'-(3-(4-hydroxy-4-(hydroxymethyl)piperidin-1-yl)propoxy)-2-methyl-[1,1'-biphenyl]-3-yl)methoxy)phenoxy)methyl)nicotinonitrile

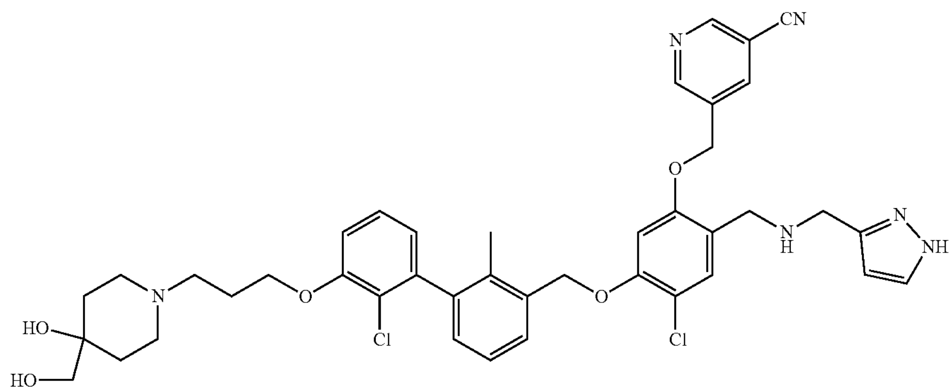 [SMILES: Cc1c(COc2cc(OCc3cncc(C#N)c3)c(CNCc3cc[nH]n3)cc2Cl)cccc1-c1cccc(OCCCN2CCC(O)(CO)CC2)c1Cl]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.8%; Observed Mass: 771.22; Retention Time: 1.57 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.2%; Observed Mass: 771.26; Retention Time: 1.42 min.

Example 2013: 5-((2-((((1H-1,2,4-triazol-5-yl)methyl)(methyl)amino)methyl)-4-chloro-5-((2'-chloro-3'-(3-(4-hydroxy-4-(hydroxymethyl)piperidin-1-yl)propoxy)-2-methyl-[1,1'-biphenyl]-3-yl)methoxy)phenoxy)methyl)nicotinonitrile

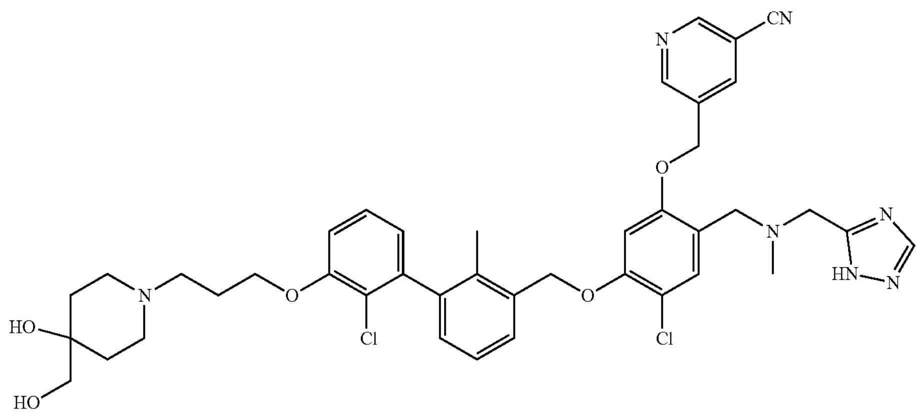

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 18-58% B over 20 minutes, then a 6-minute hold at 100% B; Flow: 20 mL/min. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.4%; Observed Mass: 786.21; Retention Time: 1.33 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.9%; Observed Mass: 786.2; Retention Time: 1.54 min.

Example 2014: 5-((2-((((1H-imidazol-4-yl)methyl)(methyl)amino)methyl)-4-chloro-5-((2'-chloro-3'-(3-(4-hydroxy-4-(hydroxymethyl)piperidin-1-yl)propoxy)-2-methyl-[1,1'-biphenyl]-3-yl)methoxy)phenoxy)methyl)nicotinonitrile

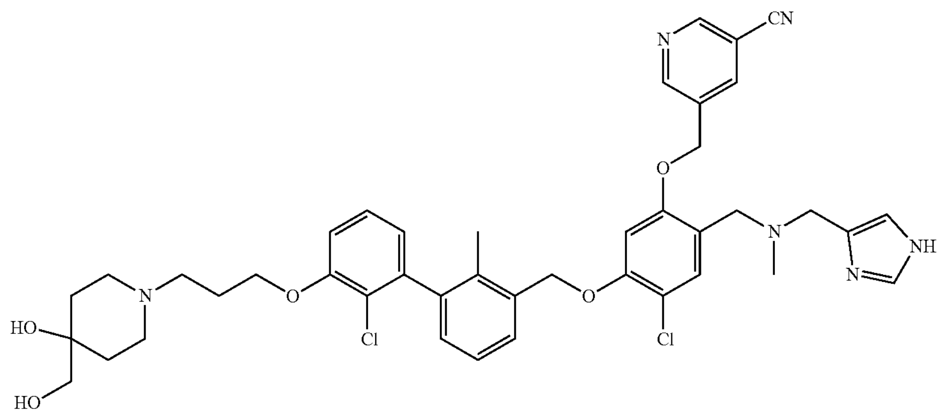 [SMILES: Cc1c(COc2cc(OCc3cncc(C#N)c3)c(CN(C)Cc3c[nH]cn3)cc2Cl)cccc1-c1cccc(OCCCN2CCC(O)(CO)CC2)c1Cl]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 14-54% B over 20 minutes, then a 6-minute hold at 100% B; Flow: 20 mL/min. Fractions containing the desired product were combined and dried via centrifugal evaporation and its estimated purity by LCMS analysis was 100%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 785.22; Retention Time: 1.37 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 785.2; Retention Time: 1.25 min.

Example 2015: 5-((2-((((1H-imidazol-2-yl)methyl)(methyl)amino)methyl)-4-chloro-5-((2'-chloro-3'-(3-(4-hydroxy-4-(hydroxymethyl)piperidin-1-yl)propoxy)-2-methyl-[1,1'-biphenyl]-3-yl)methoxy)phenoxy)methyl)nicotinonitrile

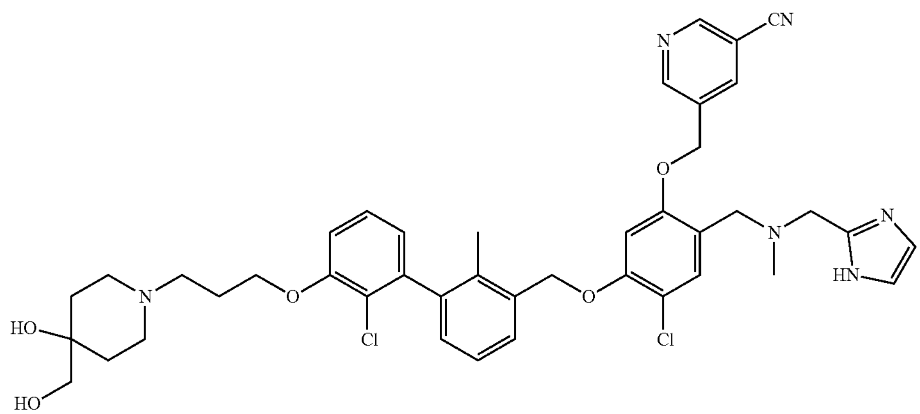 [SMILES: Cc1c(COc2cc(OCc3cncc(C#N)c3)c(CN(C)Cc3ncc[nH]3)cc2Cl)cccc1-c1cccc(OCCCN2CCC(O)(CO)CC2)c1Cl]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 14-54% B over 20 minutes, then a 5-minute hold at 100% B; Flow: 20 mL/min. Fractions containing the desired product were combined and dried via centrifugal evaporation and its estimated purity by LCMS analysis was 98%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 785.26; Retention Time: 1.68 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.0%; Observed Mass: 785.23; Retention Time: 1.38 min.

Example 2016: 5-((2-((((1H-pyrazol-3-yl)methyl)(methyl)amino)methyl)-4-chloro-5-((2'-chloro-3'-(3-(4-hydroxy-4-(hydroxymethyl)piperidin-1-yl)propoxy)-2-methyl-[1,1'-biphenyl]-3-yl)methoxy)phenoxy)methyl)nicotinonitrile

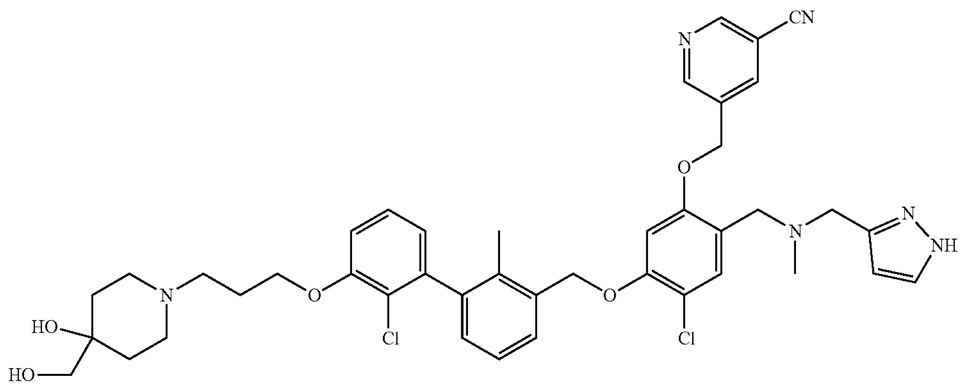 [SMILES: Cc1c(COc2cc(OCc3cncc(C#N)c3)c(CN(C)Cc3cc[nH]n3)cc2Cl)cccc1-c1cccc(OCCCN2CCC(O)(CO)CC2)c1Cl]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 22 minutes, then a 4-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 12–52% B over 20 minutes, then a 4-minute hold at 100% B; Flow: 20 mL/min. Fractions containing the desired product were combined and dried via centrifugal evaporation and its estimated purity by LCMS analysis was 97%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 785.26; Retention Time: 1.44 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.6%; Observed Mass: 785.26; Retention Time: 1.68 min.

Example 2017: (R)-5-((4-chloro-5-((3'-(3-(3-hydroxypyrrolidin-1-yl)propoxy)-2,2'-dimethyl-[1,1'-biphenyl]-3-yl)methoxy)-2-(((pyridin-2-ylmethyl)amino)methyl) phenoxy)methyl)nicotinonitrile

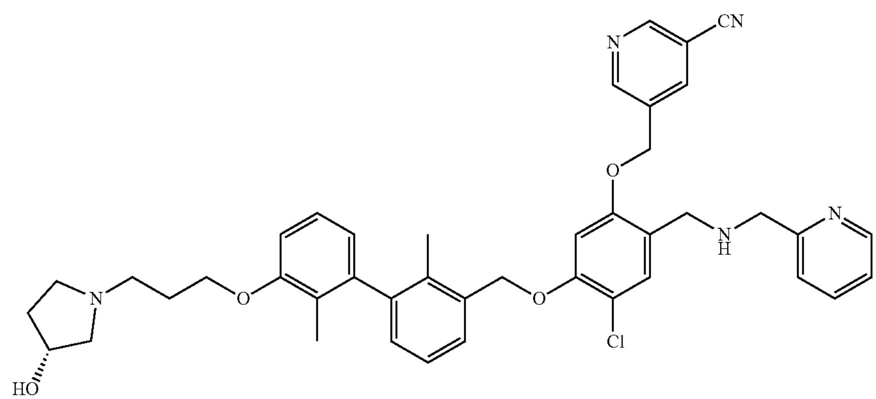 [SMILES: Cc1c(COc2cc(OCc3cncc(C#N)c3)c(CNCc3ccccn3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 23-63% B over 23 minutes, then a 6-minute hold at 100% B; Flow: 20 mL/min. Fractions containing the desired product were combined and dried via centrifugal evaporation and its estimated purity by LCMS analysis was 99%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 718.27; Retention Time: 1.78 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.6%; Observed Mass: 718.22; Retention Time: 1.55 min.

Example 2018: (R)-5-((4-chloro-5-((3'-(3-(3-hydroxypyrrolidin-1-yl)propoxy)-2,2'-dimethyl-[1,1'-biphenyl]-3-yl)methoxy)-2-(((pyridin-3-ylmethyl)amino)methyl)phenoxy)methyl)nicotinonitrile

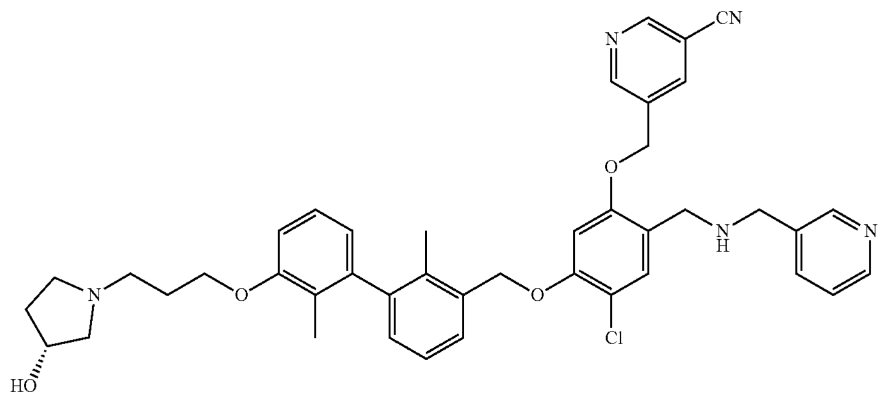

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 23-63% B over 23 minutes, then a 6-minute hold at 100% B; Flow: 20 mL/min. Fractions containing the desired product were combined and dried via centrifugal evaporation and its estimated purity by LCMS analysis was 98%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.2%; Observed Mass: 718.26; Retention Time: 1.38 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 718.3; Retention Time: 1.77 min.

Example 2019: (R)-5-((4-chloro-5-((3'-(3-(3-hydroxypyrrolidin-1-yl)propoxy)-2,2'-dimethyl-[1,1'-biphenyl]-3-yl)methoxy)-2-(((pyridin-4-ylmethyl)amino)methyl) phenoxy)methyl)nicotinonitrile

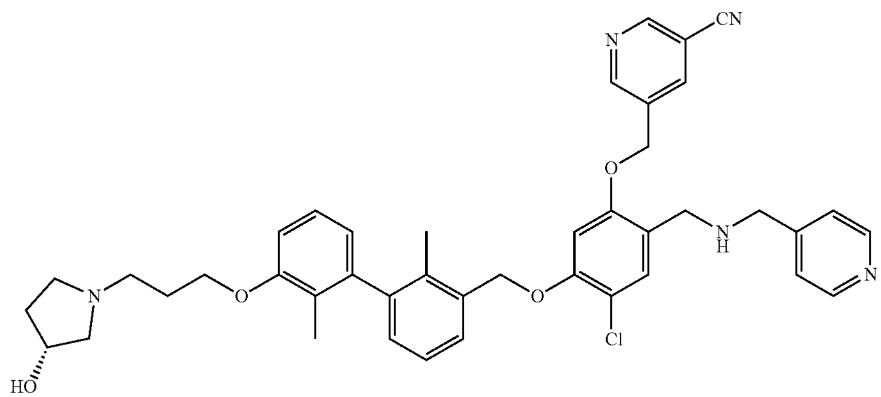 [SMILES: Cc1c(COc2cc(OCc3cncc(C#N)c3)c(CNCc3ccncc3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 28-68% B over 15 minutes, then a 5-minute hold at 100% B; Flow: 20 mL/min. Fractions containing the desired product were combined and dried via centrifugal evaporation and its estimated purity by LCMS analysis was 98%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.6%; Observed Mass: 718.25; Retention Time: 1.83 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.1%; Observed Mass: 718.29; Retention Time: 1.37 min.

Example 2020: (R)-5-((4-chloro-5-((3'-(3-(3-hydroxypyrrolidin-1-yl)propoxy)-2,2'-dimethyl-[1,1'-biphenyl]-3-yl)methoxy)-2-(((pyrazin-2-ylmethyl) amino)methyl) phenoxy)methyl)nicotinonitrile

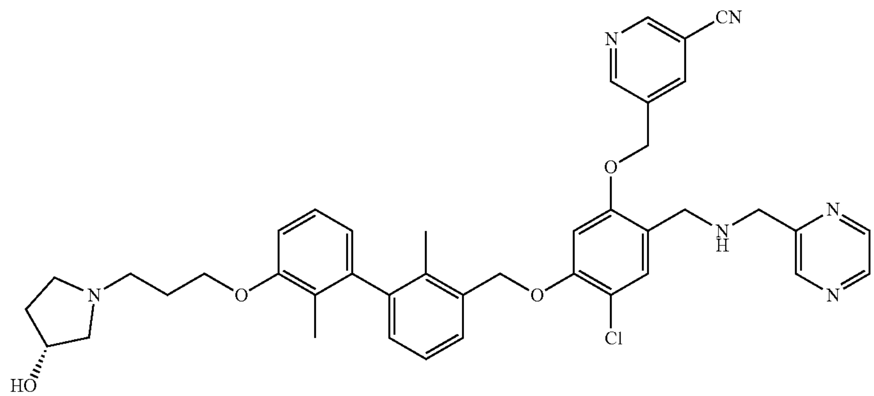 [SMILES: Cc1c(COc2cc(OCc3cncc(C#N)c3)c(CNCc3cnccn3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 20 minutes, then a 4-minute hold at 100% B; Flow: 20 mL/min. Fractions containing the desired product were combined and dried via centrifugal evaporation and its estimated purity by LCMS analysis was 99%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 719.25; Retention Time: 1.76 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.7%; Observed Mass: 719.19; Retention Time: 1.48 min.

Example 2021: (R)-5-((4-chloro-5-((3'-(3-(3-hydroxypyrrolidin-1-yl)propoxy)-2,2'-dimethyl-[1,1'-biphenyl]-3-yl)methoxy)-2-(((pyridazin-3-ylmethyl) amino)methyl) phenoxy)methyl)nicotinonitrile

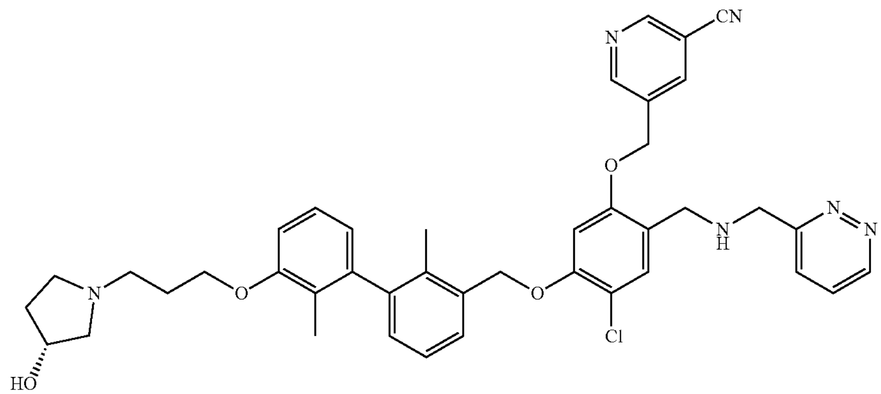 [SMILES: Cc1c(COc2cc(OCc3cncc(C#N)c3)c(CNCc3cccnn3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 24-64% B over 20 minutes, then a 6-minute hold at 100% B; Flow: 20 mL/min. Fractions containing the desired product were combined and dried via centrifugal evaporation and its estimated purity by LCMS analysis was 95%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.0%; Observed Mass: 719.18; Retention Time: 1.7 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.2%; Observed Mass: 719.19; Retention Time: 1.39 min.

Example 2022: (R)-5-((4-chloro-5-((3'-(3-(3-hydroxypyrrolidin-1-yl)propoxy)-2,2'-dimethyl-[1,1'-biphenyl]-3-yl)methoxy)-2-(((pyrimidin-5-ylmethyl) amino)methyl) phenoxy)methyl)nicotinonitrile

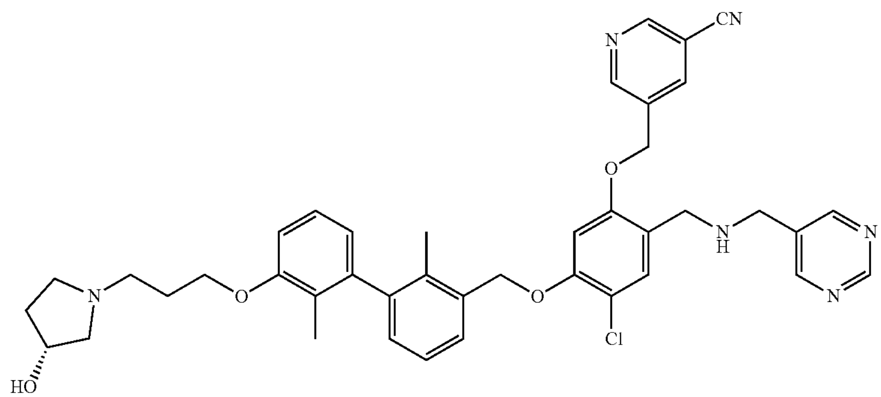 [SMILES: Cc1c(COc2cc(OCc3cncc(C#N)c3)c(CNCc3cncnc3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 25-65% B over 15 minutes, then a 5-minute hold at 100% B; Flow: 20 mL/min. Fractions containing the desired product were combined and dried via centrifugal evaporation and its estimated purity by LCMS analysis was 97%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.5%; Observed Mass: 719.33; Retention Time: 1.74 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.2%; Observed Mass: 719.29; Retention Time: 1.46 min.

Example 2023: (R)-5-((2-((((1H-benzo[d]imidazol-2-yl)methyl)(methyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile

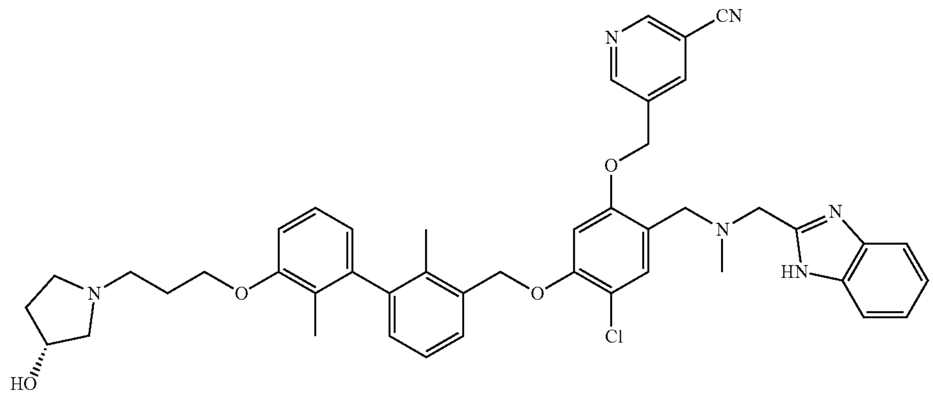 [SMILES: Cc1c(COc2cc(OCc3cncc(C#N)c3)c(CN(C)Cc3nc4ccccc4[nH]3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 31-71% B over 20 minutes, then a 6-minute hold at 100% B; Flow: 20 mL/min. Fractions containing the desired product were combined and dried via centrifugal evaporation and its estimated purity by LCMS analysis was 85%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 84.8%; Observed Mass: 771.25; Retention Time: 1.85 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 87.4%; Observed Mass: 771.29; Retention Time: 1.55 min.

Example 2024: (R)-5-((4-chloro-5-((3'-(3-(3-hydroxypyrrolidin-1-yl)propoxy)-2,2'-dimethyl-[1,1'-biphenyl]-3-yl)methoxy)-2-((methyl((4-methyl-1H-imidazol-2-yl)methyl)amino)methyl)phenoxy)methyl)nicotinonitrile

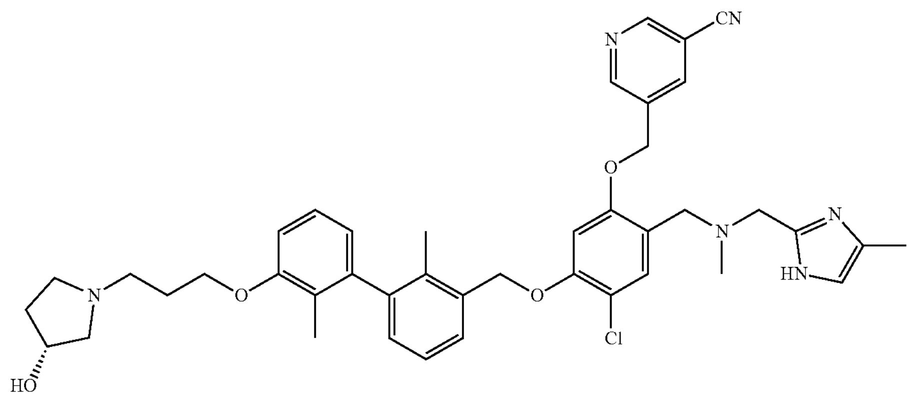 [SMILES: Cc1c[nH]c(CN(C)Cc2cc(Cl)c(OCc3cccc(-c4cccc(OCCCN5CC[C@@H](O)C5)c4C)c3C)cc2OCc2cncc(C#N)c2)n1]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 23 minutes, then a 6-minute hold at 100% B; Flow: 20 mL/min. Fractions containing the desired product were combined and dried via centrifugal evaporation and its estimated purity by LCMS analysis was 94%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.5%; Observed Mass: 735.22, 735.22; Retention Time: 1.55, 1.58 min. Injection 2 conditions: Column: Waters Xbridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 93.7%; Observed Mass: 735.24; Retention Time: 1.55 min.

Example 2025: (R)-5-((4-chloro-5-((3'-(3-(3-hydroxypyrrolidin-1-yl)propoxy)-2,2'-dimethyl-[1,1'-biphenyl]-3-yl)methoxy)-2-((methyl((3-methyl-1H-pyrazol-5-yl)methyl)amino)methyl)phenoxy)methyl)nicotinonitrile

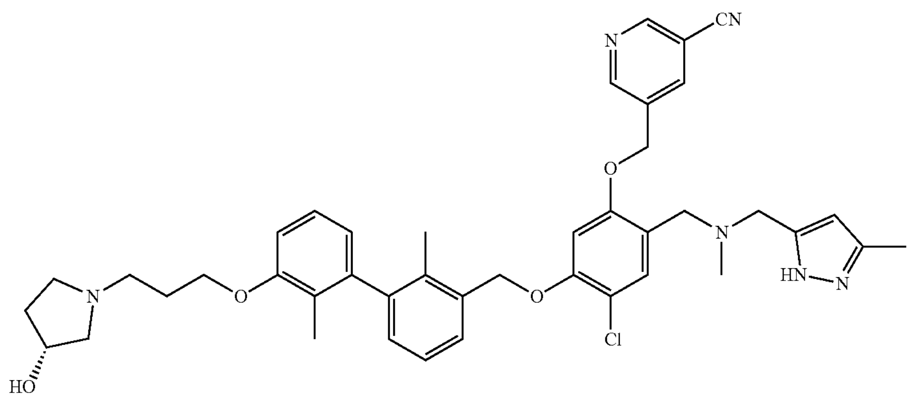 [SMILES: Cc1cc(CN(C)Cc2cc(Cl)c(OCc3cccc(-c4cccc(OCCCN5CC[C@@H](O)C5)c4C)c3C)cc2OCc2cncc(C#N)c2)[nH]n1]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 20 minutes, then a 4-minute hold at 100% B; Flow: 20 mL/min. Fractions containing the desired product were combined and dried via centrifugal evaporation and its estimated purity by LCMS analysis was 94%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 93.7%; Observed Mass: 735.3; Retention Time: 1.82 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 93.6%; Observed Mass: 735.27; Retention Time: 1.51 min.

Example 2026: (R)-5-((4-chloro-5-((3'-(3-(3-hydroxypyrrolidin-1-yl)propoxy)-2,2'-dimethyl-[1,1'-biphenyl]-3-yl)methoxy)-2-((methyl((1-methyl-1H-pyrazol-3-yl)methyl)amino)methyl)phenoxy)methyl)nicotinonitrile

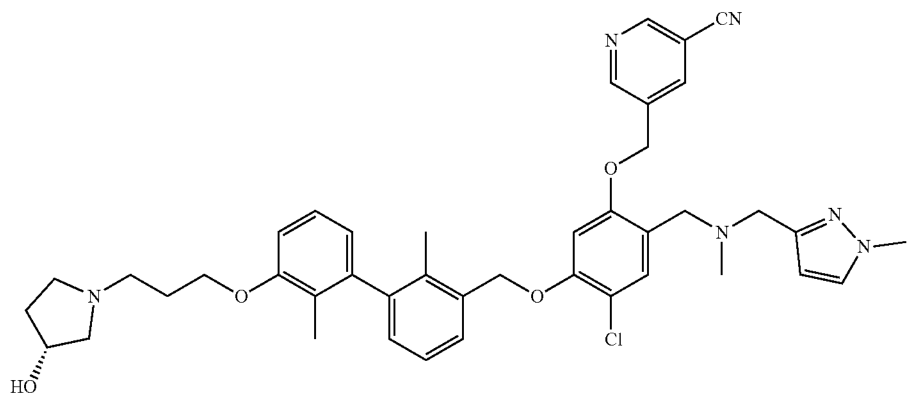 [SMILES: Cc1c(COc2cc(OCc3cncc(C#N)c3)c(CN(C)Cc3ccn(C)n3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 26-66% B over 20 minutes, then a 6-minute hold at 100% B; Flow: 20 mL/min. Fractions containing the desired product were combined and dried via centrifugal evaporation and its estimated purity by LCMS analysis was 99%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 735.26; Retention Time: 1.83 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.1%; Observed Mass: 735.27; Retention Time: 1.54 min.

Example 2027: (R)-5-((4-chloro-2-((((4-chloro-1-methyl-1H-pyrazol-3-yl)methyl)(methyl)amino)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile

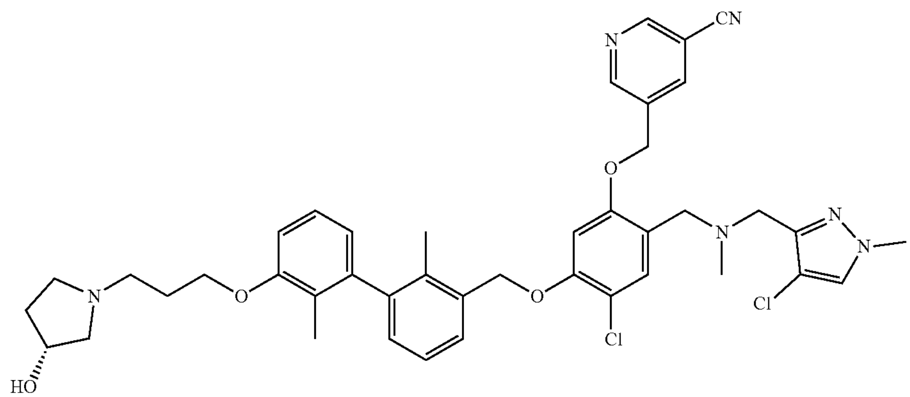 [SMILES: Cc1c(COc2cc(OCc3cncc(C#N)c3)c(CN(C)Cc3nn(C)cc3Cl)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 28-78% B over 20 minutes, then a 4-minute hold at 100% B; Flow: 20 mL/min. Fractions containing the desired product were combined and dried via centrifugal evaporation and its estimated purity by LCMS analysis was 98%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 769.2; Retention Time: 2.13 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.3%; Observed Mass: 769.22; Retention Time: 1.6 min.

Example 2028: (R)-5-((4-chloro-5-((3'-(3-(3-hydroxypyrrolidin-1-yl)propoxy)-2,2'-dimethyl-[1,1'-biphenyl]-3-yl)methoxy)-2-((methyl(pyridin-2-ylmethyl)amino)methyl)phenoxy)methyl)nicotinonitrile

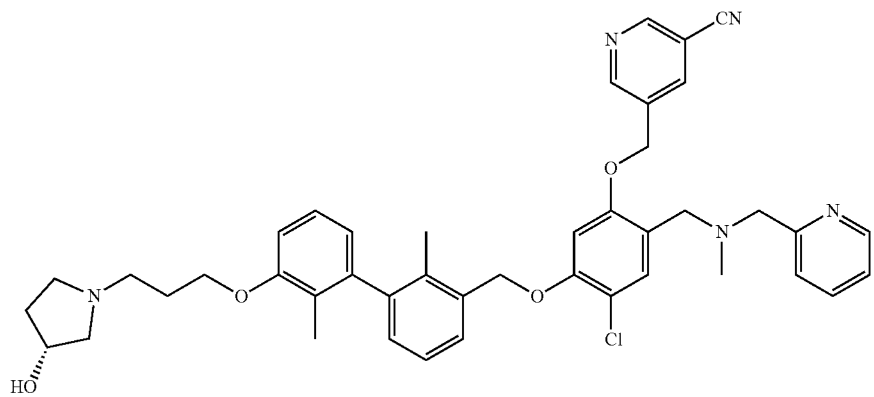

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 32-72% B over 20 minutes, then a 6-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 20 minutes, then a 6-minute hold at 100% B; Flow: 20 mL/min. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.9%; Observed Mass: 732.24; Retention Time: 1.77 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.7%; Observed Mass: 732.23; Retention Time: 1.51 min.

Example 2029: (R)-5-((4-chloro-5-((3'-(3-(3-hydroxypyrrolidin-1-yl)propoxy)-2,2'-dimethyl-[1,1'-biphenyl]-3-yl)methoxy)-2-((methyl(pyridin-4-ylmethyl)amino)methyl)phenoxy)methyl)nicotinonitrile

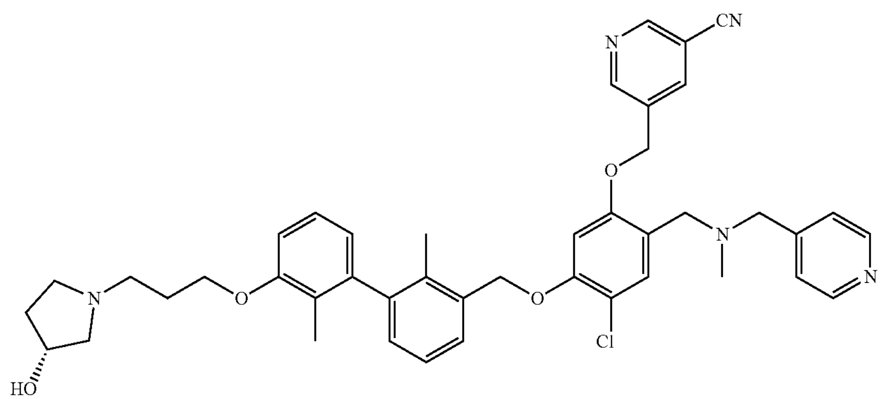

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 20 minutes, then a 5-minute hold at 100% B; Flow: 20 mL/min. Fractions containing the desired product were combined and dried via centrifugal evaporation and its estimated purity by LCMS analysis was 95%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.5%; Observed Mass: 732.25; Retention Time: 1.39 min.

Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 94.9%; Observed Mass: 732.29; Retention Time: 2.05 min.

Example 2030: (R)-5-((4-chloro-5-((3'-(3-(3-hydroxypyrrolidin-1-yl)propoxy)-2,2'-dimethyl-[1,1'-biphenyl]-3-yl)methoxy)-2-((methyl(pyrazin-2-ylmethyl)amino)methyl)phenoxy)methyl)nicotinonitrile

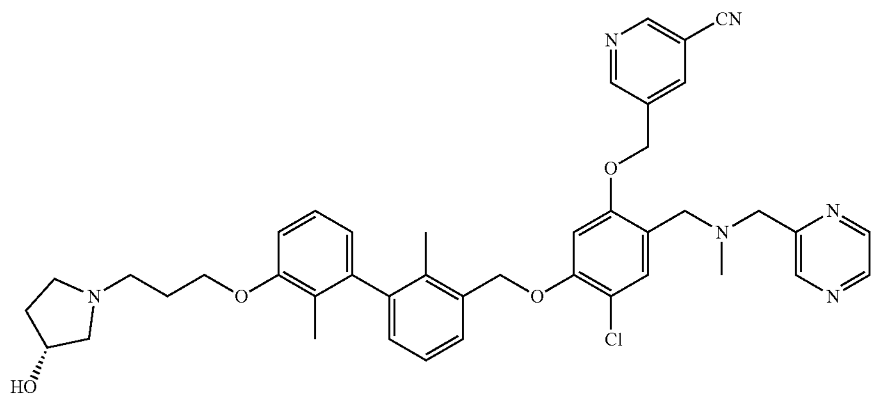

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 32-72% B over 20 minutes, then a 6-minute hold at 100% B; Flow: 20 mL/min. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.9%; Observed Mass: 733.21; Retention Time: 1.93 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.6%; Observed Mass: 733.22; Retention Time: 1.43 min.

Example 2031: (R)-5-((4-chloro-5-((3'-(3-(3-hydroxypyrrolidin-1-yl)propoxy)-2,2'-dimethyl-[1,1'-biphenyl]-3-yl)methoxy)-2-((methyl(pyridazin-3-ylmethyl)amino)methyl)phenoxy)methyl) nicotinonitrile

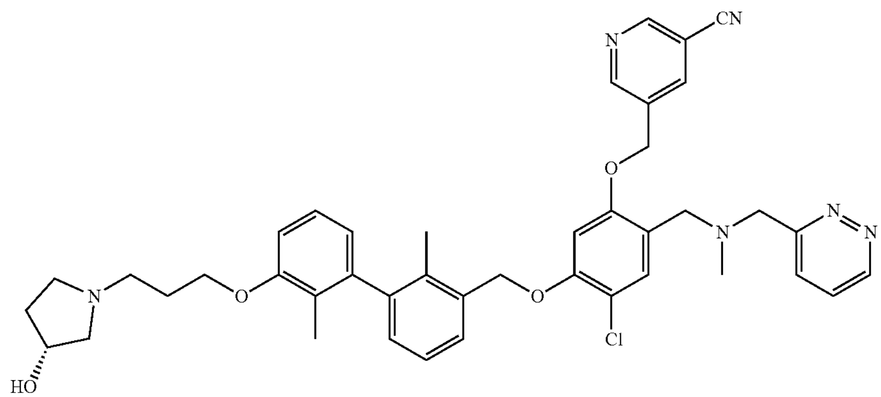

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 29-69% B over 22 minutes, then a 6-minute hold at 100% B; Flow: 20 mL/min. Fractions containing the desired product were combined and dried via centrifugal evaporation and its estimated purity by LCMS analysis was 89%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 90.7%; Observed Mass: 733.27; Retention Time: 1.47 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 89.1%; Observed Mass: 733.25; Retention Time: 1.88 min.

Example 2032: (R)-5-((4-chloro-5-((3'-(3-(3-hydroxypyrrolidin-1-yl)propoxy)-2,2'-dimethyl-[1,1'-biphenyl]-3-yl)methoxy)-2-((methyl(pyrimidin-5-ylmethyl)amino)methyl)phenoxy)methyl)nicotinonitrile

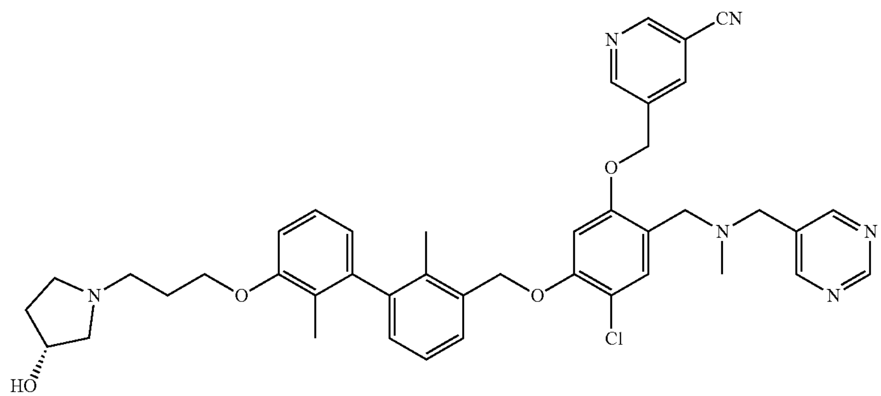

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 31-71% B over 20 minutes, then a 6-minute hold at 100% B; Flow: 20 mL/min. Fractions containing the desired product were combined and dried via centrifugal evaporation and its estimated purity by LCMS analysis was 95%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.3%; Observed Mass: 733.27; Retention Time: 1.81 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.5%; Observed Mass: 733.27; Retention Time: 1.45 min.

Example 2033: 5-((2-((((1H-imidazol-4-yl)methyl)amino)methyl)-4-chloro-5-((3'-(3-(ethyl(2-hydroxyethyl)amino)propoxy)-2,2'-dimethyl-[1,1'-biphenyl]-3-yl)methoxy)phenoxy)methyl)nicotinonitrile

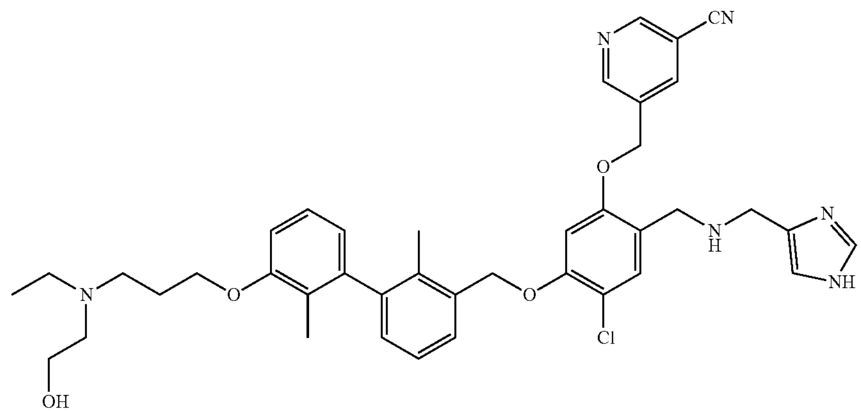 [SMILES: CCN(CCO)CCCOc1cccc(-c2cccc(COc3cc(OCc4cncc(C#N)c4)c(CNCc4c[nH]cn4)cc3Cl)c2C)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 11-51% B over 20 minutes, then a 5-minute hold at 100% B; Flow: 20 mL/min. Fractions containing the desired product were combined and dried via centrifugal evaporation and its estimated purity by LCMS analysis was 94%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 1 results: Purity: 98.4%; Observed Mass: 709.3; Retention Time: 1.58 min. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. Injection 2 results: Purity: 94.2%; Observed Mass: 709.2; Retention Time: 1.35 min.

Example 2040: (R)-4-(((5-chloro-2-((5-cyanopyridin-3-yl)methoxy)-4-((3'-(3-(3-hydroxypyrrolidin-1-yl)propoxy)-2,2'-dimethyl-[1,1'-biphenyl]-3-yl)methoxy)benzyl)amino)methyl)pyrimidine-2-carbonitrile

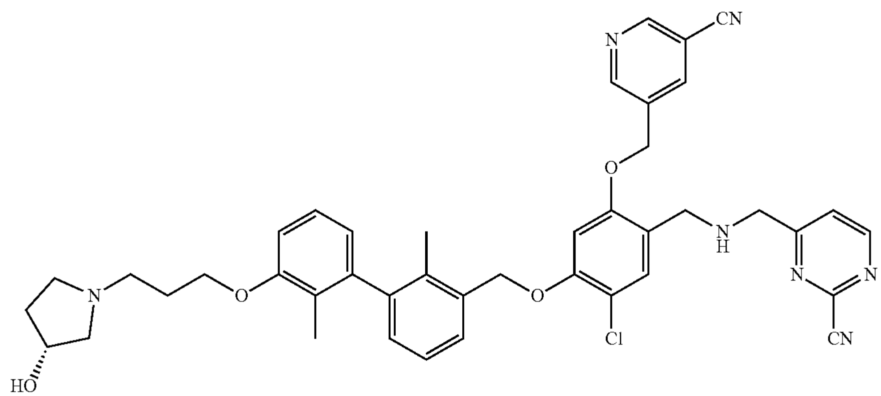 [SMILES: Cc1c(COc2cc(OCc3cncc(C#N)c3)c(CNCc3ccnc(C#N)n3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 24-71% B over 22 minutes, then a 4-minute hold at 100% B; Flow: 20 mL/min. Fractions containing the desired product were combined and dried via centrifugal evaporation and its estimated purity by LCMS analysis was 90%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 90.3%; Observed Mass: 744.2; Retention Time: 1.5 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 89.9%; Observed Mass: 744.22; Retention Time: 1.96 min.

Example 2041: (R)-4-(((5-chloro-2-((5-cyanopyridin-3-yl)methoxy)-4-((3'-(3-(3-hydroxypyrrolidin-1-yl)propoxy)-2,2'-dimethyl-[1,1'-biphenyl]-3-yl)methoxy)benzyl)amino)methyl)pyrimidine-2-carboxamide

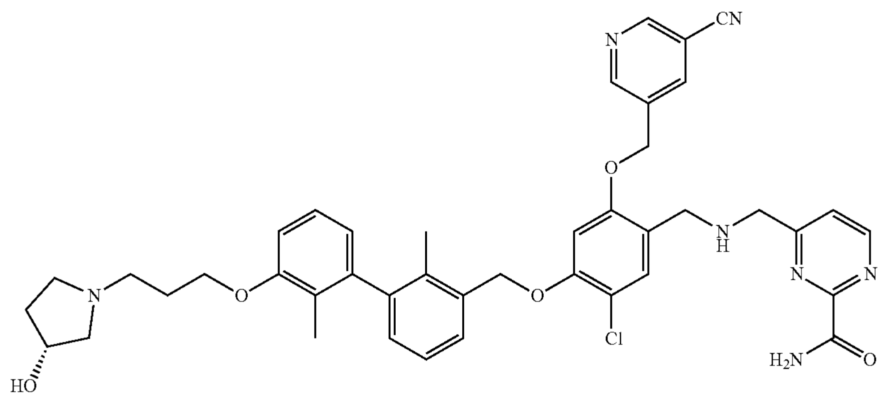 [SMILES: Cc1c(COc2cc(OCc3cncc(C#N)c3)c(CNCc3ccnc(C(N)=O)n3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 24-71% B over 22 minutes, then a 4-minute hold at 100% B; Flow: 20 mL/min. Fractions containing the desired product were combined and dried via centrifugal evaporation and its estimated purity by LCMS analysis was 87%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 86.7%; Observed Mass: 762.31; Retention Time: 1.39 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 92.4%; Observed Mass: 762.27; Retention Time: 1.66 min.

Example 2042: (R)-4-(((5-chloro-4-((3'-(3-(3-hydroxypyrrolidin-1-yl)propoxy)-2,2'-dimethyl-[1,1'-biphenyl]-3-yl)methoxy)-2-((5-methyl-1H-imidazol-4-yl)methoxy)benzyl)amino)methyl)pyrimidine-2-carbonitrile

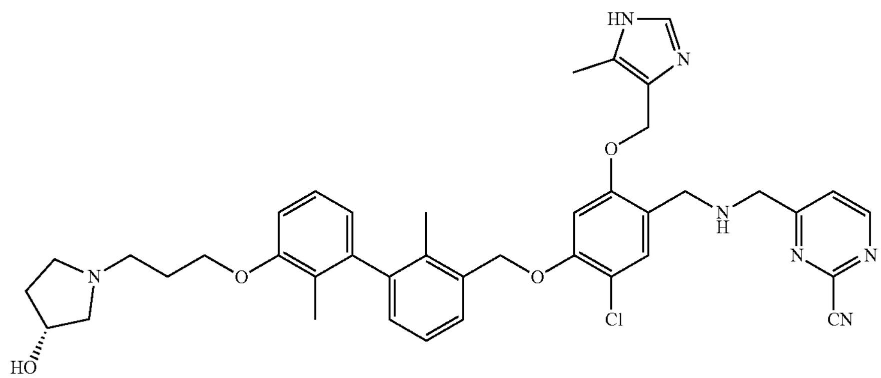 [SMILES: Cc1[nH]cnc1COc1cc(OCc2cccc(-c3cccc(OCCCN4CC[C@@H](O)C4)c3C)c2C)c(Cl)cc1CNCc1ccnc(C#N)n1]

The crude material was purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 1-40% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 18-58% B over 20 minutes, then a 5-minute hold at 100% B; Flow: 20 mL/min. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 722.26; Retention Time: 1.76 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.5%; Observed Mass: 722.3; Retention Time: 1.32 min.

Example 2043: (R)-4-(((5-chloro-4-((3'-(3-(3-hydroxypyrrolidin-1-yl)propoxy)-2,2'-dimethyl-[1,1'-biphenyl]-3-yl)methoxy)-2-((5-methyl-1-trityl-1H-imidazol-4-yl)methoxy)benzyl)amino)methyl)pyrimidine-2-carbonitrile

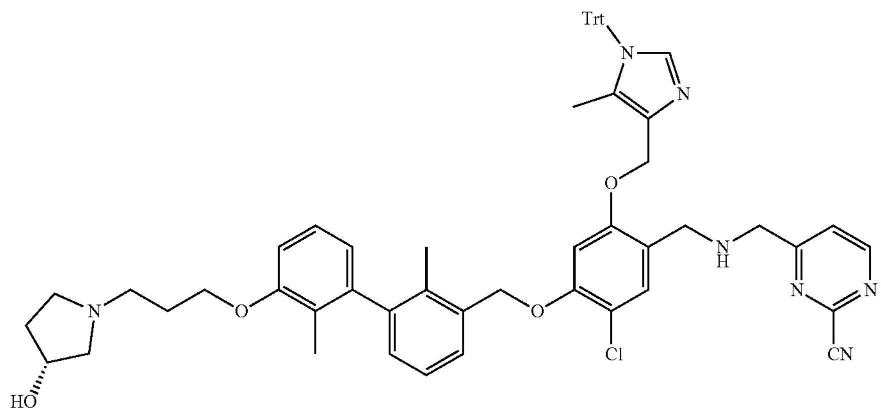

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 45-85% B over 25 minutes, then a 4-minute hold at 100% B; Flow: 20 mL/min. Fractions containing the desired product were combined and dried via centrifugal evaporation and its estimated purity by LCMS analysis was 85%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 89.4%; Observed Mass: 964.32; Retention Time: 2.55 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 84.9%; Observed Mass: 964.32; Retention Time: 1.81 min.

Example 2044: 4-(((5-chloro-4-((2'-chloro-3'-(3-(4-hydroxy-4-(hydroxymethyl) piperidin-1-yl) propoxy)-2-methyl-[1,1'-biphenyl]-3-yl)methoxy)-2-((5-cyanopyridin-3-yl)methoxy)benzyl)amino) methyl)pyrimidine-2-carbonitrile

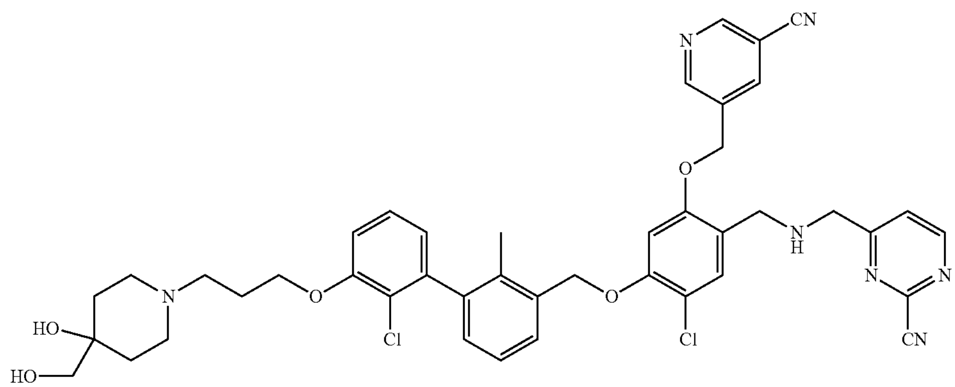 [SMILES: Cc1c(COc2cc(OCc3cncc(C#N)c3)c(CNCc3ccnc(C#N)n3)cc2Cl)cccc1-c1cccc(OCCCN2CCC(O)(CO)CC2)c1Cl]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 24-64% B over 24 minutes, then a 5-minute hold at 100% B; Flow: 20 mL/min. Fractions containing the desired product were combined and dried via centrifugal evaporation and its estimated purity by LCMS analysis was 88%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 88.3%; Observed Mass: 808.21; Retention Time: 1.42 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 92.1%; Observed Mass: 808.23; Retention Time: 1.72 min.

Example 2045: (R)-4-(((5-chloro-2-((5-cyanopyridin-3-yl)methoxy)-4-((3'-(3-(3-hydroxypyrrolidin-1-yl)propoxy)-2,2'-dimethyl-[1,1'-biphenyl]-3-yl) methoxy)benzyl) (methyl)amino)methyl)pyrimidine-2-carbonitrile

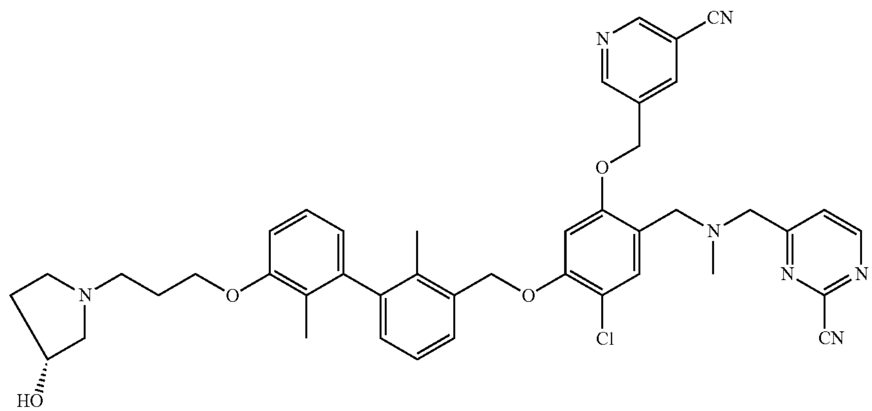 [SMILES: Cc1c(COc2cc(OCc3cncc(C#N)c3)c(CN(C)Cc3ccnc(C#N)n3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 39-79% B over 20 minutes, then a 5-minute hold at 100% B; Flow: 20 mL/min. Fractions containing the desired product were combined and dried via centrifugal evaporation and its estimated purity by LCMS analysis was 95%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 94.7%; Observed Mass: 758.29; Retention Time: 1.47 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 94.9%; Observed Mass: 758.28; Retention Time: 2.01 min.

Example 2046: 5-((4-chloro-5-((2'-chloro-2-methyl-3'-((1-methylpiperidin-4-yl)oxy)-[1,1'-biphenyl]-3-yl)methoxy)-2-(((thiazol-5-ylmethyl)amino)methyl) phenoxy)methyl)nicotinonitrile

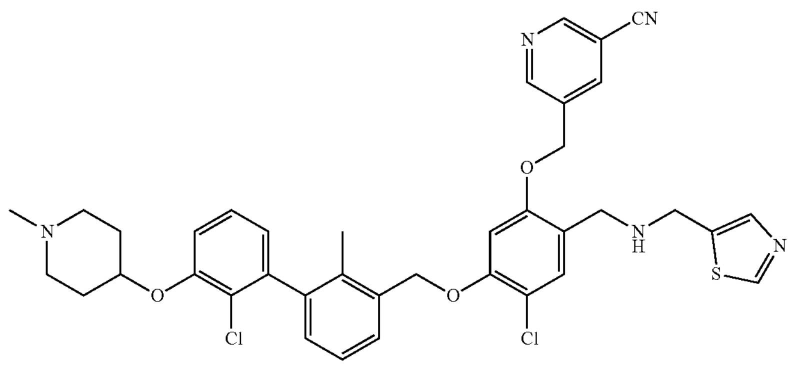 [SMILES: Cc1c(COc2cc(OCc3cncc(C#N)c3)c(CNCc3cncs3)cc2Cl)cccc1-c1cccc(OC2CCN(C)CC2)c1Cl]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 21-61% B over 20 minutes, then a 5-minute hold at 100% B; Flow: 20 mL/min. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.6%; Observed Mass: 714.17; Retention Time: 1.58 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.9%; Observed Mass: 714.15; Retention Time: 2.07 min.

Example 2047: 5-((2-((((1H-imidazol-5-yl)methyl)amino)methyl)-4-chloro-5-((2'-chloro-2-methyl-3'-((1-methylpiperidin-4-yl)oxy)-[1,1'-biphenyl]-3-yl)methoxy)phenoxy)methyl)nicotinonitrile

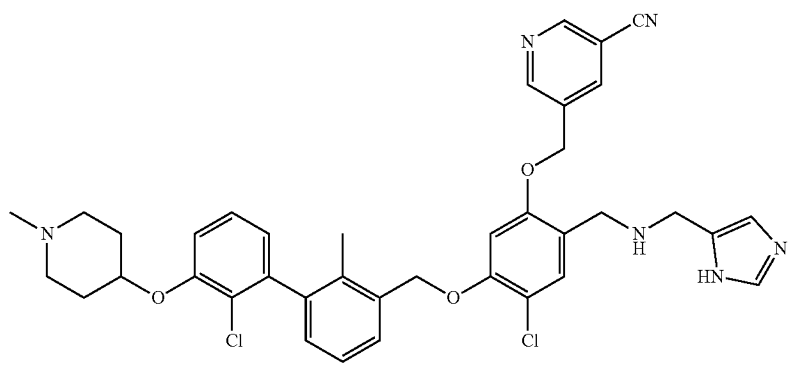 [SMILES: Cc1c(COc2cc(OCc3cncc(C#N)c3)c(CNCc3cnc[nH]3)cc2Cl)cccc1-c1cccc(OC2CCN(C)CC2)c1Cl]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 5-50% B over 20 minutes, then a 5-minute hold at 100% B; Flow: 20 mL/min. Fractions containing the desired product were combined and dried via centrifugal evaporation and its estimated purity by LCMS analysis was 98%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.3%; Observed Mass: 697.15; Retention Time: 1.47 min. Injection 2 conditions: Column: Waters XBridge C18, 2.1 mm×50 mm, 1.7 m particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.3%; Observed Mass: 697.2; Retention Time: 1.73 min.

Example 2048: 5-((4-chloro-5-((2'-chloro-2-methyl-3'-((1-methylpiperidin-4-yl)oxy)-[1,1'-biphenyl]-3-yl)methoxy)-2-((methyl(thiazol-5-ylmethyl)amino)methyl) phenoxy)methyl)nicotinonitrile

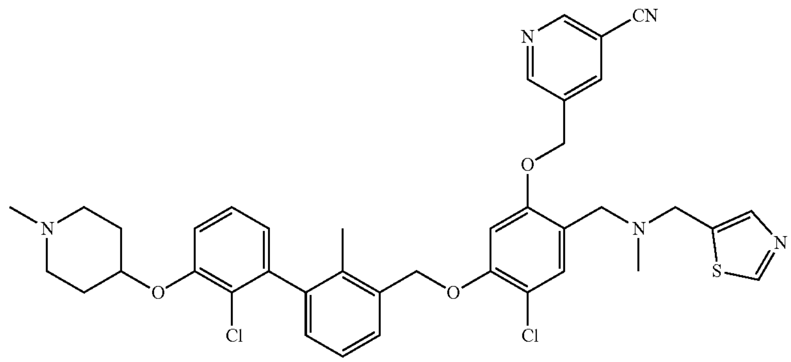 [SMILES: Cc1c(COc2cc(OCc3cncc(C#N)c3)c(CN(C)Cc3cncs3)cc2Cl)cccc1-c1cccc(OC2CCN(C)CC2)c1Cl]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 41-81% B over 20 minutes, then a 4-minute hold at 100% B; Flow: 20 mL/min. Fractions containing the desired product were combined and dried via centrifugal evaporation and its estimated purity by LCMS analysis was 98%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.3%; Observed Mass: 728.14; Retention Time: 2.32 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.8%; Observed Mass: 728.19; Retention Time: 1.56 min.

Example 2049: 5-((2-((((1H-imidazol-5-yl)methyl)(methyl)amino)methyl)-4-chloro-5-((2'-chloro-2-methyl-3'-((1-methylpiperidin-4-yl)oxy)-[1,1'-biphenyl]-3-yl)methoxy)phenoxy)methyl)nicotinonitrile

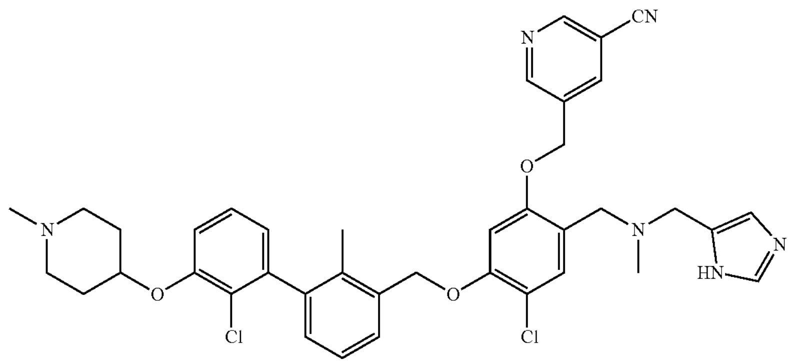 [SMILES: Cc1c(COc2cc(OCc3cncc(C#N)c3)c(CN(C)Cc3cnc[nH]3)cc2Cl)cccc1-c1cccc(OC2CCN(C)CC2)c1Cl]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 20 minutes, then a 5-minute hold at 100% B; Flow: 20 mL/min. Fractions containing the desired product were combined and dried via centrifugal evaporation and its estimated purity by LCMS analysis was 98%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.5%; Observed Mass: 711.15; Retention Time: 1.36 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.1%; Observed Mass: 711.19; Retention Time: 1.75 min Example 2050: (R)-1-(3-((3'-((4-((((1H-imidazol-2-yl)methyl)amino)methyl)-2-chloro-5-(pyrimidin-5-ylmethoxy)phenoxy)methyl)-2,2'-dimethyl-[1,1'-biphenyl]-3-yl)oxy)propyl)pyrrolidin-3-ol

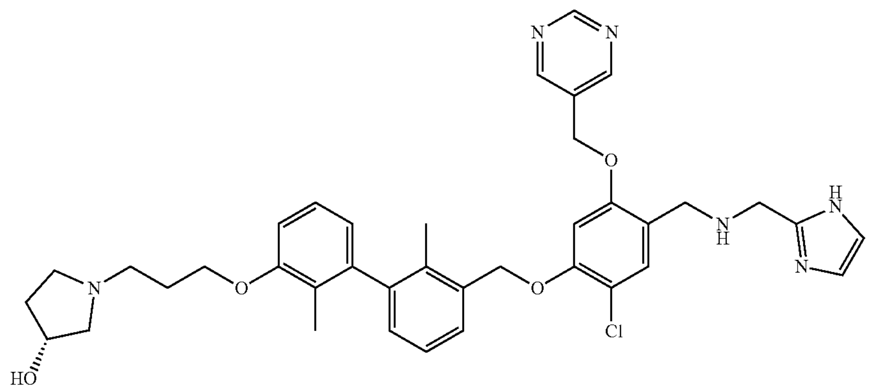 [SMILES: Cc1c(COc2cc(OCc3cncnc3)c(CNCc3ncc[nH]3)cc2Cl)cccc1-c1cccc(OCCCN2CC[C@@H](O)C2)c1C]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 20% B, 20-60% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 97%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 683.26; Retention Time: 1.68 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.7%; Observed Mass: 683.23; Retention Time: 1.25 min.

Example 2051: (R)-1-(3-((3'-((4-((((1H-pyrazol-4-yl)methyl)amino)methyl)-2-chloro-5-(pyrimidin-5-ylmethoxy)phenoxy)methyl)-2,2'-dimethyl-[1,1'-biphenyl]-3-yl)oxy)propyl)pyrrolidin-3-ol

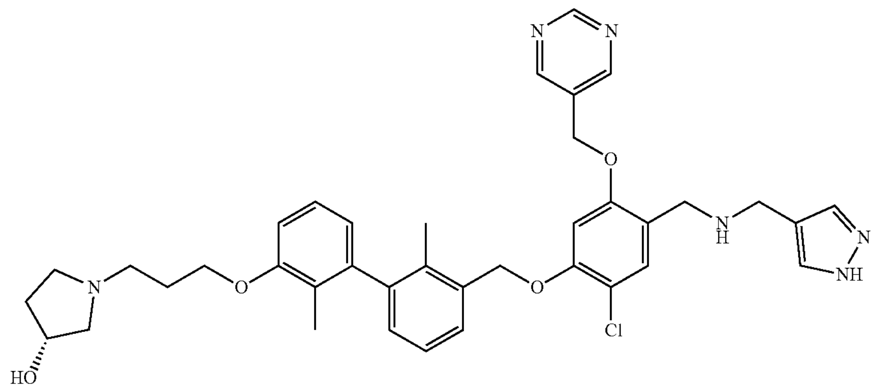 [SMILES: Cc1c(COc2cc(OCc3cncnc3)c(CNCc3cn[nH]c3)cc2Cl)cccc1-c1cccc(OCCCN2CC[C@@H](O)C2)c1C]

The crude material was purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 18% B, 18-58% B over 25 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 683.25; Retention Time: 1.32 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.2%; Observed Mass: 683.26; Retention Time: 1.58 min.

Example 2052: 5-((2-((((1H-pyrazol-4-yl)methyl)amino)methyl)-4-chloro-5-((2'-chloro-2-methyl-3'-((4-(pyrrolidin-1-yl)cyclohexyl)oxy)-[1,1'-biphenyl]-3-yl)methoxy)phenoxy)methyl)nicotinonitrile

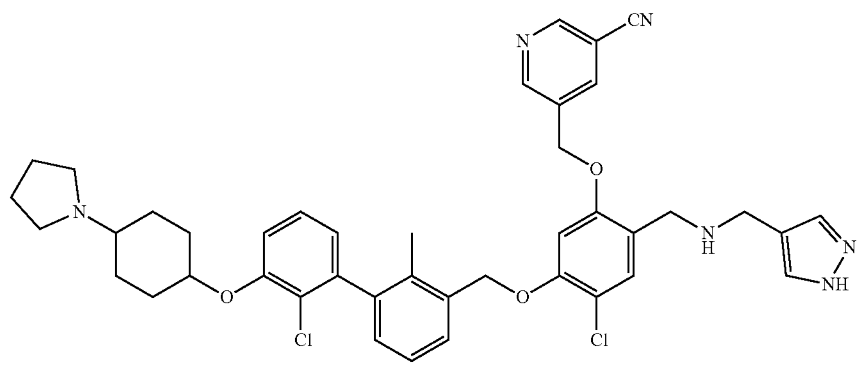 [SMILES: Cc1c(COc2cc(OCc3cncc(C#N)c3)c(CNCc3cn[nH]c3)cc2Cl)cccc1-c1cccc(OC2CCC(N3CCCC3)CC2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 17% B, 17-57% B over 25 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 94%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 751.24, 751.24; Retention Time: 1.69, 1.72 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 94.2%; Observed Mass: 751.2, 751.2; Retention Time: 1.37, 1.4 min Example 2053: 5-((2-((((1H-imidazol-2-yl)methyl)amino)methyl)-4-chloro-5-((2'-chloro-2-methyl-3'-((4-(pyrrolidin-1-yl)cyclohexyl)oxy)-[1,1'-biphenyl]-3-yl)methoxy)phenoxy)methyl)nicotinonitrile

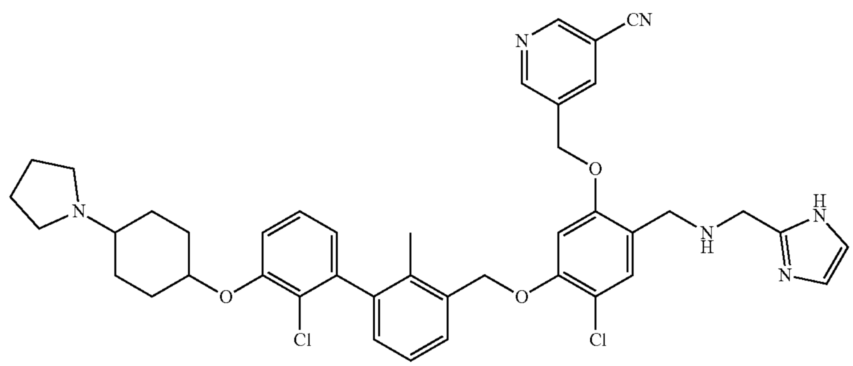 [SMILES: Cc1c(COc2cc(OCc3cncc(C#N)c3)c(CNCc3ncc[nH]3)cc2Cl)cccc1-c1cccc(OC2CCC(N3CCCC3)CC2)c1Cl]

The crude material was purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 10% B, 10-50% B over 25 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.5%; Observed Mass: 751.24; Retention Time: 1.61 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.9%; Observed Mass: 751.21; Retention Time: 1.49 min.

Example 2054: N-((1H-pyrazol-4-yl)methyl)-1-(5-chloro-4-((2'-chloro-2-methyl-3'-((1-methylpiperidin-3-yl)methoxy)-[1,1'-biphenyl]-3-yl)methoxy)-2-(pyridazin-3-ylmethoxy)phenyl)methanamine

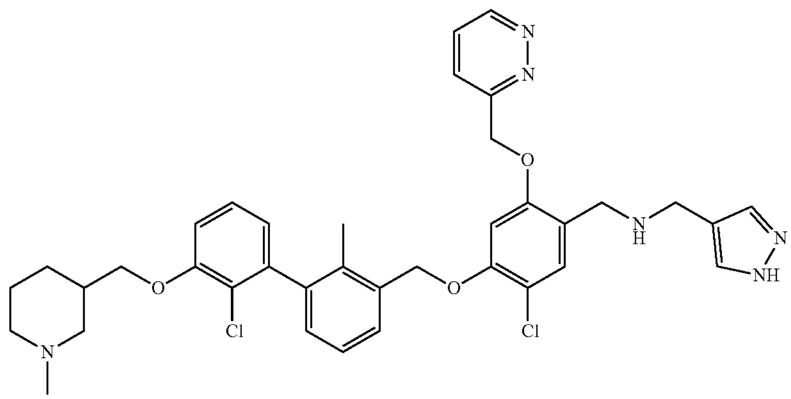 [SMILES: Cc1c(COc2cc(OCc3cccnn3)c(CNCc3cn[nH]c3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 15% B, 15-55% B over 20 minutes, then a 5-minute hold at 100% B; Flow Rate: 20 mL/min; Column Temperature: 25 C. Fraction collection was triggered by UV signals. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.6%; Observed Mass: 687.2; Retention Time: 1.26 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.7%; Observed Mass: 687.18; Retention Time: 1.66 min.

Example 2055: N-((1H-imidazol-2-yl)methyl)-1-(5-chloro-4-((2'-chloro-2-methyl-3'-((1-methylpiperidin-3-yl)methoxy)-[1,1'-biphenyl]-3-yl)methoxy)-2-(pyridazin-3-ylmethoxy)phenyl)methanamine

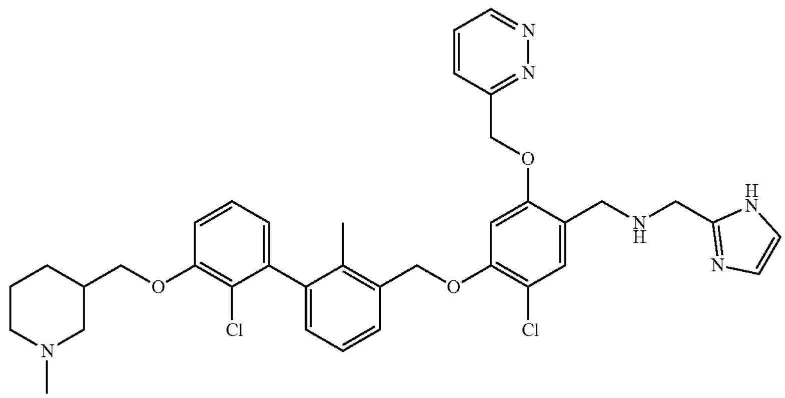 [SMILES: Cc1c(COc2cc(OCc3cccnn3)c(CNCc3ncc[nH]3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 12% B, 12-52% B over 20 minutes, then a 5-minute hold at 100% B; Flow Rate: 20 mL/min; Column Temperature: 25 C. Fraction collection was triggered by MS and UV signals. Fractions containing the desired product were combined and dried via centrifugal evaporation. The material was further purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 7% B, 7-47% B over 22 minutes, then a 5-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 86%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 687.21; Retention Time: 1.38 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 86.1%; Observed Mass: 687.21; Retention Time: 1.5 min.

Example 2056: N-((1H-pyrazol-4-yl)methyl)-1-(5-chloro-4-((2'-chloro-2-methyl-3'-((1-methylpiperidin-3-yl)methoxy)-[1,1'-biphenyl]-3-yl)methoxy)-2-methoxyphenyl)methanamine

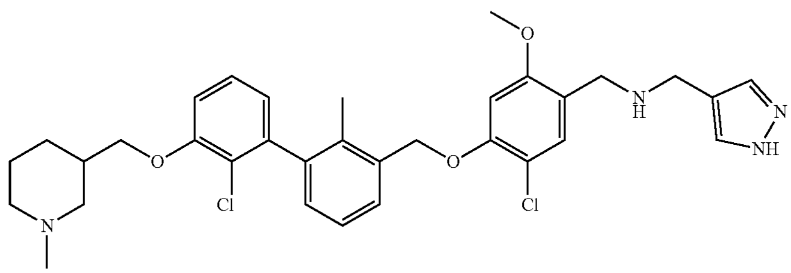 [SMILES: COc1cc(OCc2cccc(-c3cccc(OCC4CCCN(C)C4)c3Cl)c2C)c(Cl)cc1CNCc1cn[nH]c1]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 16% B, 16-56% B over 25 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 100%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 609.19; Retention Time: 1.31 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 609.21; Retention Time: 1.65 min.

Example 2057: N-((1H-imidazol-2-yl)methyl)-1-(5-chloro-4-((2'-chloro-2-methyl-3'-((1-methylpiperidin-3-yl)methoxy)-[1,1'-biphenyl]-3-yl)methoxy)-2-methoxyphenyl)methanamine

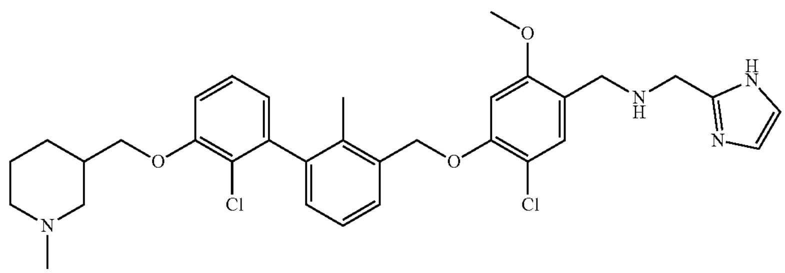 [SMILES: COc1cc(OCc2cccc(-c3cccc(OCC4CCCN(C)C4)c3Cl)c2C)c(Cl)cc1CNCc1ncc[nH]1]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 13% B, 13-53% B over 25 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.6%; Observed Mass: 609.21; Retention Time: 1.52 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.3%; Observed Mass: 609.22; Retention Time: 1.49 min.

Example 2058: N-(5-chloro-4-((2'-chloro-2-methyl-3'-((1-methylpiperidin-3-yl)methoxy)-[1,1'-biphenyl]-3-yl)methoxy)-2-(pyrazin-2-ylmethoxy)benzyl)-1-(pyridazin-3-yl)methanamine

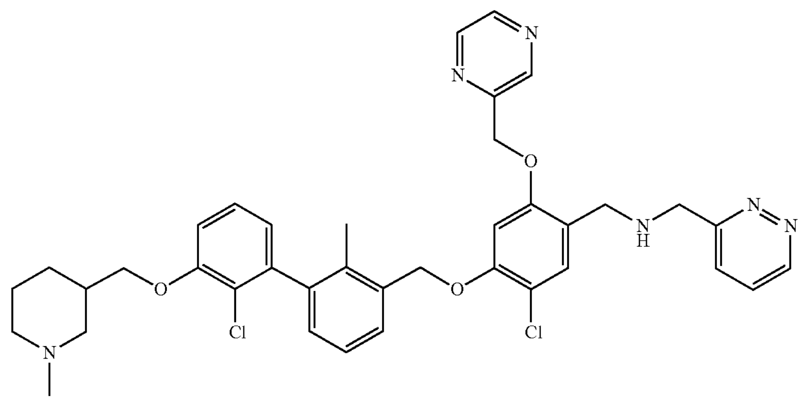 [SMILES: Cc1c(COc2cc(OCc3cnccn3)c(CNCc3cccnn3)cc2Cl)cccc1-c1cccc(OCC2CCCN(C)C2)c1Cl]

The crude material was purified via preparative LC/MS with the following conditions: Column: XBridge C18, 200 mm×19 mm, 5-µm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 30% B, 30-70% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 95%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.0%; Observed Mass: 699.13; Retention Time: 1.76 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.5%; Observed Mass: 699.13; Retention Time: 1.5 min.

Example 2059: N-(5-chloro-4-((2'-chloro-2-methyl-3'-((1-methylpiperidin-3-yl)methoxy)-[1,1'-biphenyl]-3-yl)methoxy)-2-(pyrazin-2-ylmethoxy)benzyl)-1-(pyrimidin-2-yl)methanamine

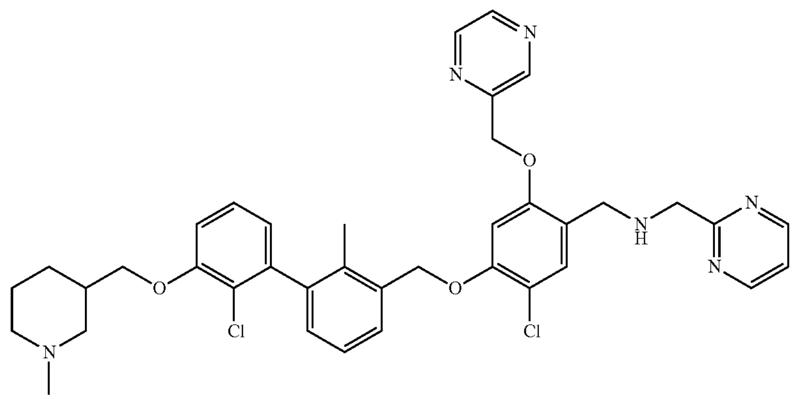 [SMILES: Cc1c(COc2cc(OCc3cnccn3)c(CNCc3ncccn3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 13% B, 13-53% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. The material was further purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 10% B, 10-100% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 99%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.2%; Observed Mass: 699.17; Retention Time: 1.84 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 699.18; Retention Time: 1.46 min.

Example 2060: N-((1H-imidazol-4-yl)methyl)-1-(5-chloro-4-((2'-chloro-2-methyl-3'-((1-methylpiperidin-3-yl)methoxy)-[1,1'-biphenyl]-3-yl)methoxy)-2-(pyrazin-2-ylmethoxy)phenyl)methanamine

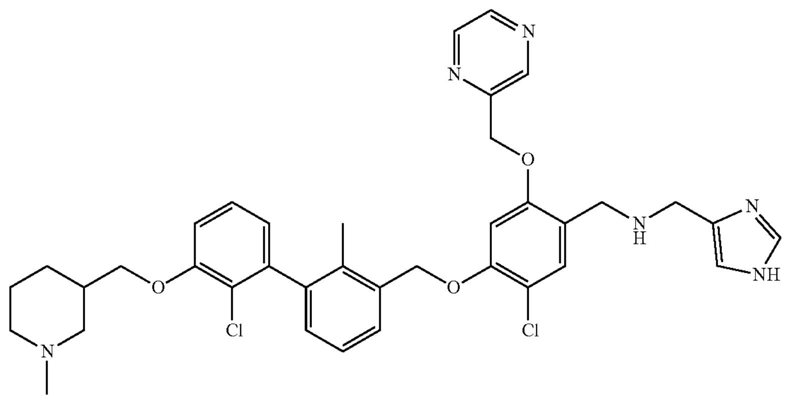 [SMILES: Cc1c(COc2cc(OCc3cnccn3)c(CNCc3c[nH]cn3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 9% B, 9-49% B over 25 minutes, then a 4-minute hold at 100% B; Flow Rate: 20 mL/min; Column Temperature: 25 C. Fraction collection was triggered by MS signals. Fractions containing the desired product were combined and dried via centrifugal evaporation. The material was further purified via preparative LC/MS with the following conditions: Column: XBridge Shield RP18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 21% B, 21-61% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 100%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 686.96; Retention Time: 1.66 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 686.98; Retention Time: 1.33 min.

Example 2061: 5-((4-chloro-5-((2'-chloro-2-methyl-3'-(pyrimidin-5-ylmethoxy)-[1,1'-biphenyl]-3-yl)methoxy)-2-(((pyridazin-3-ylmethyl)amino)methyl)phenoxy)methyl)nicotinonitrile

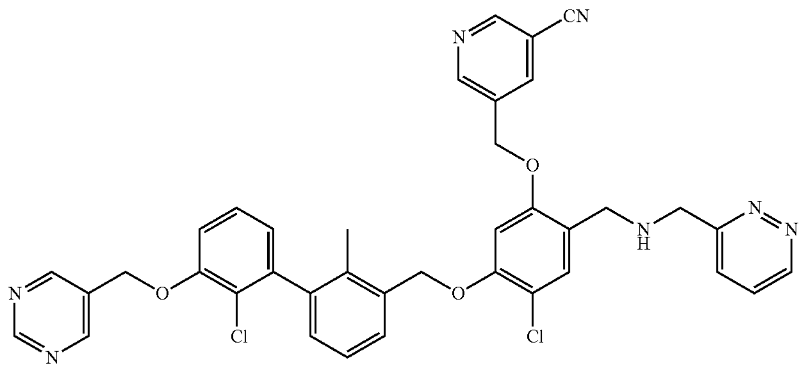 [SMILES: Cc1c(COc2cc(OCc3cncc(C#N)c3)c(CNCc3cccnn3)cc2Cl)cccc1-c1cccc(OCc2cncnc2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 33% B, 33-73% B over 20 minutes, then a 4-minute hold at 100% B; Flow Rate: 20 mL/min; Column Temperature: 25 C. Fraction collection was triggered by MS signals. Fractions containing the desired product were combined and dried via centrifugal evaporation and its estimated purity by LCMS analysis was 100%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 704.12; Retention Time: 1.85 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 704.1; Retention Time: 1.7 min.

Example 2062: 5-((2-((((1H-imidazol-4-yl)methyl)amino)methyl)-4-chloro-5-((2'-chloro-2-methyl-3'-(pyrimidin-5-ylmethoxy)-[1,1'-biphenyl]-3-yl)methoxy)phenoxy)methyl)nicotinonitrile

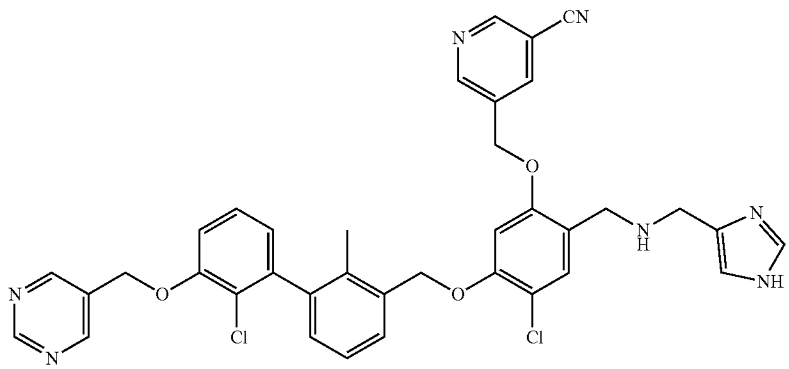 [SMILES: Cc1c(COc2cc(OCc3cncc(C#N)c3)c(CNCc3c[nH]cn3)cc2Cl)cccc1-c1cccc(OCc2cncnc2)c1Cl]

The crude material was purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 18% B, 18-58% B over 25 minutes, then a 4-minute hold at 100% B; Flow Rate: 20 mL/min; Column Temperature: 25 C. Fraction collection was triggered by MS signals. Fractions containing the desired product were combined and dried via centrifugal evaporation and its estimated purity by LCMS analysis was 95%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 94.7%; Observed Mass: 692.13; Retention Time: 1.81 min. Injection 2 conditions: Column: Waters XBridge C18, 2.1 mm×50 mm, 1.7 m particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.0%; Observed Mass: 692.12; Retention Time: 1.58 min.

Example 2063: 5-((4-chloro-5-((2'-chloro-2-methyl-3'-(pyrimidin-5-ylmethoxy)-[1,1'-biphenyl]-3-yl)methoxy)-2-(((pyrimidin-2-ylmethyl)amino)methyl)phenoxy)methyl)nicotinonitrile

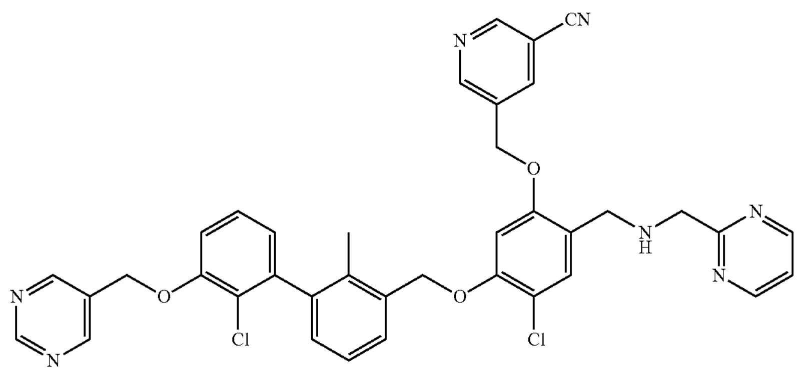 [SMILES: Cc1c(COc2cc(OCc3cncc(C#N)c3)c(CNCc3ncccn3)cc2Cl)cccc1-c1cccc(OCc2cncnc2)c1Cl]

The crude material was purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 23% B, 23-63% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 100%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 704.11; Retention Time: 1.86 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 704.11; Retention Time: 1.65 min.

Example 2064: 5-((4-chloro-5-((2'-chloro-2-methyl-3'-((1-(3,3,3-trifluoropropyl) piperidin-3-yl) methoxy)-[1,1'-biphenyl]-3-yl)methoxy)-2-(((pyridazin-3-ylmethyl)amino)methyl)phenoxy) methyl)nicotinonitrile

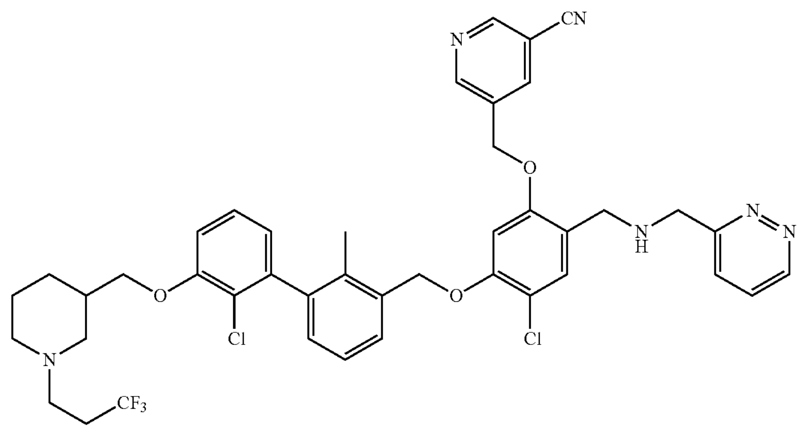 [SMILES: Cc1c(COc2cc(OCc3cncc(C#N)c3)c(CNCc3cccnn3)cc2Cl)cccc1-c1cccc(OCC2CCCN(CCC(F)(F)F)C2)c1Cl]

The crude material was purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 22% B, 22-62% B over 20 minutes, then a 4-minute hold at 100% B; Flow Rate: 20 mL/min; Column Temperature: 25 C. Fraction collection was triggered by MS signals. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.3%; Observed Mass: 805.18; Retention Time: 2.48 min. Injection 2 conditions: Column: Waters XBridge C18, 2.1 mm×50 mm, 1.7 m particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.4%; Observed Mass: 805.24; Retention Time: 1.62 min.

Example 2065: 5-((2-((((1H-imidazol-4-yl)methyl) amino)methyl)-4-chloro-5-((2'-chloro-2-methyl-3'-((1-(3,3,3-trifluoropropyl)piperidin-3-yl)methoxy)-[1,1'-biphenyl]-3-yl)methoxy)phenoxy)methyl) nicotinonitrile

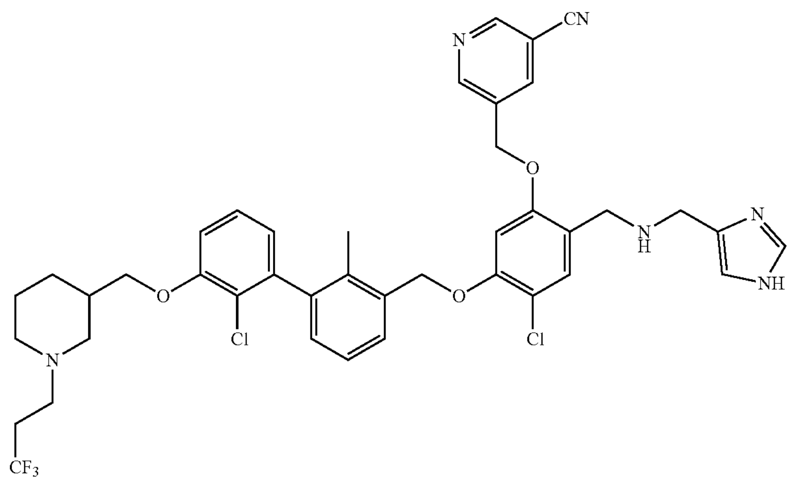 [SMILES: Cc1c(COc2cc(OCc3cncc(C#N)c3)c(CNCc3c[nH]cn3)cc2Cl)cccc1-c1cccc(OCC2CCCN(CCC(F)(F)F)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 43% B, 43-83% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. The material was further purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 12% B, 12-52% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 97%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.6%; Observed Mass: 793.35; Retention Time: 2.31 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.8%; Observed Mass: 793.32; Retention Time: 1.53 min.

Example 2066: 5-((4-chloro-5-((2'-chloro-2-methyl-3'-((1-(3,3,3-trifluoropropyl)piperidin-3-yl)methoxy)-[1,1'-biphenyl]-3-yl)methoxy)-2-(((pyrimidin-2-ylmethyl)amino)methyl)phenoxy)methyl)nicotinonitrile

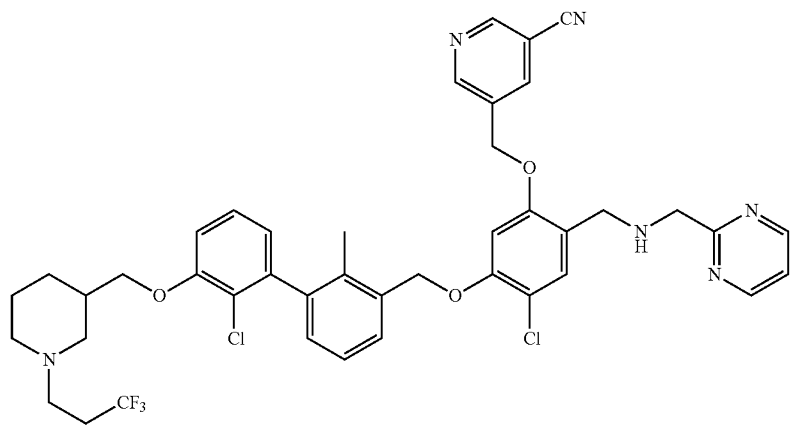 [SMILES: Cc1c(COc2cc(OCc3cncc(C#N)c3)c(CNCc3ncccn3)cc2Cl)cccc1-c1cccc(OCC2CCCN(CCC(F)(F)F)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 50% B, 50-90% B over 20 minutes, then a 4-minute hold at 100% B; Flow Rate: 20 mL/min; Column Temperature: 25 C. Fraction collection was triggered by MS signals. Fractions containing the desired product were combined and dried via centrifugal evaporation and its estimated purity by LCMS analysis was 99%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 805; Retention Time: 2.6 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.9%; Observed Mass: 805.3; Retention Time: 1.67 min.

Example 2067: 5-((2-((((1H-pyrazol-4-yl)methyl)amino)methyl)-4-chloro-5-((2'-chloro-2-methyl-3'-((1-(3,3,3-trifluoropropyl)piperidin-3-yl)methoxy)-[1,1'-biphenyl]-3-yl)methoxy)phenoxy)methyl)nicotinonitrile

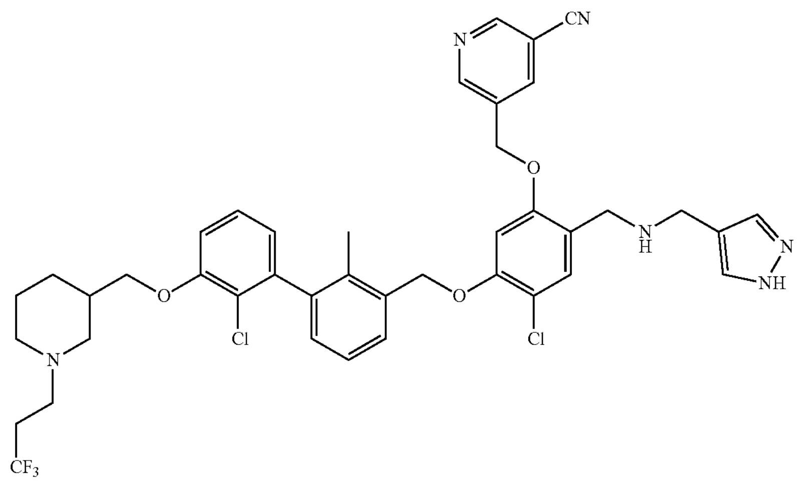 [SMILES: Cc1c(COc2cc(OCc3cncc(C#N)c3)c(CNCc3cn[nH]c3)cc2Cl)cccc1-c1cccc(OCC2CCCN(CCC(F)(F)F)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 43% B, 43-83% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. The material was further purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 20% B, 20-60% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.8%; Observed Mass: 793.09; Retention Time: 2.34 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 793.3; Retention Time: 1.64 min.

Example 2068: 5-((2-((((2H-1,2,3-triazol-4-yl)methyl)amino)methyl)-4-chloro-5-((2'-chloro-2-methyl-3'-((1-(3,3,3-trifluoropropyl)piperidin-3-yl)methoxy)-[1,1'-biphenyl]-3-yl)methoxy)phenoxy)methyl)nicotinonitrile

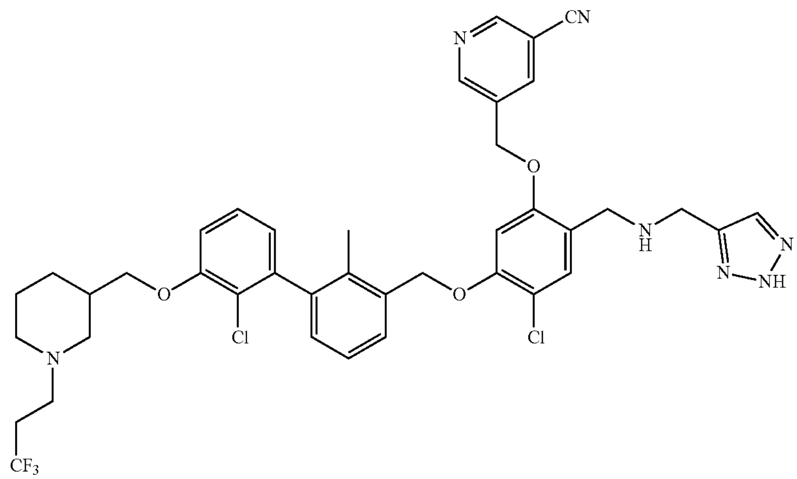 [SMILES: Cc1c(COc2cc(OCc3cncc(C#N)c3)c(CNCc3cn[nH]n3)cc2Cl)cccc1-c1cccc(OCC2CCCN(CCC(F)(F)F)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 47% B, 47-87% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 98%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.3%; Observed Mass: 794.32; Retention Time: 1.64 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.3%; Observed Mass: 794.3; Retention Time: 2.53 min.

Example 2501: (R)-5-((4-chloro-5-((3'-(3-(3-hydroxypyrrolidin-1-yl)propoxy)-2,2'-dimethyl-[1,1'-biphenyl]-3-yl)methoxy)-2-((methyl(pyridin-3-ylmethyl)amino)methyl)phenoxy)methyl)nicotinonitrile

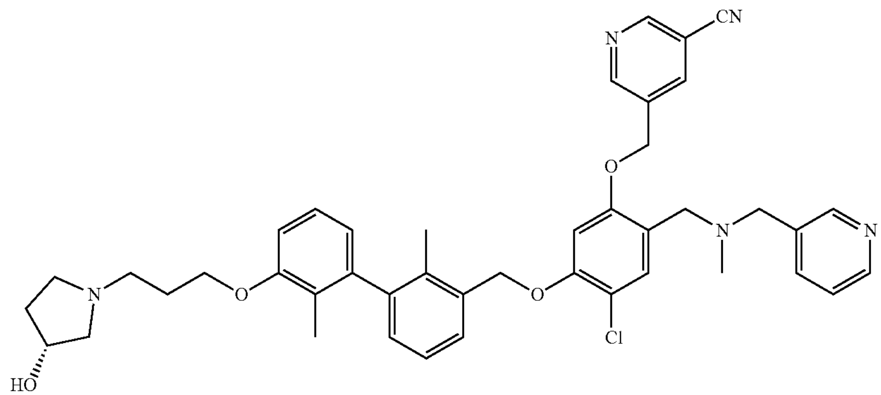

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 28-68% B over 20 minutes, then a 5-minute hold at 100% B; Flow: 20 mL/min. Fractions containing the desired product were combined and dried via centrifugal evaporation and its estimated purity by LCMS analysis was 94%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1results: Purity: 95.0%; Observed Mass: 732.23; Retention Time: 1.41 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 93.9%; Observed Mass: 732.25; Retention Time: 2.06 min.

Example 2502: ((R)-5-((4-chloro-5-((3'-(3-(3-hydroxypyrrolidin-1-yl)propoxy)-2,2'-dimethyl-[1,1'-biphenyl]-3-yl)methoxy)-2-((1-methyl-1,4,6,7-tetrahydro-5H-imidazo[4,5-c]pyridin-5-yl)methyl)phenoxy)methyl)nicotinonitrile

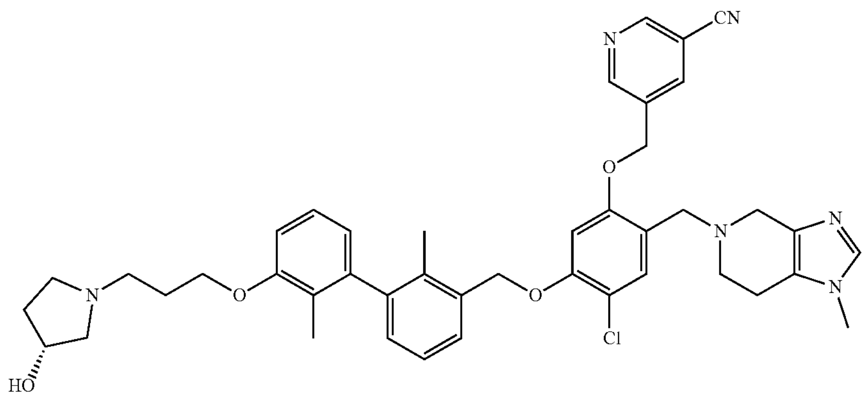 [SMILES: Cc1c(COc2cc(OCc3cncc(C#N)c3)c(CN3CCc4c(ncn4C)C3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 23-63% B over 20 minutes, then a 6-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 8-48% B over 20 minutes, then a 6-minute hold at 100% B; Flow: 20 mL/min. Fractions containing the desired product were combined and dried via centrifugal evaporation and its estimated purity by LCMS analysis was 100%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 100%; Observed Mass: 747.25; Retention Time: 1.60 min.

Example 2503: (R)-5-((4-chloro-5-((3'-(3-(3-hydroxypyrrolidin-1-yl)propoxy)-2,2'-dimethyl-[1,1'-biphenyl]-3-yl)methoxy)-2-((2-methyl-6,7-dihydrothiazolo[5,4-c]pyridin-5(4H) yl)methyl)phenoxy)methyl)nicotinonitrile

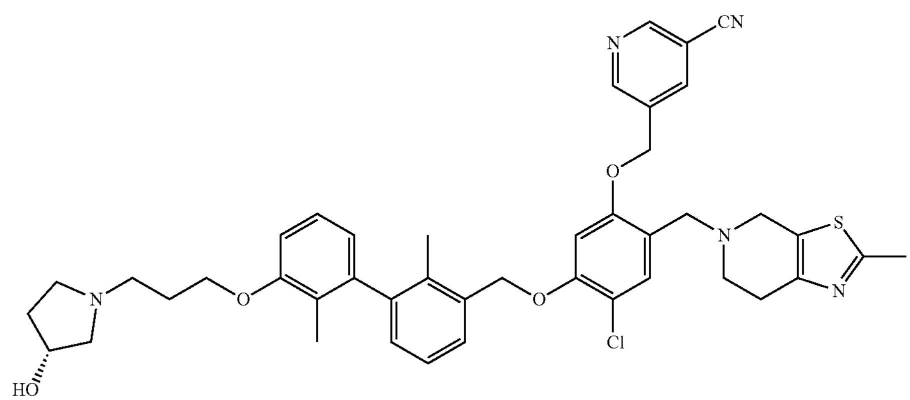 [SMILES: Cc1nc2c(s1)CN(Cc1cc(Cl)c(OCc3cccc(-c4cccc(OCCCN5CC[C@@H](O)C5)c4C)c3C)cc1OCc1cncc(C#N)c1)CC2]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 31-71% B over 20 minutes, then a 5-minute hold at 100% B; Flow: 20 mL/min. Fractions containing the desired product were combined and dried via centrifugal evaporation and its estimated purity by LCMS analysis was 97%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×

50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 97.0%; Observed Mass: 764.25; Retention Time: 1.96 min.

Example 2504: (R)-5-((4-chloro-5-((3'-(3-(3-hydroxypyrrolidin-1-yl)propoxy)-2,2'-dimethyl-[1,1'-biphenyl]-3-yl)methoxy)-2-(((2-(4-methylthiazol-5-yl)ethyl)amino)methyl)phenoxy)methyl) nicotinonitrile

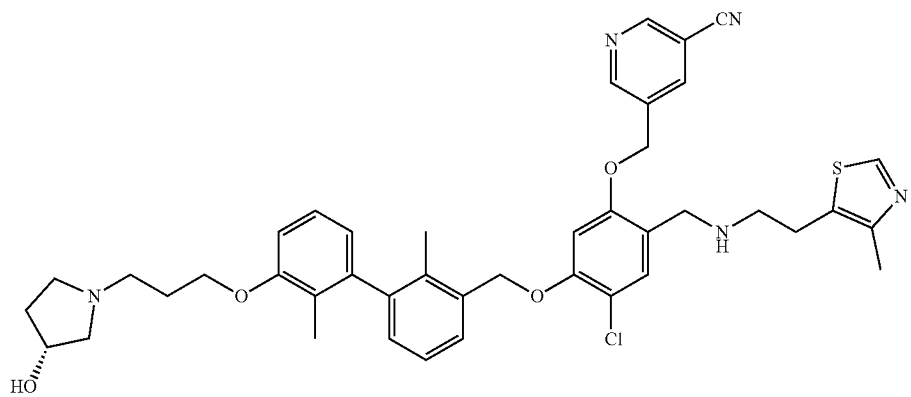

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 20 minutes, then a 5-minute hold at 100% B; Flow: 20 mL/min. Fractions containing the desired product were combined and dried via centrifugal evaporation and its estimated purity by LCMS analysis was 100%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 100.0%; Observed Mass: 752.25; Retention Time: 1.84 min.

Example 2505: (R)-5-((2-(((2-(1H-benzo[d]imidazol-2-yl)ethyl)amino)methyl)-4-chloro-5-((3'-(3-(3 hydroxypyrrolidin-1-yl)propoxy)-2,2'-dimethyl-[1, 1'-biphenyl]-3yl)methoxy)phenoxy)methyl)nicotinonitrile

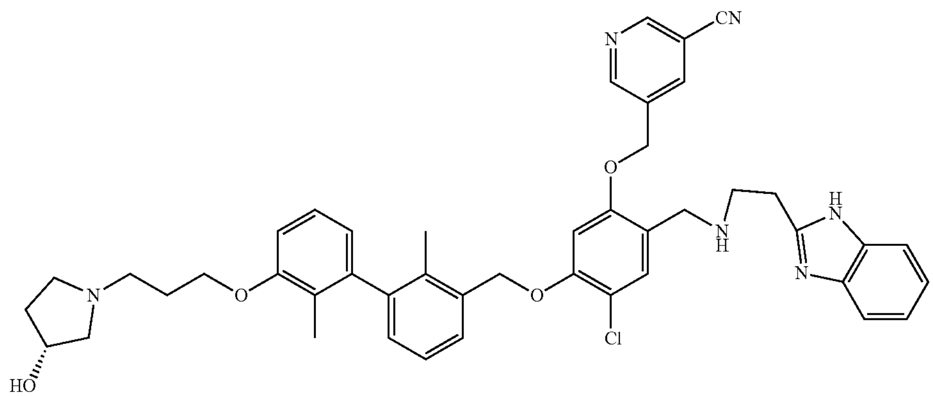 [SMILES: Cc1c(COc2cc(OCc3cncc(C#N)c3)c(CNCCc3nc4ccccc4[nH]3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 17-57% B over 20 minutes, then a 5-minute hold at 100% B; Flow: 20 mL/min. Fractions containing the desired product were combined and dried via centrifugal evaporation and its estimated purity by LCMS analysis was 96%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 96.0%; Observed Mass: 771.25; Retention Time: 1.54 min.

Example 2506: (R)-5-((4-chloro-5-((3'-(3-(3-hydroxypyrrolidin-1-yl)propoxy)-2,2'-dimethyl-[1,1'-biphenyl]-3-yl)methoxy)-2-(((2-(thiazol-4-yl)ethyl)amino)methyl)phenoxy)methyl)nicotinonitrile

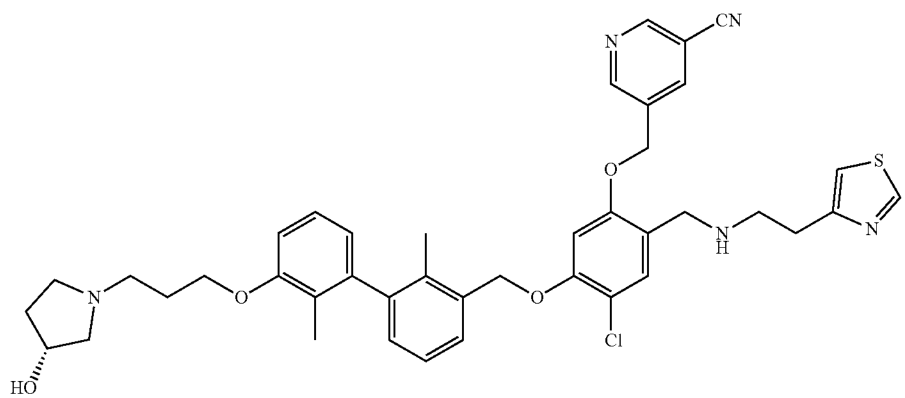 [SMILES: Cc1c(COc2cc(OCc3cncc(C#N)c3)c(CNCCc3cscn3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 16-56% B over 20 minutes, then a 5-minute hold at 100% B; Flow: 20 mL/min. Fractions containing the desired product were combined and dried via centrifugal evaporation and its estimated purity by LCMS analysis was 97%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 96.7%; Observed Mass: 738.25; Retention Time: 1.49 min.

Example 2507: (R)-5-((4-chloro-5-((3'-(3-(3-hydroxypyrrolidin-1-yl)propoxy)-2,2'-dimethyl-[1,1'-biphenyl]-3-yl)methoxy)-2-((methyl(2-(thiazol-4-yl)ethyl)amino)methyl)phenoxy)methyl)nicotinonitrile

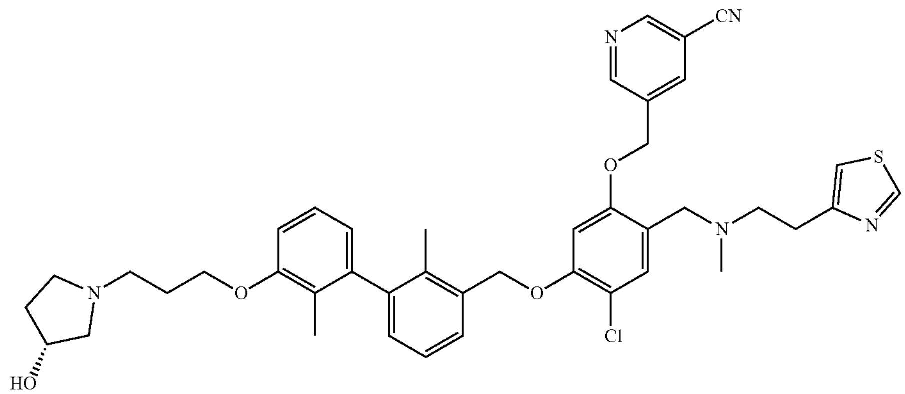 [SMILES: Cc1c(COc2cc(OCc3cncc(C#N)c3)c(CN(C)CCc3cscn3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 28-68% B over 20 minutes, then a 6-minute hold at 100% B; Flow: 20 mL/min. Fractions containing the desired product were combined and dried via centrifugal evaporation and its estimated purity by LCMS analysis was 100%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 100%; Observed Mass: 752.25; Retention Time: 1.60 min.

Example 2508: (R)-5-((2-(((2-(1H-benzo[d]imidazol-2-yl)ethyl)(methyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile

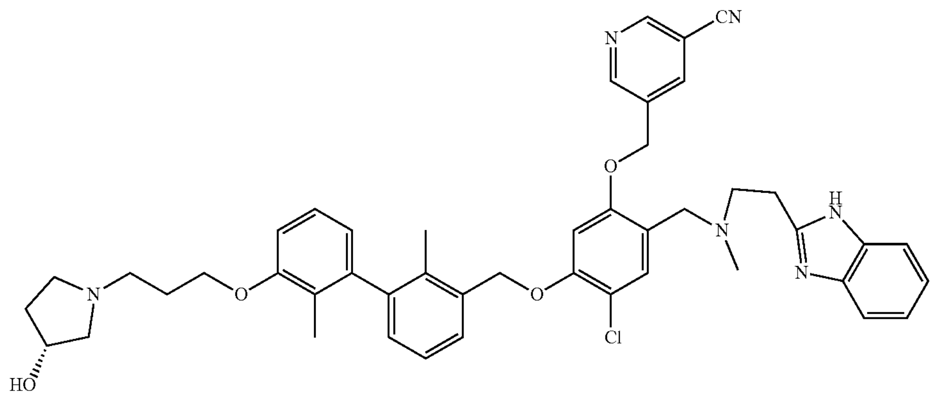 [SMILES: Cc1c(COc2cc(OCc3cncc(C#N)c3)c(CN(C)CCc3nc4ccccc4[nH]3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 28-68% B over 20 minutes, then a 6-minute hold at 100% B; Flow: 20 mL/min. Fractions containing the desired product were combined and dried via centrifugal evaporation and its estimated purity by LCMS analysis was 96%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 96.0%; Observed Mass: 785.25; Retention Time: 1.62 min.

Example 2509: (R)-5-((2-(((2-(1H-1,2,4-triazol-5-yl)ethyl)(methyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile

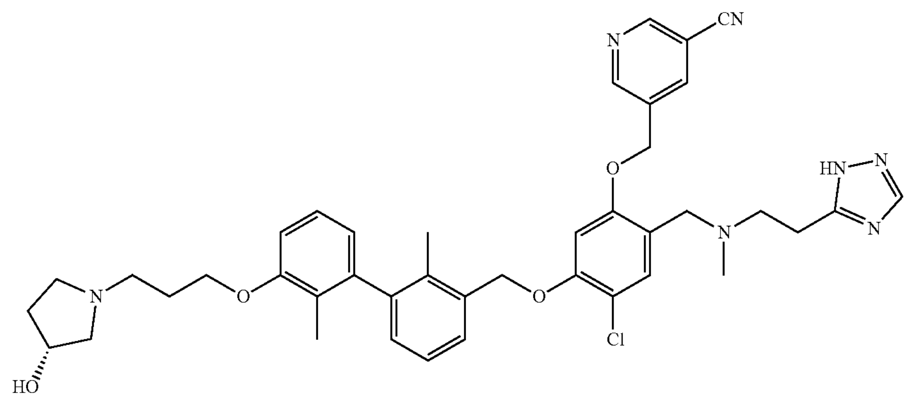 [SMILES: Cc1c(COc2cc(OCc3cncc(C#N)c3)c(CN(C)CCc3ncn[nH]3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 13-53% B over 20 minutes, then a 5-minute hold at 100% B; Flow: 20 mL/min. Fractions containing the desired product were combined and dried via centrifugal evaporation and its estimated purity by LCMS analysis was 95%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 95.4%; Observed Mass: 736.25; Retention Time: 1.42 min.

Example 2510: (R)-5-((4-chloro-5-((3'-(3-(3-hydroxypyrrolidin-1-yl)propoxy)-2,2'-dimethyl-[1,1'-biphenyl]-3-yl)methoxy)-2-((methyl(2-(1-methyl-1H-benzo[d]imidazol-2-yl)ethyl)amino)methyl)phenoxy)methyl)nicotinonitrile

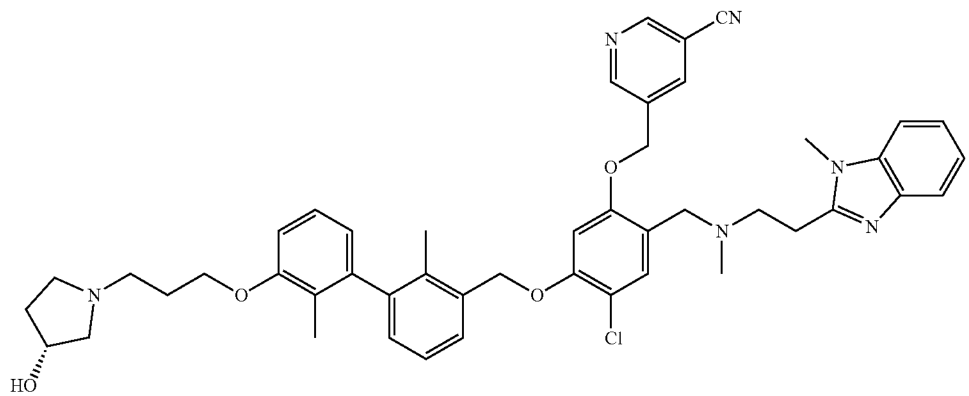 [SMILES: Cc1c(COc2cc(OCc3cncc(C#N)c3)c(CN(C)CCc3nc4ccccc4n3C)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 24-64% B over 25 minutes, then a 6-minute hold at 100% B; Flow: 20 mL/min. Fractions containing the desired product were combined and dried via centrifugal evaporation. and its estimated purity by LCMS analysis was 94%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 93.7%; Observed Mass: 799.25; Retention Time: 1.66 min.

Example 2511: (R)-5-((4-chloro-5-((3'-(3-(3-hydroxypyrrolidin-1-yl)propoxy)-2,2'-dimethyl-[1,1'-biphenyl]-3-yl)methoxy)-2-((methyl(2-(4-methylthiazol-5-yl)ethyl)amino)methyl)phenoxy)methyl)nicotinonitrile

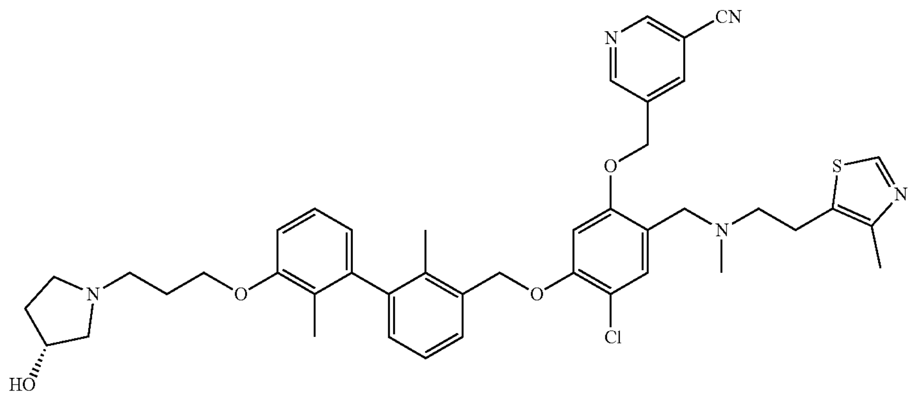 [SMILES: Cc1ncsc1CCN(C)Cc1cc(Cl)c(OCc2cccc(-c3cccc(OCCCN4CC[C@@H](O)C4)c3C)c2C)cc1OCc1cncc(C#N)c1]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 36-76% B over 20 minutes, then a 6-minute hold at 100% B; Flow: 20 mL/min. Fractions containing the desired product were combined and dried via centrifugal evaporation. and its estimated purity by LCMS analysis was 93%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 93.0%; Observed Mass: 766.25; Retention Time: 1.61 min.

Example 2512: (R)-5-((4-chloro-5-((3'-(3-(3-hydroxypyrrolidin-1-yl)propoxy)-2,2'-dimethyl-[1,1'-biphenyl]-3-yl)methoxy)-2-((1,4,6,7-tetrahydro-5H-pyrazolo[4,3-c]pyridin-5-yl)methyl)phenoxy)methyl)nicotinonitrile

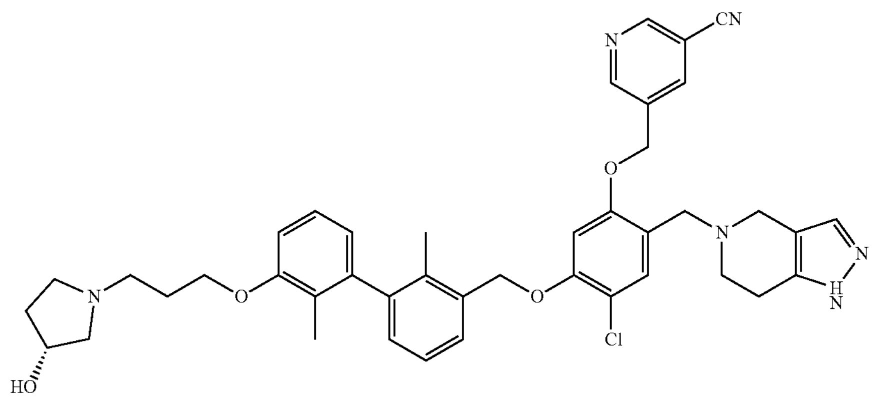 [SMILES: Cc1c(COc2cc(OCc3cncc(C#N)c3)c(CN3CCc4[nH]ncc4C3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 14-64% B over 25 minutes, then a 5-minute hold at 100% B; Flow: 20 mL/min. Fractions containing the desired product were combined and dried via centrifugal evaporation and its estimated purity by LCMS analysis was 88%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 94.9%; Observed Mass: 733.25; Retention Time: 1.45 min.

Example 2513: 5-((2-((3-(1H-pyrazol-3-yl)pyrrolidin-1-yl)methyl)-4-chloro-5-((3'-(3-((R)-3-hydroxypyrrolidin-1-yl)propoxy)-2,2'-dimethyl-[1,1'-biphenyl]-3-yl)methoxy)phenoxy)methyl)nicotinonitrile

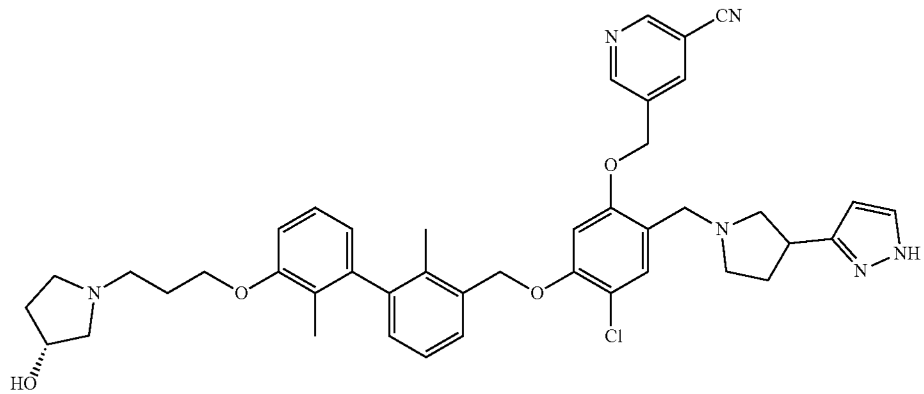 [SMILES: Cc1c(COc2cc(OCc3cncc(C#N)c3)c(CN3CCC(c4cc[nH]n4)C3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 16-56% B over 25 minutes, then a 6-minute hold at 100% B; Flow: 20 mL/min. Fractions containing the desired product were combined and dried via centrifugal evaporation and its estimated purity by LCMS analysis was 96%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 96.0%; Observed Mass: 747.25; Retention Time: 1.47 min.

Example 2514: (R)-5-((2-(((2-(1H-pyrazol-3-yl)ethyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile

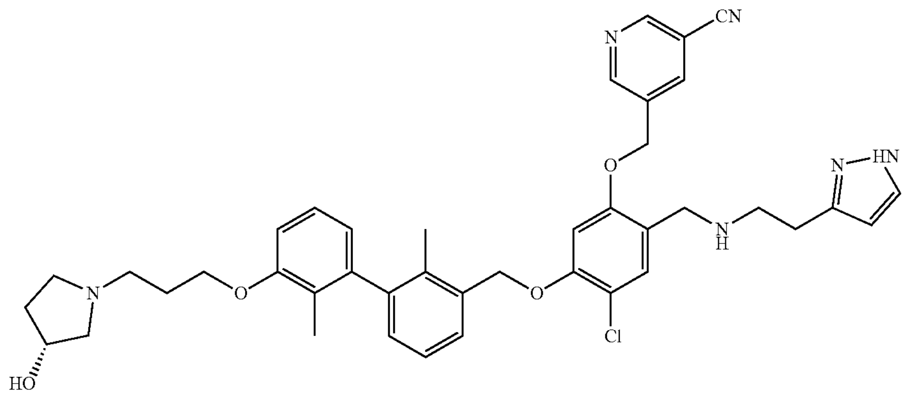 [SMILES: Cc1c(COc2cc(OCc3cncc(C#N)c3)c(CNCCc3cc[nH]n3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 19-59% B over 15 minutes, then a 5-minute hold at 100% B; Flow: 20 mL/min. Fractions containing the desired product were combined and dried via centrifugal evaporation and its estimated purity by LCMS analysis was 97%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 97.0%; Observed Mass: 721.25; Retention Time: 1.56 min.

Example 2515: (R)-5-((4-chloro-5-((3'-(3-(3-hydroxypyrrolidin-1-yl)propoxy)-2,2'-dimethyl-[1,1'-biphenyl]-3-yl)methoxy)-2-((1,4,6,7-tetrahydro-5H-imidazo[4,5-c]pyridin-5-yl)methyl)phenoxy)methyl) nicotinonitrile

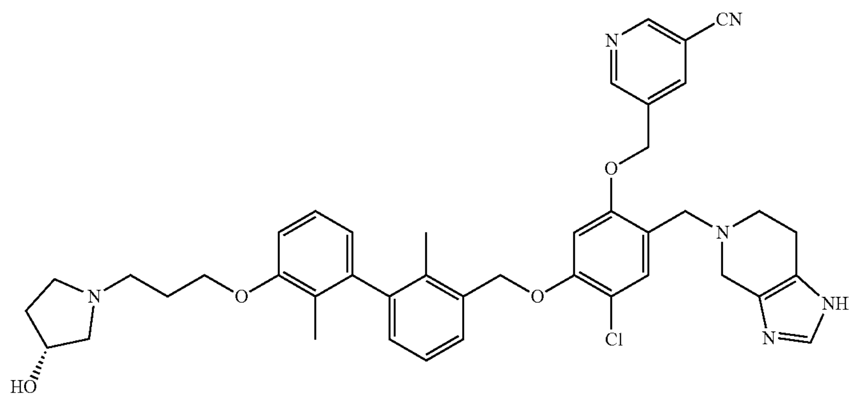 [SMILES: Cc1c(COc2cc(OCc3cncc(C#N)c3)c(CN3CCc4[nH]cnc4C3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 11-66% B over 25 minutes, then a 6-minute hold at 100% B; Flow: 20 mL/min. Fractions containing the desired product were combined and dried via centrifugal evaporation and its estimated purity by LCMS analysis was 90%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1results: Purity: 89.7%; Observed Mass: 733.22; Retention Time: 1.39 min. Injection 2 conditions: Column: Waters XBridge C18, 2.1 mm×50 mm, 1.7 m particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 91.1%; Observed Mass: 733.27; Retention Time: 1.49 min.

Example 2516: (R)-5-((4-chloro-2-(((2-(5-chloro-1H-benzo[d]imidazol-2-yl)ethyl)amino)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile

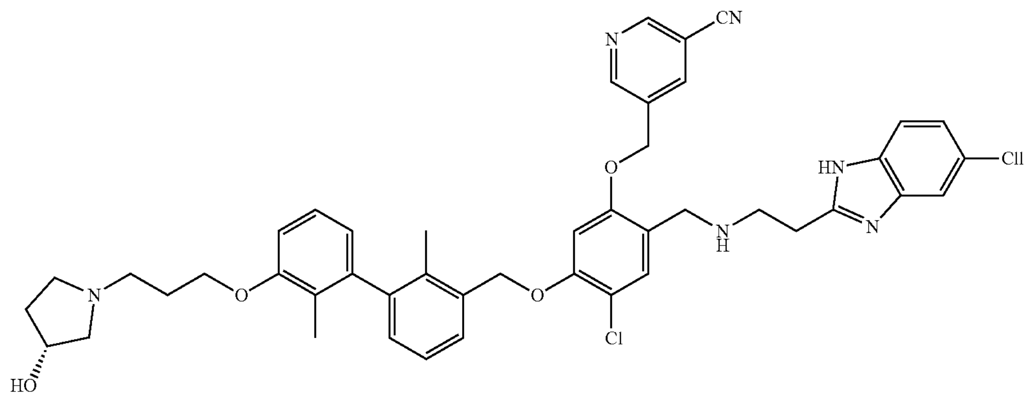

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 20 minutes, then a 5-minute hold at 100% B; Flow: 20 mL/min. Fractions containing the desired product were combined and dried via centrifugal evaporation and its estimated purity by LCMS analysis was 84%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 84.0%; Observed Mass: 805.25; Retention Time: 1.55 min.

Example 2517: (R)-5-((4-chloro-2-(((2-(5-chloro-1H-benzo[d]imidazol-2-yl)ethyl)(methyl)amino)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile

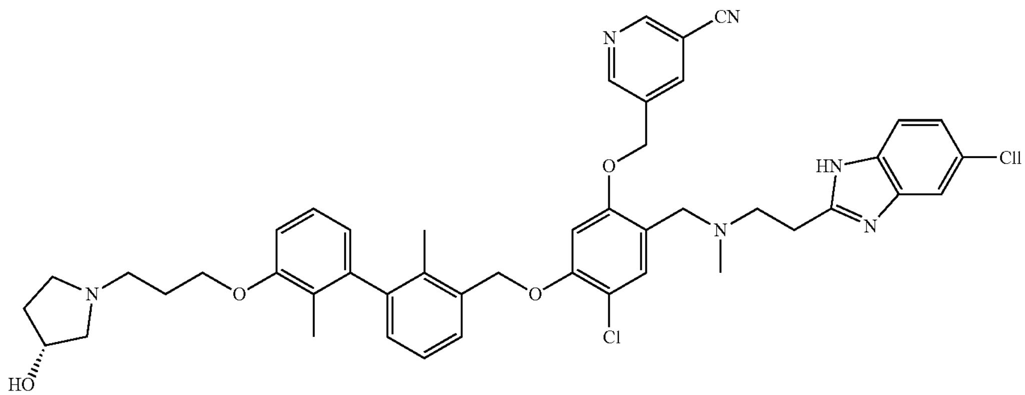

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 28-68% B over 20 minutes, then a 5-minute hold at 100% B; Flow: 20 mL/min. Fractions containing the desired product were combined and dried via centrifugal evaporation and its estimated purity by LCMS analysis was 91%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 91.0%; Observed Mass: 819.25; Retention Time: 2.01 min.

Example 2518: (R)-5-((2-(((2-(1H-pyrazol-3-yl)ethyl)(methyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile

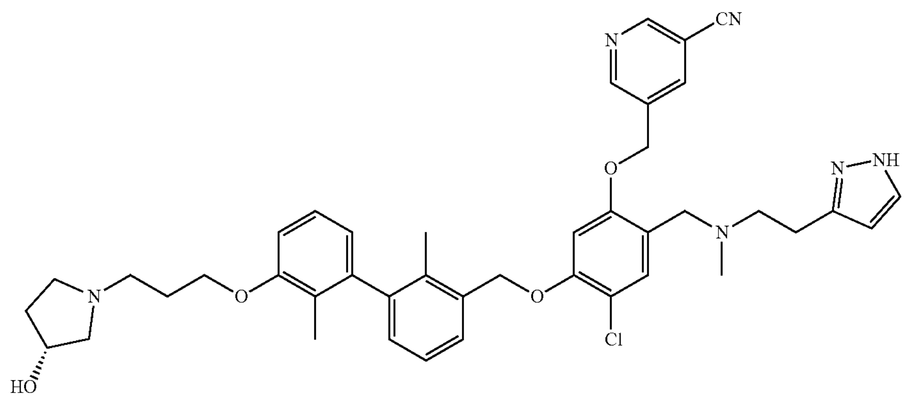 [SMILES: Cc1c(COc2cc(OCc3cncc(C#N)c3)c(CN(C)CCc3cc[nH]n3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 19-59% B over 20 minutes, then a 5-minute hold at 100% B; Flow: 20 mL/min. Fractions containing the desired product were combined and dried via centrifugal evaporation and its estimated purity by LCMS analysis was 97%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection:

MS and UV (220 nm). Injection 2 results: Purity: 97.0%; Observed Mass: 735.25; Retention Time: 1.72 min.

Example 2519: (R)-5-((2-(((2-(1H-1,2,4-triazol-5-yl)ethyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl) nicotinonitrile

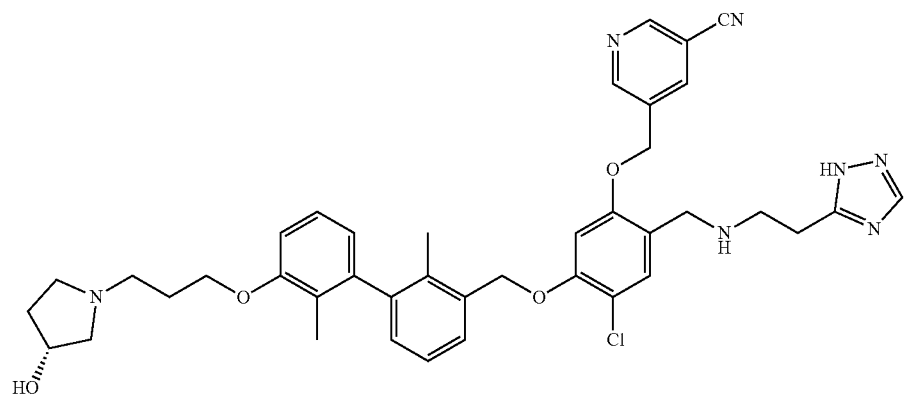 [SMILES: Cc1c(COc2cc(OCc3cncc(C#N)c3)c(CNCCc3ncn[nH]3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 11-51% B over 20 minutes, then a 6-minute hold at 100% B; Flow: 20 mL/min. Fractions containing the desired product were combined and dried via centrifugal evaporation and its estimated purity by LCMS analysis was 94%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 94.0%; Observed Mass: 722.25; Retention Time: 1.37 min.

Example 2520: (R)-5-((2-((((2-aminothiazol-4-yl) methyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl) nicotinonitrile

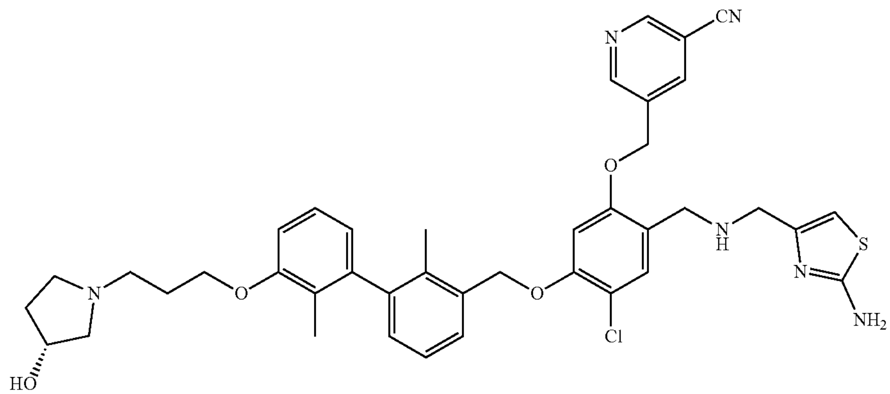 [SMILES: Cc1c(COc2cc(OCc3cncc(C#N)c3)c(CNCc3csc(N)n3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 16-56% B over 20 minutes, then a 5-minute hold at 100% B; Flow: 20 mL/min. Fractions containing the desired product were combined and dried via centrifugal evaporation and its estimated purity by LCMS analysis was 95%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 95.0%; Observed Mass: 739.25; Retention Time: 1.63 min.

Example 2521: (R)-5-((2-((((2-aminothiazol-4-yl)methyl)(methyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile

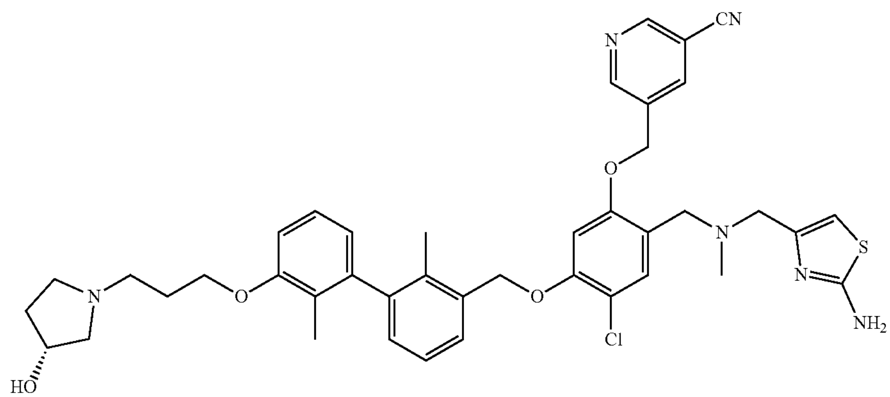 [SMILES: Cc1c(COc2cc(OCc3cncc(C#N)c3)c(CN(C)Cc3csc(N)n3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 21-61% B over 20 minutes, then a 5-minute hold at 100% B; Flow: 20 mL/min. Fractions containing the desired product were combined and dried via centrifugal evaporation and its estimated purity by LCMS analysis was 98%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 97.7%; Observed Mass: 753.25; Retention Time: 1.78 min.

Example 2522: (R)-5-((4-chloro-5-((3'-(3-(3-hydroxypyrrolidin-1-yl)propoxy)-2,2'-dimethyl-[1,1'-biphenyl]-3-yl)methoxy)-2-((((5-methyl-3-phenylisoxazol-4-yl)methyl)amino)methyl)phenoxy)methyl)nicotinonitrile

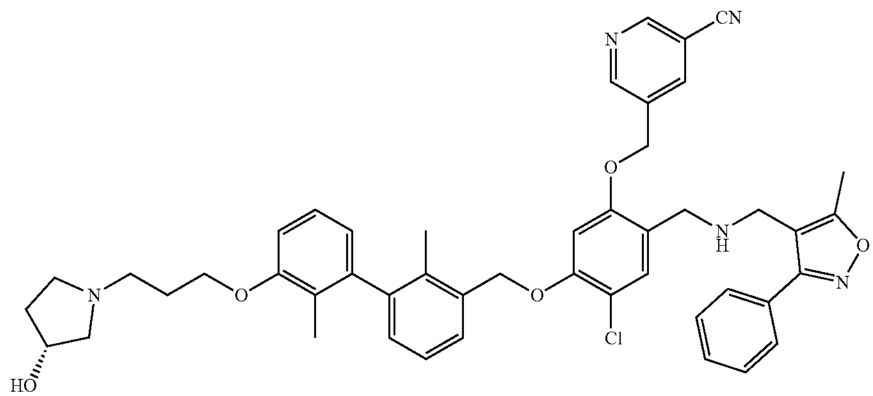 [SMILES: Cc1onc(-c2ccccc2)c1CNCc1cc(Cl)c(OCc2cccc(-c3cccc(OCCCN4CC[C@@H](O)C4)c3C)c2C)cc1OCc1cncc(C#N)c1]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 40-80% B over 20 minutes, then a 6-minute hold at 100% B; Flow: 20 mL/min. Fractions containing the desired product were combined and dried via centrifugal evaporation and its estimated purity by LCMS analysis was 93%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 93.2%; Observed Mass: 798.25; Retention Time: 1.63 min.

Example 2523: (R)-5-((4-chloro-5-((3'-(3-(3-hydroxypyrrolidin-1-yl)propoxy)-2,2'-dimethyl-[1,1'-biphenyl]-3-yl)methoxy)-2-((methyl((5-methyl-3-phenylisoxazol-4-yl)methyl)amino)methyl)phenoxy)methyl)nicotinonitrile

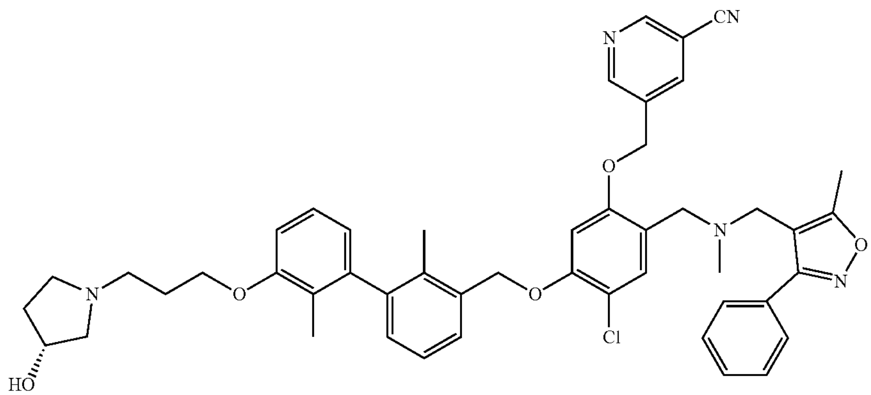 [SMILES: Cc1onc(-c2ccccc2)c1CN(C)Cc1cc(Cl)c(OCc2cccc(-c3cccc(OCCCN4CC[C@@H](O)C4)c3C)c2C)cc1OCc1cncc(C#N)c1]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 42-82% B over 25 minutes, then a 6-minute hold at 100% B; Flow: 20 mL/min. Fractions containing the desired product were combined and dried via centrifugal evaporation and its estimated purity by LCMS analysis was 92%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 92.2%; Observed Mass: 812.25; Retention Time: 2.26 min.

Example 2524: (R)-5-((2-((((1H-pyrazol-4-yl)methyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile

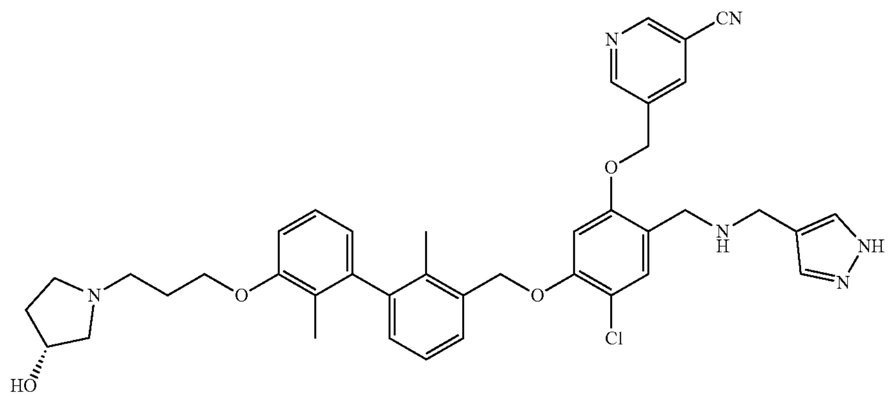 [SMILES: Cc1c(COc2cc(OCc3cncc(C#N)c3)c(CNCc3cn[nH]c3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 11-51% B over 20 minutes, then a 5-minute hold at 100% B; Flow: 20 mL/min. Fractions containing the desired product were combined and dried via centrifugal evaporation and its estimated purity by LCMS analysis was 94%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 94.0%; Observed Mass: 707.25; Retention Time: 1.50 min.

Example 2525: (R)-5-((2-((((1H-pyrazol-4-yl)methyl)(methyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile

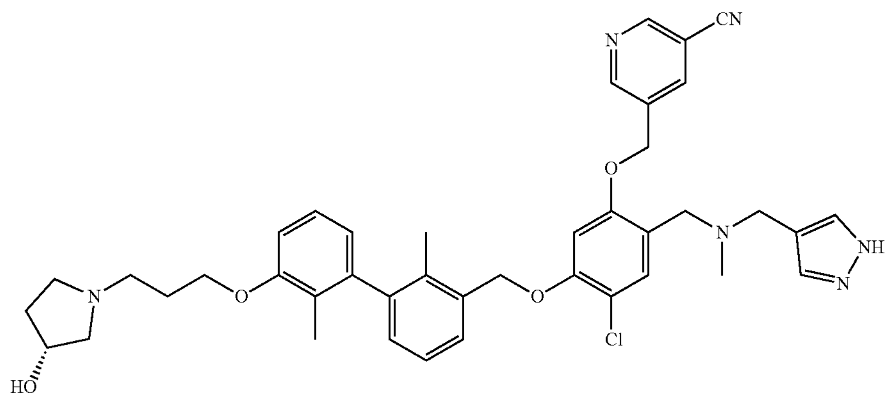 [SMILES: Cc1c(COc2cc(OCc3cncc(C#N)c3)c(CN(C)Cc3cn[nH]c3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55% B over 20 minutes, then a 5-minute hold at 100% B; Flow: 20 mL/min. Fractions containing the desired product were combined and dried via centrifugal evaporation and its estimated purity by LCMS analysis was 96%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 96.0%; Observed Mass: 721.25; Retention Time: 1.63 min.

Example 2526: (R)-5-((4-chloro-2-((((3,5-dimethylisoxazol-4-yl)methyl)amino)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile

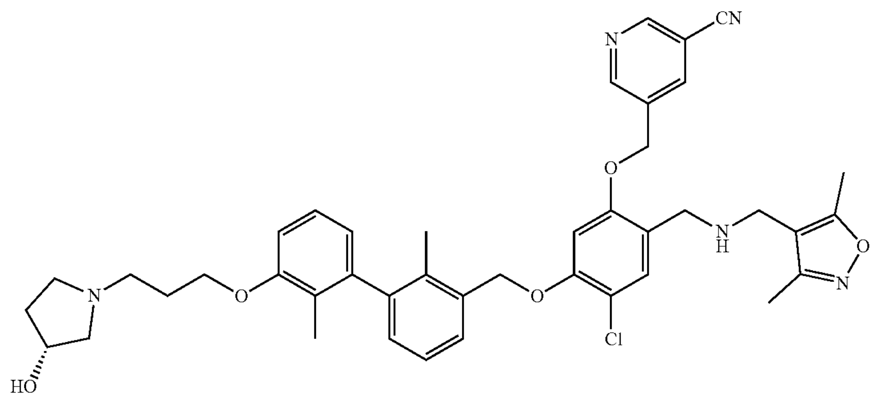 [SMILES: Cc1noc(C)c1CNCc1cc(Cl)c(OCc2cccc(-c3cccc(OCCCN4CC[C@@H](O)C4)c3C)c2C)cc1OCc1cncc(C#N)c1]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 25-65% B over 25 minutes, then a 6-minute hold at 100% B; Flow: 20 mL/min. Fractions containing the desired product were combined and dried via centrifugal evaporation and its estimated purity by LCMS analysis was 98%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 98.0%; Observed Mass: 736.25; Retention Time: 1.71 min.

Example 2527: (R)-5-((4-chloro-2-((((3,5-dimethylisoxazol-4-yl)methyl)(methyl)amino)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile

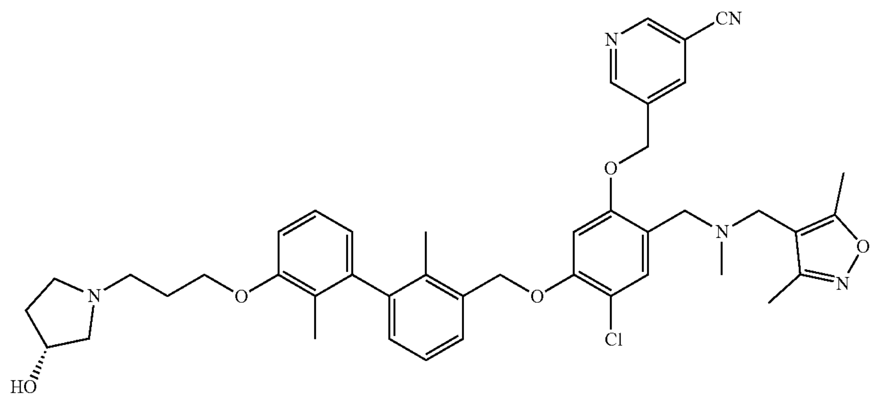 [SMILES: Cc1noc(C)c1CN(C)Cc1cc(Cl)c(OCc2cccc(-c3cccc(OCCCN4CC[C@@H](O)C4)c3C)c2C)cc1OCc1cncc(C#N)c1]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 35-75% B over 25 minutes, then a 6-minute hold at 100% B; Flow: 20 mL/min. Fractions containing the desired product were combined and dried via centrifugal evaporation and its estimated purity by LCMS analysis was 91%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 91.2%; Observed Mass: 750.23; Retention Time: 2 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 92.1%; Observed Mass: 750.27; Retention Time: 1.49 min.

Example 2528: (R)-5-((4-chloro-5-((3'-(3-(3-hydroxypyrrolidin-1-yl)propoxy)-2,2'-dimethyl-[1,1'-biphenyl]-3-yl)methoxy)-2-((((5-methylisoxazol-3-yl)methyl)amino)methyl)phenoxy)methyl)nicotinonitrile

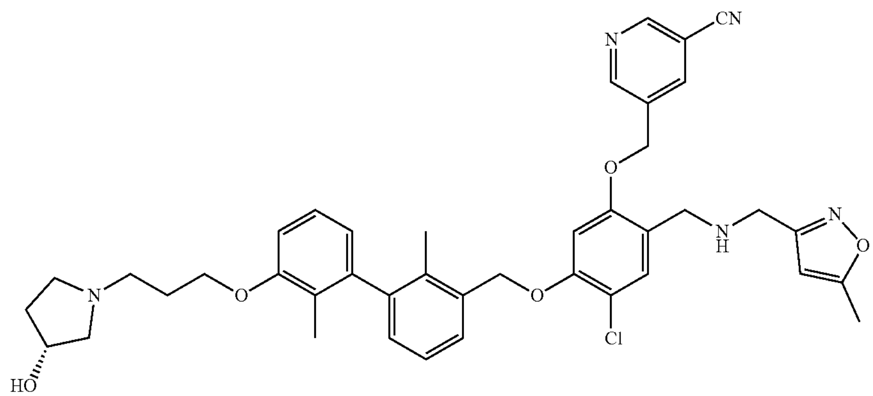 [SMILES: Cc1cc(CNCc2cc(Cl)c(OCc3cccc(-c4cccc(OCCCN5CC[C@@H](O)C5)c4C)c3C)cc2OCc2cncc(C#N)c2)no1]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 26-66% B over 20 minutes, then a 5-minute hold at 100% B; Flow: 20 mL/min. Fractions containing the desired product were combined and dried via centrifugal evaporation and its estimated purity by LCMS analysis was 98%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 98.4%; Observed Mass: 722.27; Retention Time: 1.51 min.

Example 2529: (R)-5-((4-chloro-5-((3'-(3-(3-hydroxypyrrolidin-1-yl)propoxy)-2,2'-dimethyl-[1,1'-biphenyl]-3-yl)methoxy)-2-((methyl((5-methylisoxazol-3-yl)methyl)amino)methyl)phenoxy)methyl)nicotinonitrile

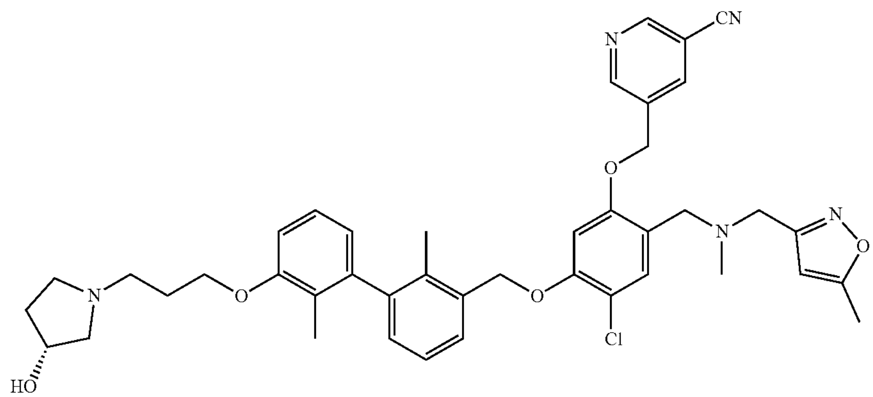 [SMILES: Cc1cc(CN(C)Cc2cc(Cl)c(OCc3cccc(-c4cccc(OCCCN5CC[C@@H](O)C5)c4C)c3C)cc2OCc2cncc(C#N)c2)no1]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 33-73% B over 20 minutes, then a 5-minute hold at 100% B; Flow: 20 mL/min. Fractions containing the desired product were combined and dried via centrifugal evaporation and its estimated purity by LCMS analysis was 94%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 93.8%; Observed Mass: 736.27; Retention Time: 1.52 min.

Example 2530: (R)-5-((4-chloro-5-((3'-(3-(3-hydroxypyrrolidin-1-yl)propoxy)-2,2'-dimethyl-[1,1'-biphenyl]-3-yl)methoxy)-2-(((thiazol-2-ylmethyl)amino)methyl) phenoxy)methyl)nicotinonitrile

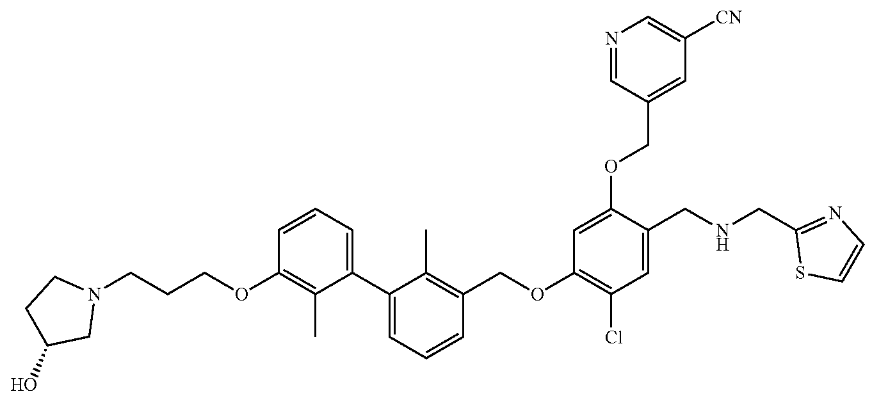 [SMILES: Cc1c(COc2cc(OCc3cncc(C#N)c3)c(CNCc3nccs3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 25-65% B over 20 minutes, then a 5-minute hold at 100% B; Flow: 20 mL/min. Fractions containing the desired product were combined and dried via centrifugal evaporation and its estimated purity by LCMS analysis was 94%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 93.5%; Observed Mass: 724.27; Retention Time: 1.52 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.0%; Observed Mass: 724.21; Retention Time: 1.95 min.

Example 2531: (R)-5-((4-chloro-5-((3'-(3-(3-hydroxypyrrolidin-1-yl)propoxy)-2,2'-dimethyl-[1,1'-biphenyl]-3-yl)methoxy)-2-(((thiazol-5-ylmethyl) amino)methyl) phenoxy)methyl)nicotinonitrile

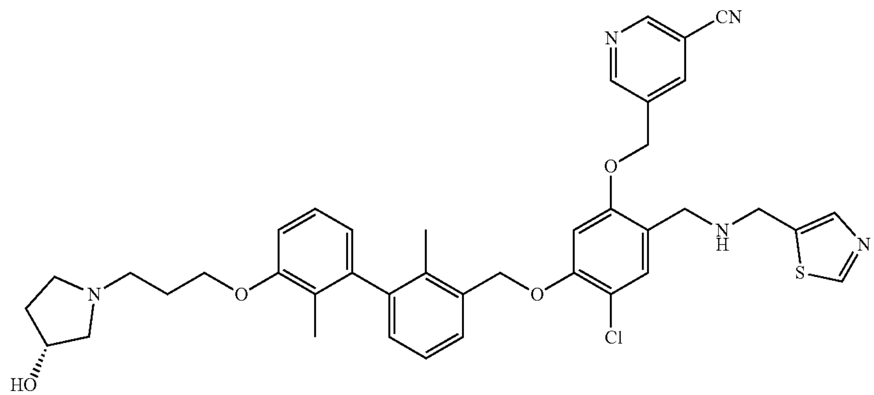 [SMILES: Cc1c(COc2cc(OCc3cncc(C#N)c3)c(CNCc3cncs3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 22-62% B over 25 minutes, then a 4-minute hold at 100% B; Flow: 20 mL/min. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.0%; Observed Mass: 724.15; Retention Time: 1.73 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.5%; Observed Mass: 724.16; Retention Time: 1.43 min.

Example 2532: (R)-5-((2-(((2-(1H-imidazol-4-yl) ethyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile

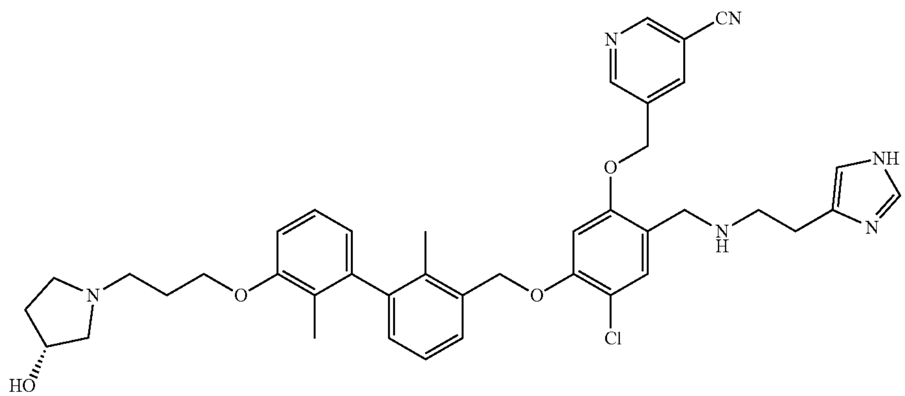

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 25 minutes, then a 4-minute hold at 100% B; Flow: 20 mL/min. Fractions containing the desired product were combined and dried via centrifugal evaporation and its estimated purity by LCMS analysis was 98%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.8%; Observed Mass: 721.18; Retention Time: 1.3 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.2%; Observed Mass: 721.21; Retention Time: 1.41 min.

Example 2533: (R)-5-((4-chloro-5-((3'-(3-(3-hydroxypyrrolidin-1-yl)propoxy)-2,2'-dimethyl-[1,1'-biphenyl]-3-yl)methoxy)-2-((methyl(thiazol-2-ylmethyl)amino)methyl)phenoxy)methyl)nicotinonitrile

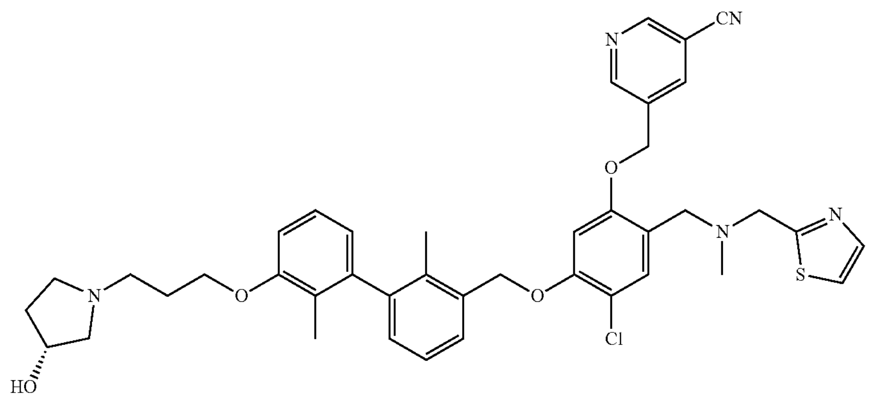 [SMILES: Cc1c(COc2cc(OCc3cncc(C#N)c3)c(CN(C)Cc3nccs3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 32-72% B over 25 minutes, then a 4-minute hold at 100% B; Flow: 20 mL/min. Fractions containing the desired product were combined and dried via centrifugal evaporation and its estimated purity by LCMS analysis was 98%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.6%; Observed Mass: 738.2; Retention Time: 2.02 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.5%; Observed Mass: 738.19; Retention Time: 1.5 min.

Example 2534: (R)-5-((4-chloro-5-((3'-(3-(3-hydroxypyrrolidin-1-yl)propoxy)-2,2'-dimethyl-[1,1'-biphenyl]-3-yl)methoxy)-2-((methyl(thiazol-5-ylmethyl)amino)methyl)phenoxy)methyl)nicotinonitrile

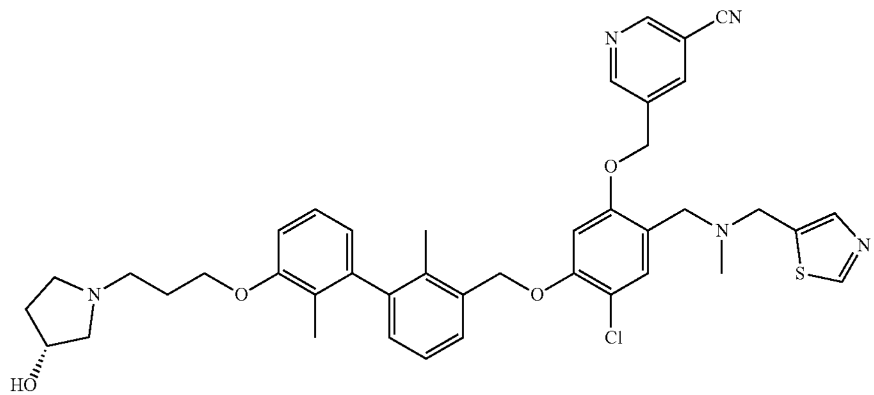 [SMILES: Cc1c(COc2cc(OCc3cncc(C#N)c3)c(CN(C)Cc3cncs3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 29-69% B over 20 minutes, then a 5-minute hold at 100% B; Flow: 20 mL/min. Fractions containing the desired product were combined and dried via centrifugal evaporation and its estimated purity by LCMS analysis was 97%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.4%; Observed Mass: 738.24; Retention Time: 1.48 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.6%; Observed Mass: 738.19; Retention Time: 2.09 min.

Example 2535: (R)-5-((2-(((2-(1H-imidazol-4-yl)ethyl)(methyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile

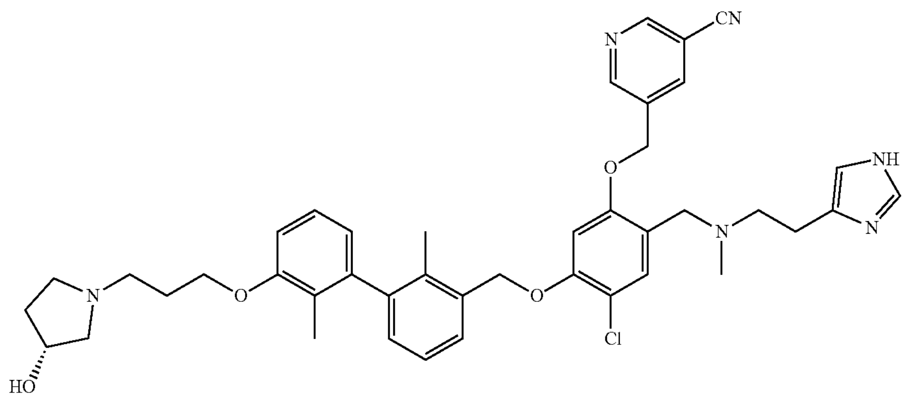

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 12-52% B over 25 minutes, then a 4-minute hold at 100% B; Flow: 20 mL/min. Fractions containing the desired product were combined and dried via centrifugal evaporation and its estimated purity by LCMS analysis was 97%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.6%; Observed Mass: 735.25; Retention Time: 1.44 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.6%; Observed Mass: 735.25; Retention Time: 1.3 min.

Example 2536: (R)-5-((4-chloro-2-((((1,5-dimethyl-1H-pyrazol-3-yl)methyl)amino)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile

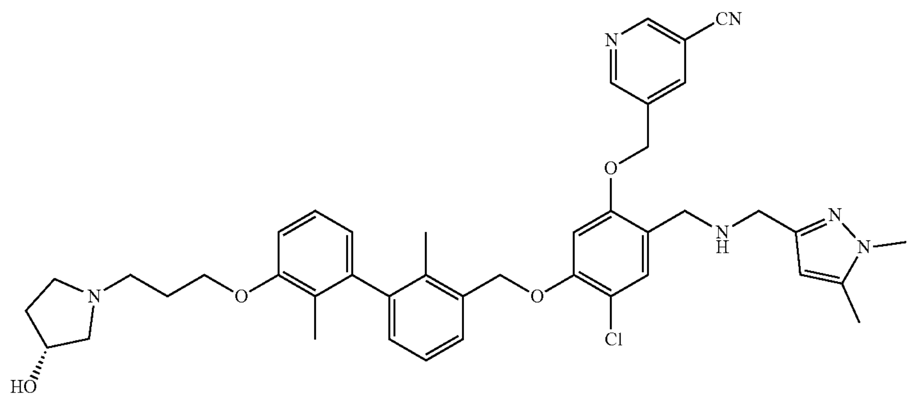 [SMILES: Cc1c(COc2cc(OCc3cncc(C#N)c3)c(CNCc3cc(C)n(C)n3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 9-49% B over 20 minutes, then a 5-minute hold at 100% B; Flow: 20 mL/min. Fractions containing the desired product were combined and dried via centrifugal evaporation and its estimated purity by LCMS analysis was 97%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.5%; Observed Mass: 735.27; Retention Time: 1.76 min. Injection 2 conditions: Column: Waters XBridge C18, 2.1 mm×50 mm, 1.7 m particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.9%; Observed Mass: 735.26; Retention Time: 1.53 min.

Example 2537: (R)-5-((4-chloro-5-((3'-(3-(3-hydroxypyrrolidin-1-yl)propoxy)-2,2'-dimethyl-[1,1'-biphenyl]-3-yl)methoxy)-2-(((pyrazolo[1,5-a]pyridin-2-ylmethyl)amino)methyl)phenoxy)methyl) nicotinonitrile

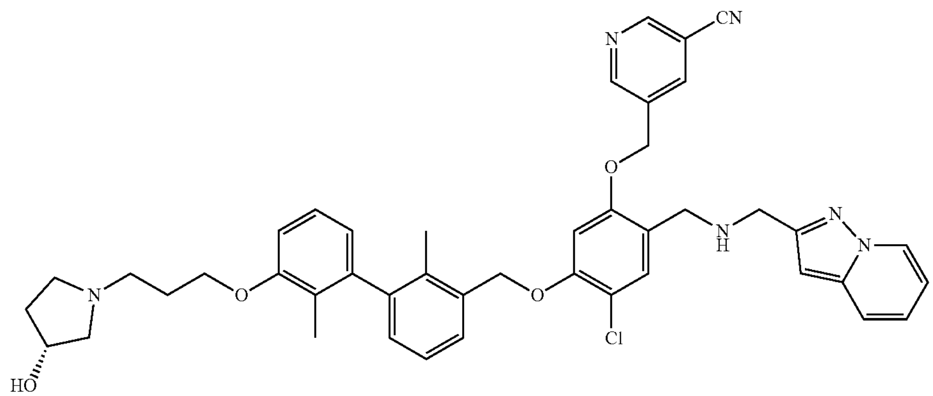 [SMILES: Cc1c(COc2cc(OCc3cncc(C#N)c3)c(CNCc3cc4ccccn4n3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 19-59% B over 20 minutes, then a 5-minute hold at 100% B; Flow: 20 mL/min. Fractions containing the desired product were combined and dried via centrifugal evaporation and its estimated purity by LCMS analysis was 98%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.5%; Observed Mass: 757.24; Retention Time: 1.57 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 757.25; Retention Time: 1.89 min.

Example 2538: (R)-5-((4-chloro-5-((3'-(3-(3-hydroxypyrrolidin-1-yl)propoxy)-2,2'-dimethyl-[1,1'-biphenyl]-3-yl)methoxy)-2-((((5-phenylisoxazol-3-yl)methyl)amino)methyl)phenoxy)methyl) nicotinonitrile

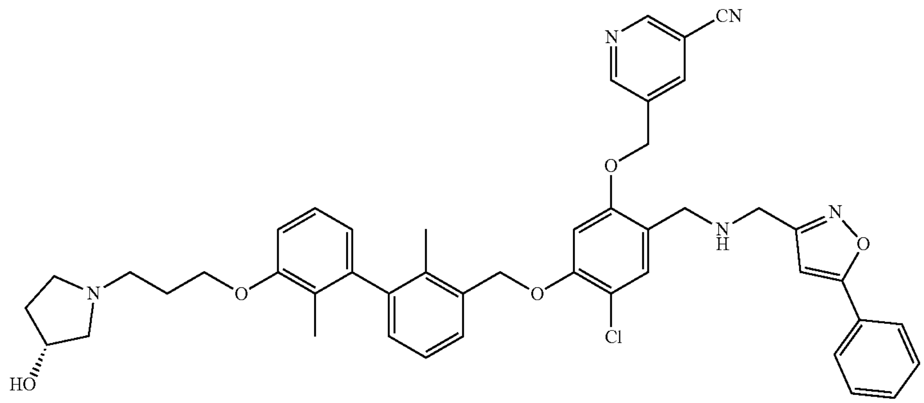 [SMILES: Cc1c(COc2cc(OCc3cncc(C#N)c3)c(CNCc3cc(-c4ccccc4)on3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 35-75% B over 20 minutes, then a 5-minute hold at 100% B; Flow: 20 mL/min. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.3%; Observed Mass: 784.27; Retention Time: 2.19 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.3%; Observed Mass: 784.26; Retention Time: 1.7 min.

Example 2539: (R)-5-((4-chloro-5-((3'-(3-(3-hydroxypyrrolidin-1-yl)propoxy)-2,2'-dimethyl-[1,1'-biphenyl]-3-yl)methoxy)-2-(((oxazol-4-ylmethyl) amino)methyl) phenoxy)methyl)nicotinonitrile

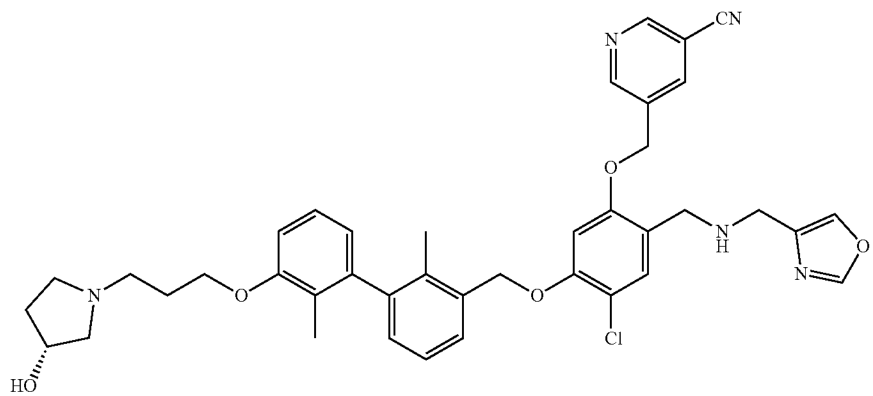 [SMILES: Cc1c(COc2cc(OCc3cncc(C#N)c3)c(CNCc3cocn3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 21-61% B over 20 minutes, then a 4-minute hold at 100% B; Flow: 20 mL/min. Fractions containing the desired product were combined and dried via centrifugal evaporation and its estimated purity by LCMS analysis was %. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.3%; Observed Mass: 708.27; Retention Time: 1.48 min.

Example 2540: (R)-5-((4-chloro-5-((3'-(3-(3-hydroxypyrrolidin-1-yl)propoxy)-2,2'-dimethyl-[1,1'-biphenyl]-3-yl)methoxy)-2-((((5-methyl-1,2,4-oxadiazol-3-yl)methyl)amino)methyl)phenoxy)methyl)nicotinonitrile

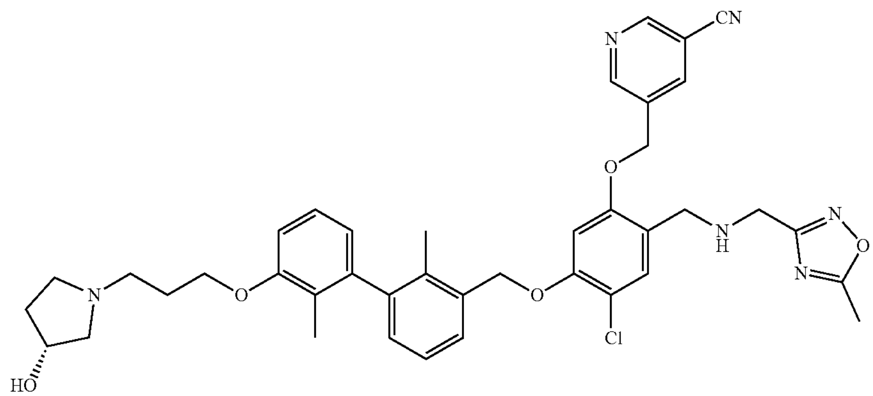

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 25-65% B over 15 minutes, then a 5-minute hold at 100% B; Flow: 20 mL/min. Fractions containing the desired product were combined and dried via centrifugal evaporation and its estimated purity by LCMS analysis was 97%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.8%; Observed Mass: 723.25; Retention Time: 1.5 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 723.25; Retention Time: 1.88 min.

Example 2541: (R)-5-((4-chloro-2-((((1,5-dimethyl-1H-pyrazol-3-yl)methyl)(methyl)amino)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile

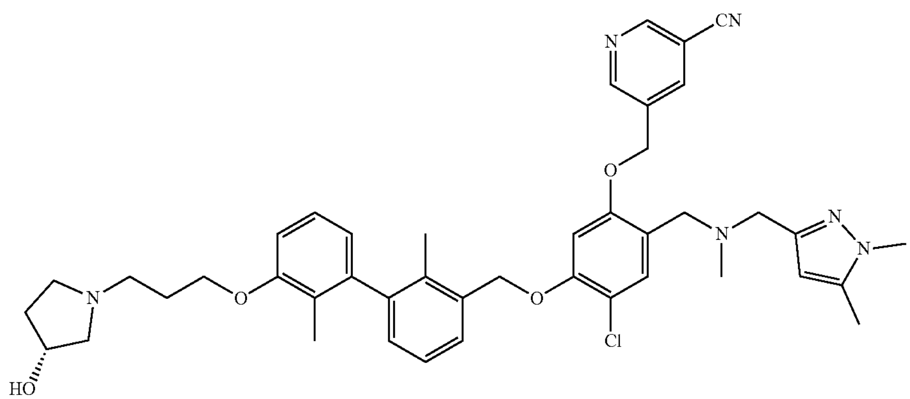 [SMILES: Cc1c(COc2cc(OCc3cncc(C#N)c3)c(CN(C)Cc3cc(C)n(C)n3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 23-63% B over 20 minutes, then a 5-minute hold at 100% B; Flow: 20 mL/min. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.3%; Observed Mass: 749.25; Retention Time: 1.91 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.7%; Observed Mass: 749.26; Retention Time: 1.55 min.

Example 2542: (R)-5-((4-chloro-5-((3'-(3-(3-hydroxypyrrolidin-1-yl)propoxy)-2,2'-dimethyl-[1,1'-biphenyl]-3-yl)methoxy)-2-((methyl(pyrazolo[1,5-a]pyridin-2-ylmethyl)amino)methyl)phenoxy)methyl)nicotinonitrile

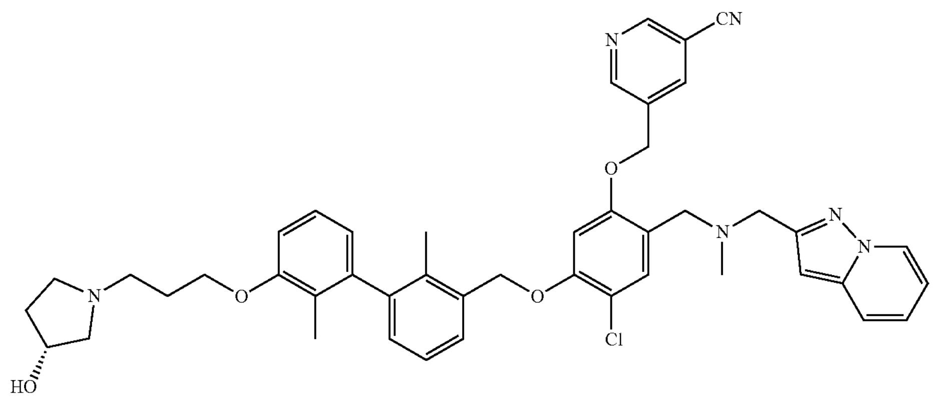 [SMILES: Cc1c(COc2cc(OCc3cncc(C#N)c3)c(CN(C)Cc3cc4ccccn4n3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 29-69% B over 20 minutes, then a 5-minute hold at 100% B; Flow: 20 mL/min. Fractions containing the desired product were combined and dried via centrifugal evaporation and its estimated purity by LCMS analysis was 98%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.3%; Observed Mass: 771.25; Retention Time: 2.14 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.2%; Observed Mass: 771.26; Retention Time: 1.6 min.

Example 2543: (R)-5-((4-chloro-5-((3'-(3-(3-hydroxypyrrolidin-1-yl)propoxy)-2,2'-dimethyl-[1,1'-biphenyl]-3-yl)methoxy)-2-((methyl((5-phenylisoxazol-3-yl)methyl)amino)methyl)phenoxy)methyl) nicotinonitrile

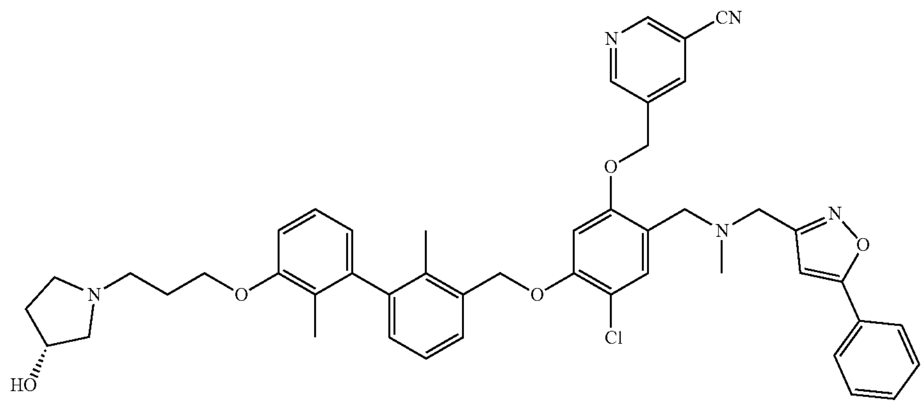

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 39-86% B over 20 minutes, then a 6-minute hold at 100% B; Flow: 20 mL/min. Fractions containing the desired product were combined and dried via centrifugal evaporation and its estimated purity by LCMS analysis was 97%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.9%; Observed Mass: 798.2; Retention Time: 2.42 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.8%; Observed Mass: 798.23; Retention Time: 1.7 min.

Example 2544: (R)-5-((4-chloro-5-((3'-(3-(3-hydroxypyrrolidin-1-yl)propoxy)-2,2'-dimethyl-[1,1'-biphenyl]-3-yl)methoxy)-2-((methyl(oxazol-4-ylmethyl)amino)methyl)phenoxy)methyl)nicotinonitrile

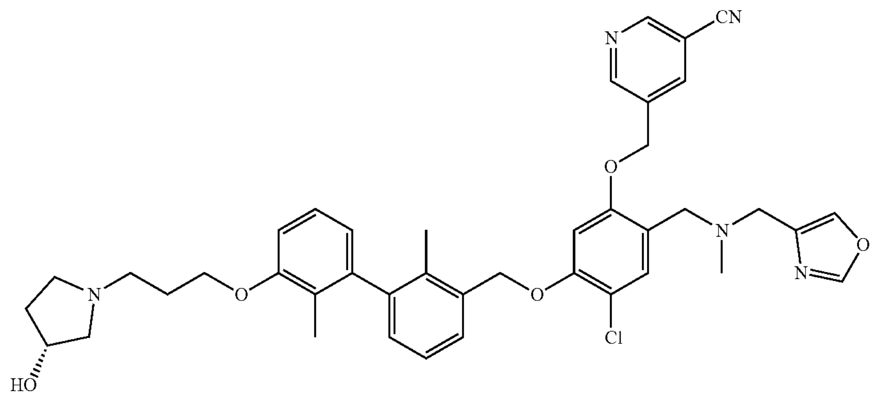

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 21-61% B over 20 minutes, then a 4-minute hold at 100% B; Flow: 20 mL/min. Fractions containing the desired product were combined and dried via centrifugal evaporation and its estimated purity by LCMS analysis was 93%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 93.7%; Observed Mass: 722.2; Retention Time: 1.48 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 92.9%; Observed Mass: 722.25; Retention Time: 1.96 min.

Example 2545: (R)-5-((4-chloro-5-((3'-(3-(3-hydroxypyrrolidin-1-yl)propoxy)-2,2'-dimethyl-[1,1'-biphenyl]-3-yl)methoxy)-2-((methyl((5-methyl-1,2,4-oxadiazol-3-yl)methyl)amino)methyl)phenoxy)methyl)nicotinonitrile

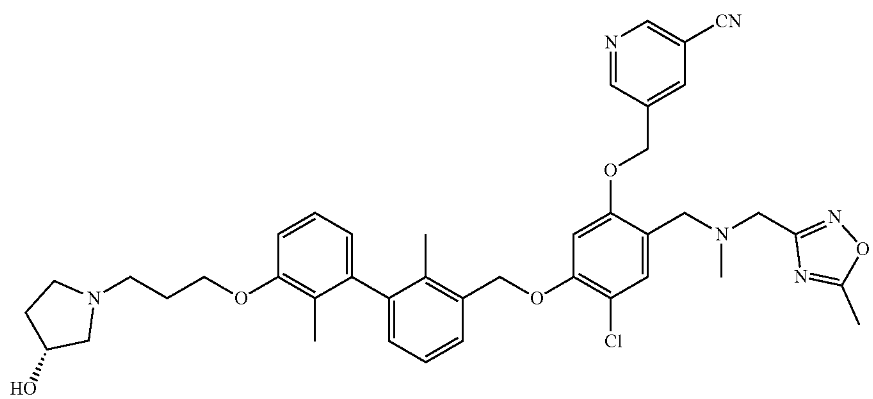 [SMILES: Cc1nc(CN(C)Cc2cc(Cl)c(OCc3cccc(-c4cccc(OCCCN5CC[C@@H](O)C5)c4C)c3C)cc2OCc2cncc(C#N)c2)no1]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 31-80% B over 20 minutes, then a 4-minute hold at 100% B; Flow: 20 mL/min. Fractions containing the desired product were combined and dried via centrifugal evaporation and its estimated purity by LCMS analysis was 93%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 93.4%; Observed Mass: 737.26; Retention Time: 1.51 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.9%; Observed Mass: 737.25; Retention Time: 2.08 min.

Example 2546: (R)-5-((4-chloro-5-((3'-(3-(3-hydroxypyrrolidin-1-yl)propoxy)-2,2'-dimethyl-[1,1'-biphenyl]-3-yl)methoxy)-2-(((oxazol-2-ylmethyl) amino)methyl) phenoxy)methyl)nicotinonitrile

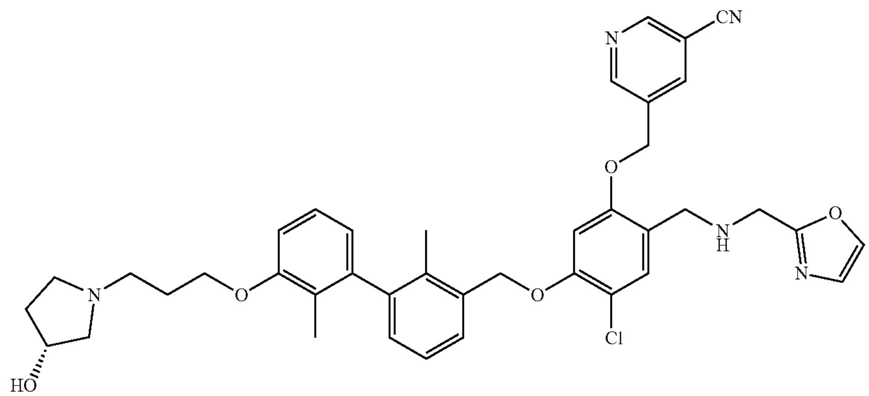

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 14-54% B over 20 minutes, then a 4-minute hold at 100% B; Flow: 20 mL/min. Fractions containing the desired product were combined and dried via centrifugal evaporation and its estimated purity by LCMS analysis was 94%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 94.0%; Observed Mass: 708.27; Retention Time: 1.84 min.

Example 2547: (R)-5-((4-chloro-5-((3'-(3-(3-hydroxypyrrolidin-1-yl)propoxy)-2,2'-dimethyl-[1,1'-biphenyl]-3-yl)methoxy)-2-(((oxazol-5-ylmethyl) amino)methyl) phenoxy)methyl)nicotinonitrile

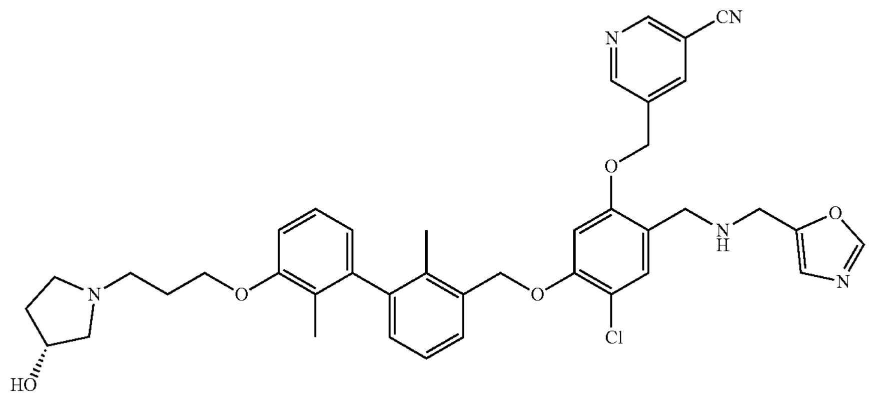 [SMILES: Cc1c(COc2cc(OCc3cncc(C#N)c3)c(CNCc3cnco3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 6-46% B over 25 minutes, then a 4-minute hold at 100% B; Flow: 20 mL/min. Fractions containing the desired product were combined and dried via centrifugal evaporation and its estimated purity by LCMS analysis was 98%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.4%; Observed Mass: 708.19; Retention Time: 1.8 min. Injection 2 conditions: Column: Waters XBridge C18, 2.1 mm×50 mm, 1.7 m particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.8%; Observed Mass: 708.17; Retention Time: 1.42 min.

Example 2548: (R)-5-((4-chloro-2-((((4-ethylthiazol-2-yl)methyl)amino)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile

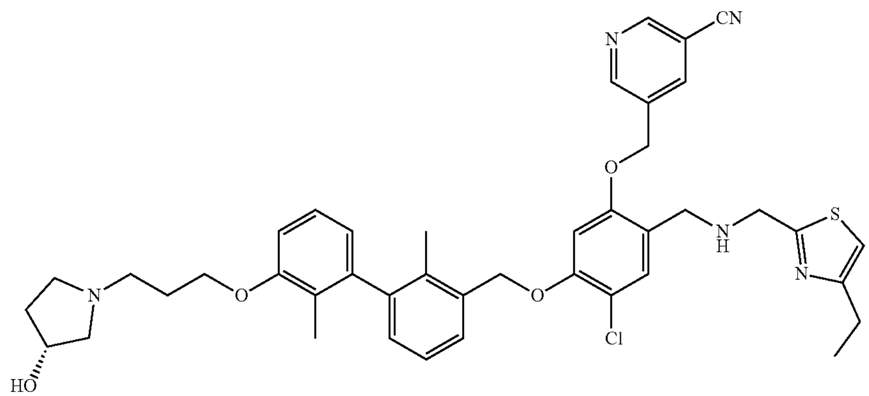 [SMILES: CCc1csc(CNCc2cc(Cl)c(OCc3cccc(-c4cccc(OCCCN5CC[C@@H](O)C5)c4C)c3C)cc2OCc2cncc(C#N)c2)n1]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-60% B over 20 minutes, then a 5-minute hold at 100% B; Flow: 20 mL/min. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.2%; Observed Mass: 752.16; Retention Time: 1.63 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.4%; Observed Mass: 752.2; Retention Time: 2.14 min.

Example 2549: (R)-5-((2-(((benzo[d]thiazol-2-ylmethyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile

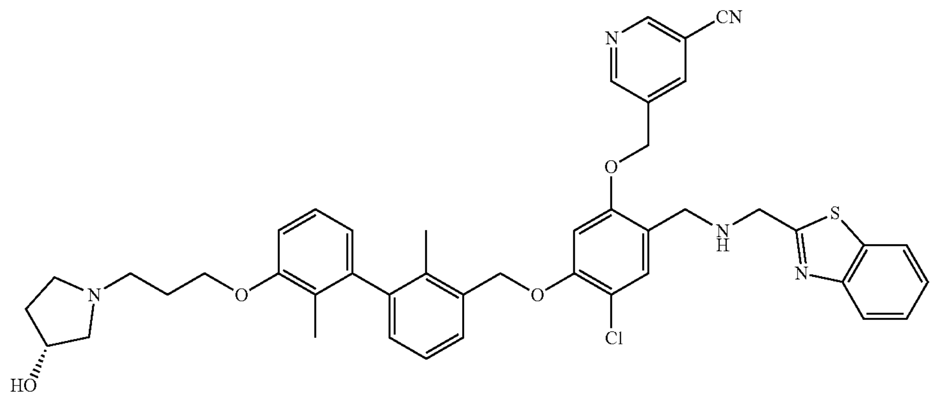

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 7-47% B over 25 minutes, then a 4-minute hold at 100% B; Flow: 20 mL/min. Fractions containing the desired product were combined and dried via centrifugal evaporation and its estimated purity by LCMS analysis was 91%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 91.6%; Observed Mass: 774.16; Retention Time: 2.21 min. Injection 2 conditions: Column: Waters XBridge C18, 2.1 mm×50 mm, 1.7 m particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 91.3%; Observed Mass: 774.15; Retention Time: 1.63 min.

Example 2550: (R)-5-((4-chloro-5-((3'-(3-(3-hydroxypyrrolidin-1-yl)propoxy)-2,2'-dimethyl-[1,1'-biphenyl]-3-yl)methoxy)-2-((methyl(oxazol-2-ylmethyl)amino)methyl)phenoxy)methyl)nicotinonitrile

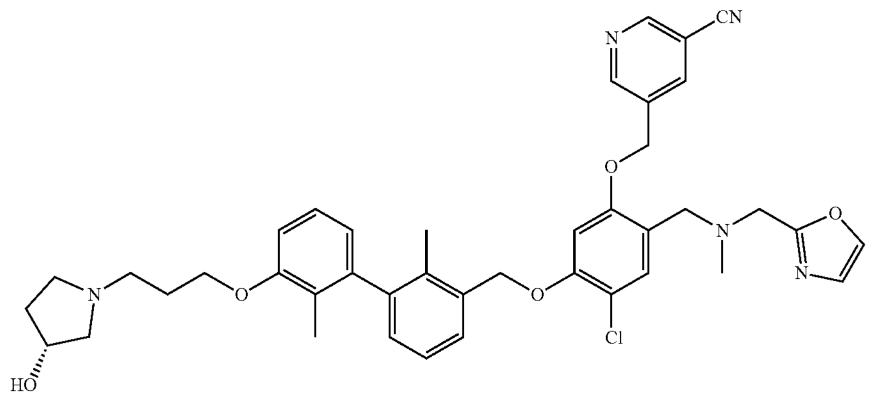

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 7-47% B over 25 minutes, then a 4-minute hold at 100% B; Flow: 20 mL/min. Fractions containing the desired product were combined and dried via centrifugal evaporation and its estimated purity by LCMS analysis was 92%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.1%; Observed Mass: 722.22; Retention Time: 2.02 min. Injection 2 conditions: Column: Waters XBridge C18, 2.1 mm×50 mm, 1.7 m particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 91.9%; Observed Mass: 722.2; Retention Time: 1.48 min.

Example 2551: (R)-5-((4-chloro-5-((3'-(3-(3-hydroxypyrrolidin-1-yl)propoxy)-2,2'-dimethyl-[1,1'-biphenyl]-3-yl)methoxy)-2-((methyl(oxazol-5-ylmethyl)amino)methyl)phenoxy)methyl)nicotinonitrile

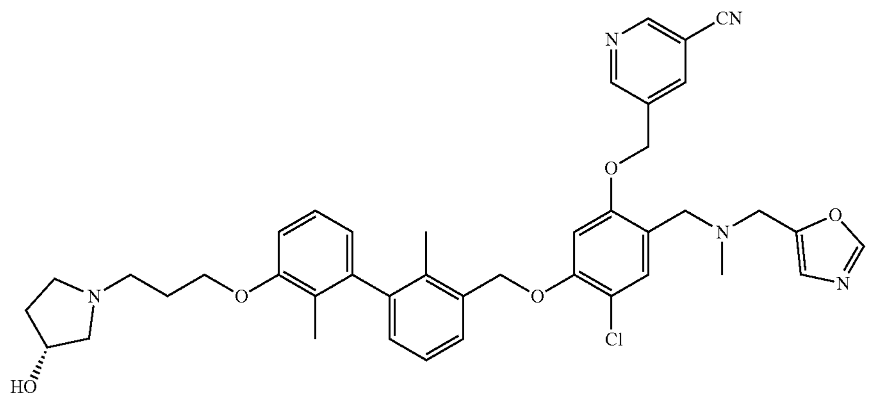 [SMILES: Cc1c(COc2cc(OCc3cncc(C#N)c3)c(CN(C)Cc3cnco3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-100% B over 20 minutes, then a 7-minute hold at 100% B; Flow: 20 mL/min. Fractions containing the desired product were combined and dried via centrifugal evaporation and its estimated purity by LCMS analysis was 88%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.4%; Observed Mass: 722.19; Retention Time: 1.84 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 88.0%; Observed Mass: 722.17; Retention Time: 1.43 min.

Example 2552: (R)-5-((4-chloro-2-((((5-cyclopropylisoxazol-3-yl)methyl)(methyl)amino)methyl)-5-((3'-(3-(3-hydroxypyrrolidin-1-yl)propoxy)-2,2'-dimethyl-[1,1'-biphenyl]-3-yl)methoxy)phenoxy)methyl) nicotinonitrile

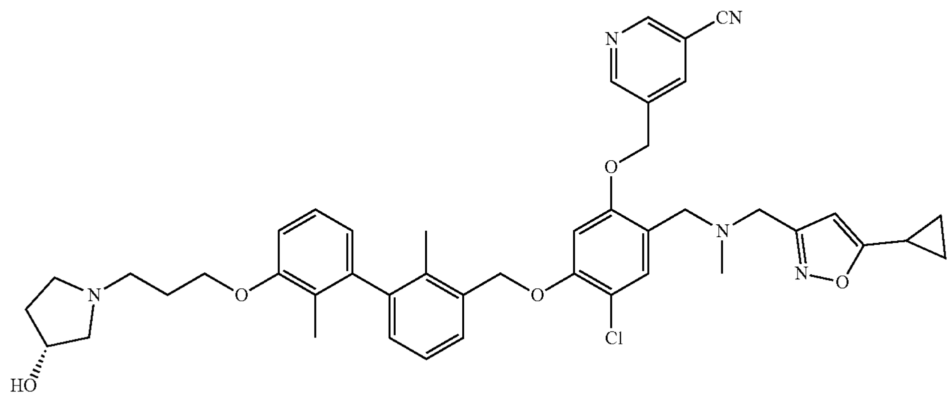 [SMILES: Cc1c(COc2cc(OCc3cncc(C#N)c3)c(CN(C)Cc3cc(C4CC4)on3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-100% B over 20 minutes, then a 7-minute hold at 100% B; Flow: 20 mL/min. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.6%; Observed Mass: 762.21; Retention Time: 2.27 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.5%; Observed Mass: 762.23; Retention Time: 1.63 min.

Example 2553: (R)-5-((4-chloro-2-((((4-ethylthiazol-2-yl)methyl)(methyl)amino)methyl)-5-((3'-(3-(3-hydroxypyrrolidin-1-yl)propoxy)-2,2'-dimethyl-[1,1'-biphenyl]-3-yl)methoxy)phenoxy)methyl) nicotinonitrile

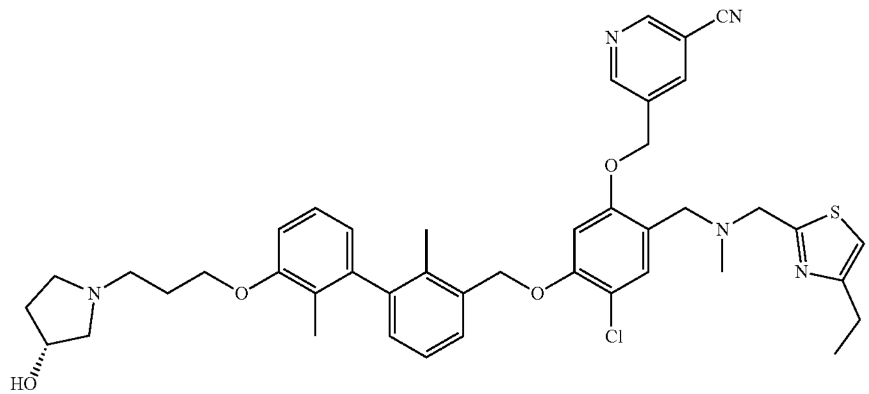 [SMILES: CCc1csc(CN(C)Cc2cc(Cl)c(OCc3cccc(-c4cccc(OCCCN5CC[C@@H](O)C5)c4C)c3C)cc2OCc2cncc(C#N)c2)n1]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-100% B over 20 minutes, then a 7-minute hold at 100% B; Flow: 20 mL/min. Fractions containing the desired product were combined and dried via centrifugal evaporation and its estimated purity by LCMS analysis was 88%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.2%; Observed Mass: 766.18; Retention Time: 2.18 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 88.3%; Observed Mass: 766.19; Retention Time: 1.62 min.

Example 2554: (R)-5-((2-(((benzo[d]thiazol-2-ylmethyl)(methyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl) nicotinonitrile

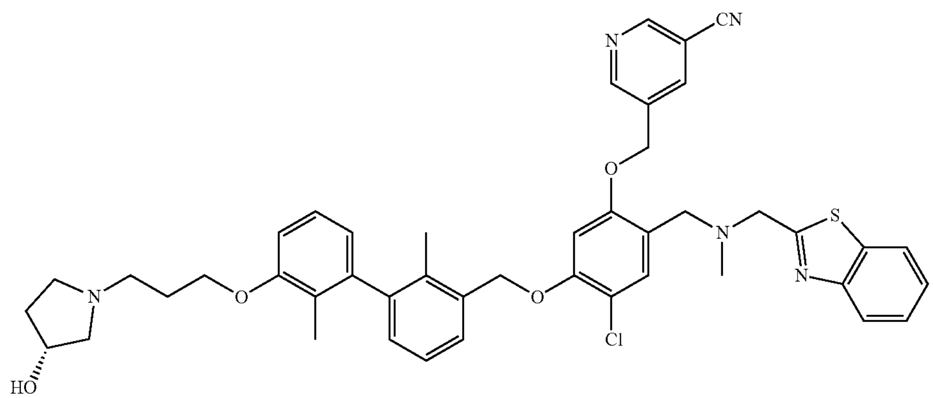 [SMILES: Cc1c(COc2cc(OCc3cncc(C#N)c3)c(CN(C)Cc3nc4ccccc4s3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-100% B over 25 minutes, then a 6-minute hold at 100% B; Flow: 20 mL/min. Fractions containing the desired product were combined and dried via centrifugal evaporation and its estimated purity by LCMS analysis was 95%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 788.15; Retention Time: 2.25 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 94.8%; Observed Mass: 788.17; Retention Time: 1.63 min.

Example 2555: (R)-5-((4-chloro-5-((3'-(3-(3-hydroxypyrrolidin-1-yl)propoxy)-2,2'-dimethyl-[1,1'-biphenyl]-3-yl)methoxy)-2-((((1-methyl-1H-indazol-3-yl)methyl)amino)methyl)phenoxy)methyl)nicotinonitrile

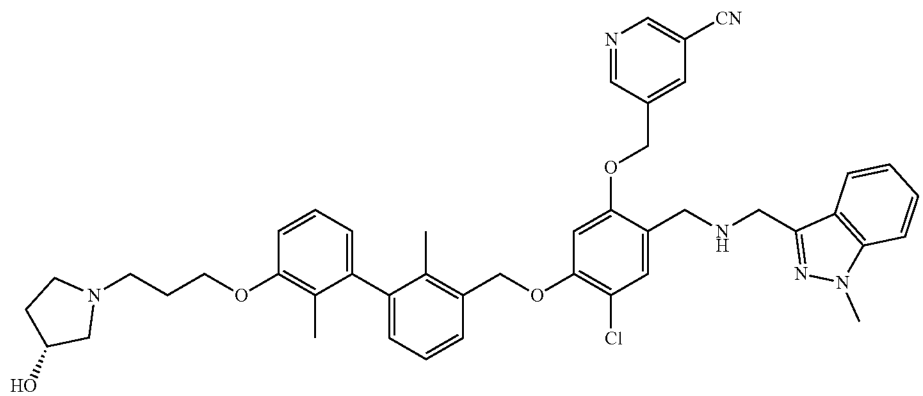 [SMILES: Cc1c(COc2cc(OCc3cncc(C#N)c3)c(CNCc3nn(C)c4ccccc34)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 22-62% B over 20 minutes, then a 4-minute hold at 100% B; Flow: 20 mL/min. Fractions containing the desired product were combined and dried via centrifugal evaporation and its estimated purity by LCMS analysis was 87%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 86.8%; Observed Mass: 771.25; Retention Time: 2.01 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 93.3%; Observed Mass: 771.26; Retention Time: 1.64 min.

Example 2556: (R)-5-((4-chloro-5-((3'-(3-(3-hydroxypyrrolidin-1-yl)propoxy)-2,2'-dimethyl-[1,1'-biphenyl]-3-yl)methoxy)-2-((((1-methyl-1H-pyrazol-5-yl)methyl)amino)methyl)phenoxy)methyl)nicotinonitrile

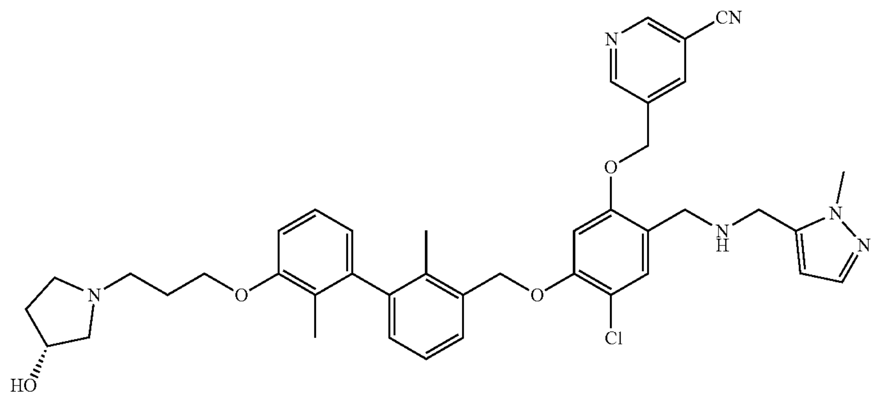 [SMILES: Cc1c(COc2cc(OCc3cncc(C#N)c3)c(CNCc3ccnn3C)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-100% B over 20 minutes, then a 5-minute hold at 100% B; Flow: 20 mL/min. Fractions containing the desired product were combined and dried via centrifugal evaporation and its estimated purity by LCMS analysis was 97%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.9%; Observed Mass: 721.22; Retention Time: 1.47 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.0%; Observed Mass: 721.27; Retention Time: 1.83 min.

Example 2557: (R)-5-((2-((((1-benzyl-1H-benzo[d]imidazol-2-yl)methyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile

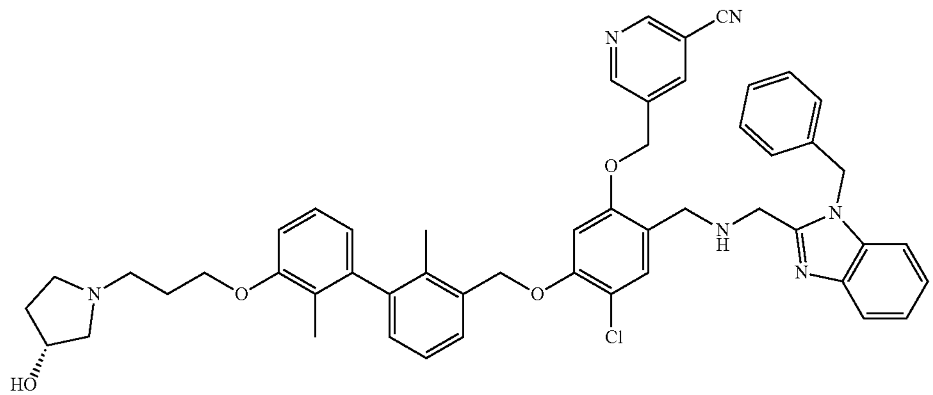 [SMILES: Cc1c(COc2cc(OCc3cncc(C#N)c3)c(CNCc3nc4ccccc4n3Cc3ccccc3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-100% B over 20 minutes, then a 5-minute hold at 100% B; Flow: 20 mL/min. Fractions containing the desired product were combined and dried via centrifugal evaporation and its estimated purity by LCMS analysis was 99%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 847.25; Retention Time: 2.2 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.8%; Observed Mass: 847.25; Retention Time: 1.78 min.

Example 2558: (R)-5-((4-chloro-5-((3'-(3-(3-hydroxypyrrolidin-1-yl)propoxy)-2,2'-dimethyl-[1,1'-biphenyl]-3-yl)methoxy)-2-((((3-(methoxymethyl)-1,2,4-oxadiazol-5-yl)methyl)amino)methyl)phenoxy)methyl)nicotinonitrile

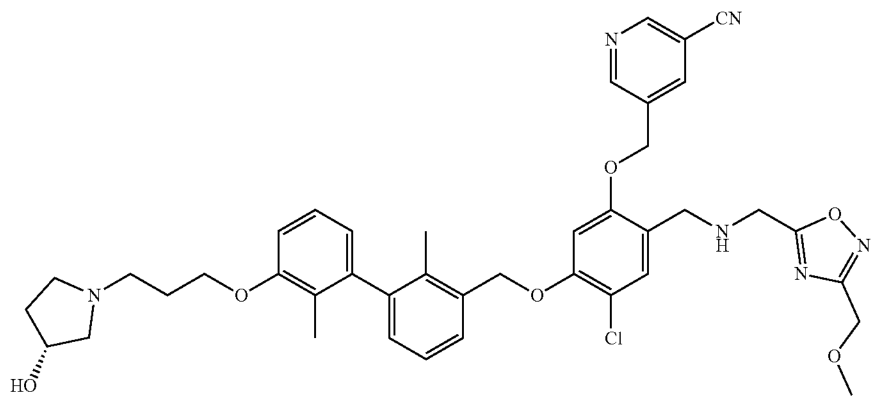 [SMILES: COCc1noc(CNCc2cc(Cl)c(OCc3cccc(-c4cccc(OCCCN5CC[C@@H](O)C5)c4C)c3C)cc2OCc2cncc(C#N)c2)n1]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 19-100% B over 22 minutes, then a 4-minute hold at 100% B; Flow: 20 mL/min. Fractions containing the desired product were combined and dried via centrifugal evaporation and its estimated purity by LCMS analysis was 89%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 90.6%; Observed Mass: 753.19; Retention Time: 1.79 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 88.9%; Observed Mass: 753.19; Retention Time: 1.49 min.

Example 2559: (R)-5-((4-chloro-5-((3'-(3-(3-hydroxypyrrolidin-1-yl)propoxy)-2,2'-dimethyl-[1,1'-biphenyl]-3-yl)methoxy)-2-((methyl((1-methyl-1H-pyrazol-5-yl)methyl)amino)methyl)phenoxy)methyl)nicotinonitrile

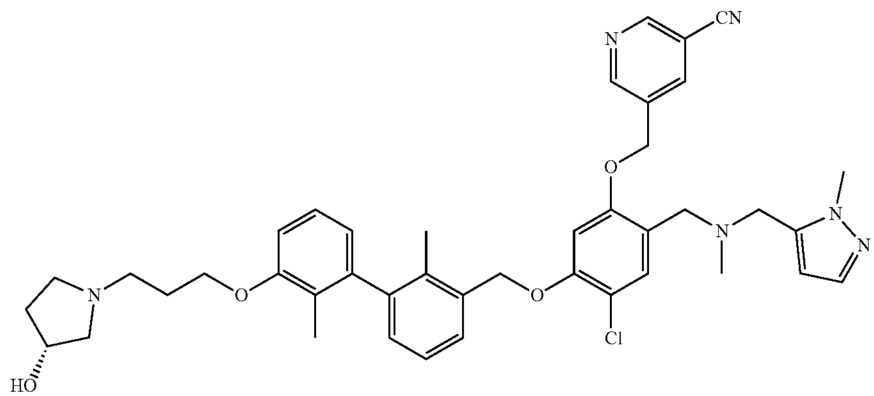 [SMILES: Cc1c(COc2cc(OCc3cncc(C#N)c3)c(CN(C)Cc3ccnn3C)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-100% B over 20 minutes, then a 6-minute hold at 100% B; Flow: 20 mL/min. Fractions containing the desired product were combined and dried via centrifugal evaporation and its estimated purity by LCMS analysis was 93%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 92.8%; Observed Mass: 735.25; Retention Time: 1.99 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 92.7%; Observed Mass: 735.29; Retention Time: 1.45 min.

Example 2560: (R)-5-((4-chloro-5-((3'-(3-(3-hydroxypyrrolidin-1-yl)propoxy)-2,2'-dimethyl-[1,1'-biphenyl]-3-yl)methoxy)-2-((((3-(methoxymethyl)-1,2,4-oxadiazol-5-yl)methyl)(methyl)amino)methyl)phenoxy)methyl)nicotinonitrile

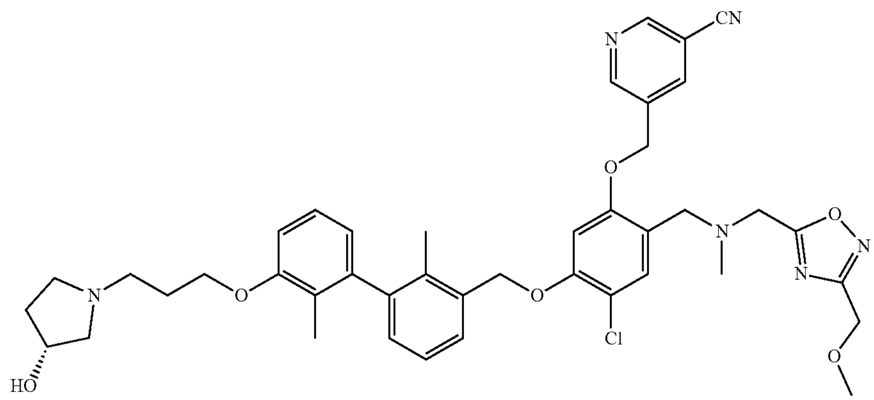 [SMILES: COCc1noc(CN(C)Cc2cc(Cl)c(OCc3cccc(-c4cccc(OCCCN5CC[C@@H](O)C5)c4C)c3C)cc2OCc2cncc(C#N)c2)n1]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 24-64% B over 25 minutes, then a 4-minute hold at 100% B; Flow: 20 mL/min. Fractions containing the desired product were combined and dried via centrifugal evaporation and its estimated purity by LCMS analysis was 84%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 89.2%; Observed Mass: 767.25; Retention Time: 2.07 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 84.4%; Observed Mass: 767.24; Retention Time: 1.56 min.

Example 2561: (R)-5-((2-((((1-benzyl-1H-benzo[d]imidazol-2-yl)methyl)(methyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile

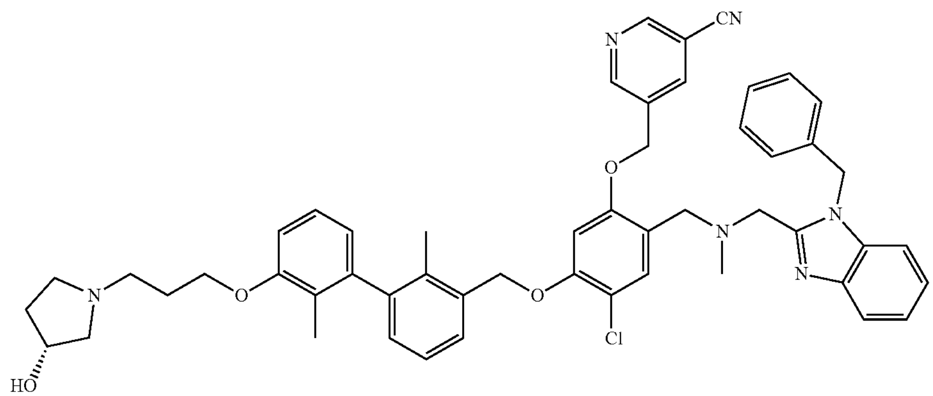 [SMILES: Cc1c(COc2cc(OCc3cncc(C#N)c3)c(CN(C)Cc3nc4ccccc4n3Cc3ccccc3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-100% B over 20 minutes, then a 6-minute hold at 100% B; Flow: 20 mL/min. Fractions containing the desired product were combined and dried via centrifugal evaporation and its estimated purity by LCMS analysis was 93%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 92.6%; Observed Mass: 861.28; Retention Time: 1.78 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 93.4%; Observed Mass: 861.29; Retention Time: 2.21 min.

Example 2562: (R)-5-((4-chloro-5-((3'-(3-(3-hydroxypyrrolidin-1-yl)propoxy)-2,2'-dimethyl-[1,1'-biphenyl]-3-yl)methoxy)-2-((methyl((1-methyl-1H-indazol-3-yl)methyl)amino)methyl)phenoxy)methyl)nicotinonitrile

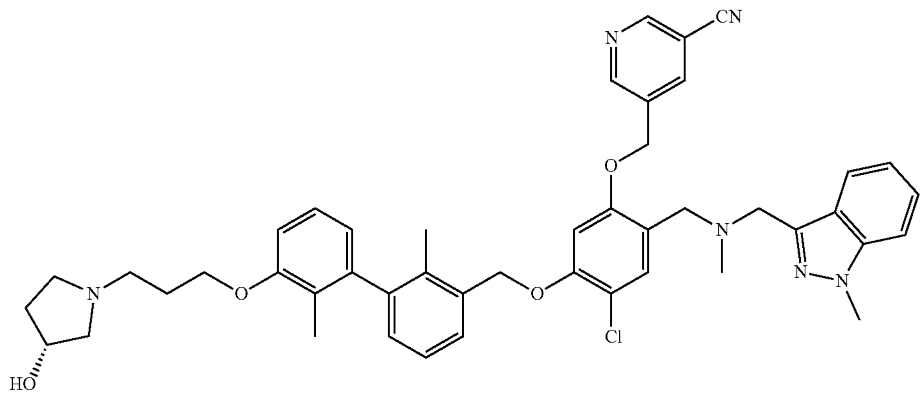 [SMILES: Cc1c(COc2cc(OCc3cncc(C#N)c3)c(CN(C)Cc3nn(C)c4ccccc34)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 12-57% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 27-72% B over 20 minutes, then a 5-minute hold at 100% B; Flow: 20 mL/min. Fractions containing the desired product were combined and dried via centrifugal evaporation and its estimated purity by LCMS analysis was 99%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.9%; Observed Mass: 785.35; Retention Time: 1.64 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 785.28; Retention Time: 2.29 min.

Example 2563: 5-((4-chloro-5-((3'-(3-((R)-3-hydroxypyrrolidin-1-yl)propoxy)-2,2'-dimethyl-[1,1'-biphenyl]-3-yl)methoxy)-2-(((4,5,6,7-tetrahydro-1H-indazol-5-yl)amino)methyl)phenoxy)methyl) nicotinonitrile

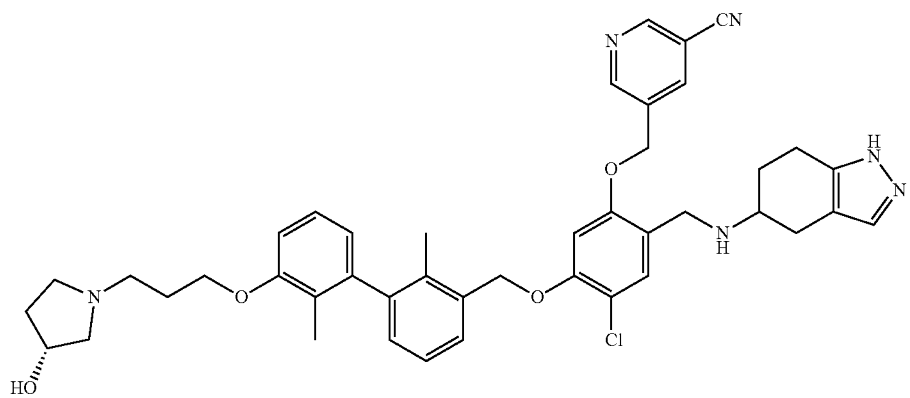 [SMILES: Cc1c(COc2cc(OCc3cncc(C#N)c3)c(CNC3CCc4[nH]ncc4C3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 13-53% B over 25 minutes, then a 6-minute hold at 100% B; Flow: 20 mL/min. Fractions containing the desired product were combined and dried via centrifugal evaporation and its estimated purity by LCMS analysis was 95%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.1%; Observed Mass: 747.21; Retention Time: 1.45 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow:

1 mL/min; Detection: MS and UV (220 nm). Injection 2 results: Purity: 94.9%; Observed Mass: 747.22; Retention Time: 1.39 min.

Example 2564: 5-((4-chloro-5-((3'-(3-((R)-3-hydroxypyrrolidin-1-yl)propoxy)-2,2'-dimethyl-[1,1'-biphenyl]-3-yl)methoxy)-2-((methyl(4,5,6,7-tetrahydro-1H-indazol-5-yl)amino)methyl)phenoxy)methyl)nicotinonitrile

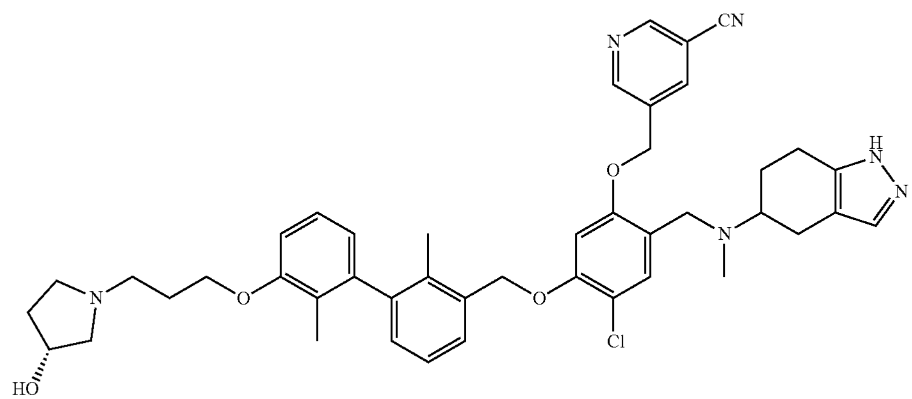 [SMILES: Cc1c(COc2cc(OCc3cncc(C#N)c3)c(CN(C)C3CCc4[nH]ncc4C3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 25-65% B over 22 minutes, then a 4-minute hold at 100% B; Flow: 20 mL/min. Fractions containing the desired product were combined and dried via centrifugal evaporation and its estimated purity by LCMS analysis was 95%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.4%; Observed Mass: 761.24; Retention Time: 1.42 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.1%; Observed Mass: 761.26; Retention Time: 1.67 min.

Example 2565: (R)-5-((4-chloro-5-((3'-(3-(3-hydroxypyrrolidin-1-yl)propoxy)-2,2'-dimethyl-[1,1'-biphenyl]-3-yl)methoxy)-2-(((imidazo[1,5-a]pyridin-3-ylmethyl)amino)methyl)phenoxy)methyl)nicotinonitrile

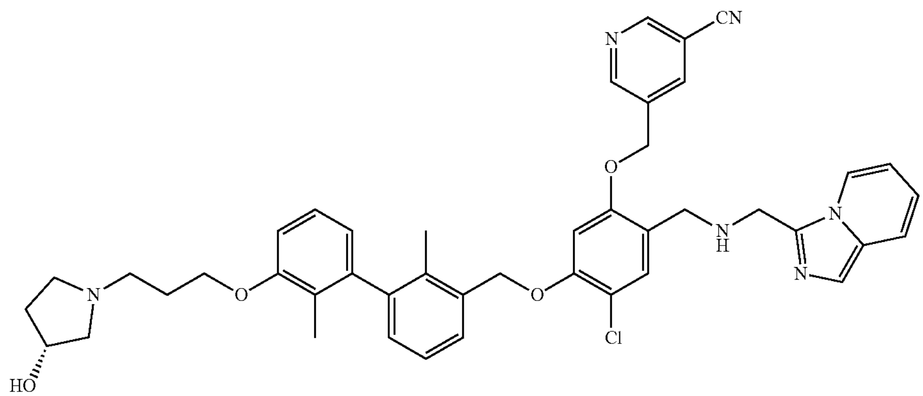 [SMILES: Cc1c(COc2cc(OCc3cncc(C#N)c3)c(CNCc3ncc4ccccn34)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 25 minutes, then a 4-minute hold at 100% B; Flow: 20 mL/min. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.1%; Observed Mass: 757.17; Retention Time: 1.63 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 757.2; Retention Time: 1.75 min.

Example 2566: (R)-5-((4-chloro-5-((3'-(3-(3-hydroxypyrrolidin-1-yl)propoxy)-2,2'-dimethyl-[1,1'-biphenyl]-3-yl)methoxy)-2-((((5-phenyloxazol-2-yl)methyl)amino)methyl)phenoxy)methyl)nicotinonitrile

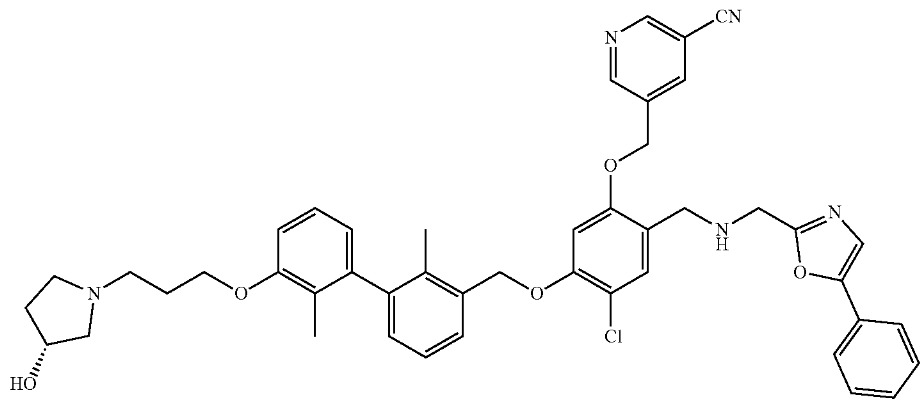 [SMILES: Cc1c(COc2cc(OCc3cncc(C#N)c3)c(CNCc3ncc(-c4ccccc4)o3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 38-78% B over 20 minutes, then a 4-minute hold at 100% B; Flow: 20 mL/min. Fractions containing the desired product were combined and dried via centrifugal evaporation and its estimated purity by LCMS analysis was 100%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 784.21; Retention Time: 1.99 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 784.22; Retention Time: 1.61 min.

Example 2567: (R)-5-((4-chloro-5-((3'-(3-(3-hydroxypyrrolidin-1-yl)propoxy)-2,2'-dimethyl-[1,1'-biphenyl]-3-yl)methoxy)-2-((1-phenyl-1,4,6,7-tetrahydro-5H-pyrazolo[4,3-c]pyridin-5-yl)methyl)phenoxy)methyl)nicotinonitrile

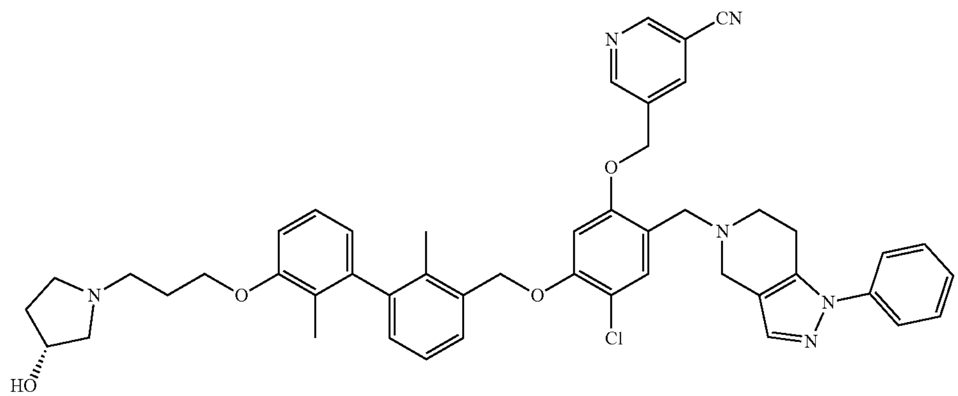 [SMILES: Cc1c(COc2cc(OCc3cncc(C#N)c3)c(CN3CCc4c(cnn4-c4ccccc4)C3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 42-82% B over 20 minutes, then a 4-minute hold at 100% B; Flow: 20 mL/min. Fractions containing the desired product were combined and dried via centrifugal evaporation and its estimated purity by LCMS analysis was 97%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.7%; Observed Mass: 809.26; Retention Time: 2.28 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.7%; Observed Mass: 809.27; Retention Time: 1.61 min.

Example 2568: 5-((2-((3-(1H-pyrazol-3-yl)piperidin-1-yl)methyl)-4-chloro-5-((3'-(3-((R)-3-hydroxypyrrolidin-1-yl)propoxy)-2,2'-dimethyl-[1,1'-biphenyl]-3-yl)methoxy)phenoxy)methyl)nicotinonitrile

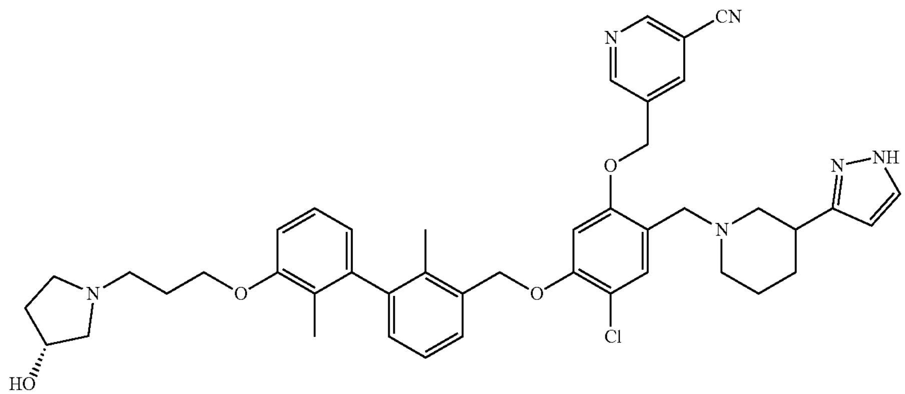 [SMILES: Cc1c(COc2cc(OCc3cncc(C#N)c3)c(CN3CCCC(c4cc[nH]n4)C3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 8-48% B over 20 minutes, then a 5-minute hold at 100% B; Flow: 20 mL/min. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.7%; Observed Mass: 761.23; Retention Time: 1.49 min. Injection 2 conditions: Column: Waters XBridge C18, 2.1 mm×50 mm, 1.7 m particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.6%; Observed Mass: 761.28; Retention Time: 1.91 min.

Example 2569: (R)-5-((4-chloro-5-((3'-(3-(3-hydroxypyrrolidin-1-yl)propoxy)-2,2'-dimethyl-[1,1'-biphenyl]-3-yl)methoxy)-2-((1,4,5,7-tetrahydro-6H-pyrazolo[3,4-c]pyridin-6-yl)methyl)phenoxy)methyl)nicotinonitrile

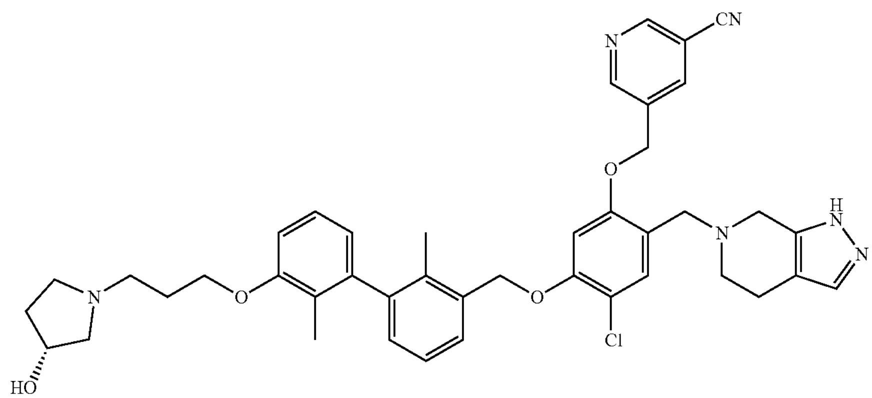 [SMILES: Cc1c(COc2cc(OCc3cncc(C#N)c3)c(CN3CCc4cn[nH]c4C3)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 15-55% B over 23 minutes, then a 5-minute hold at 100% B; Flow: 20 mL/min. Fractions containing the desired product were combined and dried via centrifugal evaporation and its estimated purity by LCMS analysis was 98%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 733.19; Retention Time: 1.93 min. Injection 2 conditions: Column: Waters XBridge C18, 2.1 mm×50 mm, 1.7 m particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.1%; Observed Mass: 733.22; Retention Time: 1.52 min.

Example 2570: (R)-5-((4-chloro-2-((((3,5-dimethyl-1H-pyrazol-4-yl)methyl)amino)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile

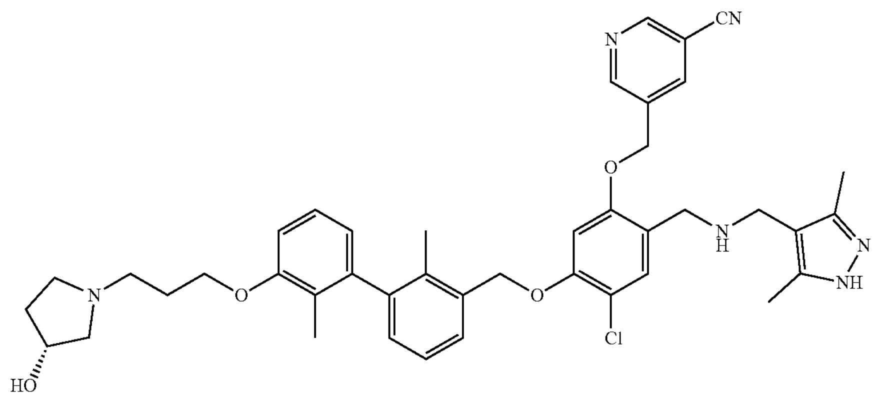 [SMILES: Cc1n[nH]c(C)c1CNCc1cc(Cl)c(OCc2cccc(-c3cccc(OCCCN4CC[C@@H](O)C4)c3C)c2C)cc1OCc1cncc(C#N)c1]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 8-48% B over 25 minutes, then a 6-minute hold at 100% B; Flow: 20 mL/min. Fractions containing the desired product were combined and dried via centrifugal evaporation and its estimated purity by LCMS analysis was 97%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.6%; Observed Mass: 735.25; Retention Time: 1.65 min. Injection 2 conditions: Column: Waters XBridge C18, 2.1 mm×50 mm, 1.7 m particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.8%; Observed Mass: 735.28; Retention Time: 1.41 min.

Example 2571: (R)-5-((4-chloro-2-((((4,5-diethyl-1H-imidazol-2-yl)methyl)(2-methoxyethyl)amino)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile

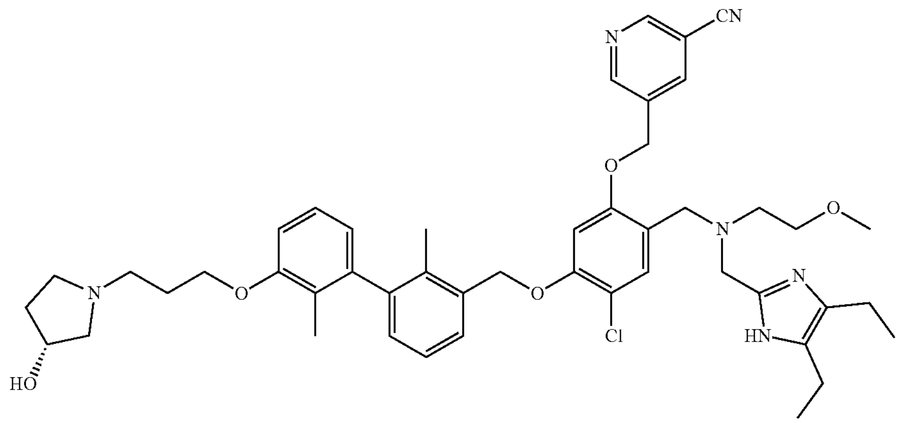 [SMILES: CCc1nc(CN(CCOC)Cc2cc(Cl)c(OCc3cccc(-c4cccc(OCCCN5CC[C@@H](O)C5)c4C)c3C)cc2OCc2cncc(C#N)c2)[nH]c1CC]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 23-63% B over 25 minutes, then a 4-minute hold at 100% B; Flow: 20 mL/min. Fractions containing the desired product were combined and dried via centrifugal evaporation and its estimated purity by LCMS analysis was 94%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.6%; Observed Mass: 821.38; Retention Time: 1.69 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 94.5%; Observed Mass: 821.35; Retention Time: 1.99 min.

Example 2572: (R)-5-((4-chloro-2-((((3,5-dimethyl-1H-pyrazol-4-yl)methyl)(methyl)amino)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile

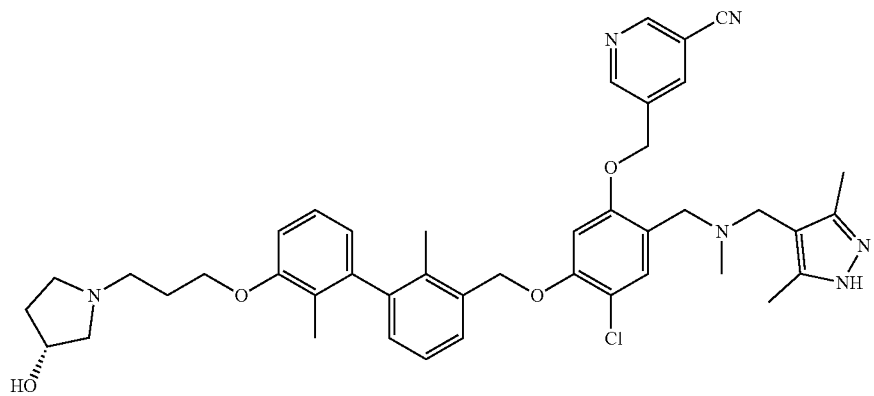 [SMILES: Cc1n[nH]c(C)c1CN(C)Cc1cc(Cl)c(OCc2cccc(-c3cccc(OCCCN4CC[C@@H](O)C4)c3C)c2C)cc1OCc1cncc(C#N)c1]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 19-64% B over 20 minutes, then a 5-minute hold at 100% B; Flow: 20 mL/min. Fractions containing the desired product were combined and dried via centrifugal evaporation and its estimated purity by LCMS analysis was 92%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 92.3%; Observed Mass: 749.22; Retention Time: 1.43 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 94.8%; Observed Mass: 749.3; Retention Time: 1.78 min.

Example 2575: 5-((4-chloro-5-((2'-chloro-2-methyl-3'-((1-methylpiperidin-3-yl)methoxy)-[1,1'-biphenyl]-3-yl)methoxy)-2-((((5-methylisoxazol-3-yl)methyl)amino)methyl)phenoxy)methyl)nicotinonitrile

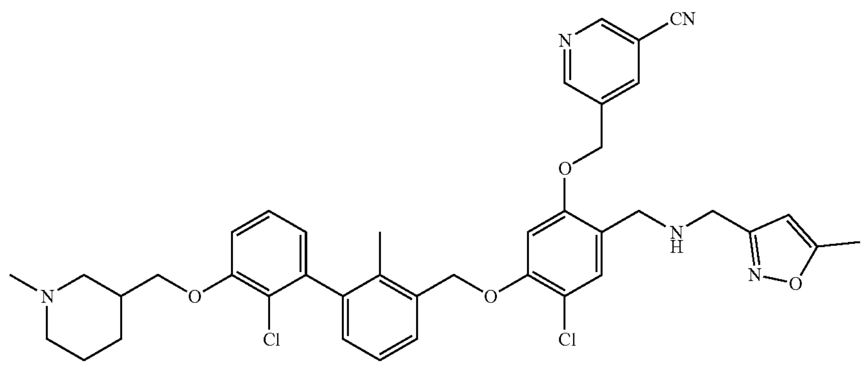

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 40% B, 40-80% B over 20 minutes, then a 5-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 100%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 726.2; Retention Time: 1.56 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 726.17; Retention Time: 2.08 min.

Example 2576: 5-((4-chloro-5-((2'-chloro-2-methyl-3'-((1-methylpiperidin-3-yl)methoxy)-[1,1'-biphenyl]-3-yl)methoxy)-2-(((thiazol-5-ylmethyl)amino)methyl) phenoxy)methyl)nicotinonitrile

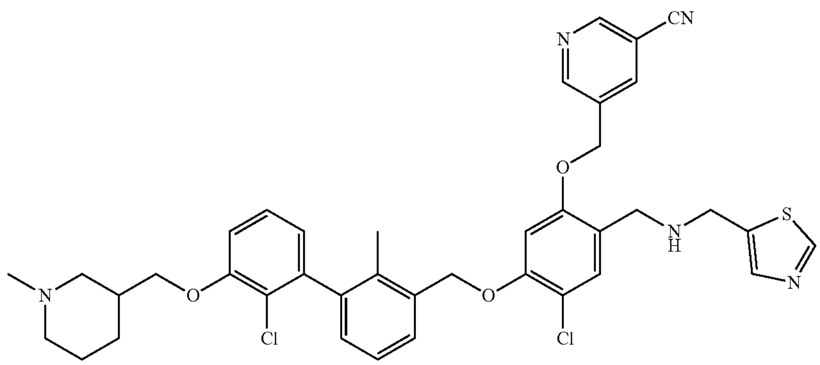 [SMILES: Cc1c(COc2cc(OCc3cncc(C#N)c3)c(CNCc3cncs3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 32% B, 32-72% B over 22 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 95%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.4%; Observed Mass: 728.14; Retention Time: 1.48 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.4%; Observed Mass: 728.13; Retention Time: 2.02 min.

Example 2577: 5-((2-((((1H-imidazol-2-yl)methyl)amino)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile

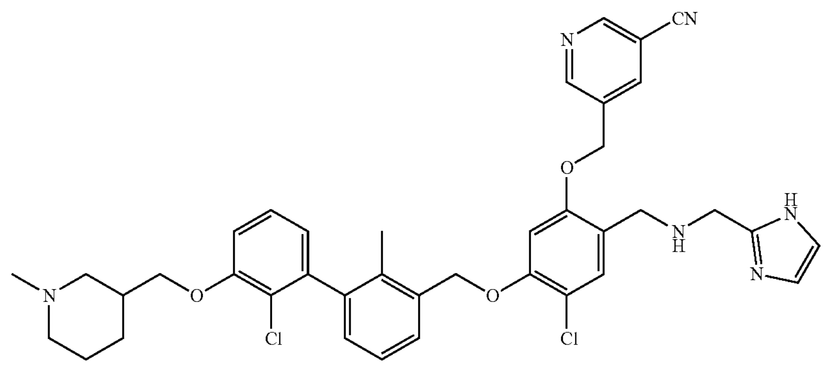 [SMILES: Cc1c(COc2cc(OCc3cncc(C#N)c3)c(CNCc3ncc[nH]3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 21% B, 21-61% B over 25 minutes, then a 5-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 95%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 94.7%; Observed Mass: 711.19; Retention Time: 1.38 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.8%; Observed Mass: 711.17; Retention Time: 1.8 min.

Example 2578: 5-((2-((((1H-1,2,4-triazol-5-yl)methyl)amino)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile

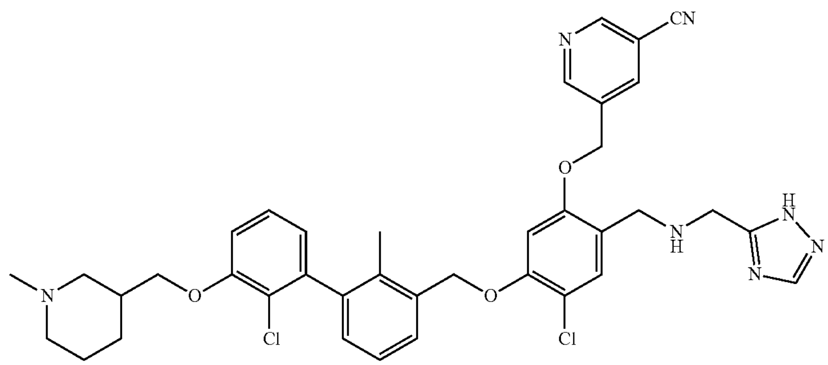 [SMILES: Cc1c(COc2cc(OCc3cncc(C#N)c3)c(CNCc3ncn[nH]3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 20% B, 20-60% B over 20 minutes, then a 5-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 95%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.0%; Observed Mass: 712.16; Retention Time: 1.74 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.1%; Observed Mass: 712.14; Retention Time: 1.43 min.

Example 2579: 5-((2-(((2-(1H-1,2,4-triazol-5-yl)ethyl)amino)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile

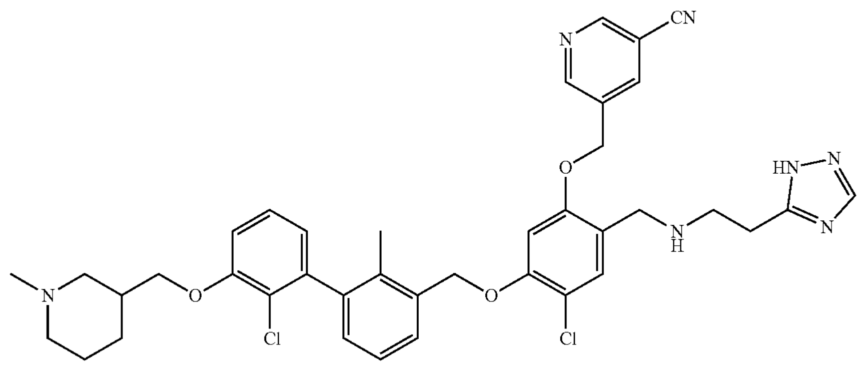 [SMILES: Cc1c(COc2cc(OCc3cncc(C#N)c3)c(CNCCc3ncn[nH]3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 20% B, 20-60% B over 20 minutes, then a 5-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 98%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 726.2; Retention Time: 1.76 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.0%; Observed Mass: 726.16; Retention Time: 1.43 min.

Example 2580: 5-((2-(((2-(1H-imidazol-4-yl)ethyl)amino)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile

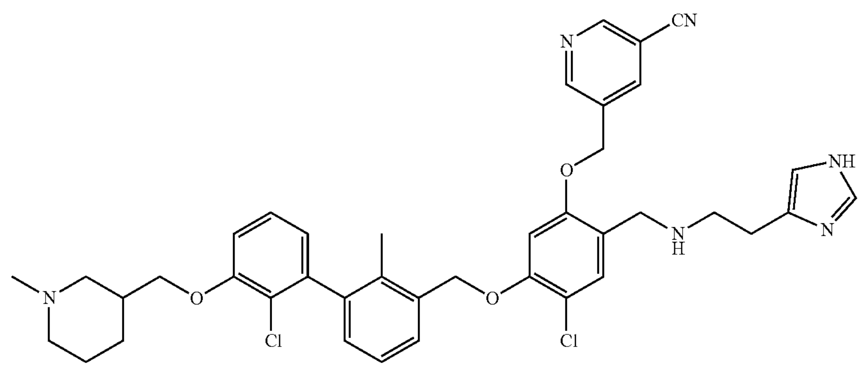 [SMILES: Cc1c(COc2cc(OCc3cncc(C#N)c3)c(CNCCc3c[nH]cn3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 20% B, 20-60% B over 20 minutes, then a 5-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 99%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 725.2; Retention Time: 1.83 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.9%; Observed Mass: 725.25; Retention Time: 1.34 min.

Example 2581: 5-((2-((((1H-pyrazol-4-yl)methyl)(methyl)amino)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile

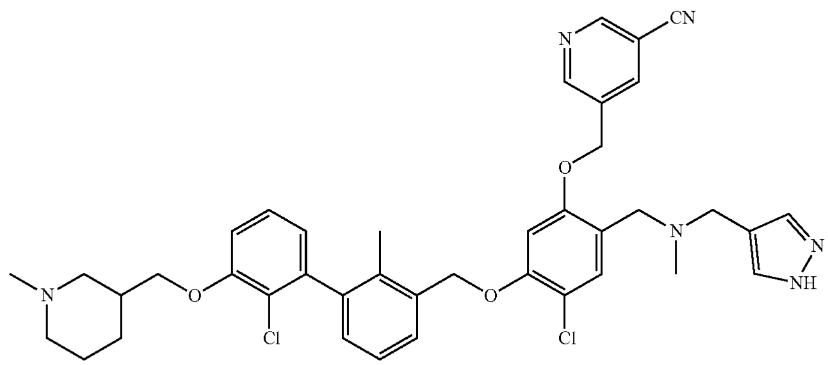 [SMILES: Cc1c(COc2cc(OCc3cncc(C#N)c3)c(CN(C)Cc3cn[nH]c3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 22% B, 22-62% B over 25 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 97%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.4%; Observed Mass: 725.19; Retention Time: 1.85 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.0%; Observed Mass: 725.19; Retention Time: 1.46 min.

Example 2582: 5-((2-(((2-(1H-pyrazol-3-yl)ethyl)amino)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile

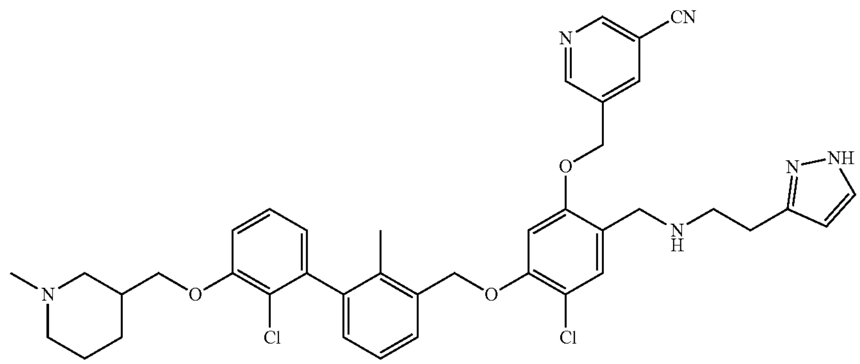 [SMILES: Cc1c(COc2cc(OCc3cncc(C#N)c3)c(CNCCc3cc[nH]n3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 26% B, 26-66% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 97%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.1%; Observed Mass: 725.2; Retention Time: 1.49 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.7%; Observed Mass: 725.2; Retention Time: 1.88 min.

Example 2583: 5-((4-chloro-5-((2'-chloro-2-methyl-3'-((1-methylpiperidin-3-yl)methoxy)-[1,1'-biphenyl]-3-yl)methoxy)-2-((1,4,6,7-tetrahydro-5H-imidazo[4,5-c]pyridin-5-yl)methyl)phenoxy)methyl) nicotinonitrile

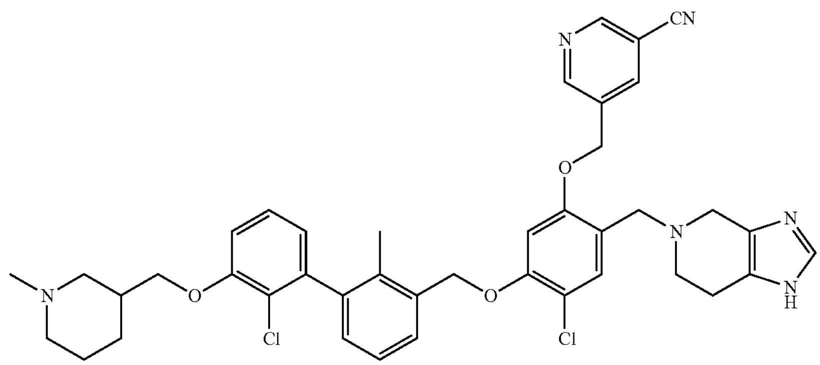 [SMILES: Cc1c(COc2cc(OCc3cncc(C#N)c3)c(CN3CCc4[nH]cnc4C3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 25% B, 25-65% B over 25 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.6%; Observed Mass: 737.18; Retention Time: 1.89 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.4%; Observed Mass: 737.2; Retention Time: 1.34 min.

Example 2584: 5-((4-chloro-5-((2'-chloro-2-methyl-3'-((1-methylpiperidin-3-yl)methoxy)-[1,1'-biphenyl]-3-yl)methoxy)-2-(((pyrimidin-5-ylmethyl)amino)methyl)phenoxy)methyl)nicotinonitrile

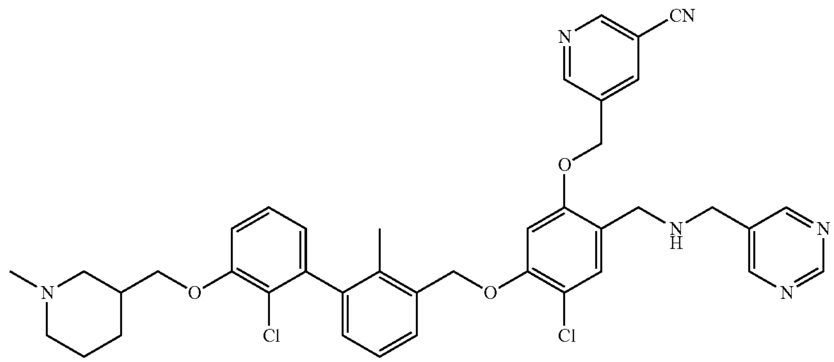 [SMILES: Cc1c(COc2cc(OCc3cncc(C#N)c3)c(CNCc3cncnc3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 16% B, 16-56% B over 23 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 99%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 723.16; Retention Time: 1.45 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.4%; Observed Mass: 723.22; Retention Time: 1.77 min.

Example 2585: 5-((4-chloro-5-((2'-chloro-2-methyl-3'-((1-methylpiperidin-3-yl)methoxy)-[1,1'-biphenyl]-3-yl)methoxy)-2-(((thiazol-2-ylmethyl)amino)methyl) phenoxy)methyl)nicotinonitrile

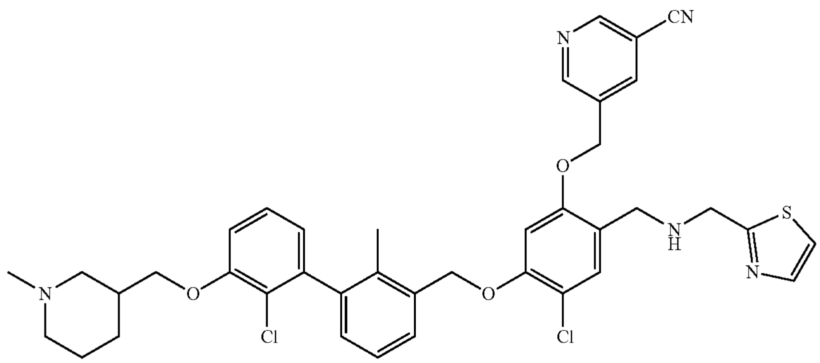 [SMILES: Cc1c(COc2cc(OCc3cncc(C#N)c3)c(CNCc3nccs3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 33% B, 33-73% B over 25 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 99%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 728.14; Retention Time: 2.11 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.7%; Observed Mass: 728.11; Retention Time: 1.52 min.

Example 2586: 5-((2-((((2-aminothiazol-4-yl)methyl)amino)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile

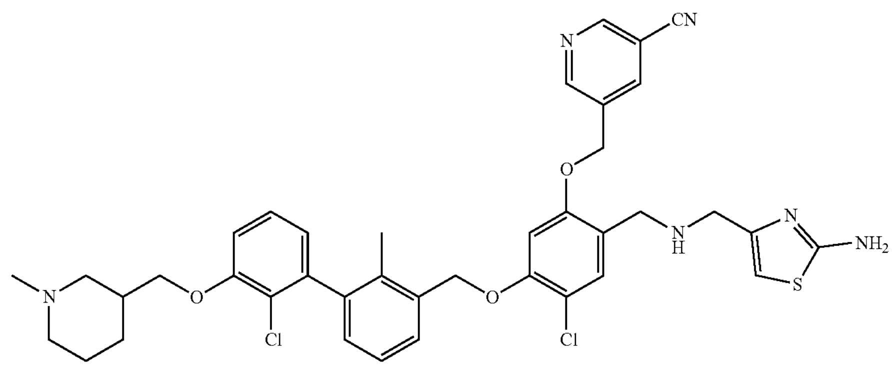 [SMILES: Cc1c(COc2cc(OCc3cncc(C#N)c3)c(CNCc3csc(N)n3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 29% B, 29-69% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 95%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.4%; Observed Mass: 743.18; Retention Time: 1.46 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.2%; Observed Mass: 743.18; Retention Time: 1.87 min.

Example 2587: 5-((4-chloro-5-((2'-chloro-2-methyl-3'-((1-methylpiperidin-3-yl)methoxy)-[1,1'-biphenyl]-3-yl)methoxy)-2-((1,4,6,7-tetrahydro-5H-pyrazolo[4,3-c]pyridin-5-yl)methyl)phenoxy)methyl) nicotinonitrile

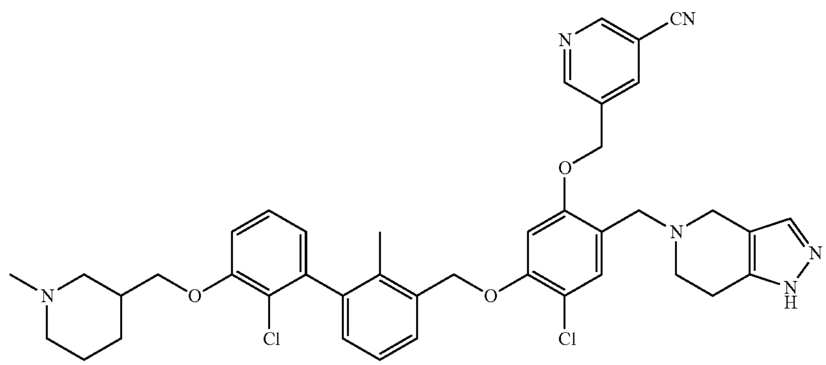 [SMILES: Cc1c(COc2cc(OCc3cncc(C#N)c3)c(CN3CCc4[nH]ncc4C3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 18% B, 18-58% B over 23 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 88%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.8%; Observed Mass: 737.21; Retention Time: 1.46 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 88.4%; Observed Mass: 737.19; Retention Time: 1.98 min.

Example 2588: 5-((2-((((1H-pyrazol-3-yl)methyl) amino)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile

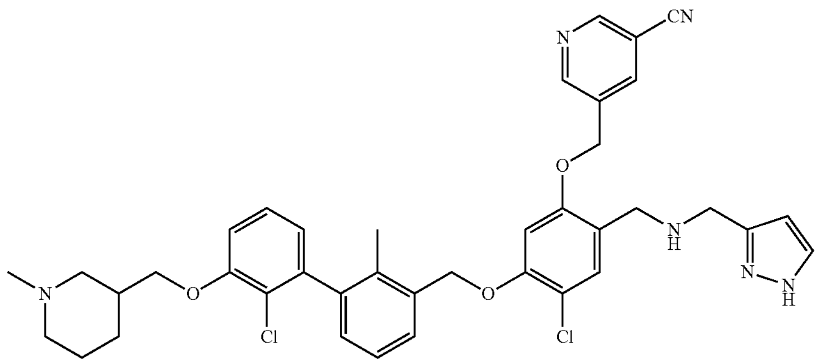 [SMILES: Cc1c(COc2cc(OCc3cncc(C#N)c3)c(CNCc3cc[nH]n3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 28% B, 28-69% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 98%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.7%; Observed Mass: 711.19; Retention Time: 1.47 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.8%; Observed Mass: 711.18; Retention Time: 1.8 min.

Example 2589: 5-((4-chloro-5-((2'-chloro-2-methyl-3'-((1-methylpiperidin-3-yl)methoxy)-[1,1'-biphenyl]-3-yl)methoxy)-2-((1,4,5,7-tetrahydro-6H-pyrazolo[3,4-c]pyridin-6-yl)methyl)phenoxy)methyl) nicotinonitrile

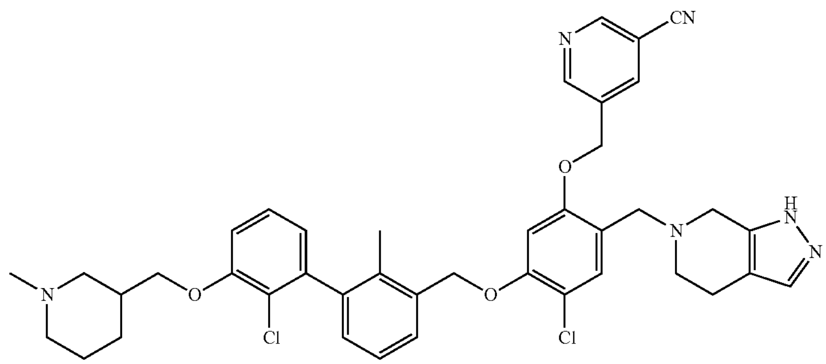 [SMILES: Cc1c(COc2cc(OCc3cncc(C#N)c3)c(CN3CCc4cn[nH]c4C3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 42% B, 42-83% B over 23 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 98%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.0%; Observed Mass: 737.2; Retention Time: 2.1 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.6%; Observed Mass: 737.22; Retention Time: 1.57 min.

Example 2590: 5-((4-chloro-5-((2'-chloro-2-methyl-3'-((1-methylpiperidin-3-yl)methoxy)-[1,1'-biphenyl]-3-yl)methoxy)-2-(((oxazol-2-ylmethyl)amino) methyl) phenoxy)methyl)nicotinonitrile

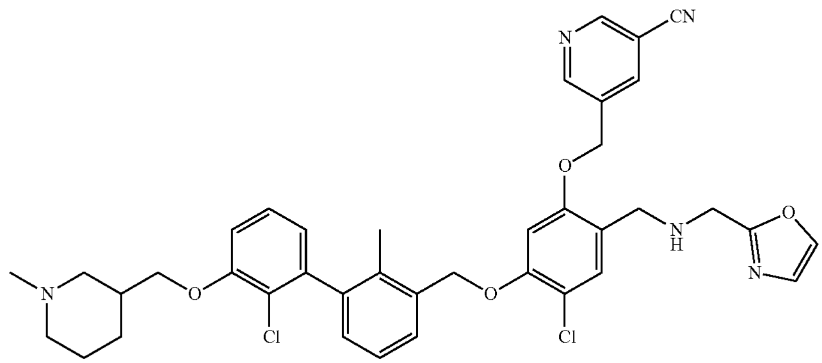 [SMILES: Cc1c(COc2cc(OCc3cncc(C#N)c3)c(CNCc3ncco3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 35% B, 35-75% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 95%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.4%; Observed Mass: 712.16; Retention Time: 1.49 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.3%; Observed Mass: 712.17; Retention Time: 1.98 min.

Example 2591: 5-((4-chloro-5-((2'-chloro-2-methyl-3'-((1-methylpiperidin-3-yl)methoxy)-[1,1'-biphenyl]-3-yl)methoxy)-2-(((oxazol-5-ylmethyl)amino) methyl) phenoxy)methyl)nicotinonitrile

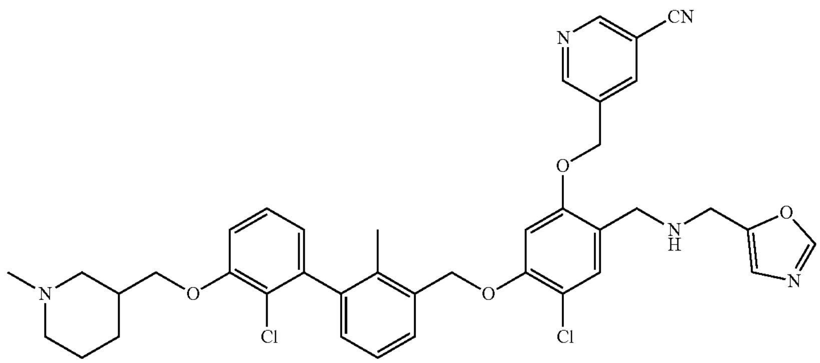

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 34% B, 34-74% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 712.23; Retention Time: 1.8 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.5%; Observed Mass: 712.22; Retention Time: 1.44 min.

Example 2592: 5-((4-chloro-5-((2'-chloro-2-methyl-3'-((1-methylpiperidin-3-yl)methoxy)-[1,1'-biphenyl]-3-yl)methoxy)-2-((1-methyl-1,4,6,7-tetrahydro-5H-imidazo[4,5-c]pyridin-5-yl)methyl)phenoxy)methyl)nicotinonitrile

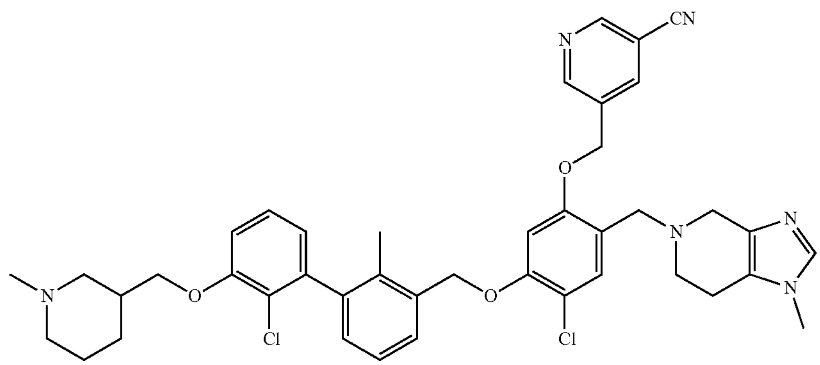 [SMILES: Cc1c(COc2cc(OCc3cncc(C#N)c3)c(CN3CCc4c(ncn4C)C3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 16% B, 16-56% B over 22 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. The material was further purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 26% B, 26-66% B over 25 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 95%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 751.19; Retention Time: 1.99 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100%

B; Flow: 1 mL/min; Detection: MS and UV (220 nm). Injection 2 results: Purity: 95.4%; Observed Mass: 751.22; Retention Time: 1.35 min.

Example 2593: 5-((2-(((2-(1H-benzo[d]imidazol-2-yl)ethyl)amino)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile

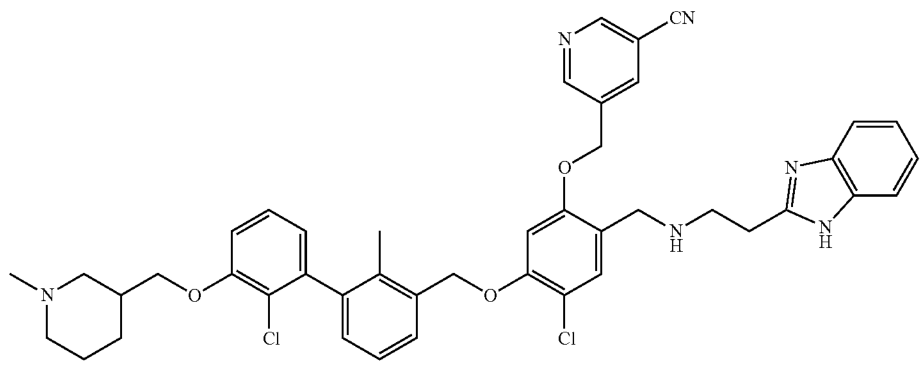 [SMILES: Cc1c(COc2cc(OCc3cncc(C#N)c3)c(CNCCc3nc4ccccc4[nH]3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 31% B, 31-71% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 90%. Analytical LC/MS was used to determine the final purity. Injection 1 conditions: Column: Waters XBridge Phenyl, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 92.3%; Observed Mass: 775.25; Retention Time: 1.9 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 90.4%; Observed Mass: 775.19; Retention Time: 1.43 min.

Example 2594: 5-((4-chloro-5-((2'-chloro-2-methyl-3'-((1-methylpiperidin-3-yl)methoxy)-[1,1'-biphenyl]-3-yl)methoxy)-2-(((2-(4-methylthiazol-5-yl)ethyl)amino)methyl)phenoxy)methyl)nicotinonitrile

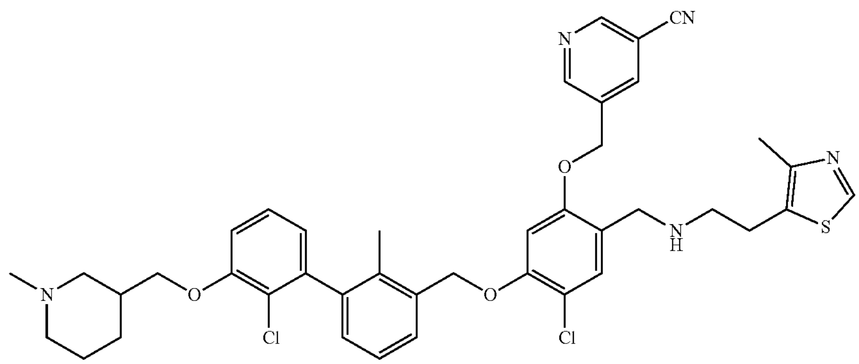 [SMILES: Cc1ncsc1CCNCc1cc(Cl)c(OCc2cccc(-c3cccc(OCC4CCCN(C)C4)c3Cl)c2C)cc1OCc1cncc(C#N)c1]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 35% B, 35-75% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 97%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.4%; Observed Mass: 756.18; Retention Time: 2.04 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.1%; Observed Mass: 756.14; Retention Time: 1.48 min.

Example 2595: 5-((4-chloro-5-((2'-chloro-2-methyl-3'-((1-methylpiperidin-3-yl)methoxy)-[1,1'-biphenyl]-3-yl)methoxy)-2-((((3-(methoxymethyl)-1,2,4-oxadiazol-5-yl)methyl)amino)methyl)phenoxy)methyl)nicotinonitrile

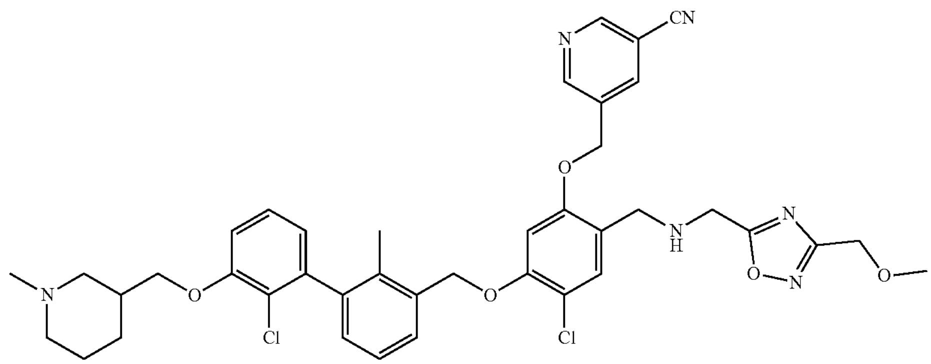

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 35% B, 35-75% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 100%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 757.18; Retention Time: 2.03 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 757.21; Retention Time: 1.53 min.

Example 2596: 5-((4-chloro-5-((2'-chloro-2-methyl-3'-((1-methylpiperidin-3-yl)methoxy)-[1,1'-biphenyl]-3-yl)methoxy)-2-((((1,5-dimethyl-1H-pyrazol-3-yl)methyl)amino)methyl)phenoxy)methyl) nicotinonitrile

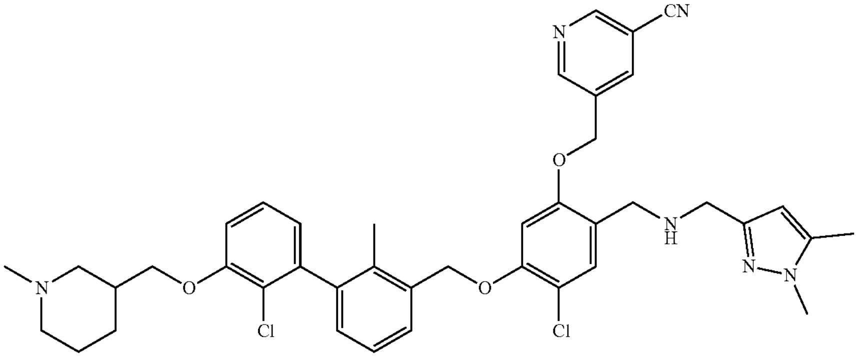

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 30% B, 30-70% B over 25 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 98%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.5%; Observed Mass: 739.19; Retention Time: 1.55 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.2%; Observed Mass: 739.22; Retention Time: 1.93 min.

Example 2597: 5-((4-chloro-5-((2'-chloro-2-methyl-3'-((1-methylpiperidin-3-yl)methoxy)-[1,1'-biphenyl]-3-yl)methoxy)-2-((((3,5-dimethylisoxazol-4-yl) methyl)amino)methyl)phenoxy)methyl) nicotinonitrile

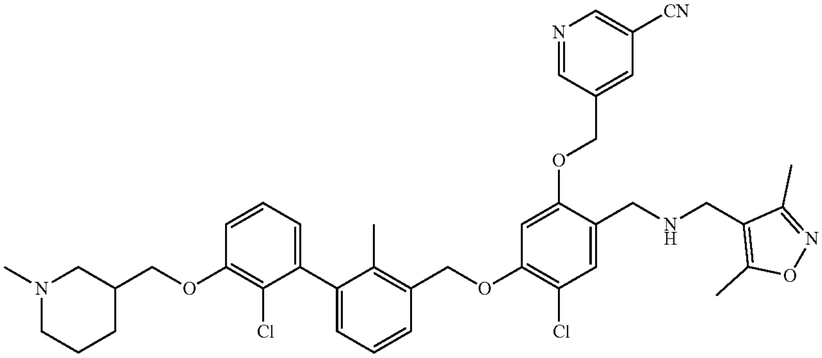 [SMILES: Cc1noc(C)c1CNCc1cc(Cl)c(OCc2cccc(-c3cccc(OCC4CCCN(C)C4)c3Cl)c2C)cc1OCc1cncc(C#N)c1]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 37% B, 37-77% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 99%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.3%; Observed Mass: 740.22; Retention Time: 2.1 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.4%; Observed Mass: 740.23; Retention Time: 1.53 min.

Example 2598: 5-((4-chloro-5-((2'-chloro-2-methyl-3'-((1-methylpiperidin-3-yl)methoxy)-[1,1'-biphenyl]-3-yl)methoxy)-2-(((2-(thiazol-4-yl)ethyl)amino)methyl) phenoxy)methyl)nicotinonitrile

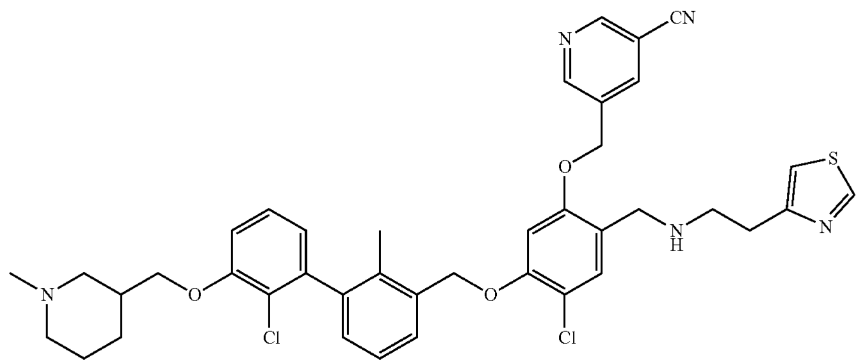 [SMILES: Cc1c(COc2cc(OCc3cncc(C#N)c3)c(CNCCc3cscn3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 30% B, 30-70% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 98%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.3%; Observed Mass: 742.2; Retention Time: 1.95 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.3%; Observed Mass: 742.18; Retention Time: 1.55 min.

Example 2599: 5-((4-chloro-5-((2'-chloro-2-methyl-3'-((1-methylpiperidin-3-yl)methoxy)-[1,1'-biphenyl]-3-yl)methoxy)-2-((((3,5-dimethyl-1H-pyrazol-4-yl)methyl)amino)methyl)phenoxy)methyl)nicotinonitrile

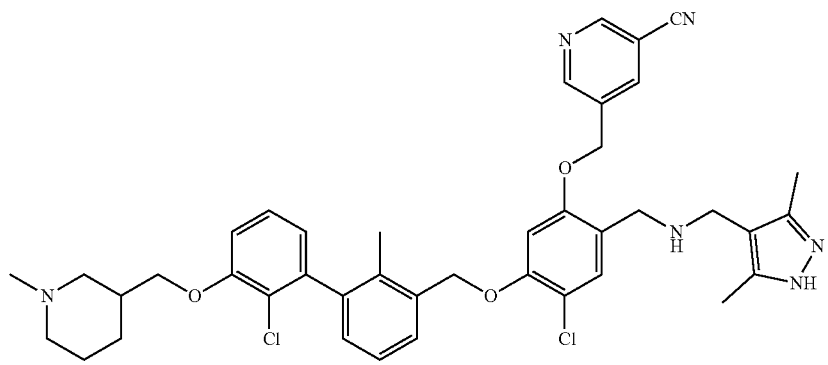 [SMILES: Cc1n[nH]c(C)c1CNCc1cc(Cl)c(OCc2cccc(-c3cccc(OCC4CCCN(C)C4)c3Cl)c2C)cc1OCc1cncc(C#N)c1]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 27% B, 27-67% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 97%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.0%; Observed Mass: 739.25; Retention Time: 1.82 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.2%; Observed Mass: 739.26; Retention Time: 1.46 min.

Example 2600: 5-((4-chloro-5-((2'-chloro-2-methyl-3'-((1-methylpiperidin-3-yl)methoxy)-[1,1'-biphenyl]-3-yl)methoxy)-2-((2-methyl-6,7-dihydrothiazolo[5,4-c]pyridin-5(4H)-yl)methyl)phenoxy)methyl)nicotinonitrile

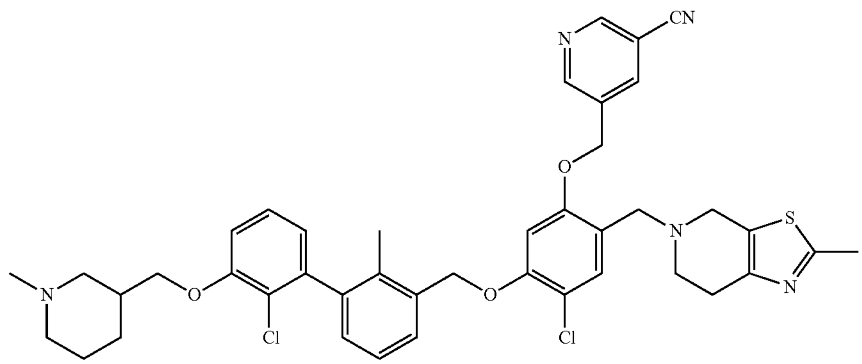

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 45% B, 45-85% B over 22 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 95%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 94.9%; Observed Mass: 768.19; Retention Time: 2.19 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.5%; Observed Mass: 768.22; Retention Time: 1.51 min.

Example 2601: 5-((4-chloro-5-((2'-chloro-2-methyl-3'-((1-methylpiperidin-3-yl)methoxy)-[1,1'-biphenyl]-3-yl)methoxy)-2-(((4,5,6,7-tetrahydro-1H-indazol-5-yl)amino)methyl)phenoxy)methyl)nicotinonitrile

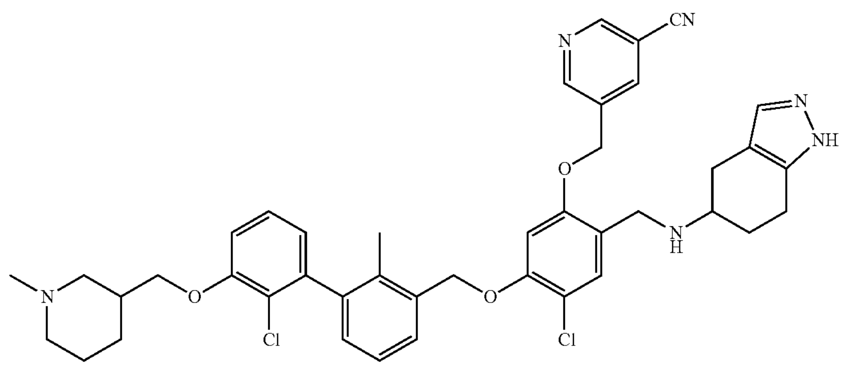 [SMILES: Cc1c(COc2cc(OCc3cncc(C#N)c3)c(CNC3CCc4[nH]ncc4C3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 25% B, 25-65% B over 22 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 97%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: MS and UV (220 nm). Injection 2 results: Purity: 97.0%; Observed Mass: 751.3; Retention Time: 1.77 min.

Example 2602: 5-((4-chloro-5-((2'-chloro-2-methyl-3'-((1-methylpiperidin-3-yl)methoxy)-[1,1'-biphenyl]-3-yl)methoxy)-2-(((pyrazolo[1,5-a]pyridin-2-ylmethyl)amino)methyl)phenoxy)methyl) nicotinonitrile

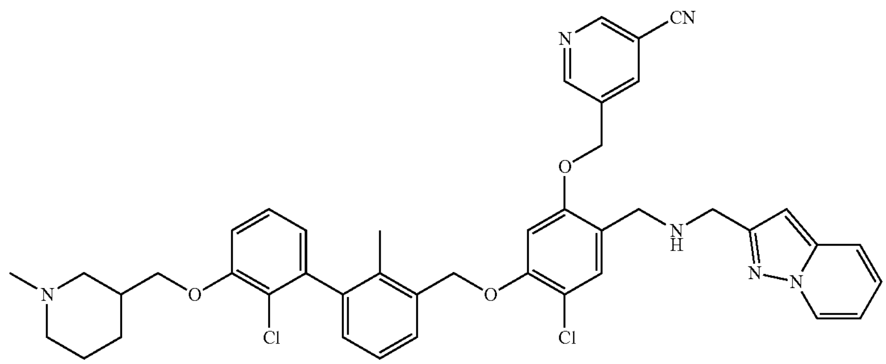 [SMILES: Cc1c(COc2cc(OCc3cncc(C#N)c3)c(CNCc3cc4ccccn4n3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 39% B, 39-79% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 99%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 761.22; Retention Time: 1.95 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.3%; Observed Mass: 761.23; Retention Time: 1.57 min.

Example 2603: 5-((4-chloro-5-((2'-chloro-2-methyl-3'-((1-methylpiperidin-3-yl)methoxy)-[1,1'-biphenyl]-3-yl)methoxy)-2-((((5-methyl-1,2,4-oxadiazol-3-yl)methyl)amino)methyl)phenoxy)methyl) nicotinonitrile

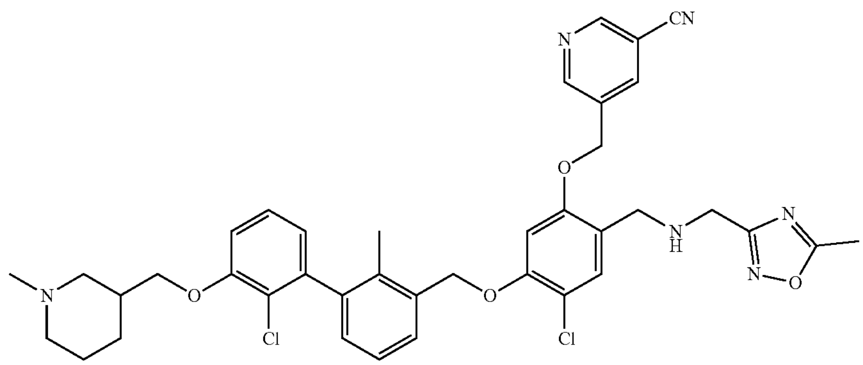

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 38% B, 38-78% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 99%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.9%; Observed Mass: 727.19; Retention Time: 1.53 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.0%; Observed Mass: 727.18; Retention Time: 1.9 min Example 2604: 5-((4-chloro-5-((2'-chloro-2-methyl-3'-((1-methylpiperidin-3-yl)methoxy)-[1,1'-biphenyl]-3-yl)methoxy)-2-((((5-methyl-4H-1,2,4-triazol-3-yl)methyl)amino)methyl)phenoxy)methyl) nicotinonitrile

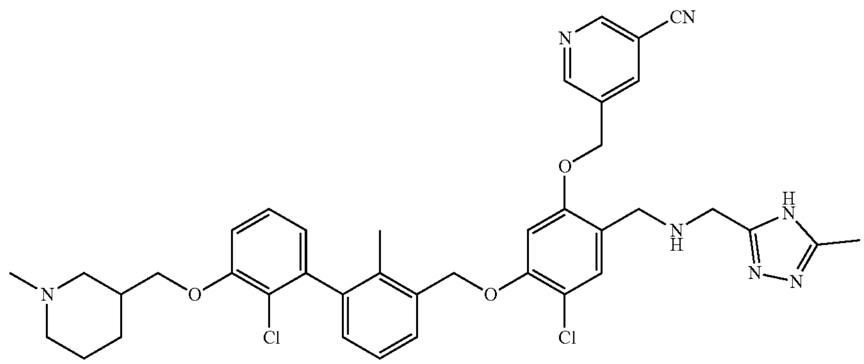

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 29% B, 29-69% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 93%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 93.7%; Observed Mass: 726.2; Retention Time: 1.78 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 92.7%; Observed Mass: 726.24; Retention Time: 1.46 min.

Example 2605: 5-((4-chloro-5-((2'-chloro-2-methyl-3'-((1-methylpiperidin-3-yl)methoxy)-[1,1'-biphenyl]-3-yl)methoxy)-2-(((2-(1-methyl-1H-benzo[d]imidazol-2-yl)ethyl)amino)methyl)phenoxy)methyl)nicotinonitrile

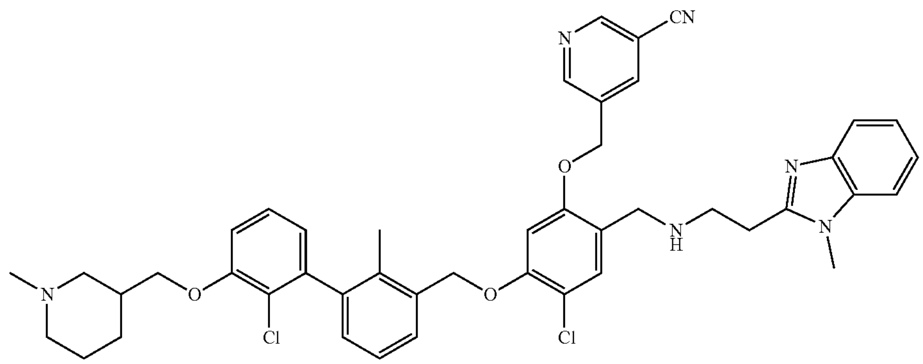 [SMILES: Cc1c(COc2cc(OCc3cncc(C#N)c3)c(CNCCc3nc4ccccc4n3C)cc2Cl)cccc1-c1cccc(OCC2CCCN(C)C2)c1Cl]

The crude material was purified via preparative LC/MS with the following conditions: Column: XBridge C18, 200 mm×19 mm, 5-µm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 36% B, 36-76% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 99%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.2%; Observed Mass: 789.19; Retention Time: 1.47 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 789.24; Retention Time: 1.87 min.

Example 2606: 5-((2-((((1H-indol-6-yl)methyl)amino)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile

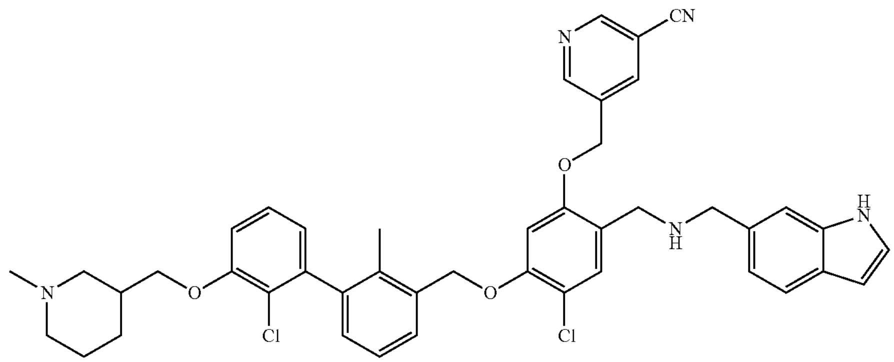 [SMILES: Cc1c(COc2cc(OCc3cncc(C#N)c3)c(CNCc3ccc4cc[nH]c4c3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 32% B, 32-74% B over 24 minutes, then a 5-minute hold at 100% B; Flow Rate: 20 mL/min; Column Temperature: 25 C. Fraction collection was triggered by UV signals. Fractions containing the desired product were combined and dried via centrifugal evaporation. The material was further purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 10% B, 10-52% B over 27 minutes, then a 5-minute hold at 100% B; Flow Rate: 20 mL/min; Column Temperature: 25 C. Fraction collection was triggered by UV signals. Fractions containing the desired product were combined and dried via centrifugal evaporation and its estimated purity by LCMS analysis was 100%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 760.21; Retention Time: 1.65 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 760.21; Retention Time: 2.1 min.

Example 2607: 5-((4-chloro-5-((2'-chloro-2-methyl-3'-((1-methylpiperidin-3-yl)methoxy)-[1,1'-biphenyl]-3-yl)methoxy)-2-((((5-cyclopropylisoxazol-3-yl)methyl)amino)methyl)phenoxy)methyl) nicotinonitrile

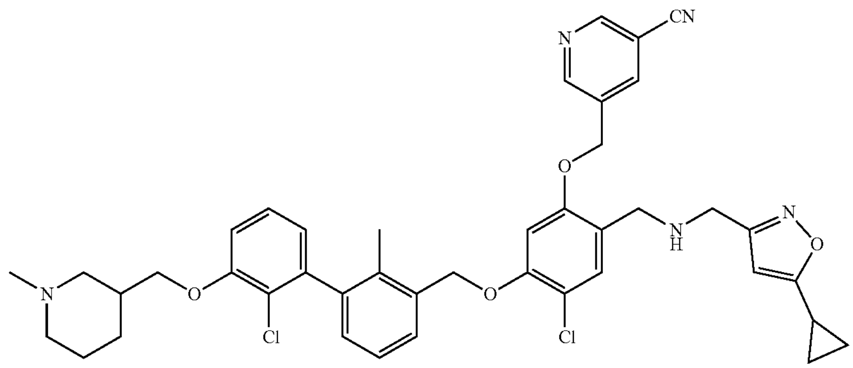 [SMILES: Cc1c(COc2cc(OCc3cncc(C#N)c3)c(CNCc3cc(C4CC4)on3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 43% B, 43-83% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 97%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.3%; Observed Mass: 752.2; Retention Time: 1.6 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 752.2; Retention Time: 2.17 min.

Example 2608: 5-((2-((3-(1H-pyrazol-3-yl)pyrrolidin-1-yl)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile

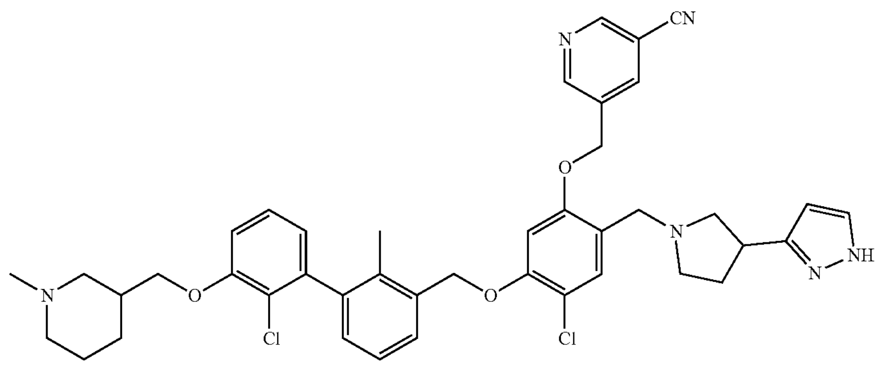 [SMILES: Cc1c(COc2cc(OCc3cncc(C#N)c3)c(CN3CCC(c4cc[nH]n4)C3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 20% B, 20-60% B over 20 minutes, then a 5-minute hold at 100% B; Flow Rate: 20 mL/min; Column Temperature: 25 C. Fraction collection was triggered by UV signals. Fractions containing the desired product were combined and dried via centrifugal evaporation and its estimated purity by LCMS analysis was 100%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 751.22; Retention Time: 1.49 min. Injection 2 conditions: Column: Waters XBridge C18, 2.1 mm×50 mm, 1.7 m particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 751.22; Retention Time: 1.89 min.

Example 2609: 5-((4-chloro-5-((2'-chloro-2-methyl-3'-((1-methylpiperidin-3-yl)methoxy)-[1,1'-biphenyl]-3-yl)methoxy)-2-((((2-methyl-1H-benzo[d]imidazol-6-yl)methyl)amino)methyl)phenoxy)methyl) nicotinonitrile

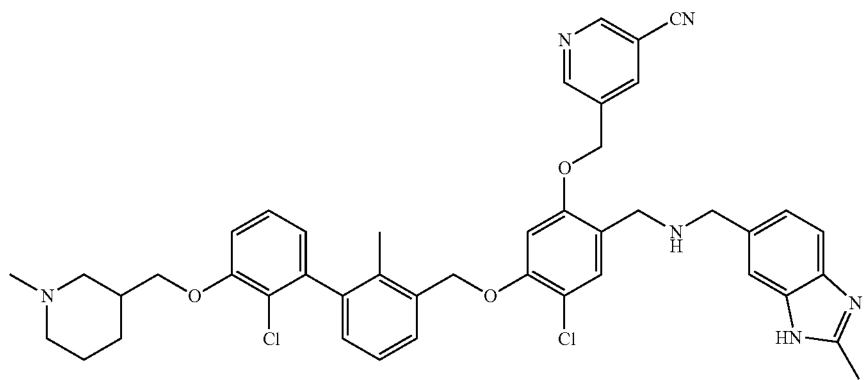

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 30% B, 30-70% B over 23 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 99%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.1%; Observed Mass: 775.18; Retention Time: 1.33 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 775.22; Retention Time: 1.8 min.

Example 2610: 5-((2-((((3-amino-1H-indazol-6-yl)methyl)amino)methyl)-4-chloro-5-((2'-chloro-2-methyl-3'-((1-methylpiperidin-3-yl)methoxy)-[1,1'-biphenyl]-3-yl)methoxy)phenoxy)methyl) nicotinonitrile

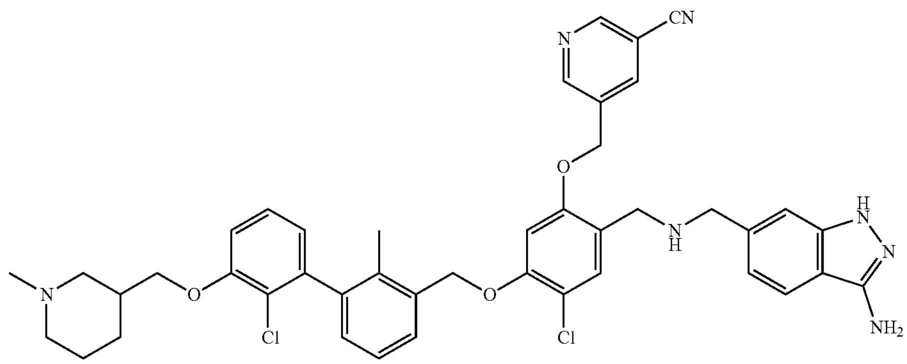 [SMILES: Cc1c(COc2cc(OCc3cncc(C#N)c3)c(CNCc3ccc4c(N)n[nH]c4c3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 27% B, 27-67% B over 25 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 98%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.1%; Observed Mass: 776.2; Retention Time: 1.84 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.9%; Observed Mass: 776.24; Retention Time: 1.38 min.

Example 2611: 5-((2-(((benzo[d]thiazol-2-ylmethyl)amino)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile

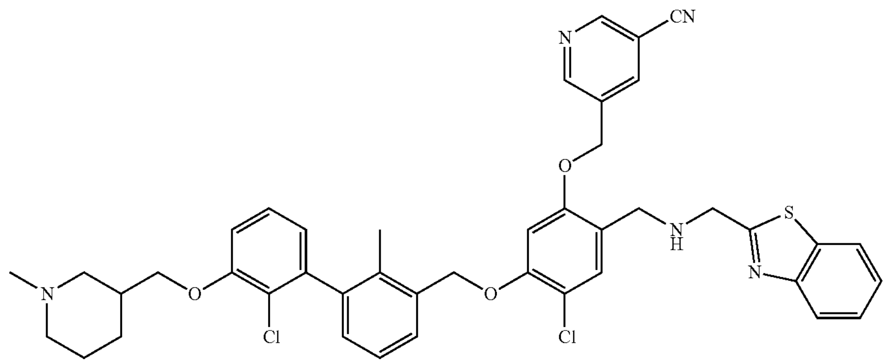 [SMILES: Cc1c(COc2cc(OCc3cncc(C#N)c3)c(CNCc3nc4ccccc4s3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 48% B, 48-88% B over 23 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 95%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.5%; Observed Mass: 778.17; Retention Time: 2.34 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 94.6%; Observed Mass: 778.15; Retention Time: 1.62 min.

Example 2612: 5-((4-chloro-5-((2'-chloro-2-methyl-3'-((1-methylpiperidin-3-yl)methoxy)-[1,1'-biphenyl]-3-yl)methoxy)-2-((((5-phenyloxazol-2-yl)methyl)amino)methyl)phenoxy)methyl)nicotinonitrile

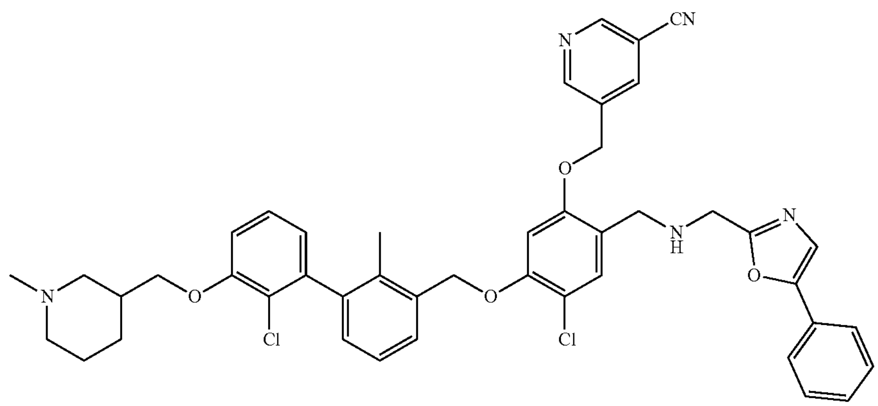 [SMILES: Cc1c(COc2cc(OCc3cncc(C#N)c3)c(CNCc3ncc(-c4ccccc4)o3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 46% B, 46-86% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.5%; Observed Mass: 788.21; Retention Time: 1.64 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.7%; Observed Mass: 788.22; Retention Time: 2.1 min.

Example 2613: 5-((4-chloro-2-(((2-(5-chloro-1H-benzo[d]imidazol-2-yl)ethyl)amino)methyl)-5-((2'-chloro-2-methyl-3'-((1-methylpiperidin-3-yl)methoxy)-[1,1'-biphenyl]-3-yl)methoxy)phenoxy)methyl)nicotinonitrile

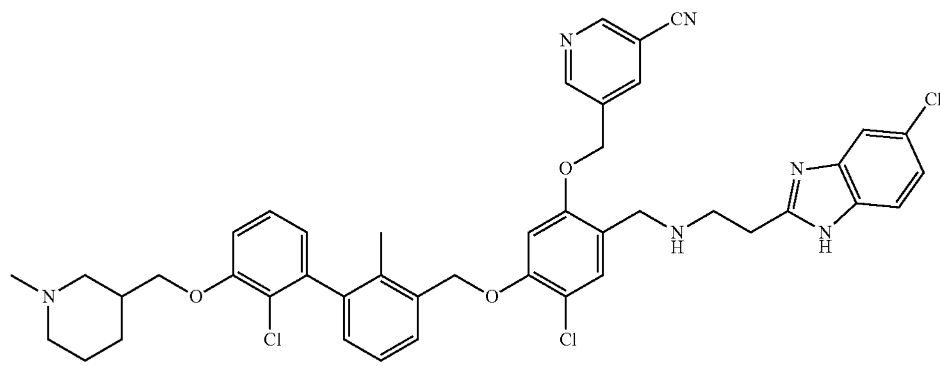 [SMILES: Cc1c(COc2cc(OCc3cncc(C#N)c3)c(CNCCc3nc4cc(Cl)ccc4[nH]3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 37% B, 37-77% B over 22 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 98%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 809.22; Retention Time: 1.57 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.0%; Observed Mass: 809.2; Retention Time: 2.26 min.

Example 2614: 5-((4-chloro-5-((2'-chloro-2-methyl-3'-((1-methylpiperidin-3-yl)methoxy)-[1,1'-biphenyl]-3-yl)methoxy)-2-((((1-methyl-1H-pyrazol-5-yl)methyl)amino)methyl)phenoxy)methyl)nicotinonitrile

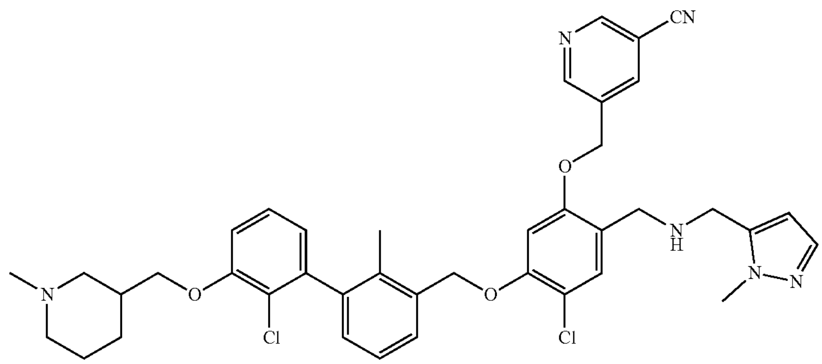 [SMILES: Cc1c(COc2cc(OCc3cncc(C#N)c3)c(CNCc3ccnn3C)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 37% B, 37-77% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.8%; Observed Mass: 725.22; Retention Time: 1.97 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.1%; Observed Mass: 725.24; Retention Time: 1.45 min.

Example 2615: 5-((4-chloro-5-((2'-chloro-2-methyl-3'-((1-methylpiperidin-3-yl)methoxy)-[1,1'-biphenyl]-3-yl)methoxy)-2-((((1-methyl-1H-indazol-3-yl)methyl)amino)methyl)phenoxy)methyl)nicotinonitrile

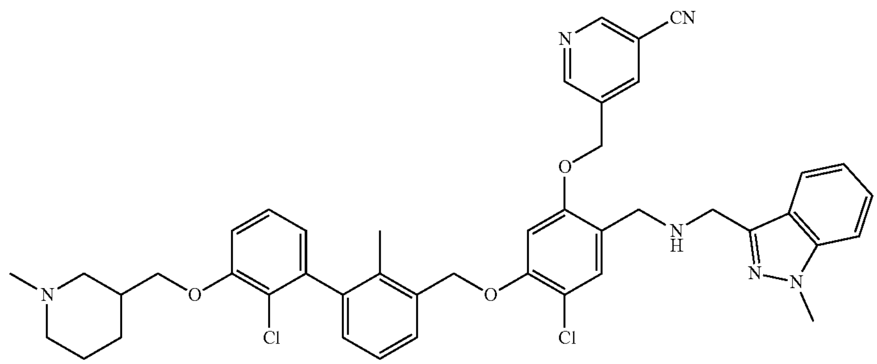 [SMILES: Cc1c(COc2cc(OCc3cncc(C#N)c3)c(CNCc3nn(C)c4ccccc34)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 45% B, 45-90% B over 25 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. The material was further purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 18% B, 18-58% B over 22 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 100%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 775.22; Retention Time: 1.61 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 775.24; Retention Time: 1.98 min.

Example 2616: 5-((2-((((1H-benzo[d]imidazol-2-yl)methyl)amino)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile

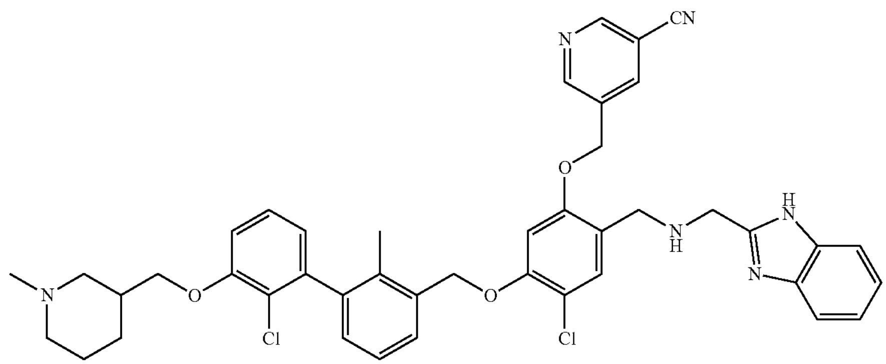 [SMILES: Cc1c(COc2cc(OCc3cncc(C#N)c3)c(CNCc3nc4ccccc4[nH]3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 36% B, 36-76% B over 23 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 99%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.2%; Observed Mass: 761.2; Retention Time: 1.52 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.9%; Observed Mass: 761.22; Retention Time: 2 min.

Example 2617: 5-((2-((((2-aminothiazol-4-yl)methyl)(methyl)amino)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile

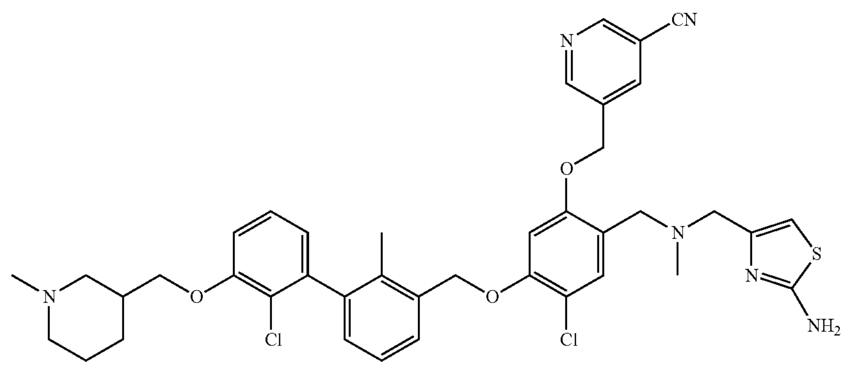 [SMILES: Cc1c(COc2cc(OCc3cncc(C#N)c3)c(CN(C)Cc3csc(N)n3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 30% B, 30-70% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.2%; Observed Mass: 757.16; Retention Time: 1.99 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.4%; Observed Mass: 757.16; Retention Time: 1.46 min.

Example 2618: 5-((2-((((1H-1,2,4-triazol-3-yl)methyl)(methyl)amino)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile

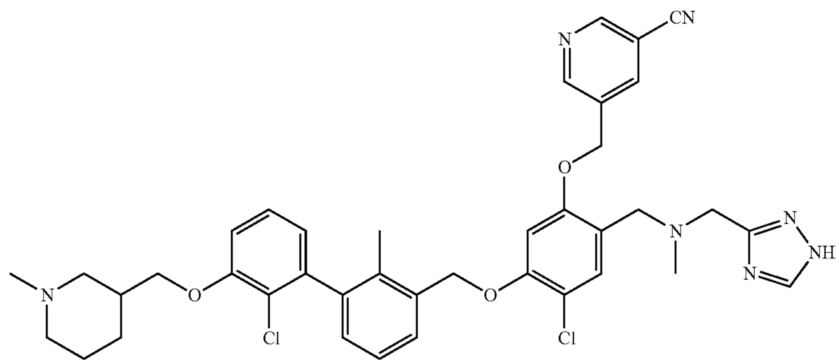 [SMILES: Cc1c(COc2cc(OCc3cncc(C#N)c3)c(CN(C)Cc3nc[nH]n3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 34% B, 34-74% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.6%; Observed Mass: 726.21; Retention Time: 1.42 min. Injection 2 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 726.22; Retention Time: 1.84 min.

Example 2619: 5-((4-chloro-5-((2'-chloro-2-methyl-3'-((1-methylpiperidin-3-yl)methoxy)-[1,1'-biphenyl]-3-yl)methoxy)-2-((((6-(trifluoromethyl)-[1,2,4]triazolo[4,3-a]pyridin-3-yl)methyl)amino)methyl)phenoxy)methyl)nicotinonitrile

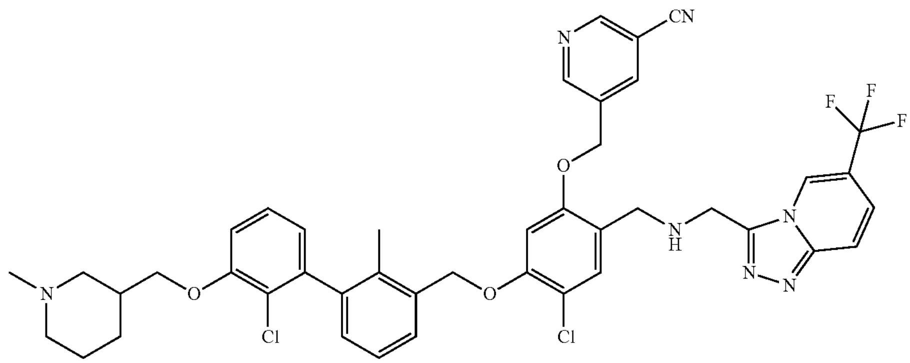 [SMILES: Cc1c(COc2cc(OCc3cncc(C#N)c3)c(CNCc3nnc4ccc(C(F)(F)F)cn34)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 16% B, 16-56% B over 22 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 100%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 830.19; Retention Time: 1.92 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 830.2; Retention Time: 1.63 min.

Example 2620: 5-((2-(((2-(1,2,4-oxadiazol-3-yl)propan-2-yl)amino)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile

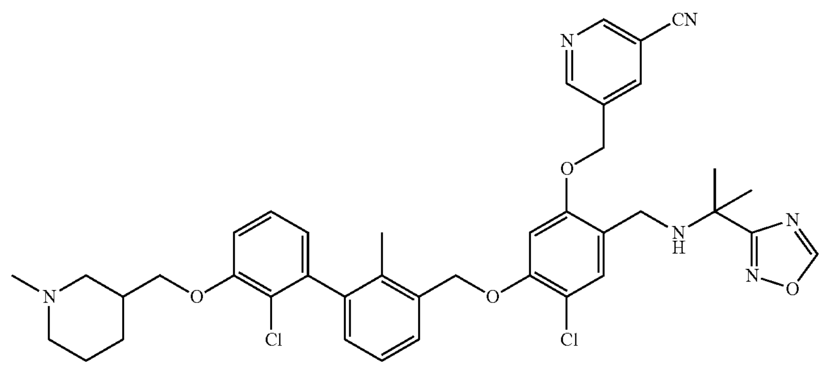 [SMILES: Cc1c(COc2cc(OCc3cncc(C#N)c3)c(CNC(C)(C)c3ncon3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 39% B, 39-79% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.1%; Observed Mass: 741.3; Retention Time: 2.24 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.5%; Observed Mass: 741.33; Retention Time: 1.54 min.

Example 2621: 5-((4-chloro-5-((2'-chloro-2-methyl-3'-((1-methylpiperidin-3-yl)methoxy)-[1,1'-biphenyl]-3-yl)methoxy)-2-((((2-chloropyridin-3-yl)methyl)amino)methyl)phenoxy)methyl)nicotinonitrile

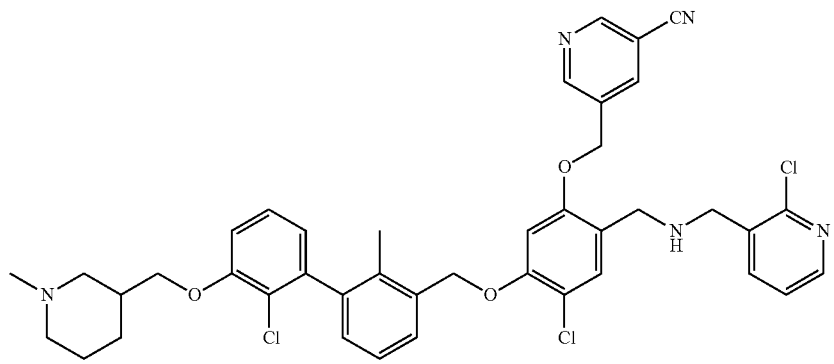 [SMILES: Cc1c(COc2cc(OCc3cncc(C#N)c3)c(CNCc3cccnc3Cl)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 16% B, 16-56% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 100%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 756.29; Retention Time: 2.21 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 756.01; Retention Time: 1.56 min.

Example 2622: 5-((4-chloro-5-((2'-chloro-2-methyl-3'-((1-methylpiperidin-3-yl)methoxy)-[1,1'-biphenyl]-3-yl)methoxy)-2-((((4-ethylthiazol-2-yl)methyl)amino)methyl)phenoxy)methyl)nicotinonitrile

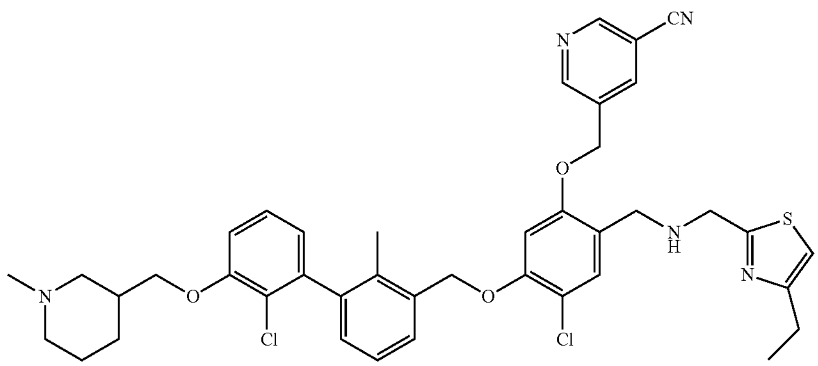 [SMILES: CCc1csc(CNCc2cc(Cl)c(OCc3cccc(-c4cccc(OCC5CCCN(C)C5)c4Cl)c3C)cc2OCc2cncc(C#N)c2)n1]

The crude material was purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 19% B, 19-59% B over 20 minutes, then a 4-minute hold at 100% B; Flow Rate: 20 mL/min; Column Temperature: 25 C. Fraction collection was triggered by UV signals. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 756.43; Retention Time: 2.22 min. Injection 2 conditions: Column: Waters XBridge C18, 2.1 mm×50 mm, 1.7 m particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.7%; Observed Mass: 756.44; Retention Time: 1.62 min.

Example 2623: 5-((4-chloro-5-((2'-chloro-2-methyl-3'-((1-methylpiperidin-3-yl)methoxy)-[1,1'-biphenyl]-3-yl)methoxy)-2-(((imidazo[1,5-a]pyridin-3-ylmethyl)amino)methyl)phenoxy)methyl) nicotinonitrile

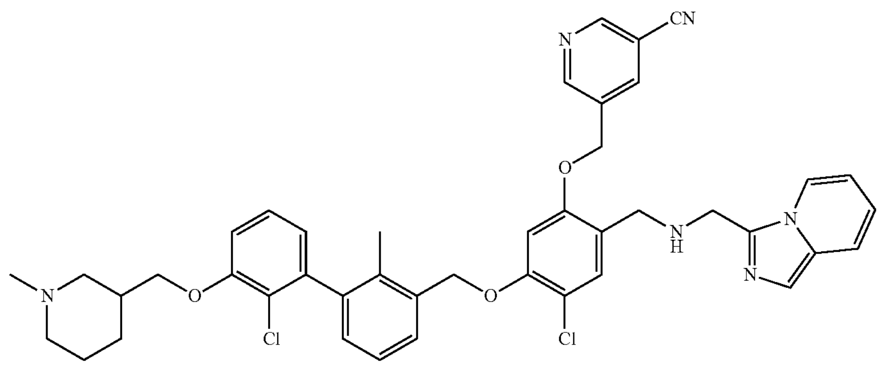 [SMILES: Cc1c(COc2cc(OCc3cncc(C#N)c3)c(CNCc3ncc4ccccn34)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 34% B, 34-74% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.5%; Observed Mass: 761.48; Retention Time: 1.97 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.2%; Observed Mass: 761.13; Retention Time: 1.62 min.

Example 2624: 5-((2-(((2-(1,2,4-oxadiazol-3-yl) propan-2-yl-1,1,1,3,3,3-d6)amino)methyl)-4-chloro-5-((2'-chloro-2-methyl-3'-((1-methylpiperidin-3-yl) methoxy)-[1,1'-biphenyl]-3-yl)methoxy)phenoxy) methyl)nicotinonitrile

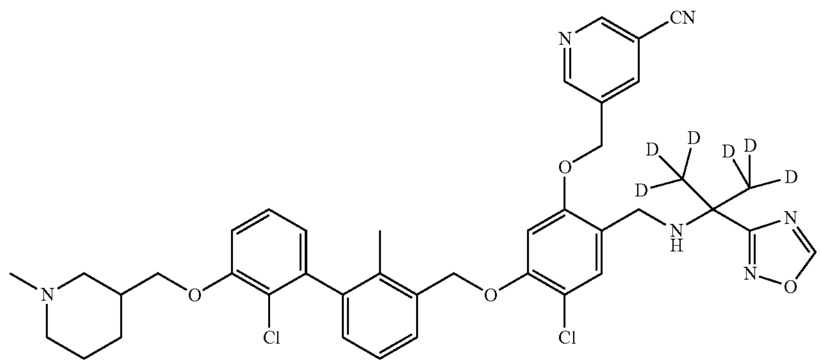 [SMILES: [2H]C([2H])([2H])C(NCc1cc(Cl)c(OCc2cccc(-c3cccc(OCC4CCCN(C)C4)c3Cl)c2C)cc1OCc1cncc(C#N)c1)(c1ncon1)C([2H])([2H])[2H]]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 39% B, 39-79% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 97%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 747.09; Retention Time: 2.24 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.7%; Observed Mass: 747.11; Retention Time: 1.54 min.

Example 2625: 5-((2-(((3-(benzyloxy)-1-(1,2,4-oxadiazol-3-yl)cyclobutyl)amino)methyl)-4-chloro-5-((2'-chloro-2-methyl-3'-((1-methylpiperidin-3-yl) methoxy)-[1,1'-biphenyl]-3-yl)methoxy)phenoxy) methyl)nicotinonitrile

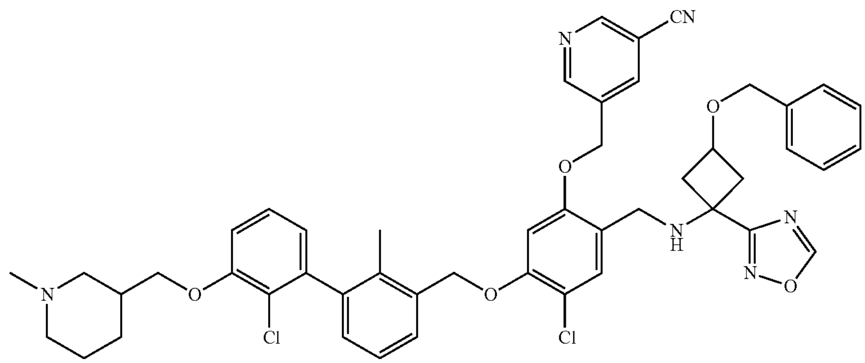 [SMILES: Cc1c(COc2cc(OCc3cncc(C#N)c3)c(CNC3(c4ncon4)CC(OCc4ccccc4)C3)cc2Cl)cccc1-c1cccc(OCC2CCCN(C)C2)c1Cl]

The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 48% B, 48-88% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation and its estimated purity by LCMS analysis was 96%. Analytical LC/MS was used to determine the final purity. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.7%; Observed Mass: 859.04; Retention Time: 2.49 min. Injection 2 conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.8%; Observed Mass: 859.32; Retention Time: 1.8 min.

BIOLOGICAL ASSAY

The ability of the compounds of the invention to bind to PD-L1 was investigated using a PD-1/PD-L1 Homogenous Time-Resolved Fluorescence (HTRF) binding assay.

Homogenous Time-Resolved Fluorescence (HTRF) binding assay.

The interaction of PD-1 and PD-L1 can be assessed using soluble, purified preparations of the extracellular domains of the two proteins. The PD-1 and PD-L1 protein extracellular domains were expressed as fusion proteins with detection tags, for PD-1, the tag was the Fc portion of Immunoglobulin (PD-1-Ig) and for PD-L1 it was the 6 histidine motif (PD-L1-His). All binding studies were performed in an HTRF assay buffer consisting of dPBS supplemented with 0.1% (with) bovine serum albumin and 0.05% (v/v) Tween-20. For the h/PD-L1-His binding assay, inhibitors were pre-incubated with PD-L1-His (10 nM final) for 15 m in 4 μl of assay buffer, followed by addition of PD-1-Ig (20 nM final) in 1 μl of assay buffer and further incubation for 15 m. HTRF detection was achieved using europium crypate-labeled anti-Ig (1 nM final) and allophycocyanin (APC) labeled anti-His (20 nM final). Antibodies were diluted in HTRF detection buffer and 5 μl was dispensed on top of the binding reaction. The reaction mixture was allowed to equilibrate for 30 minutes and the resulting signal (665 nm/620 nm ratio) was obtained using an EnVision fluorometer. Additional binding assays were established between the human proteins PD-1-Ig/PD-L2-His (20 & 5 nM, respectively) and $CD_{80}$-His/PD-L1-Ig (100 & 10 nM, respectively).

Recombinant Proteins: Human PD-1 (25-167) with a C-terminal human Fc domain of immunoglobulin G (Ig) epitope tag [hPD-1 (25-167)-3S-IG] and human PD-L1 (18-239) with a C-terminal His epitope tag [hPD-L1(18-239)-TVMV-His] were expressed in HEK293T cells and purified sequentially by ProteinA affinity chromatography and size exclusion chromatography. Human PD-L2-His and $CD_{80}$-His was obtained through commercial sources.

The table below lists the $IC_{50}$ values for representative examples of this disclosure measured in the PD-1/PD-L1 Homogenous Time-Resolved Fluorescence (HTRF) binding assay.

| Example Number | $IC_{50}$ (μM) |
|---|---|
| 1001 | 0.0049 |
| 1002 | 0.0029 |
| 1003 | 0.0014 |
| 1004 | 0.0011 |
| 1005 | 0.0023 |
| 1006 | 0.0027 |
| 1007 | 0.0030 |
| 1008 | 0.0042 |
| 1009 | 0.0005 |
| 1010 | 0.0053 |
| 1011 | 0.0175 |
| 1012 | 0.0007 |
| 1013 | 0.0032 |
| 1014 | 0.0029 |
| 1015 | 0.0029 |
| 1016 | 0.0019 |
| 1017 | 0.0019 |
| 1018 | 0.0005 |
| 1020 | 0.0028 |
| 1021 | 0.0018 |
| 1022 | 0.0013 |
| 1023 | 0.0002 |
| 1024 | 0.0007 |
| 1025 | 0.0005 |
| 1026 | 0.0015 |
| 1027 | 0.0011 |
| 1028 | 0.0019 |
| 1029 | 0.0020 |
| 1030 | 0.0002 |
| 1031 | |
| 1032 | 0.0008 |
| 1033 | 0.0021 |
| 1034 | 0.0004 |
| 1035 | 0.0013 |
| 1036 | 0.0042 |
| 1037 | 0.0028 |
| 1038 | 0.0037 |
| 1039 | 0.0027 |
| 1040 | 0.0023 |
| 1041 | 0.0005 |
| 1042 | 0.0002 |
| 1043 | 0.0031 |
| 1044 | 0.0005 |
| 1045 | 0.0038 |
| 1046 | 0.0019 |
| 1047 | 0.0024 |
| 1048 | 0.0005 |
| 1049 | 0.0025 |
| 1050 | 0.0007 |
| 1051 | 0.0021 |
| 1052 | 0.0034 |
| 1053 | 0.0076 |
| 1054 | 0.0030 |
| 1055 | 0.0012 |
| 1056 | 0.0018 |
| 1057 | 0.0007 |
| 1058 | 0.0019 |
| 1059 | 0.0036 |
| 2001 | 0.0002 |
| 2002 | 0.0093 |
| 2003 | 0.0072 |
| 2004 | 0.0041 |
| 2005 | 0.0025 |
| 2006 | 0.0002 |
| 2007 | 0.0006 |
| 2008 | 0.0005 |
| 2009 | 0.0021 |
| 2010 | 0.0021 |
| 2011 | 0.0028 |

-continued

| Example Number | $IC_{50}$ (μM) |
|---|---|
| 2012 | 0.0026 |
| 2013 | 0.0011 |
| 2014 | 0.0005 |
| 2015 | 0.0031 |
| 2016 | 0.0002 |
| 2017 | 0.0021 |
| 2018 | 0.0008 |
| 2019 | 0.0041 |
| 2020 | 0.0027 |
| 2021 | 0.0060 |
| 2022 | 0.0008 |
| 2023 | 0.0088 |
| 2024 | 0.0006 |
| 2025 | 0.0016 |
| 2026 | 0.0019 |
| 2027 | 0.0023 |
| 2028 | 0.0002 |
| 2029 | 0.0041 |
| 2030 | 0.0011 |
| 2031 | 0.0002 |
| 2032 | 0.0025 |
| 2033 | 0.0029 |
| 2040 | 0.0082 |
| 2041 | 0.0019 |
| 2042 | 0.0895 |
| 2043 | >10 |
| 2044 | 0.0014 |
| 2045 | 0.0164 |
| 2046 | 0.0323 |
| 2047 | 0.0035 |
| 2048 | 0.3547 |
| 2049 | 0.0016 |
| 2050 | 0.0017 |
| 2051 | 0.0020 |
| 2052 | 0.0096 |
| 2053 | 0.0029 |
| 2054 | 0.0056 |
| 2055 | 0.0031 |
| 2056 | 0.0035 |
| 2057 | 0.0063 |
| 2058 | 0.0039 |
| 2059 | 0.0044 |
| 2060 | 0.0019 |
| 2061 | 0.0169 |
| 2062 | 0.0076 |
| 2063 | 0.0285 |
| 2064 | 0.1788 |
| 2065 | 0.0280 |
| 2066 | 0.0759 |
| 2067 | 0.0531 |
| 2068 | 0.0896 |
| 2501 | 0.0023 |
| 2502 | 0.0009 |
| 2503 | 0.0039 |
| 2504 | 0.0018 |
| 2505 | 0.0067 |
| 2506 | 0.0004 |
| 2507 | 0.0017 |
| 2508 | 0.0062 |
| 2509 | 0.0002 |
| 2510 | 0.0033 |
| 2511 | 0.0033 |
| 2512 | 0.0039 |
| 2513 | 0.0036 |
| 2514 | 0.0019 |
| 2515 | 0.0038 |
| 2516 | 0.0045 |
| 2517 | 0.0124 |
| 2518 | 0.0044 |
| 2519 | 0.0010 |
| 2520 | 0.0031 |
| 2521 | 0.0007 |
| 2522 | 0.0232 |
| 2523 | 0.1783 |
| 2524 | 0.0055 |
| 2525 | 0.0022 |

-continued

| Example Number | $IC_{50}$ (μM) |
|---|---|
| 2526 | 0.0030 |
| 2527 | 0.0054 |
| 2528 | 0.0031 |
| 2529 | 0.0011 |
| 2530 | 0.0062 |
| 2531 | 0.0034 |
| 2532 | 0.0048 |
| 2533 | 0.0027 |
| 2534 | 0.0034 |
| 2535 | 0.0039 |
| 2536 | 0.0074 |
| 2537 | 0.0065 |
| 2538 | 0.0438 |
| 2539 | 0.0007 |
| 2540 | 0.0031 |
| 2541 | 0.0039 |
| 2542 | 0.0039 |
| 2543 | 0.1917 |
| 2544 | 0.0016 |
| 2545 | 0.0119 |
| 2546 | 0.0018 |
| 2547 | 0.0025 |
| 2548 | <0.000038 |
| 2549 | 0.0332 |
| 2550 | 0.0005 |
| 2551 | 0.0027 |
| 2552 | 0.0073 |
| 2553 | 0.0301 |
| 2554 | 0.2581 |
| 2555 | 0.0004 |
| 2556 | 0.0008 |
| 2557 | 0.0733 |
| 2558 | 0.0064 |
| 2559 | 0.0041 |
| 2560 | 0.0045 |
| 2561 | 0.7464 |
| 2562 | 0.0095 |
| 2563 | 0.0005 |
| 2564 | 0.0027 |
| 2565 | 0.0047 |
| 2566 | 0.0486 |
| 2567 | 0.0228 |
| 2568 | 0.0025 |
| 2569 | 0.0055 |
| 2570 | 0.0015 |
| 2571 | 0.0038 |
| 2572 | 0.0033 |
| 2575 | 0.0028 |
| 2576 | 0.0025 |
| 2577 | 0.0016 |
| 2578 | 0.0019 |
| 2579 | 0.0005 |
| 2580 | 0.0002 |
| 2581 | 0.0034 |
| 2582 | 0.0037 |
| 2583 | 0.0023 |
| 2584 | 0.0026 |
| 2585 | 0.0028 |
| 2586 | 0.0007 |
| 2587 | 0.0009 |
| 2588 | 0.0020 |
| 2589 | 0.0079 |
| 2590 | 0.0020 |
| 2591 | 0.0019 |
| 2592 | 0.0036 |
| 2593 | 0.0030 |
| 2594 | 0.0007 |
| 2595 | 0.0020 |
| 2596 | 0.0029 |
| 2597 | 0.0029 |
| 2598 | 0.0010 |
| 2599 | 0.0017 |
| 2600 | 0.0072 |
| 2601 | 0.0006 |
| 2602 | 0.0016 |
| 2603 | 0.0009 |

-continued

| Example Number | $IC_{50}$ (μM) |
|---|---|
| 2604 | 0.0023 |
| 2605 | 0.0006 |
| 2606 | 0.0014 |
| 2607 | 0.0042 |
| 2608 | 0.0023 |
| 2609 | 0.0011 |
| 2610 | 0.0008 |
| 2611 | 0.0059 |
| 2612 | 0.0073 |
| 2613 | 0.0022 |
| 2614 | 0.0017 |
| 2615 | |
| 2616 | 0.0019 |
| 2617 | 0.0018 |
| 2618 | 0.0007 |
| 2619 | 0.0031 |
| 2620 | 0.0047 |
| 2621 | 0.0089 |
| 2622 | 0.0083 |
| 2623 | 0.0061 |
| 2624 | 0.0030 |
| 2625 | 0.0353 |

The compounds of formula (I) possess activity as inhibitors of the PD-1/PD-L1 interaction, and therefore, may be used in the treatment of diseases or deficiencies associated with the PD-1/PD-L1 interaction. Via inhibition of the PD-1/PD-L1 interaction, the compounds of the present disclosure may be employed to treat infectious diseases such as HIV, septic shock, Hepatitis A, B, C, or D and cancer.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All publications, patents, and patent applications disclosed herein are incorporated by reference to the same extent as if each individual publication, patent or patent application was specifically and individually indicated to be incorporated by reference.

We claim:

1. A compound which is

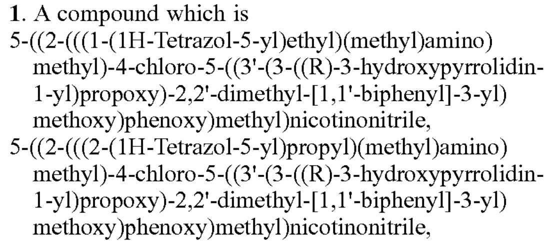

5-((2-(((1-(1H-Tetrazol-5-yl)ethyl)(methyl)amino)methyl)-4-chloro-5-((3'-(3-((R)-3-hydroxypyrrolidin-1-yl)propoxy)-2,2'-dimethyl-[1,1'-biphenyl]-3-yl)methoxy)phenoxy)methyl)nicotinonitrile, 5-((2-(((2-(1H-Tetrazol-5-yl)propyl)(methyl)amino)methyl)-4-chloro-5-((3'-(3-((R)-3-hydroxypyrrolidin-1-yl)propoxy)-2,2'-dimethyl-[1,1'-biphenyl]-3-yl)methoxy)phenoxy)methyl)nicotinonitrile, 5-((4-Chloro-5-((3'-(3-((R)-3-hydroxypyrrolidin-1-yl)propoxy)-2,2'-dimethyl-[1,1'-biphenyl]-3-yl)methoxy)-2-((2-(5-oxo-2,5-dihydro-1H-1,2,4-triazol-3-yl)piperidin-1-yl)-methyl)phenoxy)methyl)nicotinonitrile, 5-((2-(((2-(1H-Tetrazol-5-yl)propyl)amino)methyl)-4-chloro-5-((3'-(3-((R)-3-hydroxy-pyrrolidin-1-yl)propoxy)-2,2'-dimethyl-[1,1'-biphenyl]-3-yl)methoxy)phenoxy)methyl)-nicotinonitrile, 2-((5-Chloro-4-((2'-chloro-2-methyl-3'-((1-methylpiperidin-3-yl)methoxy)-[1,1'-biphenyl]-3-yl)methoxy)-2-((5-cyanopyridin-3-yl)methoxy)benzyl)amino)-2-(3,5-dimethyl-1H-pyrazol-4-yl)acetic acid, 2-((5-Chloro-4-((2'-chloro-2-methyl-3'-((1-methylpiperidin-3-yl)methoxy)-[1,1'-biphenyl]-3-yl)methoxy)-2-((5-cyanopyridin-3-yl)methoxy)benzyl)amino)-2-(1-methyl-1H-pyrazol-4-yl)acetic acid, 5-((4-Chloro-5-((2'-chloro-2-methyl-3'-((1-methylpiperidin-3-yl)methoxy)-[1,1'-biphenyl]-3-yl)methoxy)-2-((3-(hydroxymethyl)-1-methyl-1,3a,4,6,7,7a-hexahydro-5H-pyrazolo[4,3-c]pyridin-5-yl)methyl)phenoxy)methyl)nicotinonitrile, 5-((2-(((1-(1H-Tetrazol-5-yl)ethyl)(methyl)amino)methyl)-4-chloro-5-((3'-(3-(((S)-2,3-dihydroxypropyl)amino)propoxy)-2,2'-dimethyl-[1,1'-biphenyl]-3-yl)methoxy)-phenoxy)methyl)nicotinonitrile, 5-((2-(((2-(1H-Tetrazol-5-yl)propyl)(methyl)amino)methyl)-4-chloro-5-((3'-(3-(((S)-2,3-dihydroxy-propyl)amino)propoxy)-2,2'-dimethyl-[1,1'-biphenyl]-3-yl)methoxy)-phenoxy)methyl)nicotinonitrile, 5-((2-(((1-(1H-Tetrazol-5-yl)ethyl)(methyl)amino)methyl)-4-chloro-5-((2'-chloro-3'-(3-(((S)-2,3-dihydroxypropyl)amino)propoxy)-2-methyl-[1,1'-biphenyl]-3-yl)methoxy)-phenoxy)methyl)-nicotinonitrile, 5-((2-(((2-(1H-Tetrazol-5-yl)propyl)(methyl)amino)methyl)-4-chloro-5-((2'-chloro-3'-(3-(((S)-2,3-dihydroxypropyl)amino)propoxy)-2-methyl-[1,1'-biphenyl]-3-yl)methoxy)-phenoxy)methyl)nicotinonitrile, N-(1-(3-((3'-((4-(((1-(1H-Tetrazol-5-yl)ethyl)(methyl)amino)methyl)-2-chloro-5-((5-cyanopyridin-3-yl)methoxy)phenoxy)methyl)-2,2'-dimethyl-[1,1'-biphenyl]-3-yl)oxy)-propyl)piperidin-4-yl)acetamide, N-(1-(3-((3'-((4-(((1-(1H-Tetrazol-5-yl)ethyl)amino)methyl)-2-chloro-5-((5-cyanopyridin-3-yl)methoxy)phenoxy)methyl)-2,2'-dimethyl-[1,1'-biphenyl]-3-yl)oxy)propyl)piperidin-4-yl)acetamide, N-(1-(3-((3'-((4-(((2-(2H-Tetrazol-5-yl)propyl)(methyl)amino)methyl)-2-chloro-5-((5-cyanopyridin-3-yl)methoxy)phenoxy)methyl)-2,2'-dimethyl-[1,1'-biphenyl]-3-yl)oxy)-propyl)piperidin-4-yl)acetamide, (R)-4-(((5-chloro-4-((3'-(3-(3-hydroxypyrrolidin-1-yl)propoxy)-2,2'-dimethyl-[1,1'-biphenyl]-3-yl)methoxy)-2-((5-methyl-1H-imidazol-4-yl)methoxy)benzyl)amino)methyl)pyrimidine-2-carbonitrile, N-(1-(3-((3'-((4-(((2-(1H-Tetrazol-5-yl)propyl)amino)methyl)-2-chloro-5-((5-cyano-pyridin-3-yl)methoxy)phenoxy)methyl)-2,2'-dimethyl-[1,1'-biphenyl]-3-yl)oxy)propyl)-piperidin-4-yl)acetamide, (R)-4-(((5-chloro-4-((3'-(3-(3-hydroxypyrrolidin-1-yl)propoxy)-2,2'-dimethyl-[1,1'-biphenyl]-3-yl)methoxy)-2-((5-methyl-1-trityl-1H-imidazol-4-yl)methoxy)benzyl)amino)methyl)pyrimidine-2-carbonitrile, (R)-1-(3-((3'-((4-((((1H-imidazol-2-yl)methyl)amino)methyl)-2-chloro-5-(pyrimidin-5-ylmethoxy)phenoxy)methyl)-2,2'-dimethyl-[1,1'-biphenyl]-3-yl)oxy)propyl)pyrrolidin-3-ol, (R)-1-(3-((3'-((4-((((1H-pyrazol-4-yl)methyl)amino)methyl)-2-chloro-5-(pyrimidin-5-ylmethoxy)phenoxy)methyl)-2,2'-dimethyl-[1,1'-biphenyl]-3-yl)oxy)propyl)pyrrolidin-3-ol, N-((1H-pyrazol-4-yl)methyl)-1-(5-chloro-4-((2'-chloro-2-methyl-3'-((1-methylpiperidin-3-yl)methoxy)-[1,1'-biphenyl]-3-yl)methoxy)-2-(pyridazin-3-ylmethoxy)phenyl)methanamine, N-((1H-imidazol-2-yl)methyl)-1-(5-chloro-4-((2'-chloro-2-methyl-3'-((1-methylpiperidin-3-yl)methoxy)-[1,1'-biphenyl]-3-yl)methoxy)-2-(pyridazin-3-ylmethoxy)phenyl)methanamine, N-((1H-pyrazol-4-yl)methyl)-1-(5-chloro-4-((2'-chloro-2-methyl-3'-((1-methylpiperidin-3-yl)methoxy)-[1,1'-biphenyl]-3-yl)methoxy)-2-methoxyphenyl)methanamine, N-((1H-imidazol-2-yl)methyl)-1-(5-chloro-4-((2'-chloro-2-methyl-3'-((1-methylpiperidin-3-yl)methoxy)-[1,1'-biphenyl]-3-yl)methoxy)-2-methoxyphenyl)methanamine, N-(5-chloro-4-((2'-chloro-2-methyl-3'-((1-methylpiperidin-3-yl)methoxy)-[1,1'-biphenyl]-3-yl)methoxy)-2-(pyrazin-2-ylmethoxy)benzyl)-1-(pyridazin-3-yl)methanamine, N-(5-chloro-4-((2'-chloro-2-methyl-3'-((1-methylpiperidin-3-yl)methoxy)-[1,1'-biphenyl]-3-yl)methoxy)-2-(pyrazin-2-ylmethoxy)benzyl)-1-(pyrimidin-2-yl)methanamine, N-((1H-imidazol-4-yl)methyl)-1-(5-chloro-4-((2'-chloro-2-methyl-3'-((1-methylpiperidin-3-yl)methoxy)-[1,1'-biphenyl]-3-yl)methoxy)-2-(pyrazin-2-ylmethoxy)phenyl)methanamine, ((R)-5-((4-chloro-5-((3'-(3-(3-hydroxypyrrolidin-1-yl)propoxy)-2,2'-dimethyl-[1,1'-biphenyl]-3-yl)methoxy)-2-((1-methyl-1,4,6,7-tetrahydro-5H-imidazo[4,5-c]pyridin-5-yl)methyl)phenoxy)methyl)nicotinonitrile, (R)-5-((4-chloro-5-((3'-(3-(3-hydroxypyrrolidin-1-yl)propoxy)-2,2'-dimethyl-[1,1'-biphenyl]-3-yl)methoxy)-2-((2-methyl-6,7-dihydrothiazolo[5,4-c]pyridin-5 (4H)yl)methyl)phenoxy)methyl)nicotinonitrile, (R)-5-((4-chloro-5-((3'-(3-(3-hydroxypyrrolidin-1-yl)propoxy)-2,2'-dimethyl-[1,1'-biphenyl]-3-yl)methoxy)-2-((1,4,6,7-tetrahydro-5H-pyrazolo[4,3-c]pyridin-5-yl)methyl)phenoxy)methyl)nicotinonitrile, (R)-5-((4-chloro-5-((3'-(3-(3-hydroxypyrrolidin-1-yl)propoxy)-2,2'-dimethyl-[1,1'-biphenyl]-3-yl)methoxy)-2-((1,4,6,7-tetrahydro-5H-imidazo[4,5-c]pyridin-5-yl)methyl)phenoxy)methyl)nicotinonitrile, (R)-5-((4-chloro-2-(((2-(5-chloro-1H-benzo[d]imidazol-2-yl)ethyl)amino)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile, (R)-5-((2-(((benzo[d]thiazol-2-ylmethyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile, (R)-5-((2-(((benzo[d]thiazol-2-ylmethyl)(methyl)amino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile, (R)-5-((4-chloro-5-((3'-(3-(3-hydroxypyrrolidin-1-yl)propoxy)-2,2'-dimethyl-[1,1'-biphenyl]-3-yl)methoxy)-2-((((1-methyl-1H-indazol-3-yl)methyl)amino)methyl)phenoxy)methyl)nicotinonitrile, 5-((4-chloro-5-((3'-(3-((R)-3-hydroxypyrrolidin-1-yl)propoxy)-2,2'-dimethyl-[1,1'-biphenyl]-3-yl)methoxy)-2-(((4,5,6,7-tetrahydro-1H-indazol-5-yl)amino)methyl)phenoxy)methyl)nicotinonitrile, 5-((4-chloro-5-((3'-(3-((R)-3-hydroxypyrrolidin-1-yl)propoxy)-2,2'-dimethyl-[1,1'-biphenyl]-3-yl)methoxy)-2-((methyl (4,5,6,7-tetrahydro-1H-indazol-5-yl)amino)methyl)phenoxy)methyl)nicotinonitrile, (R)-5-((4-chloro-5-((3'-(3-(3-hydroxypyrrolidin-1-yl)propoxy)-2,2'-dimethyl-[1,1'-biphenyl]-3-yl)methoxy)-2-(((imidazo[1,5-a]pyridin-3-ylmethyl)amino)methyl)phenoxy)methyl)nicotinonitrile, (R)-5-((4-chloro-5-((3'-(3-(3-hydroxypyrrolidin-1-yl)propoxy)-2,2'-dimethyl-[1,1'-biphenyl]-3-yl)methoxy)-2-((1-phenyl-1,4,6,7-tetrahydro-5H-pyrazolo[4,3-c]pyridin-5-yl)methyl)phenoxy)methyl)nicotinonitrile, (R)-5-((4-chloro-5-((3'-(3-(3-hydroxypyrrolidin-1-yl)propoxy)-2,2'-dimethyl-[1,1'-biphenyl]-3-yl)methoxy)-2-((1,4,5,7-tetrahydro-6H-pyrazolo[3,4-c]pyridin-6-yl)methyl)phenoxy)methyl)nicotinonitrile, (R)-5-((4-chloro-2-((((4,5-diethyl-1H-imidazol-2-yl)methyl)(2-methoxyethyl)amino)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile, 5-((4-chloro-5-((2'-chloro-2-methyl-3'-((1-methylpiperidin-3-yl)methoxy)-[1,1'-biphenyl]-3-yl)methoxy)-2-((1,4,6,7-tetrahydro-5H-imidazo[4,5-c]pyridin-5-yl)methyl)phenoxy)methyl)nicotinonitrile, 5-((4-chloro-5-((2'-chloro-2-methyl-3'-((1-methylpiperidin-3-yl)methoxy)-[1,1'-biphenyl]-3-yl)methoxy)-2-((1,4,6,7-tetrahydro-5H-pyrazolo[4,3-c]pyridin-5-yl)methyl)phenoxy)methyl)nicotinonitrile, 5-((4-chloro-5-((2'-chloro-2-methyl-3'-((1-methylpiperidin-3-yl)methoxy)-[1,1'-biphenyl]-3-yl)methoxy)-2-((1,4,5,7-tetrahydro-6H-pyrazolo[3,4-c]pyridin-6-yl)methyl)phenoxy)methyl)nicotinonitrile, 5-((4-chloro-5-((2'-chloro-2-methyl-3'-((1-methylpiperidin-3-yl)methoxy)-[1,1'-biphenyl]-3-yl)methoxy)-2-((1,4,5,7-tetrahydro-6H-pyrazolo[3,4-c]12yridine-6-yl)methyl)phenoxy)methyl)nicotinonitrile, 5-((4-chloro-5-((2'-chloro-2-methyl-3'-((1-methylpiperidin-3-yl)methoxy)-[1,1'-biphenyl]-3-yl)methoxy)-2-((1-methyl-1,4,6,7-tetrahydro-5H-imidazo[4,5-c]pyridin-5-yl)methyl)phenoxy)methyl)nicotinonitrile, 5-((2-(((2-(1H-benzo[d]imidazol-2-yl)ethyl)amino)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile, 5-((4-chloro-5-((2'-chloro-2-methyl-3'-((1-methylpiperidin-3-yl)methoxy)-[1,1'-biphenyl]-3-yl)methoxy)-2-((2-methyl-6,7-dihydrothiazolo[5,4-c]pyridin-5 (4H)-yl)methyl)phenoxy)methyl)nicotinonitrile, 5-((4-chloro-5-((2'-chloro-2-methyl-3'-((1-methylpiperidin-3-yl)methoxy)-[1,1'-biphenyl]-3-yl)methoxy)-2-(((4,5,6,7-tetrahydro-1H-indazol-5-yl)amino)methyl)phenoxy)methyl)nicotinonitrile, 5-((2-(((benzo[d]thiazol-2-ylmethyl)amino)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile, 5-((4-chloro-5-((2'-chloro-2-methyl-3'-((1-methylpiperidin-3-yl)methoxy)-[1,1'-biphenyl]-3-yl)methoxy)-2-(((((6-(trifluoromethyl)-[1,2,4]triazolo[4,3-a]pyridin-3-yl)methyl)amino)methyl)phenoxy)methyl)nicotinonitrile, 5-((2-(((2-(1,2,4-oxadiazol-3-yl)propan-2-yl)amino)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile, 5-((4-chloro-5-((2'-chloro-2-methyl-3'-((1-methylpiperidin-3-yl)methoxy)-[1,1'-biphenyl]-3-yl)methoxy)-2-(((imidazo[1,5-a]pyridin-3-ylmethyl)amino)methyl)phenoxy)methyl)nicotinonitrile, 5-((2-(((2-(1,2,4-oxadiazol-3-yl)propan-2-yl-1,1,1,3,3,3-d6)amino)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile, 5-((2-(((3-(benzyloxy)-1-(1,2,4-oxadiazol-3-yl)cyclobutyl)amino)methyl)-4-chloro-5-((2'-chloro-2-methyl-3'-((1-methylpiperidin-3-yl)methoxy)-[1,1'-biphenyl]-3-yl)methoxy)phenoxy)methyl)nicotinonitrile, 5-((2-((2-(1H-Pyrazol-4-yl)piperidin-1-yl)methyl)-4-chloro-5-((3'-(3-((R)-3-hydroxy-pyrrolidin-1-yl)propoxy)-2,2'-dimethyl-[1,1'-biphenyl]-3-yl)methoxy)phenoxy)methyl)-nicotinonitrile, 5-((2-((2-(1H-Pyrazol-4-yl)piperidin-1-yl)methyl)-4-chloro-5-((2'-chloro-2-methyl-3'-((1-methylpiperidin-3-yl)methoxy)-[1,1'-biphenyl]-3-yl)methoxy)phenoxy)methyl)-nicotinonitrile, or 5-((2-((2-(1H-Pyrazol-3-yl)piperidin-1-yl)methyl)-4-chloro-5-((2'-chloro-2-methyl-3'-((1-methylpiperidin-3-yl)methoxy)-[1,1'-biphenyl]-3-yl)methoxy)phenoxy)methyl)-nicotinonitrile, or a pharmaceutically acceptable salt thereof.

2. A pharmaceutical composition comprising a compound of claim 1, or a pharmaceutically acceptable salt thereof, and a pharmaceutically acceptable carrier.

* * * * *